United States Patent
Scutt et al.

(10) Patent No.: US 11,618,743 B2
(45) Date of Patent: Apr. 4, 2023

(54) HERBICIDAL COMPOUNDS

(71) Applicant: SYNGENTA PARTICIPATIONS AG, Basel (CH)

(72) Inventors: James Nicholas Scutt, Bracknell (GB); Nigel James Willetts, Bracknell (GB); Ravindra Sonawane, Goa (IN); Mangala Phadte, Goa (IN); Sandeep Reddy Kandukuri, Goa (IN); Swarnendu Sasmal, Goa (IN); Sarah Armstrong, Bracknell (GB); Andrea McGranaghan, Bracknell (GB); Sean Ng, Bracknell (GB)

(73) Assignee: SYNGENTA PARTICIPATIONS AG, Basel (CH)

( * ) Notice: Subject to any disclaimer, the term of this patent is extended or adjusted under 35 U.S.C. 154(b) by 315 days.

(21) Appl. No.: 16/639,723

(22) PCT Filed: Aug. 16, 2018

(86) PCT No.: PCT/EP2018/072280
§ 371 (c)(1),
(2) Date: Feb. 17, 2020

(87) PCT Pub. No.: WO2019/034757
PCT Pub. Date: Feb. 21, 2019

(65) Prior Publication Data
US 2021/0009561 A1    Jan. 14, 2021

(30) Foreign Application Priority Data

Aug. 17, 2017  (IN) .............................. 201711029217

(51) Int. Cl.
| | | |
|---|---|---|
| *C07D 403/04* | (2006.01) | |
| *A01N 43/58* | (2006.01) | |
| *A01N 43/60* | (2006.01) | |
| *A01N 57/24* | (2006.01) | |

(52) U.S. Cl.
CPC ........... *C07D 403/04* (2013.01); *A01N 43/58* (2013.01); *A01N 43/60* (2013.01); *A01N 57/24* (2013.01)

(58) Field of Classification Search
None
See application file for complete search history.

(56) References Cited

U.S. PATENT DOCUMENTS

| | | |
|---|---|---|
| 3,702,361 A | 11/1972 | Phillips |
| 5,466,697 A | 11/1995 | Wilhelm et al. |
| 7,329,757 B2 | 2/2008 | Muller et al. |
| 2021/0053957 A1* | 2/2021 | Scutt ...................... A01N 43/82 |

FOREIGN PATENT DOCUMENTS

| | | |
|---|---|---|
| GB | 1334272 A | 10/1973 |
| WO | 2016071360 A1 | 5/2016 |

OTHER PUBLICATIONS

Heldmann, D. K. et al. "Synthesis of Metallated . . . " Tetrahedron Letters, V. 38, No. 33, 5791-5794, 1997 (Year: 1997).*
Patani, G. A. et al. "Bioisosterism . . . " Chemical Reviews, 1996, 96, 3147-3176. (Year: 1996).*
Heldmann, D. K. et al. "Synthesis of Metallated . . . " Tetrahedron Letters, 1997, v. 38, No. 33, 5791-5794 (Year: 1997).*
Patani, G. et al. "Bioisosterism: . . . " Chemical Reviews, 1996, 96, 3147-3176 (Year: 1996).*
McDouall, J. J. W. "Theoretical and computational chemistry" Taken from Sciencedirect pseudohalogen topics, p. 1, section 4.1, first sentence, 2002. (Year: 2002).*
Duke et al. Toxins, 2011, 3, 1038-1064. (Year: 2011).*
IUPAC goldbook "pseudohalogens" entry, https://goldbook.iupac.org/terms/view/P04930#:~:text=Compounds%20that%20resemble%20the%20halogen,e.g.%20N%20%2C%20SCN%20%2C%20CN%20, 2014 no pagination.*
International Search Report for International Application No. PCT/EP2018/072280 dated Oct. 8, 2018.

* cited by examiner

*Primary Examiner* — Erin E Hirt
(74) *Attorney, Agent, or Firm* — BakerHostetler; Toni-Junell Herbert

(57) ABSTRACT

Compounds of the formula (I) wherein the substituents are as defined in claim 1, useful as a pesticides, especially as herbicides.

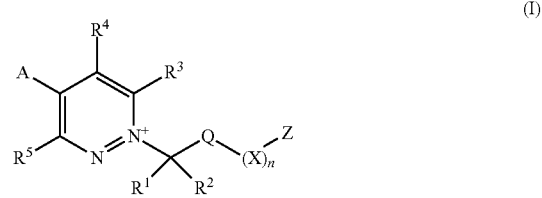

(I)

29 Claims, No Drawings

HERBICIDAL COMPOUNDS

CROSS-REFERENCE TO RELATED APPLICATIONS

This application is a 371 National Stage application of International Application No. PCT/EP2018/072280 filed Aug. 16, 2018 which claims priority to IN 201711029217, filed Aug. 17, 2017, the entire contents of which applications are hereby incorporated by reference.

The present invention relates to herbicidally active pyridazine derivatives, as well as to processes and intermediates used for the preparation of such derivatives. The invention further extends to herbicidal compositions comprising such derivatives, as well as to the use of such compounds and compositions for controlling undesirable plant growth: in particular the use for controlling weeds, in crops of useful plants.

The present invention is based on the finding that pyridazine derivatives of Formula (I) as defined herein, exhibit surprisingly good herbicidal activity. Thus, according to the present invention there is provided a compound of formula (I) or an agronomically acceptable salt or zwitterionic species thereof:

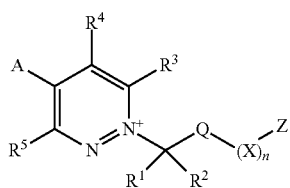

(I)

wherein $R^1$ is selected from the group consisting of hydrogen, halogen, $C_1$-$C_6$alkyl, $C_2$-$C_6$alkenyl, $C_2$-$C_6$alkynyl, $C_3$-$C_6$cycloalkyl, $C_1$-$C_6$haloalkyl, —$OR^7$, —$OR^{15a}$, —$N(R^6)S(O)_2R^{15}$, —$N(R^6)C(O)R^{15}$, —$N(R^6)C(O)OR^{15}$, —$N(R^6)C(O)NR^{16}R^{17}$, —$N(R^6)CHO$, —$N(R^{7a})_2$ and —$S(O)_rR^{15}$;

$R^2$ is selected from the group consisting of hydrogen, halogen, $C_1$-$C_6$alkyl and $C_1$-$C_6$haloalkyl;

and wherein when $R^1$ is selected from the group consisting of —$OR^7$, —$OR^{15a}$, —$N(R^6)S(O)_2R^{15}$, —$N(R^6)C(O)R^{15}$, —$N(R^6)C(O)OR^{15}$, —$N(R^6)C(O)NR^{16}R^{17}$, —$N(R^6)CHO$, —$N(R^{7a})_2$ and —$S(O)_rR^{15}$, $R^2$ is selected from the group consisting of hydrogen and $C_1$-$C_6$alkyl; or $R^1$ and $R^2$ together with the carbon atom to which they are attached form a $C_3$-$C_6$cycloalkyl ring or a 3- to 6-membered heterocyclyl, which comprises 1 or 2 heteroatoms individually selected from N and O;

Q is $(CR^{1a}R^{2b})_m$;

m is 0, 1, 2 or 3;

each $R^{1a}$ and $R^{2b}$ are independently selected from the group consisting of hydrogen, halogen, $C_1$-$C_6$alkyl, $C_1$-$C_6$haloalkyl, —OH, —$OR^7$, —$OR^{15a}$, —$NH_2$, —$NHR^7$, —$NHR^{15a}$, —$N(R^6)CHO$, —$NR^{7b}R^{7c}$ and —$S(O)_rR^{15}$; or each $R^{1a}$ and $R^{2b}$ together with the carbon atom to which they are attached form a $C_3$-$C_6$cycloalkyl ring or a 3- to 6-membered heterocyclyl, which comprises 1 or 2 heteroatoms individually selected from N and O;

$R^3$, $R^4$ and $R^5$ are independently selected from the group consisting of hydrogen, halogen, cyano, nitro, —$S(O)_rR^{15}$, $C_1$-$C_6$alkyl, $C_1$-$C_6$fluoroalkyl, $C_1$-$C_6$fluoroalkoxy, $C_1$-$C_6$alkoxy, $C_3$-$C_6$cycloalkyl and —$N(R^6)_2$;

each $R^6$ is independently selected from hydrogen and $C_1$-$C_6$alkyl;

each $R^7$ is independently selected from the group consisting of $C_1$-$C_6$alkyl, —$S(O)_2R^{15}$, —$C(O)R^{15}$, —$C(O)OR^{15}$ and —$C(O)NR^{16}R^{17}$;

each $R^{7a}$ is independently selected from the group consisting of —$S(O)_2R^{15}$, —$C(O)R^{15}$, —$C(O)OR^{15}$ —$C(O)NR^{16}R^{17}$ and —$C(O)NR^6R^{15a}$;

$R^{7b}$ and $R^{7c}$ are independently selected from the group consisting of $C_1$-$C_6$alkyl, —$S(O)_2R^{15}$, —$C(O)R^{15}$, —$C(O)OR^{15}$, —$C(O)NR^{16}R^{17}$ and phenyl, and wherein said phenyl is optionally substituted by 1, 2 or 3 $R^9$ substituents, which may be the same or different; or $R^{7b}$ and $R^{7c}$ together with the nitrogen atom to which they are attached form a 4- to 6-membered heterocyclyl ring which optionally comprises one additional heteroatom individually selected from N, O and S; and A is a 6-membered heteroaryl, which comprises 1, 2, 3 or 4 nitrogen atoms and wherein the heteroaryl may be optionally substituted by 1, 2, 3 or 4 $R^8$ substituents, which may be the same or different, and wherein when A is substituted by 1 or 2 substituents, each $R^8$ is independently selected from the group consisting of halogen, nitro, cyano, —$NH_2$, —$NHR^7$, —$N(R^7)_2$, —OH, —$OR^7$, —$S(O)_rR^{15}$, —$NR^6S(O)_2R^{15}$, —$C(O)OR^{10}$, —$C(O)R^{15}$, —$C(O)NR^{16}R^{17}$, —$S(O)_2NR^{16}R^{17}$, $C_1$-$C_6$alkyl, $C_1$-$C_6$haloalkyl, $C_3$-$C_6$cycloalkyl, $C_3$-$C_6$halocycloalkyl, $C_3$-$C_6$cycloalkoxy, $C_2$-$C_6$alkenyl, $C_2$-$C_6$haloalkenyl, $C_2$-$C_6$alkynyl, $C_1$-$C_3$alkoxy$C_1$-$C_3$alkyl-, hydroxy$C_1$-$C_6$alkyl-, $C_1$-$C_3$alkoxy$C_1$-$C_3$alkoxy-, $C_1$-$C_6$haloalkoxy, $C_1$-$C_3$haloalkoxy$C_1$-$C_3$alkyl-, $C_3$-$C_6$alkenyloxy, $C_3$-$C_6$alkynyloxy, N—$C_3$-$C_6$cycloalkylamino, —$C(R^6)$=$NOR^6$, phenyl, a 3- to 6-membered heterocyclyl, which comprises 1 or 2 heteroatoms individually selected from N and O, and a 5- or 6-membered heteroaryl, which comprises 1, 2, 3 or 4 heteroatoms individually selected from N, O and S, and wherein said phenyl, heterocyclyl or heteroaryl are optionally substituted by 1, 2 or 3 $R^9$ substituents, which may be the same or different;

or when A is substituted by 3 or 4 substituents, each $R^8$ is independently selected from the group consisting of halogen, —$NH_2$, —$NHR^7$, —$N(R^7)_2$, —OH, —$OR^7$, —$C(O)NR^{16}R^{17}$, —$S(O)_2NR^{16}R^{17}$, $C_1$-$C_6$alkyl and $C_1$-$C_6$haloalkyl; and each $R^9$ is independently selected from the group consisting of halogen, cyano, —OH, —$N(R^6)_2$, $C_1$-$C_4$alkyl, $C_1$-$C_4$alkoxy, $C_1$-$C_4$haloalkyl and $C_1$-$C_4$haloalkoxy;

X is selected from the group consisting of $C_3$-$C_6$cycloalkyl, phenyl, a 5- or 6-membered heteroaryl, which comprises 1, 2, 3 or 4 heteroatoms individually selected from N, O and S, and a 4- to 6-membered heterocyclyl, which comprises 1, 2 or 3 heteroatoms individually selected from N, O and S, and wherein said cycloalkyl, phenyl, heteroaryl or heterocyclyl moieties are optionally substituted by 1 or 2 substituents, which may be the same or different, selected from $R^9$, and wherein the aforementioned $CR^1R^2$, Q and Z moieties may be attached at any position of said cycloalkyl, phenyl, heteroaryl or heterocyclyl moieties;

n is 0 or 1;

Z is selected from the group consisting of —C(O)OR$^{10}$, —CH$_2$OH, —CHO, —C(O)NHOR$^{11}$, —C(O)NHCN, —OC(O)NHOR$^{11}$, —OC(O)NHCN, —NR$^6$C(O)NHOR$^{11}$, —NR$^6$C(O)NHCN, —C(O)NHS(O)$_2$R$^{12}$, —OC(O)NHS(O)$_2$R$^{12}$, —NR$^6$C(O)NHS(O)$_2$R$^{12}$, —S(O)$_2$OR$^{10}$, —OS(O)$_2$OR$^{10}$, —NR$^6$S(O)$_2$OR$^{10}$, —NR$^6$S(O)OR$^{10}$, —NHS(O)$_2$R$^{14}$, —S(O)OR$^{10}$, —OS(O)OR$^{10}$, —S(O)$_2$NHCN, —S(O)$_2$NHC(O)R$^{18}$, —S(O)$_2$NHS(O)$_2$R$^{12}$, —OS(O)$_2$NHCN, —OS(O)$_2$NHS(O)$_2$R$^{12}$, —OS(O)$_2$NHC(O)R$^{18}$, —NR$^6$S(O)$_2$NHCN, —NR$^6$S(O)$_2$NHC(O)R$^{18}$, —N(OH)C(O)R$^{15}$, —ONHC(O)R$^{15}$, —NR$^6$S(O)$_2$NHS(O)$_2$R$^{12}$, —P(O)(R$^{13}$)(OR$^{10}$), —P(O)H(OR$^{10}$), —OP(O)(R$^{13}$)(OR$^{10}$), —NR$^6$P(O)(R$^{13}$)(OR$^{10}$) and tetrazole;

R$^{10}$ is selected from the group consisting of hydrogen, C$_1$-C$_6$alkyl, phenyl and benzyl, and wherein said phenyl or benzyl are optionally substituted by 1, 2 or 3 R$^9$ substituents, which may be the same or different;

R$^{11}$ is selected from the group consisting of hydrogen, C$_1$-C$_6$alkyl and phenyl, and wherein said phenyl is optionally substituted by 1, 2 or 3 R$^9$ substituents, which may be the same or different;

R$^{12}$ is selected from the group consisting of C$_1$-C$_6$alkyl, C$_1$-C$_6$haloalkyl, C$_1$-C$_6$alkoxy, —OH, —N(R$^6$)$_2$ and phenyl, and wherein said phenyl is optionally substituted by 1, 2 or 3 R$^9$ substituents, which may be the same or different;

R$^{13}$ is selected from the group consisting of —OH, C$_1$-C$_6$alkyl, C$_1$-C$_6$alkoxy and phenyl;

R$^{14}$ is C$_1$-C$_6$haloalkyl;

R$^{15}$ is selected from the group consisting of C$_1$-C$_6$alkyl and phenyl, and wherein said phenyl is optionally substituted by 1, 2 or 3 R$^9$ substituents, which may be the same or different;

R$^{15a}$ is phenyl, wherein said phenyl is optionally substituted by 1, 2 or 3 R$^9$ substituents, which may be the same or different;

R$^{16}$ and R$^{17}$ are independently selected from the group consisting of hydrogen and C$_1$-C$_6$alkyl; or R$^{16}$ and R$^{17}$ together with the nitrogen atom to which they are attached form a 4- to 6-membered heterocyclyl ring which optionally comprises one additional heteroatom individually selected from N, O and S;

R$^{18}$ is selected from the group consisting of hydrogen, C$_1$-C$_6$alkyl, C$_1$-C$_6$haloalkyl, C$_1$-C$_6$alkoxy, —N(R$^6$)$_2$ and phenyl, and wherein said phenyl is optionally substituted by 1, 2 or 3 R$^9$ substituents, which may be the same or different;

and r is 0, 1 or 2.

According to a second aspect of the invention, there is provided an agrochemical composition comprising a herbicidally effective amount of a compound of Formula (I) and an agrochemically-acceptable diluent or carrier. Such an agricultural composition may further comprise at least one 25 additional active ingredient.

According to a third aspect of the invention, there is provided a method of controlling or preventing undesirable plant growth, wherein a herbicidally effective amount of a compound of Formula (I), or a composition comprising this compound as active ingredient, is applied to the plants, to parts thereof or 30 the locus thereof.

According to a fourth aspect of the invention, there is provided the use of a compound of formula (I) as a herbicide.

According to a fifth aspect of the invention, there is provided a process for the preparation of compounds of formula (I).

As used herein, the term "halogen" or "halo" refers to fluorine (fluoro), chlorine (chloro), bromine (bromo) or iodine (iodo), preferably fluorine, chlorine or bromine.

As used herein, cyano means a —CN group.

As used herein, hydroxy means an —OH group.

As used herein, nitro means an —NO$_2$ group.

As used herein, the term "C$_1$-C$_6$alkyl" refers to a straight or branched hydrocarbon chain radical consisting solely of carbon and hydrogen atoms, containing no unsaturation, having from one to six carbon atoms, and which is attached to the rest of the molecule by a single bond. C$_1$-C$_4$alkyl and C$_1$-C$_2$alkyl are to be construed accordingly. Examples of C$_1$-C$_6$alkyl include, but are not limited to, methyl (Me), ethyl (Et), n-propyl, 1-methylethyl (iso-propyl), n-butyl, and 1-dimethylethyl (t-butyl).

As used herein, the term "C$_1$-C$_6$alkoxy" refers to a radical of the formula —OR$_a$ where R$_a$ is a C$_1$-C$_6$alkyl radical as generally defined above. C$_1$-C$_4$alkoxy is to be construed accordingly. Examples of C$_{1-4}$ alkoxy include, but are not limited to, methoxy, ethoxy, propoxy, iso-propoxy and t-butoxy.

As used herein, the term "C$_1$-C$_6$haloalkyl" refers to a C$_1$-C$_6$alkyl radical as generally defined above substituted by one or more of the same or different halogen atoms. C$_1$-C$_4$haloalkyl is to be construed accordingly. Examples of C$_1$-C$_6$haloalkyl include, but are not limited to chloromethyl, fluoromethyl, fluoroethyl, difluoromethyl, trifluoromethyl and 2,2,2-trifluoroethyl.

As used herein, the term "C$_2$-C$_6$alkenyl" refers to a straight or branched hydrocarbon chain radical group consisting solely of carbon and hydrogen atoms, containing at least one double bond that can be of either the (E)- or (Z)-configuration, having from two to six carbon atoms, which is attached to the rest of the molecule by a single bond. C$_2$-C$_4$alkenyl is to be construed accordingly. Examples of C$_2$-C$_6$alkenyl include, but are not limited to, prop-1-enyl, allyl (prop-2-enyl) and but-1-enyl.

As used herein, the term "C$_2$-C$_6$haloalkenyl" refers to a C$_2$-C$_6$alkenyl radical as generally defined above substituted by one or more of the same or different halogen atoms. Examples of C$_2$-C$_6$haloalkenyl include, but are not limited to chloroethylene, fluoroethylene, 1,1-difluoroethylene, 1,1-dichloroethylene and 1,1,2-trichloroethylene.

As used herein, the term "C$_2$-C$_6$alkynyl" refers to a straight or branched hydrocarbon chain radical group consisting solely of carbon and hydrogen atoms, containing at least one triple bond, having from two to six carbon atoms, and which is attached to the rest of the molecule by a single bond. C$_2$-C$_4$alkynyl is to be construed accordingly. Examples of C$_2$-C$_4$alkynyl include, but are not limited to, prop-1-ynyl, propargyl (prop-2-ynyl) and but-1-ynyl.

As used herein, the term "C$_1$-C$_6$haloalkoxy" refers to a C$_1$-C$_6$alkoxy group as defined above substituted by one or more of the same or different halogen atoms. C$_1$-C$_4$haloalkoxy is to be construed accordingly. Examples of C$_1$-C$_6$haloalkoxy include, but are not limited to, fluoromethoxy, difluoromethoxy, fluoroethoxy, trifluoromethoxy and trifluoroethoxy.

As used herein, the term "C$_1$-C$_3$haloalkoxyC$_1$-C$_3$alkyl" refers to a radical of the formula R$_b$—O—R$_a$— where R$_b$ is a $C_1$-$C_3$haloalkyl radical as generally defined above, and $R_a$ is a $C_1$-$C_3$alkylene radical as generally defined above.

As used herein, the term "$C_1$-$C_3$alkoxy$C_1$-$C_3$alkyl" refers to a radical of the formula $R_b$—O—$R_a$— where $R_b$ is a $C_1$-$C_3$alkyl radical as generally defined above, and $R_a$ is a $C_1$-$C_3$alkylene radical as generally defined above.

As used herein, the term "$C_1$-$C_3$alkoxy$C_1$-$C_3$alkoxy-" refers to a radical of the formula $R_b$—O—$R_a$—O— where $R_b$ is a $C_1$-$C_3$alkyl radical as generally defined above, and $R_a$ is a $C_1$-$C_3$alkylene radical as generally defined above.

As used herein, the term "$C_3$-$C_6$alkenyloxy" refers to a radical of the formula —O$R_a$ where $R_a$ is a $C_3$-$C_6$alkenyl radical as generally defined above.

As used herein, the term "$C_3$-$C_6$alkynyloxy" refers to a radical of the formula —O$R_a$ where $R_a$ is a $C_3$-$C_6$alkynyl radical as generally defined above.

As used herein, the term "hydroxy$C_1$-$C_6$alkyl" refers to a $C_1$-$C_6$alkyl radical as generally defined above substituted by one or more hydroxy groups.

As used herein, the term "$C_1$-$C_6$alkylcarbonyl" refers to a radical of the formula —C(O)$R_a$ where $R_a$ is a $C_1$-$C_6$alkyl radical as generally defined above.

As used herein, the term "$C_1$-$C_6$alkoxycarbonyl" refers to a radical of the formula —C(O)O$R_a$ where $R_a$ is a $C_1$-$C_6$alkyl radical as generally defined above.

As used herein, the term "aminocarbonyl" refers to a radical of the formula —C(O)$NH_2$.

As used herein, the term "$C_3$-$C_6$cycloalkyl" refers to a stable, monocyclic ring radical which is saturated or partially unsaturated and contains 3 to 6 carbon atoms. $C_3$-$C_4$cycloalkyl is to be construed accordingly. Examples of $C_3$-$C_6$cycloalkyl include, but are not limited to, cyclopropyl, cyclobutyl, cyclopentyl and cyclohexyl.

As used herein, the term "$C_3$-$C_6$halocycloalkyl" refers to a $C_3$-$C_4$cycloalkyl radical as generally defined above substituted by one or more of the same or different halogen atoms. $C_3$-$C_4$halocycloalkyl is to be construed accordingly.

As used herein, the term "$C_3$-$C_6$cycloalkoxy" refers to a radical of the formula —O$R_a$ where $R_a$ is a $C_3$-$C_6$cycloalkyl radical as generally defined above.

As used herein, the term "N—$C_3$-$C_6$cycloalkylamino" refers to a radical of the formula —NH$R_a$ where $R_a$ is a $C_3$-$C_6$cycloalkyl radical as generally defined above.

As used herein, except where explicitly stated otherwise, the term "heteroaryl" refers to a 5- or 6-membered monocyclic aromatic ring which comprises 1, 2, 3 or 4 heteroatoms individually selected from nitrogen, oxygen and sulfur. The heteroaryl radical may be bonded to the rest of the molecule via a carbon atom or heteroatom. Examples of heteroaryl include, furyl, pyrrolyl, imidazolyl, thienyl, pyrazolyl, thiazolyl, isothiazolyl, oxazolyl, isoxazolyl, triazolyl, tetrazolyl, pyrazinyl, pyridazinyl, pyrimidyl or pyridyl.

As used herein, except where explicitly stated otherwise, the term "heterocyclyl" or "heterocyclic" refers to a stable 4- to 6-membered non-aromatic monocyclic ring radical which comprises 1, 2, or 3 heteroatoms individually selected from nitrogen, oxygen and sulfur. The heterocyclyl radical may be bonded to the rest of the molecule via a carbon atom or heteroatom. Examples of heterocyclyl include, but are not limited to, pyrrolinyl, pyrrolidyl, tetrahydrofuryl, tetrahydrothienyl, tetrahydrothiopyranyl, piperidyl, piperazinyl, tetrahydropyranyl, dihydroisoxazolyl, dioxolanyl, morpholinyl or δ-lactamyl.

The presence of one or more possible asymmetric carbon atoms in a compound of formula (I) means that the compounds may occur in chiral isomeric forms, i.e., enantiomeric or diastereomeric forms. Also atropisomers may occur as a result of restricted rotation about a single bond. Formula (I) is intended to include all those possible isomeric forms and mixtures thereof. The present invention includes all those possible isomeric forms and mixtures thereof for a compound of formula (I). Likewise, formula (I) is intended to include all possible tautomers (including lactam-lactim tautomerism and keto-enol tautomerism) where present. The present invention includes all possible tautomeric forms for a compound of formula (I). Similarly, where there are di-substituted alkenes, these may be present in E or Z form or as mixtures of both in any proportion. The present invention includes all these possible isomeric forms and mixtures thereof for a compound of formula (I).

The compounds of formula (I) will typically be provided in the form of an agronomically acceptable salt, a zwitterion or an agronomically acceptable salt of a zwitterion. This invention covers all such agronomically acceptable salts, zwitterions and mixtures thereof in all proportions.

For example a compound of formula (I) wherein Z comprises an acidic proton, may exist as a zwitterion, a compound of formula (I-I), or as an agronomically acceptable salt, a compound of formula (I-I) as shown below:

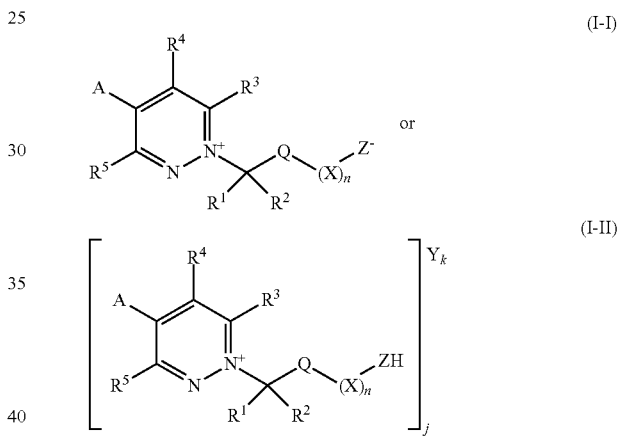

wherein, Y represents an agronomically acceptable anion and j and k represent integers that may be selected from 1, 2 or 3, dependent upon the charge of the respective anion Y.

A compound of formula (I) may also exist as an agronomically acceptable salt of a zwitterion, a compound of formula (I-III) as shown below:

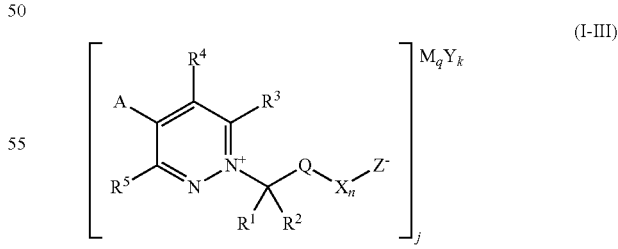

wherein, Y represents an agronomically acceptable anion, M represents an agronomically acceptable cation (in addition to the pyridazinium cation) and the integers j, k and q may be selected from 1, 2 or 3, dependent upon the charge of the respective anion Y and respective cation M.

Thus where a compound of formula (I) is drawn in protonated form herein, the skilled person would appreciate that it could equally be represented in unprotonated or salt form with one or more relevant counter ions.

In one embodiment of the invention there is provided a compound of formula (I-II) wherein k is 2, j is 1 and Y is selected from the group consisting of halogen, trifluoroacetate and pentafluoropropionate.

In this embodiment a nitrogen atom in ring A may be protonated or a nitrogen atom comprised in $R^1$, $R^2$, Q or X may be protonated (for example see compound A234 or A235 in table A). Preferably, in a compound of formula (I-II), k is 2, j is 1 and Y is chloride, wherein a nitrogen atom in ring A is protonated.

Suitable agronomically acceptable salts of the present invention, represented by an anion Y, include but are not limited chloride, bromide, iodide, fluoride, 2-naphthalenesulfonate, acetate, adipate, methoxide, ethoxide, propoxide, butoxide, aspartate, benzenesulfonate, benzoate, bicarbonate, bisulfate, bitartrate, butylsulfate, butylsulfonate, butyrate, camphorate, camsylate, caprate, caproate, caprylate, carbonate, citrate, diphosphate, edetate, edisylate, enanthate, ethanedisulfonate, ethanesulfonate, ethylsulfate, formate, fumarate, gluceptate, gluconate, glucoronate, glutamate, glycerophosphate, heptadecanoate, hexadecanoate, hydrogen sulfate, hydroxide, hydroxynaphthoate, isethionate, lactate, lactobionate, laurate, malate, maleate, mandelate, mesylate, methanedisulfonate, methylsulfate, mucate, myristate, napsylate, nitrate, nonadecanoate, octadecanoate, oxalate, pelargonate, pentadecanoate, pentafluoropropionate, perchlorate, phosphate, propionate, propylsulfate, propylsulfonate, succinate, sulfate, tartrate, tosylate, tridecylate, triflate, trifluoroacetate, undecylinate and valerate.

Suitable cations represented by M include, but are not limited to, metals, conjugate acids of amines and organic cations. Examples of suitable metals include aluminium, calcium, cesium, copper, lithium, magnesium, manganese, potassium, sodium, iron and zinc. Examples of suitable amines include allylamine, ammonia, amylamine, arginine, benethamine, benzathine, butenyl-2-amine, butylamine, butylethanolamine, cyclohexylamine, decylamine, diamylamine, dibutylamine, diethanolamine, diethylamine, diethylenetriamine, diheptylamine, dihexylamine, diisoamylamine, diisopropylamine, dimethylamine, dioctylamine, dipropanolamine, dipropargylamine, dipropylamine, dodecylamine, ethanolamine, ethylamine, ethylbutylamine, ethylenediamine, ethylheptylamine, ethyloctylamine, ethylpropanolamine, heptadecylamine, heptylamine, hexadecylamine, hexenyl-2-amine, hexylamine, hexylheptylamine, hexyloctylamine, histidine, indoline, isoamylamine, isobutanolamine, isobutylamine, isopropanolamine, isopropylamine, lysine, meglumine, methoxyethylamine, methylamine, methylbutylamine, methylethylamine, methylhexylamine, methylisopropylamine, methylnonylamine, methyloctadecylamine, methylpentadecylamine, morpholine, N,N-diethylethanolamine, N-methylpiperazine, nonylamine, octadecylamine, octylamine, oleylamine, pentadecylamine, pentenyl-2-amine, phenoxyethylamine, picoline, piperazine, piperidine, propanolamine, propylamine, propylenediamine, pyridine, pyrrolidine, sec-butylamine, stearylamine, tallowamine, tetradecylamine, tributylamine, tridecylamine, trimethylamine, triheptylamine, trihexylamine, triisobutylamine, triisodecylamine, triisopropylamine, trimethylamine, tripentylamine, tripropylamine, tris(hydroxymethyl)aminomethane, and undecylamine. Examples of suitable organic cations include benzyltributylammonium, benzyltrimethylammonium, benzyltriphenylphosphonium, choline, tetrabutylammonium, tetrabutylphosphonium, tetraethylammonium, tetraethylphosphonium, tetramethylammonium, tetramethylphosphonium, tetrapropylammonium, tetrapropylphosphonium, tributylsulfonium, tributylsulfoxonium, triethylsulfonium, triethylsulfoxonium, trimethylsulfonium, trimethylsulfoxonium, tripropylsulfonium and tripropylsulfoxonium.

Preferred compounds of formula (I), wherein Z comprises an acidic proton, can be represented as either (I-I) or (I-II). For compounds of formula (I-II) emphasis is given to salts when Y is chloride, bromide, iodide, hydroxide, bicarbonate, acetate, pentafluoropropionate, triflate, trifluoroacetate, methylsulfate, tosylate and nitrate, wherein j and k are 1. Preferably, Y is chloride, bromide, iodide, hydroxide, bicarbonate, acetate, trifluoroacetate, methylsulfate, tosylate and nitrate, wherein j and k are 1. For compounds of formula (I-II) emphasis is also given to salts when Y is carbonate and sulfate, wherein j is 2 and k is 1, and when Y is phosphate, wherein j is 3 and k is 1.

Where appropriate compounds of formula (I) may also be in the form of (and/or be used as) an N-oxide.

Compounds of formula (I) wherein m is 0 and n is 0 may be represented by a compound of formula (I-Ia) as shown below:

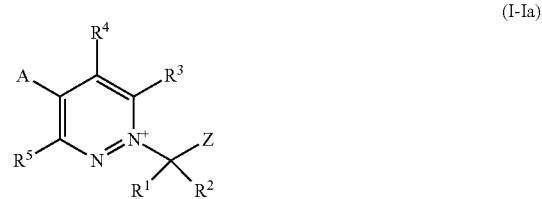

(I-Ia)

wherein $R^1$, $R^2$, $R^3$, $R^4$, $R^5$, A and Z are as defined for compounds of formula (I).

Compounds of formula (I) wherein m is 1 and n is 0 may be represented by a compound of formula (I-Ib) as shown below:

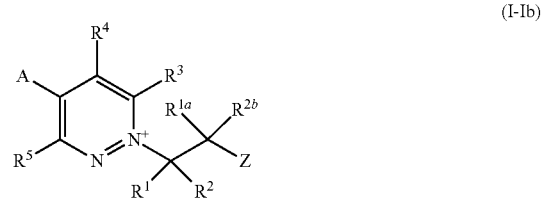

(I-Ib)

wherein $R^1$, $R^2$, $R^{1a}$, $R^{2b}$, $R^3$, $R^4$, $R^5$, A and Z are as defined for compounds of formula (I).

Compounds of formula (I) wherein m is 2 and n is 0 may be represented by a compound of formula (I-Ic) as shown below:

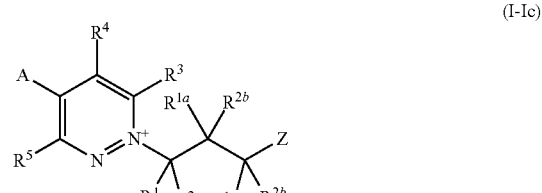

(I-Ic)

wherein $R^1$, $R^2$, $R^{1a}$, $R^{2b}$, $R^3$, $R^4$, $R^5$, A and Z are as defined for compounds of formula (I).

Compounds of formula (I) wherein m is 3 and n is 0 may be represented by a compound of formula (I-Id) as shown below:

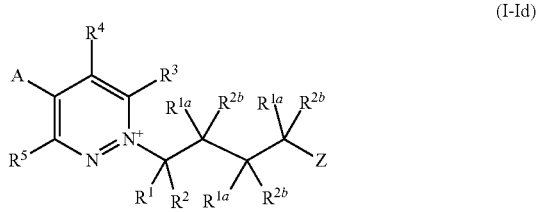

(I-Id)

wherein $R^1$, $R^2$, $R^{1a}$, $R^{2b}$, $R^3$, $R^4$, $R^5$, A and Z are as defined for compounds of formula (I).

The following list provides definitions, including preferred definitions, for substituents n, m, r, A, Q, X, Z, $R^1$, $R^2$, $R^{1a}$, $R^{2b}$, $R^2$, $R^3$, $R^4$, $R^5$, $R^6$, $R^7$, $R^{7a}$, $R^{7b}$, $R^7$, $R^8$, $R^9$, $R^{10}$, $R^{11}$, $R^{12}$, $R^{13}$, $R^{14}$, $R^{15}$, $R^{15a}$, $R^{16}$, $R^{17}$ and $R^{18}$ with reference to the compounds of Formula (I) according to the invention. For any one of these substituents, any of the definitions given below may be combined with any definition of any other substituent given below or elsewhere in this document.

$R^1$ is selected from the group consisting of hydrogen, halogen, $C_1$-$C_6$alkyl, $C_2$-$C_6$alkenyl, $C_2$-$C_6$alkynyl, $C_3$-$C_6$cycloalkyl, $C_1$-$C_6$haloalkyl, —$OR^7$, —$OR^{15a}$, —$N(R^6)S(O)_2R^{15}$, —$N(R^6)C(O)R^{15}$, —$N(R^6)C(O)OR^{15}$, —$N(R^6)C(O)NR^{16}R^{17}$, —$N(R^6)CHO$, —$N(R^{7a})_2$ and —$S(O)_rR^{15}$. Preferably, $R^1$ is selected from the group consisting of hydrogen, halogen, $C_1$-$C_6$alkyl, $C_1$-$C_6$fluoroalkyl, —$OR^7$, —$NHS(O)_2R^{15}$, —$NHC(O)R^{15}$, —$NHC(O)OR^{15}$, —$NHC(O)NR^{16}R^{17}$, —$N(R^{7a})_2$ and —$S(O)_rR^{15}$. More preferably, $R^1$ is selected from the group consisting of hydrogen, halogen, $C_1$-$C_6$alkyl, $C_1$-$C_6$fluoroalkyl, —$OR^7$ and —$N(R^{7a})_2$. Even more preferably, $R^1$ is selected from the group consisting of hydrogen, $C_1$-$C_6$alkyl, —$OR^7$ and —$N(R^{7a})_2$. Even more preferably still, $R^1$ is hydrogen or $C_1$-$C_6$alkyl. Yet even more preferably still, $R^1$ is hydrogen or methyl. Most preferably $R^1$ is hydrogen.

$R^2$ is selected from the group consisting of hydrogen, halogen, $C_1$-$C_6$alkyl and $C_1$-$C_6$haloalkyl. Preferably, $R^2$ is selected from the group consisting of hydrogen, halogen, $C_1$-$C_6$alkyl and $C_1$-$C_6$fluoroalkyl. More preferably, $R^2$ is hydrogen or $C_1$-$C_6$alkyl. Even more preferably, $R^2$ is hydrogen or methyl. Most preferably $R^2$ is hydrogen.

Wherein when $R^1$ is selected from the group consisting of —$OR^7$, —$OR^{15a}$, —$N(R^6)S(O)_2R^{15}$, —$N(R^6)C(O)R^{15}$, —$N(R^6)C(O)OR^{15}$, —$N(R^6)C(O)NR^{16}R^{17}$, —$N(R^6)CHO$, —$N(R^{7a})_2$ and —$S(O)_rR^{15}$, $R^2$ is selected from the group consisting of hydrogen and $C_1$-$C_6$alkyl. Preferably, when $R^1$ is selected from the group consisting of —$OR^7$, —$NHS(O)_2R^{15}$, —$NHC(O)R^{15}$, —$NHC(O)OR^{15}$, —$NHC(O)NR^{16}R^{17}$, —$N(R^{7a})_2$ and —$S(O)_rR^{15}$, $R^2$ is selected from the group consisting of hydrogen and methyl.

Alternatively, $R^1$ and $R^2$ together with the carbon atom to which they are attached form a $C_3$-$C_6$cycloalkyl ring or a 3- to 6-membered heterocyclyl, which comprises 1 or 2 heteroatoms individually selected from N and O. Preferably, $R^1$ and $R^2$ together with the carbon atom to which they are attached form a $C_3$-$C_6$cycloalkyl ring. More preferably, $R^1$ and $R^2$ together with the carbon atom to which they are attached form a cyclopropyl ring.

In one embodiment $R^1$ and $R^2$ are hydrogen.
In another embodiment $R^1$ is methyl and $R^2$ is hydrogen.
In another embodiment $R^1$ is methyl and $R^2$ is methyl.
Q is $(CR^{1a}R^{2b})_m$.
m is 0, 1, 2 or 3. Preferably, m is 0, 1 or 2. More preferably, m is 1 or 2. Most preferably, m is 1.

Each $R^{1a}$ and $R^{2b}$ are independently selected from the group consisting of hydrogen, halogen, $C_1$-$C_6$alkyl, $C_1$-$C_6$haloalkyl, —OH, —$OR^7$, —$OR^{15a}$, —$NH_2$, —$NHR^7$, —$NHR^{15a}$, —$N(R^6)CHO$, —$NR^{7b}R^{7c}$ and —$S(O)_rR^{15}$. Preferably, each $R^{1a}$ and $R^{2b}$ are independently selected from the group consisting of hydrogen, halogen, $C_1$-$C_6$alkyl, $C_1$-$C_6$fluoroalkyl, —OH, —$NH_2$ and —$NHR^7$. More preferably, each $R^{1a}$ and $R^{2b}$ are independently selected from the group consisting of hydrogen, $C_1$-$C_6$alkyl, —OH and —$NH_2$. Even more preferably, each $R^{1a}$ and $R^{2b}$ are independently selected from the group consisting of hydrogen, methyl, —OH and —$NH_2$. Even more preferably still, each $R^{1a}$ and $R^{2b}$ are independently selected from the group consisting of hydrogen and methyl. Most preferably $R^{1a}$ and $R^{2b}$ are hydrogen.

In another embodiment each $R^{1a}$ and $R^{2b}$ are independently selected from the group consisting of hydrogen and $C_1$-$C_6$alkyl.

Alternatively, each $R^{1a}$ and $R^{2b}$ together with the carbon atom to which they are attached form a $C_3$-$C_6$cycloalkyl ring or a 3- to 6-membered heterocyclyl, which comprises 1 or 2 heteroatoms individually selected from N and O. Preferably, each $R^{1a}$ and $R^{2b}$ together with the carbon atom to which they are attached form a $C_3$-$C_6$cycloalkyl ring. More preferably, each $R^{1a}$ and $R^{2b}$ together with the carbon atom to which they are attached form a cyclopropyl ring.

$R^3$, $R^4$ and $R^5$ are independently selected from the group consisting of hydrogen, halogen, cyano, nitro, —$S(O)_rR^{15}$, $C_1$-$C_6$alkyl, $C_1$-$C_6$fluoroalkyl, $C_1$-$C_6$fluoroalkoxy, $C_1$-$C_6$alkoxy, $C_3$-$C_6$cycloalkyl and —$N(R^6)_2$. Preferably, $R^3$, $R^4$ and $R^5$ are independently selected from the group consisting of hydrogen, $C_1$-$C_6$alkyl, $C_1$-$C_6$fluoroalkyl, $C_1$-$C_6$fluoroalkoxy, $C_1$-$C_6$alkoxy, $C_3$-$C_6$cycloalkyl and —$N(R^6)_2$. More preferably, $R^3$, $R^4$ and $R^5$ are independently selected from the group consisting of hydrogen, $C_1$-$C_6$alkyl and $C_1$-$C_6$alkoxy. Even more preferably, $R^3$, $R^4$ and $R^5$ are independently selected from the group consisting of hydrogen and $C_1$-$C_6$alkyl. Even more preferably still, $R^3$, $R^4$ and $R^5$ are independently selected from the group consisting of hydrogen and methyl. Most preferably, $R^3$, $R^4$ and $R^5$ are hydrogen.

Each $R^6$ is independently selected from hydrogen and $C_1$-$C_6$alkyl. Preferably, each $R^6$ is independently selected from hydrogen and methyl.

Each $R^7$ is independently selected from the group consisting of $C_1$-$C_6$alkyl, —$S(O)_2R^{15}$, —$C(O)R^{15}$, —$C(O)OR^{15}$ and —$C(O)NR^{16}R^{17}$. Preferably, each $R^7$ is independently selected from the group consisting of $C_1$-$C_6$alkyl, —$C(O)R^{15}$ and —$C(O)NR^{16}R^{17}$. More preferably, each $R^7$ is $C_1$-$C_6$alkyl. Most preferably, each $R^7$ is methyl.

Each $R^{7a}$ is independently selected from the group consisting of —$S(O)_2R^{15}$, —$C(O)R^{15}$, —$C(O)OR^{15}$—$C(O)NR^{16}R^{17}$ and —$C(O)NR^6R^{15a}$. Preferably, each $R^{7a}$ is independently —$C(O)R^{15}$ or —$C(O)NR^{16}R^{17}$.

$R^{7b}$ and $R^{7c}$ are independently selected from the group consisting of $C_1$-$C_6$alkyl, —$S(O)_2R^{15}$, —$C(O)R^{15}$, —$C(O)OR^{15}$, —$C(O)NR^{16}R^{17}$ and phenyl, and wherein said phenyl is optionally substituted by 1, 2 or 3 $R^9$ substituents, which may be the same or different. Preferably, $R^{7b}$ and $R^{7c}$ are independently selected from the group consisting of $C_1$-$C_6$alkyl, —C(O)R$^{15}$ and —C(O)NR$^{16}$R$^{17}$. More preferably, R$^{7b}$ and R$^{7c}$ are $C_1$-$C_6$alkyl. Most preferably, R$^{7b}$ and R$^{7c}$ are methyl.

Alternatively, R$^{7b}$ and R$^{7c}$ together with the nitrogen atom to which they are attached form a 4- to 6-membered heterocyclyl ring which optionally comprises one additional heteroatom individually selected from N, O and S. Preferably, R$^{7b}$ and R$^{7c}$ together with the nitrogen atom to which they are attached form a 5- to 6-membered heterocyclyl ring which optionally comprises one additional heteroatom individually selected from N and O. More preferably, R$^{7b}$ and R$^{7c}$ together with the nitrogen atom to which they are attached form an pyrrolidyl, oxazolidinyl, imidazolidinyl, piperidyl, piperazinyl or morpholinyl group.

A is a 6-membered heteroaryl, which comprises 1, 2, 3 or 4 nitrogen atoms and wherein the heteroaryl may, where feasible, be optionally substituted by 1, 2, 3 or 4 R$^8$ substituents, which may be the same or different.

Preferably, A is a 6-membered heteroaryl, which comprises 1, 2, 3 or 4 nitrogen atoms and wherein the heteroaryl may, where feasible, be optionally substituted by 1 or 2 R$^8$ substituents, which may be the same or different.

More preferably, A is a 6-membered heteroaryl, which comprises 1 or 2 nitrogen atoms and wherein the heteroaryl may be optionally substituted by 1 or 2 R$^8$ substituents, which may be the same or different.

Further more preferably, A is selected from the group consisting of formula A-I to A-VIII below

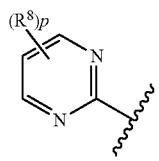

A-I

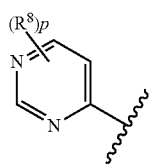

A-II

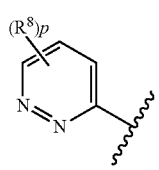

A-III

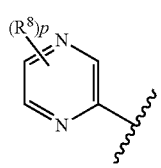

A-IV

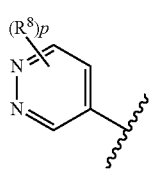

A-V

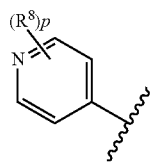

A-VI

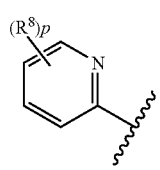

A-VII

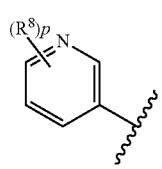

A-VIII wherein the jagged line defines the point of attachment to the remaining part of a compound of Formula (I) and p is 0, 1 or 2.

Even more preferably, A is selected from the group consisting of formula A-I to A-VII below

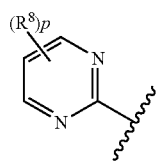

A-I

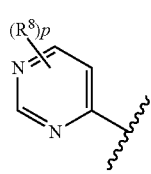

A-II

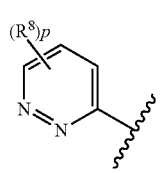

A-III

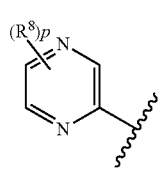

A-IV

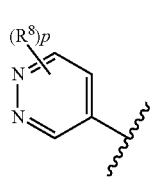

A-V

-continued

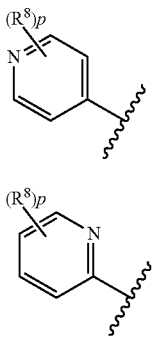

A-VI

A-VII wherein the jagged line defines the point of attachment to the remaining part of a compound of Formula (I) and p is 0, 1 or 2.

Even more preferably still, A is selected from the group consisting of formula A-I to A-V below

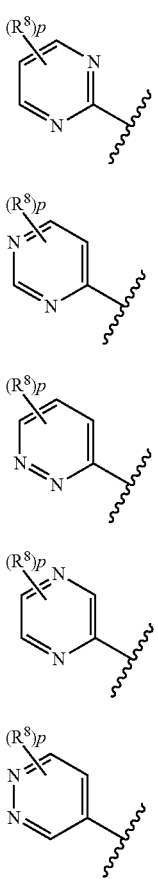

A-I

A-II

A-III

A-IV

A-V wherein the jagged line defines the point of attachment to the remaining part of a compound of Formula (I) and p is 0, 1, or 2.

Yet, even more preferably still, A is selected from the group consisting of formula A-I to A-V and p is 0 or 1.

Most preferably, A is selected from the group consisting of formula A-I to A-V and p is 0.

When A is substituted by 1 or 2 substituents each $R^8$ is independently selected from the group consisting of halogen, nitro, cyano, —NH$_2$, —NHR$^7$, —N(R$^7$)$_2$, —OH, —OR$^7$, —S(O)$_r$R$^{15}$, —NR$^6$S(O)$_2$R$^{15}$, —C(O)OR$^1$, —C(O)R$^{15}$, —C(O)NR$^{16}$R$^{17}$, —S(O)$_2$NR$^{16}$R$^{17}$, C$_1$-C$_6$alkyl, C$_1$-C$_6$haloalkyl, C$_3$-C$_6$cycloalkyl, C$_3$-C$_6$halocycloalkyl, C$_3$-C$_6$cycloalkoxy, C$_2$-C$_6$alkenyl, C$_2$-C$_6$haloalkenyl, C$_2$-C$_6$alkynyl, C$_1$-C$_3$alkoxyC$_1$-C$_3$alkyl-, hydroxyC$_1$-C$_6$alkyl-, C$_1$-C$_3$alkoxyC$_1$-C$_3$alkoxy-, C$_1$-C$_6$haloalkoxy, C$_1$-C$_3$haloalkoxyC$_1$-C$_6$alkyl-, C$_3$-C$_6$alkenyloxy, C$_3$-C$_6$alkynyloxy, N—C$_3$-C$_6$cycloalkylamino, —C(R$^6$)=NOR$^6$, phenyl, a 3- to 6-membered heterocyclyl, which comprises 1 or 2 heteroatoms individually selected from N and O, and a 5- or 6-membered heteroaryl, which comprises 1, 2, 3 or 4 heteroatoms individually selected from N, O and S, and wherein said phenyl, heterocyclyl or heteroaryl are optionally substituted by 1, 2 or 3 R$^9$ substituents, which may be the same or different.

Preferably, when A is substituted by 1 or 2 substituents each $R^8$ is independently selected from the group consisting of halogen, nitro, cyano, —NH$_2$, —NHR$^7$, —N(R$^7$)$_2$, —OH, —OR$^7$, —S(O)$_r$R$^{15}$, —NR$^6$S(O)$_2$R$^{15}$, —C(O)OR$^{10}$, —C(O)R$^{15}$, —C(O)NR$^{16}$R$^{17}$, —S(O)$_2$NR$^{16}$R$^{17}$, C$_1$-C$_6$alkyl, C$_1$-C$_6$haloalkyl, C$_3$-C$_6$cycloalkyl, C$_3$-C$_6$halocycloalkyl, C$_3$-C$_6$cycloalkoxy, C$_2$-C$_6$alkenyl, C$_2$-C$_6$haloalkenyl, C$_2$-C$_6$alkynyl, C$_1$-C$_3$alkoxyC$_1$-C$_3$alkyl-, hydroxyC$_1$-C$_6$alkyl-, C$_1$-C$_3$alkoxyC$_1$-C$_3$alkoxy-, C$_1$-C$_6$haloalkoxy, C$_1$-C$_3$haloalkoxyC$_1$-C$_6$alkyl-, C$_3$-C$_6$alkenyloxy, C$_3$-C$_6$alkynyloxy, —C(R$^6$)=NOR$^6$, phenyl and a 5- or 6-membered heteroaryl, which comprises 1, 2, 3 or 4 heteroatoms individually selected from N, O and S, and wherein said phenyl or heteroaryl are optionally substituted by 1, 2 or 3 R$^9$ substituents, which may be the same or different.

More preferably, when A is substituted by 1 or 2 substituents, each $R^8$ is independently selected from the group consisting of halogen, nitro, cyano, —NH$_2$, —NHR$^7$, —N(R$^7$)$_2$, —OH, —OR$^7$, —S(O)$_r$R$^{15}$, —NR$^6$S(O)$_2$R$^{15}$, —C(O)OR$^{10}$, —C(O)R$^{15}$, —C(O)NR$^{16}$R$^{17}$, —S(O)$_2$NR$^{16}$R$^{17}$, C$_1$-C$_6$alkyl, C$_1$-C$_6$haloalkyl, C$_3$-C$_6$cycloalkyl, C$_1$-C$_3$alkoxyC$_1$-C$_3$alkyl-, hydroxyC$_1$-C$_6$alkyl-, C$_1$-C$_3$alkoxyC$_1$-C$_3$alkoxy-, C$_1$-C$_6$haloalkoxy, phenyl and a 6-membered heteroaryl, which comprises 1 or 2 nitrogen atoms, and wherein said phenyl or heteroaryl are optionally substituted by 1 or 2 R$^9$ substituents, which may be the same or different.

Even more preferably, when A is substituted by 1 or 2 substituents, each $R^8$ is independently selected from the group consisting of halogen, nitro, cyano, —NH$_2$, —NHR$^7$, —N(R$^7$)$_2$, —OH, —OR$^7$, —S(O)$_r$R$^{15}$, —NR$^6$S(O)$_2$R$^{15}$, —C(O)OR$^{10}$, —C(O)R$^{15}$, —C(O)NR$^{16}$R$^{17}$, —S(O)$_2$NR$^{16}$R$^{17}$, C$_1$-C$_6$alkyl, C$_1$-C$_6$haloalkyl, C$_3$-C$_6$cycloalkyl, hydroxyC$_1$-C$_6$alkyl-, C$_1$-C$_6$haloalkoxy and a 6-membered heteroaryl, which comprises 1 or 2 nitrogen atoms, and wherein said heteroaryl is optionally substituted by 1 R$^9$ substituent.

Even more preferably still, when A is substituted by 1 or 2 substituents, each $R^8$ is independently selected from the group consisting of halogen, nitro, cyano, —NH$_2$, —NHR$^7$, —N(R$^7$)$_2$, —OH, —OR$^7$, —S(O)$_r$R$^{15}$, —NR$^6$S(O)$_2$R$^{15}$, —C(O)OR$^{10}$, —C(O)R$^{15}$, —C(O)NR$^{16}$R$^{17}$, —S(O)$_2$NR$^{16}$R$^{17}$, C$_1$-C$_6$alkyl and C$_1$-C$_6$haloalkyl.

Further more preferably still, when A is substituted by 1 or 2 substituents, each $R^8$ is independently selected from the group consisting of chloro, fluoro, cyano, —NH$_2$, —N(Me)$_2$, —OH, —OMe, —S(O)$_2$Me, —C(O)OMe, —C(O)OH, —C(O)Me, —C(O)NH$_2$, —C(O)NHMe, —C(O)N(Me)$_2$, methyl and trifluoromethyl.

Most preferably, when A is substituted by 1 or 2 substituents, each $R^8$ is independently selected from the group consisting of chloro, fluoro, cyano, —$NH_2$, —$N(Me)_2$, —OMe, —$S(O)_2Me$, —C(O)NHMe, —$C(O)N(Me)_2$, methyl and trifluoromethyl.

In one embodiment, when A is substituted by 1 or 2 substituents, each $R^8$ is independently selected from the group consisting of halogen, cyano, —$NH_2$, —$NHR^7$, —$N(R^7)_2$, —OH, —$OR^7$, —$S(O)_rR^{15}$, —$NR^6S(O)_2R^{15}$, —$C(O)OR^{10}$, —$C(O)R^{15}$, —$C(O)NR^{16}R^{17}$, —$S(O)_2NR^{16}R^{17}$, $C_1$-$C_6$alkyl, $C_1$-$C_6$haloalkyl, $C_3$-$C_6$cycloalkyl, hydroxy$C_1$-$C_6$alkyl-, and a 6-membered heteroaryl, which comprises 2 nitrogen atoms, and wherein said heteroaryl is optionally substituted by 1 $R^9$ substituent. Preferably, when A is substituted by 1 or 2 substituents, each $R^8$ is independently selected from the group consisting of chloro, fluoro, cyano, —$NH_2$, —$N(Me)_2$, —OH, —OMe, —$S(O)_2Me$, —C(O)OMe, —C(O)OH, —C(O)Me, —$C(O)NH_2$, —C(O)NHMe, —$C(O)N(Me)_2$, —$S(O)_2NHMe$, methyl, trifluoromethyl, cyclopropyl, hydroxymethyl- and 6-chloro-pyridazin-3-yl.

Alternatively when A is substituted by 3 or 4 substituents, each $R^8$ is independently selected from the group consisting of halogen, —$NH_2$, —$NHR^7$, —$N(R^7)_2$, —OH, —$OR^7$, —$C(O)NR^{16}R^{17}$, —$S(O)_2NR^{16}R^{17}$, $C_1$-$C_6$alkyl and $C_1$-$C_6$haloalkyl. Preferably, each $R^8$ is independently selected from the group consisting of —$NH_2$, —$NHR^7$, —$N(R^7)_2$, —OH, —$OR^7$, $C_1$-$C_6$alkyl and $C_1$-$C_6$haloalkyl. More preferably, each $R^8$ is independently selected from the group consisting of —$NH_2$, —$NHR^7$, —$OR^7$, $C_1$-$C_6$alkyl and $C_1$-$C_6$haloalkyl.

Even more preferably still, each $R^8$ is independently selected from the group consisting of $C_1$-$C_6$alkyl and $C_1$-$C_6$haloalkyl.

Each $R^9$ is independently selected from the group consisting of halogen, cyano, —OH, —$N(R^6)_2$, $C_1$-$C_4$alkyl, $C_1$-$C_4$alkoxy, $C_1$-$C_4$haloalkyl and $C_1$-$C_4$haloalkoxy. Preferably, each $R^9$ is independently selected from the group consisting of halogen, cyano, —$N(R^6)_2$, $C_1$-$C_4$alkyl, $C_1$-$C_4$alkoxy, $C_1$-$C_4$haloalkyl and $C_1$-$C_4$haloalkoxy. More preferably, each $R^9$ is independently selected from the group consisting of halogen, $C_1$-$C_4$alkyl, $C_1$-$C_4$alkoxy and $C_1$-$C_4$haloalkyl. Even more preferably, each $R^9$ is independently selected from the group consisting of halogen and $C_1$-$C_4$alkyl.

X is selected from the group consisting of $C_3$-$C_6$cycloalkyl, phenyl, a 5- or 6-membered heteroaryl, which comprises 1, 2, 3 or 4 heteroatoms individually selected from N, O and S, and a 4- to 6-membered heterocyclyl, which comprises 1, 2 or 3 heteroatoms individually selected from N, O and S, and wherein said cycloalkyl, phenyl, heteroaryl or heterocyclyl moieties are optionally substituted by 1 or 2 substituents, which may be the same or different, selected from $R^9$, and wherein the aforementioned $CR^1R^2$, Q and Z moieties may be attached at any position of said cycloalkyl, phenyl, heteroaryl or heterocyclyl moieties.

Preferably, X is selected from the group consisting of phenyl and a 4- to 6-membered heterocyclyl, which comprises 1 or 2 heteroatoms individually selected from N and O, and wherein said phenyl or heterocyclyl moieties are optionally substituted by 1 or 2 substituents, which may be the same or different, selected from $R^9$, and wherein the aforementioned $CR^1R^2$, Q and Z moieties may be attached at any position of said phenyl or heterocyclyl moieties.

More preferably, X is a 4- to 6-membered heterocyclyl, which comprises 1 or 2 heteroatoms individually selected from N and O, and wherein said heterocyclyl moieties is optionally substituted by 1 or 2 substituents, which may be the same or different, selected from $R^9$, and wherein the aforementioned $CR^1R^2$, Q and Z moieties may be attached at any position of said heterocyclyl moiety.

In one embodiment, X is a 5-membered heterocyclyl, which comprises 1 heteroatom, wherein said heteroatom is N, and wherein the aforementioned $CR^1R^2$, Q and Z moieties may be attached at any position of said heterocyclyl moiety. Preferably, X is a 5-membered heterocyclyl, which comprises 1 heteroatom, wherein said heteroatom is N, and wherein the aforementioned $CR^1R^2$ and Q moieties are attached adjacent to the N atom and the Z moiety is attached to the N atom.

In another embodiment, X is phenyl optionally substituted by 1 or 2 substituents, which may be the same or different, selected from $R^9$, and wherein the aforementioned $CR^1R^2$, Q and Z moieties may be attached at any position of said phenyl moiety. Preferably, X is phenyl and the aforementioned $CR^1R^2$ and Q moieties are attached in a position para to the Z moiety.

n is 0 or 1. Preferably, n is 0.

Z is selected from the group consisting of —$C(O)OR^{10}$, —$CH_2OH$, —CHO, —$C(O)NHOR^{11}$, —C(O)NHCN, —$OC(O)NHOR^{11}$, —OC(O)NHCN, —$NR^6C(O)NHOR^{11}$, —$NR^6C(O)NHCN$, —$C(O)NHS(O)_2R^{12}$, —$OC(O)NHS(O)_2R^{12}$, —$NR^6C(O)NHS(O)_2R^{12}$, —$S(O)_2OR^{10}$, —$OS(O)_2 OR^{10}$, —$NR^6S(O)_2OR^{10}$, —$NR^6S(O)OR^{10}$, —$NHS(O)_2 R^{14}$, —$S(O)OR^{10}$, —$OS(O)OR^{10}$, —$S(O)_2NHCN$, —$S(O)_2 NHC(O)R^{18}$, —$S(O)_2NHS(O)_2R^{12}$, —$OS(O)_2 NHCN$, —$OS(O)_2NHS(O)_2R^{12}$, —$OS(O)_2NHC(O)R^{18}$, —$NR^6S(O)_2NHCN$, —$NR^6S(O)_2NHC(O)R^{18}$, —$N(OH)C(O)R^{15}$, —$ONHC(O)R^{15}$, —$NR^6S(O)_2NHS(O)_2R^{12}$, —$P(O)(R^{13})(OR^{10})$, —$P(O)H(OR^{10})$, —$OP(O)(R^{13})(OR^{10})$, —$NR^6P(O)(R^{13})(OR^{10})$ and tetrazole.

Preferably, Z is selected from the group consisting of —$C(O)OR^{10}$, —$C(O)NHOR^{11}$, —$OC(O)NHOR^{11}$, —$NR^6C(O)NHOR^{11}$, —$C(O)NHS(O)_2R^{12}$, —$OC(O)NHS(O)_2R^{12}$, —$NR^6C(O)NHS(O)_2R^{12}$, —$S(O)_2OR^{10}$, —$OS(O)_2 OR^{10}$, —$NR^6S(O)_2OR^{10}$, —$NR^6S(O)OR^{10}$, —$NHS(O)_2 R^{14}$, —$S(O)OR^{10}$, —$OS(O)OR^{10}$, —$S(O)_2NHC(O)R^{18}$, —$S(O)_2NHS(O)_2R^{12}$, —$OS(O)_2NHS(O)_2R^{12}$, —$OS(O)_2 NHC(O)R^{18}$, —$NR^6S(O)_2NHC(O)R^{18}$, —$N(OH)C(O)R^{15}$, —$ONHC(O)R^{15}$, —$NR^6S(O)_2NHS(O)_2R^{12}$, —$P(O)(R^{13})(OR^{10})$, —$P(O)H(OR^{10})$, —$OP(O)(R^{13})(OR^{10})$ and —$NR^6P(O)(R^3)(OR^{10})$.

More preferably, Z is selected from the group consisting of —$C(O)OR^{10}$, —$C(O)NHOR^{11}$, —$C(O)NHS(O)_2R^{12}$, —$S(O)_2OR^{10}$, —$OS(O)_2OR^{10}$, —$NR^6S(O)_2OR^{10}$, —$NHS(O)_2R^{14}$, —$S(O)OR^{10}$ and —$P(O)(R^{13})(OR^{10})$.

Even more preferably Z is selected from the group consisting of —$C(O)OR^{10}$, —$C(O)NHS(O)_2R^{12}$, —$S(O)_2 OR^{10}$, and —$P(O)(R^{13})(OR^{10})$.

Even more preferably still Z is selected from the group consisting of —C(O)OH, —$C(O)OCH_3$, —$C(O)OCH_2CH_3$, —$C(O)OCH(CH_3)_2$, —$C(O)OC(CH_3)_3$, —$C(O)OCH_2C_6H_5$, —$C(O)OC_6H_5$, —$C(O)NHS(O)_2CH_3$, —$S(O)_2OH$, —$P(O)(OH)(OCH_2CH_3)$ and —$P(O)(OCH_2CH_3)(OCH_2CH_3)$.

Most preferably Z is —C(O)OH or —$S(O)_2OH$.

In one embodiment Z is selected from the group consisting of —$C(O)OR^{10}$, —$CH_2OH$, —C(O)NHOR, —C(O)NHCN, —$C(O)NHS(O)_2R^{12}$, —$S(O)_2OR^{10}$, —$OS(O)_2 OR^{10}$, —$NR^6S(O)_2OR^{10}$, —$NHS(O)_2R^{14}$, —$P(O)(R^{13})(OR^{10})$ and tetrazole. Preferably, Z is selected from the group consisting of —C(O)OH, —$C(O)OCH_3$, —$C(O)OCH_2CH_3$, —$C(O)OCH(CH_3)_2$, —$C(O)OC(CH_3)_3$, —$C(O)OCH_2C_6H_5$, —$C(O)OC_6H_5$, —$CH_2OH$, —C(O)NHOMe, —C(O)NHCN, —C(O)NHS(O)$_2$N(Me)$_2$, —C(O)NHS(O)$_2$Me, —C(O)NHS(O)$_2$CH$_3$, —S(O)$_2$OH, —OS(O)$_2$OH, —NHS(O)$_2$OH, —NHS(O)$_2$CF$_3$, —P(O)(OH)(OH), —P(O)(OCH$_3$)(OCH$_3$), —P(O)(OH)(OCH$_3$), —P(O)(OH)(OCH$_2$CH$_3$), —P(O)(OCH$_2$CH$_3$)(OCH$_2$CH$_3$) and tetrazole.

$R^{10}$ is selected from the group consisting of hydrogen, C$_1$-C$_6$alkyl, phenyl and benzyl, and wherein said phenyl or benzyl are optionally substituted by 1, 2 or 3 $R^9$ substituents, which may be the same or different. Preferably, $R^{10}$ is selected from the group consisting of hydrogen, C$_1$-C$_6$alkyl, phenyl and benzyl. More preferably, $R^{10}$ is selected from the group consisting of hydrogen and C$_1$-C$_6$alkyl. Most preferably, $R^{10}$ is hydrogen.

$R^{11}$ is selected from the group consisting of hydrogen, C$_1$-C$_6$alkyl and phenyl, and wherein said phenyl is optionally substituted by 1, 2 or 3 $R^9$ substituents, which may be the same or different. Preferably, $R^{11}$ is selected from the group consisting of hydrogen, C$_1$-C$_6$alkyl and phenyl. More preferably, $R^{11}$ is selected from the group consisting of hydrogen and C$_1$-C$_6$alkyl. Even more preferably, $R^{11}$ is C$_1$-C$_6$alkyl. Most preferably, $R^{11}$ is methyl.

$R^{12}$ is selected from the group consisting of C$_1$-C$_6$alkyl, C$_1$-C$_6$haloalkyl, C$_1$-C$_6$alkoxy, —OH, —N(R$^6$)$_2$ and phenyl, and wherein said phenyl is optionally substituted by 1, 2 or 3 $R^9$ substituents, which may be the same or different. Preferably, $R^{12}$ is selected from the group consisting of C$_1$-C$_6$alkyl, C$_1$-C$_6$haloalkyl, C$_1$-C$_6$alkoxy, —OH, —N(R$^6$)$_2$ and phenyl. More preferably, $R^{12}$ is selected from the group consisting of C$_1$-C$_6$alkyl, C$_1$-C$_6$haloalkyl and —N(R$^6$)$_2$. Even more preferably, $R^{12}$ is selected from the group consisting of methyl, —N(Me)$_2$ and trifluoromethyl. Most preferably, $R^{12}$ is methyl.

$R^{13}$ is selected from the group consisting of —OH, C$_1$-C$_6$alkyl, C$_1$-C$_6$alkoxy and phenyl. Preferably $R^{13}$ is selected from the group consisting of —OH, C$_1$-C$_6$alkyl and C$_1$-C$_6$alkoxy. More preferably, $R^{13}$ is selected from the group consisting of —OH and C$_1$-C$_6$alkoxy. Even more preferably, $R^{13}$ is selected from the group consisting of —OH, methoxy and ethoxy. Most preferably, $R^{13}$ is —OH.

$R^{14}$ is C$_1$-C$_6$haloalkyl. Preferably, $R^{14}$ is trifluoromethyl.

$R^{15}$ is selected from the group consisting of C$_1$-C$_6$alkyl and phenyl, and wherein said phenyl is optionally substituted by 1, 2 or 3 $R^9$ substituents, which may be the same or different. Preferably, $R^{15}$ is selected from the group consisting of C$_1$-C$_6$alkyl and phenyl. More preferably, $R^{15}$ is C$_1$-C$_6$alkyl. Most preferably $R^{15}$ is methyl.

$R^{15a}$ is phenyl, wherein said phenyl is optionally substituted by 1, 2 or 3 $R^9$ substituents, which may be the same or different. Preferably, $R^{15a}$ is phenyl optionally substituted by 1 $R^9$ substituent. More preferably, $R^{15a}$ is phenyl.

$R^{16}$ and $R^{17}$ are independently selected from the group consisting of hydrogen and C$_1$-C$_6$alkyl. Preferably, $R^{16}$ and $R^{17}$ are independently selected from the group consisting of hydrogen and methyl.

Alternatively, $R^{16}$ and $R^{17}$ together with the nitrogen atom to which they are attached form a 4- to 6-membered heterocyclyl ring which optionally comprises one additional heteroatom individually selected from N, O and S. Preferably, $R^{16}$ and $R^{17}$ together with the nitrogen atom to which they are attached form a 5- to 6-membered heterocyclyl ring which optionally comprises one additional heteroatom individually selected from N and O. More preferably, $R^{16}$ and $R^{17}$ together with the nitrogen atom to which they are attached form an pyrrolidyl, oxazolidinyl, imidazolidinyl, piperidyl, piperazinyl or morpholinyl group.

$R^{18}$ is selected from the group consisting of hydrogen, C$_1$-C$_6$alkyl, C$_1$-C$_6$haloalkyl, C$_1$-C$_6$alkoxy, —N(R$^6$)$_2$ and phenyl, and wherein said phenyl is optionally substituted by 1, 2 or 3 $R^9$ substituents, which may be the same or different. Preferably, $R^{18}$ is selected from the group consisting of hydrogen, C$_1$-C$_6$alkyl, C$_1$-C$_6$haloalkyl, C$_1$-C$_6$alkoxy, —N(R$^6$)$_2$ and phenyl. More preferably, $R^{18}$ is selected from the group consisting of hydrogen, C$_1$-C$_6$alkyl and C$_1$-C$_6$haloalkyl. Further more preferably, $R^{18}$ is selected from the group consisting of C$_1$-C$_6$alkyl and C$_1$-C$_6$haloalkyl. Most preferably, $R^{18}$ is methyl or trifluoromethyl.

r is 0, 1 or 2. Preferably, r is 0 or 2.

In a set of preferred embodiments, in a compound according to Formula (I) of the invention, $R^1$ is hydrogen or C$_1$-C$_6$alkyl;
$R^2$ is hydrogen or methyl;
Q is (CR$^{1a}$R$^{2b}$)$_m$;
m is 0, 1 or 2;
$R^{1a}$ and $R^{2b}$ are independently selected from the group consisting of hydrogen, C$_1$-C$_6$alkyl, —OH and —NH$_2$;
$R^3$, $R^4$ and $R^5$ are independently selected from the group consisting of hydrogen and C$_1$-C$_6$alkyl; each $R^6$ is independently selected from hydrogen and methyl;
each $R^7$ is C$_1$-C$_6$alkyl;
A is a 6-membered heteroaryl, which comprises 1 or 2 nitrogen atoms and wherein the heteroaryl may be optionally substituted by 1 or 2 $R^8$ substituents, which may be the same or different; each $R^8$ is independently selected from the group consisting of halogen, nitro, cyano, —NH$_2$, —NHR$^7$, —N(R$^7$)$_2$, —OH, —OR$^7$, —S(O)$_r$R$^{15}$, —NR$^6$S(O)$_2$R$^{15}$, —C(O)OR$^{10}$, —C(O)R$^{15}$, —C(O)NR$^{16}$R$^{17}$, —S(O)$_2$NR$^{16}$R$^{17}$, C$_1$-C$_6$alkyl and C$_1$-C$_6$haloalkyl;
n is 0;
Z is selected from the group consisting of —C(O)OR$^{10}$, —C(O)NHS(O)$_2$R$^{12}$, —S(O)$_2$OR$^{10}$, and —P(O)(R$^{13}$)(OR$^{10}$);
$R^{10}$ is selected from the group consisting of hydrogen, C$_1$-C$_6$alkyl, phenyl and benzyl;
$R^{12}$ is selected from the group consisting of C$_1$-C$_6$alkyl, C$_1$-C$_6$haloalkyl and —N(R$^6$)$_2$;
$R^{13}$ is selected from the group consisting of —OH and C$_1$-C$_6$alkoxy;
$R^{15}$ is C$_1$-C$_6$alkyl;
$R^{16}$ and $R^{17}$ are independently selected from the group consisting of hydrogen and methyl; and
r is 0 or 2.

More preferably,
$R^1$ is hydrogen or methyl;
$R^2$ is hydrogen or methyl;
Q is (CR$^{1a}$R$^{2b}$)$_m$;
m is 1 or 2;
$R^{1a}$ and $R^{2b}$ are independently selected from the group consisting of hydrogen and methyl;
$R^3$, $R^4$ and $R^5$ are independently selected from the group consisting of hydrogen and methyl;
A is selected from the group consisting of formula A-I to A-V and p is 0, 1, or 2;
each $R^8$ is independently selected from the group consisting of chloro, fluoro, cyano, —NH$_2$, —N(Me)$_2$, —OH, —OMe, —S(O)$_2$Me, —C(O)OMe, —C(O)OH, —C(O)Me, —C(O)NH$_2$, —C(O)NHMe, —C(O)N(Me)$_2$, methyl and trifluoromethyl;
n is 0; and
Z is selected from the group consisting of —C(O)OH, —C(O)OCH$_3$, —C(O)OCH$_2$CH$_3$, —C(O)OCH(CH$_3$)$_2$, —C(O)OC(CH$_3$)$_3$, —C(O)OCH$_2$C$_6$H$_5$, —C(O)OC$_6$H$_5$, —C(O)NHS(O)$_2$CH$_3$, —S(O)$_2$OH, —P(O)(OH)(OCH$_2$CH$_3$) and —P(O)(OCH$_2$CH$_3$)(OCH$_2$CH$_3$).

In a further set of preferred embodiments, the compound according to Formula (I) is selected from a compound of Formula (I-a), (I-b), (I-c), (I-d), (I-e), (I-f), (I-g), (I-h), (I-j) or (I-k),

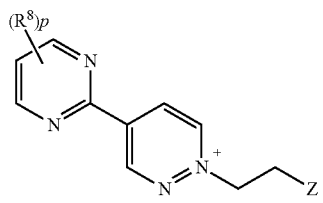
(I-a)

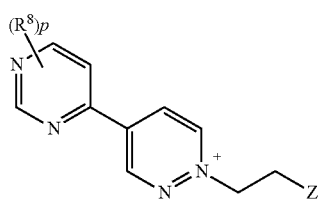
(I-b)

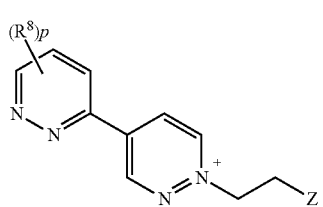
(I-c)

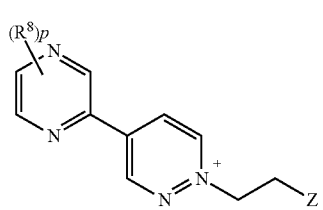
(I-d)

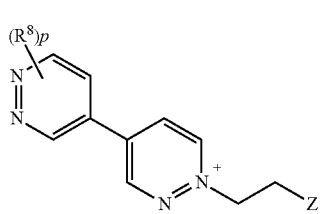
(I-e)

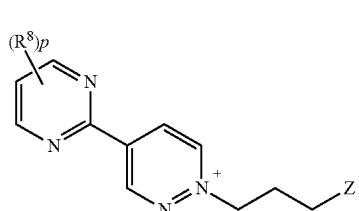
(I-f)

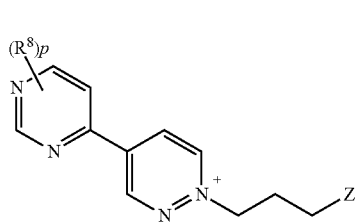
(I-g)

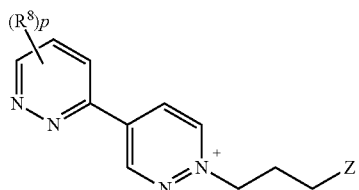
(I-h)

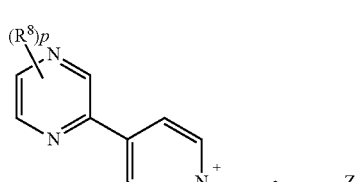
(I-j)

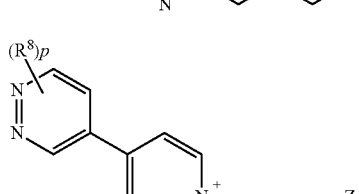
(I-k)

wherein in a compound of Formula (I-a), (I-b), (I-c), (I-d), (I-e), (I-f), (I-g), (I-h), (I-j) or (I-k), p is 0, 1 or 2;

each $R^8$ is independently selected from the group consisting of chloro, fluoro, cyano, —NH$_2$, —N(Me)$_2$, —OH, —OMe, —S(O)$_2$Me, —C(O)OMe, —C(O)OH, —C(O)Me, —C(O)NH$_2$, —C(O)NHMe, —C(O)N(Me)$_2$, methyl and trifluoromethyl; and Z is selected from the group consisting of —C(O)OH, —C(O)OCH$_3$, —C(O)OCH$_2$CH$_3$, —C(O)OCH(CH$_3$)$_2$, —C(O)OC(CH$_3$)$_3$, —C(O)OCH$_2$C$_6$H$_5$, —C(O)OC$_6$H$_5$, —C(O)NHS(O)$_2$CH$_3$, —S(O)$_2$OH, —P(O)(OH)(OCH$_2$CH$_3$) and —P(O)(OCH$_2$CH$_3$)(OCH$_2$CH$_3$).

In a further more preferred set of embodiments, the compound according to Formula (I) is selected from a compound of Formula (I-m), (I-n), (I-p), (I-q), (I-r), (I-s), (I-t), (I-u), (I-v) or (I-w),

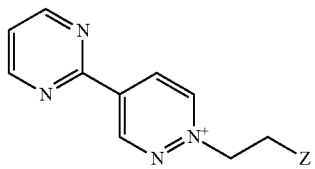
(I-m)

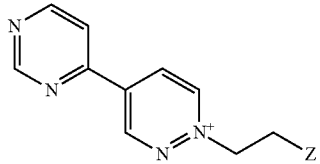
(I-n)

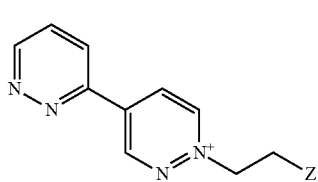
(I-p)

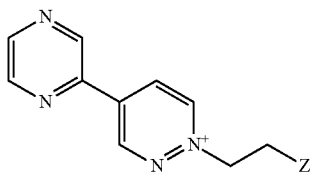
(I-q)

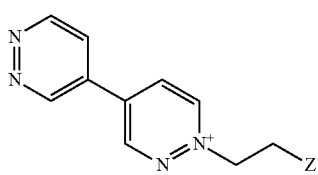
(I-r)

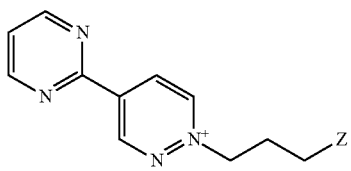
(I-s)

(I-t)

(I-u)

(I-w)

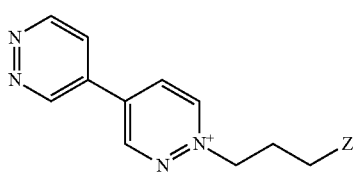

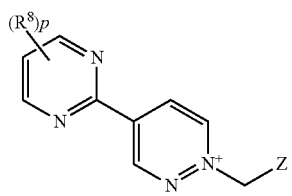
(I-aa)

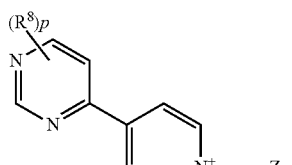
(I-bb)

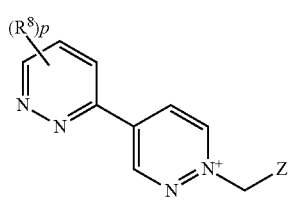
(I-cc)

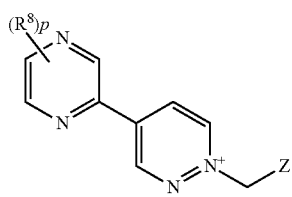
(I-dd)

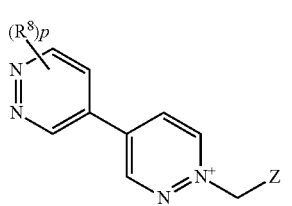
(I-ee)

wherein in a compound of Formula (I-aa), (I-bb), (I-cc), (I-dd), or (I-ee), p is 0, 1 or 2;

each $R^8$ is independently selected from the group consisting of chloro, fluoro, cyano, —NH$_2$, —N(Me)$_2$, —OH, —OMe, —S(O)$_2$Me, —C(O)OMe, —C(O)OH, —C(O)Me, —C(O)NH$_2$, —C(O)NHMe, —C(O)N(Me)$_2$, methyl and trifluoromethyl; and Z is selected from the group consisting of —C(O)OH, —C(O)OCH$_3$, —C(O)OCH$_2$CH$_3$, —C(O)OCH(CH$_3$)$_2$, —C(O)OC(CH$_3$)$_3$, —C(O)OCH$_2$C$_6$H$_5$, —C(O)OC$_6$H$_5$, —C(O)NHS(O)$_2$CH$_3$, —S(O)$_2$OH, —P(O)(OH)(OCH$_2$CH$_3$) and —P(O)(OCH$_2$CH$_3$)(OCH$_2$CH$_3$).

wherein in a compound of Formula (I-m), (I-n), (I-p), (I-q), (I-r), (I-s), (I-t), (I-u), (I-v) or (I-w), Z is —C(O)OH or —S(O)$_2$OH.

In another preferred set of embodiments, the compound according to Formula (I) is selected from a compound of Formula (I-aa), (I-bb), (I-cc), (I-dd) or (I-ee), In one set of embodiments, the compound according to Formula (I) is selected from a compound A1 to A251 listed in Table A.

In another more preferred set of embodiments, the compound according to Formula (I) is selected from a compound of Formula (I-ff), (I-gg), (I-hh), (I-jj) or (I-kk), (I-ff)

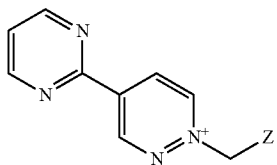

(I-gg)

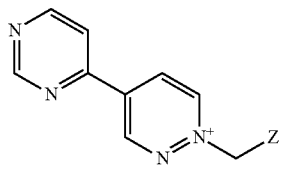

(I-hh)

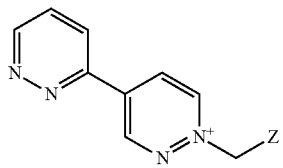

(I-jj)

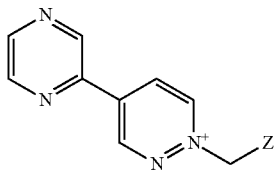

(I-kk)

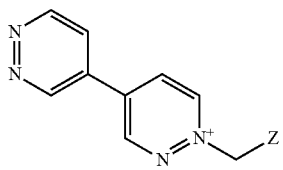

wherein in a compound of Formula (I-ff), (I-gg), (I-hh), (I-jj) or (I-kk), Z is —C(O)OH or —S(O)$_2$OH.

There is also provided a process for the preparation of compounds of formula (I):

(I)

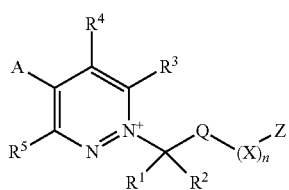

Wherein Q, Z, X, n, $R^1$, $R^2$, $R^3$, $R^4$, $R^5$ and A are as defined herein; comprising (i) either (a) reacting a compound of formula (H)

A-Hal     formula (H)

wherein
A is as defined herein and Hal is a halogen or pseudo halogen, with a compound of formula (J)

formula (J)

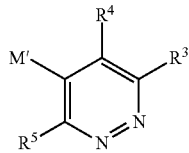

wherein
$R^3$, $R^4$ and $R^5$ are as defined herein and M' is an organostannane or an organoborane (e.g organoboronic acid, organoboronic ester or organotrifluoroborate), in the presence of a palladium catalyst, to give a compound of formula (X)

formula (X)

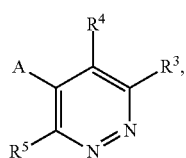

or
(b) reacting a compound of formula (K)

formula (K)

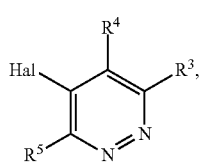

wherein $R^3$, $R^4$ and $R^5$ are as defined herein and Hal is a halogen or pseudo halogen, with a compound of formula (L)

A-M'     formula (L)

wherein
A is as defined herein and M' is an organostannane or an organoborane (e.g organoboronic acid, organoboronic ester or organotrifluoroborate), in the presence of a palladium catalyst, to give a compound of formula (X);
(ii) reacting a compound of formula (X) with an alkylating agent of formula (W)

formula (W)

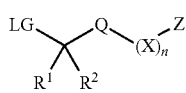

wherein $R^1$, $R^2$, Q, X, Z and n are as defined herein, and LG is a suitable leaving group, in an inert solvent or mixture of inert solvents, at a temperature of from −78° C. to 150° C., to give a compound of formula (I);
(iii) optionally,
partially or fully hydrolysing a compound of formula (I) in the presence of a suitable acid.

According to the invention there is also provided the use of a compound of formula (J) as defined herein, in a process for the manufacture of a compound of formula (I) as defined herein. Preferably, in a compound of formula (J) M' is an organostannane, organoboronic acid, organoboronic ester or organotrifluoroborate. More preferably, in a compound of formula (J) M' is an organostannane. Most preferably, in a compound of formula (J) M' is tributylstannane.

In another embodiment of the invention there is also provided the use of a compound of formula (X) as defined herein, in a process for the manufacture of a compound of formula (I) as defined herein. Preferably, the compound of formula (X) is selected from the group consisting of 2-pyridazin-4-ylpyrimidine, 4-pyridazin-4-ylpyrimidine, 3-pyridazin-4-ylpyridazine, 2-pyridazin-4-ylpyrazine and 4-pyridazin-4-ylpyridazine.

According to the invention there is also provided novel intermediates of formula (X), wherein a compound of formula (X) selected from the group consisting of 2-pyridazin-4-ylpyrimidine, 4-pyridazin-4-ylpyrimidine, 3-pyridazin-4-ylpyridazine and 2-pyridazin-4-ylpyrazine.

It should be understood that compounds of Formula (I) may exist/be manufactured in 'procidal form', wherein they comprise a group 'G'. Such compounds are referred to herein as compounds of Formula (I-IV).

G is a group which may be removed in a plant by any appropriate mechanism including, but not limited to, metabolism and chemical degradation to give a compound of Formula (I-I), (I-II) or (I-III) wherein Z contains an acidic proton, for example see the scheme below:

(I-IV)

(I-I)

Whilst such G groups may be considered as 'procidal', and thus yield active herbicidal compounds once removed, compounds comprising such groups may also exhibit herbicidal activity in their own right. In such cases in a compound of Formula (I-IV), Z-G may include but is not limited to, anyone of (G1) to (G7) below and E indicates the point of attachment to the remaining part of a compound of Formula (I):

(G1)

(G2)

(G3)

(G4)

(G5)

(G6)

(G7)

In embodiments where Z-G is (G1) to (G7), G, $R^{19}$, $R^{20}$, $R^{21}$, $R^{22}$ and $R^{23}$ are defined as follows:

G is $C_1$-$C_6$alkyl, $C_2$-$C_6$alkenyl, $C_2$-$C_6$alkynyl, —C($R^{21}R^{22}$)OC(O)$R^{19}$, phenyl or phenyl-$C_1$-$C_4$alkyl-, wherein said phenyl moiety is optionally substituted by 1 to 5 substituents independently selected from halo, cyano, nitro, $C_1$-$C_6$alkyl, $C_1$-$C_6$haloalkyl or $C_1$-$C_6$alkoxy.

$R^{19}$ is $C_1$-$C_6$alkyl or phenyl, $R^{20}$ is hydroxy, $C_1$-$C_6$alkyl, $C_1$-$C_6$alkoxy or phenyl, $R^{21}$ is hydrogen or methyl, $R^{22}$ is hydrogen or methyl, $R^{23}$ is hydrogen or $C_1$-$C_6$alkyl.

The compounds in Tables 1 to 27 below illustrate the compounds of the invention. The skilled person would understand that the compounds of formula (I) may exist as anagronomically acceptable salt, a zwitterion or anagronomically acceptable salt of a zwitterion as described hereinbefore.

TABLE 1

This table discloses 53 specific compounds of the formula (T-1):

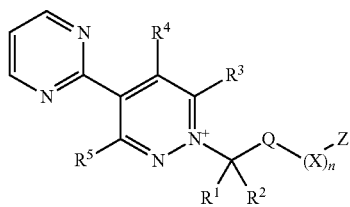

Wherein m, Q, $R^3$, $R^4$, $R^5$ and Z are as defined in Table 1, $R^1$ and $R^2$ are hydrogen and n is 0.

| Compound number | $R^3$ | $R^4$ | $R^5$ | Z | m | Q |
|---|---|---|---|---|---|---|
| 1.001 | H | H | H | —C(O)OH | 0 | — |
| 1.002 | H | H | H | —C(O)OMe | 0 | — |
| 1.003 | H | H | H | —C(O)NHOMe | 0 | — |
| 1.004 | H | H | H | —OC(O)NHOMe | 0 | — |
| 1.005 | H | H | H | —NHC(O)NHOMe | 0 | — |
| 1.006 | H | H | H | —NMeC(O)NHOMe | 0 | — |
| 1.007 | H | H | H | —C(O)NHS(O)$_2$Me | 0 | — |
| 1.008 | H | H | H | —OC(O)NHS(O)$_2$Me | 0 | — |
| 1.009 | H | H | H | —NHC(O)NHS(O)$_2$Me | 0 | — |
| 1.010 | H | H | H | —NMeC(O)NHS(O)$_2$Me | 0 | — |
| 1.011 | H | H | H | —S(O)$_2$OH | 0 | — |
| 1.012 | H | H | H | —OS(O)$_2$OH | 0 | — |
| 1.013 | H | H | H | —NHS(O)$_2$OH | 0 | — |
| 1.014 | H | H | H | —NMeS(O)$_2$OH | 0 | — |
| 1.015 | H | H | H | —S(O)OH | 0 | — |
| 1.016 | H | H | H | —OS(O)OH | 0 | — |
| 1.017 | H | H | H | —NHS(O)OH | 0 | — |
| 1.018 | H | H | H | —NMeS(O)OH | 0 | — |
| 1.019 | H | H | H | —NHS(O)$_2$CF$_3$ | 0 | — |
| 1.020 | H | H | H | —S(O)$_2$NHC(O)Me | 0 | — |
| 1.021 | H | H | H | —OS(O)$_2$NHC(O)Me | 0 | — |
| 1.022 | H | H | H | —NHS(O)$_2$NHC(O)Me | 0 | — |
| 1.023 | H | H | H | —NMeS(O)$_2$NHC(O)Me | 0 | — |
| 1.024 | H | H | H | —P(O)(OH)(OMe) | 0 | — |
| 1.025 | H | H | H | —P(O)(OH)(OH) | 0 | — |
| 1.026 | H | H | H | —OP(O)(OH)(OMe) | 0 | — |
| 1.027 | H | H | H | —OP(O)(OH)(OH) | 0 | — |
| 1.028 | H | H | H | —NHP(O)(OH)(OMe) | 0 | — |
| 1.029 | H | H | H | —NHP(O)(OH)(OH) | 0 | — |
| 1.030 | H | H | H | —NMeP(O)(OH)(OMe) | 0 | — |
| 1.031 | H | H | H | —NMeP(O)(OH)(OH) | 0 | — |
| 1.032 | H | H | H | -tetrazole | 0 | — |
| 1.033 | H | H | H | —S(O)$_2$OH | 1 | CH(NH$_2$) |
| 1.033 | H | H | H | —C(O)OH | 1 | CH(NH$_2$) |
| 1.035 | H | H | H | —S(O)$_2$OH | 2 | CH(OH)CH$_2$ |
| 1.036 | H | H | H | —C(O)OH | 2 | CH(OH)CH$_2$ |
| 1.037 | H | H | H | —S(O)$_2$OH | 1 | CH(OH) |
| 1.038 | H | H | H | —C(O)OH | 1 | CH(OH) |
| 1.039 | H | H | H | —C(O)NHCN | 0 | — |
| 1.040 | H | H | H | —OC(O)NHCN | 0 | — |
| 1.041 | H | H | H | —NHC(O)NHCN | 0 | — |
| 1.042 | H | H | H | —NMeC(O)NHCN | 0 | — |
| 1.043 | H | H | H | —S(O)$_2$NHCN | 0 | — |
| 1.044 | H | H | H | —OS(O)$_2$NHCN | 0 | — |
| 1.045 | H | H | H | —NHS(O)$_2$NHCN | 0 | — |
| 1.046 | H | H | H | —NMeS(O)$_2$NHCN | 0 | — |
| 1.047 | H | H | H | —S(O)$_2$NHS(O)$_2$Me | 0 | — |
| 1.048 | H | H | H | —OS(O)$_2$NHS(O)$_2$Me | 0 | — |
| 1.049 | H | H | H | —NHS(O)$_2$NHS(O)$_2$Me | 0 | — |
| 1.050 | H | H | H | —NMeS(O)$_2$NHS(O)$_2$Me | 0 | — |
| 1.051 | H | H | H | —P(O)H(OH) | 0 | — |
| 1.052 | H | H | H | —N(OH)C(O)Me | 0 | — |
| 1.053 | H | H | H | —ONHC(O)Me | 0 | — |

TABLE 2

This table discloses 49 specific compounds of the formula (T-2):

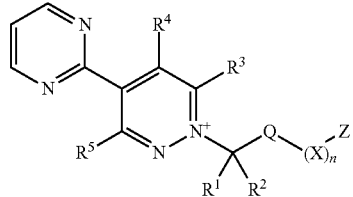

Wherein m, Q, $R^3$, $R^4$, $R^5$ and Z are as defined in Table 2, $R^1$ and $R^2$ are hydrogen and n is 0.

| Compound number | $R^3$ | $R^4$ | $R^5$ | Z | m | Q |
|---|---|---|---|---|---|---|
| 2.001 | H | H | H | —C(O)OH | 1 | CH$_2$ |
| 2.002 | H | H | H | —C(O)OMe | 1 | CH$_2$ |
| 2.003 | H | H | H | —C(O)NHOMe | 1 | CH$_2$ |
| 2.004 | H | H | H | —OC(O)NHOMe | 1 | CH$_2$ |
| 2.005 | H | H | H | —NHC(O)NHOMe | 1 | CH$_2$ |
| 2.006 | H | H | H | —NMeC(O)NHOMe | 1 | CH$_2$ |
| 2.007 | H | H | H | —C(O)NHS(O)$_2$Me | 1 | CH$_2$ |
| 2.008 | H | H | H | —OC(O)NHS(O)$_2$Me | 1 | CH$_2$ |
| 2.009 | H | H | H | —NHC(O)NHS(O)$_2$Me | 1 | CH$_2$ |
| 2.010 | H | H | H | —NMeC(O)NHS(O)$_2$Me | 1 | CH$_2$ |
| 2.011 | H | H | H | —S(O)$_2$OH | 1 | CH$_2$ |
| 2.012 | H | H | H | —OS(O)$_2$OH | 1 | CH$_2$ |
| 2.013 | H | H | H | —NHS(O)$_2$OH | 1 | CH$_2$ |
| 2.014 | H | H | H | —NMeS(O)$_2$OH | 1 | CH$_2$ |
| 2.015 | H | H | H | —S(O)OH | 1 | CH$_2$ |
| 2.016 | H | H | H | —OS(O)0H | 1 | CH$_2$ |
| 2.017 | H | H | H | —NHS(O)OH | 1 | CH$_2$ |
| 2.018 | H | H | H | —NMeS(O)OH | 1 | CH$_2$ |
| 2.019 | H | H | H | —NHS(O)$_2$CF$_3$ | 1 | CH$_2$ |
| 2.020 | H | H | H | —S(O)$_2$NHC(O)Me | 1 | CH$_2$ |
| 2.021 | H | H | H | —OS(O)$_2$NHC(O)Me | 1 | CH$_2$ |
| 2.022 | H | H | H | —NHS(O)$_2$NHC(O)Me | 1 | CH$_2$ |
| 2.023 | H | H | H | —NMeS(O)$_2$NHC(O)Me | 1 | CH$_2$ |
| 2.024 | H | H | H | —P(O)(OH)(OMe) | 1 | CH$_2$ |
| 2.025 | H | H | H | —P(O)(OH)(OH) | 1 | CH$_2$ |
| 2.026 | H | H | H | —OP(O)(OH)(OMe) | 1 | CH$_2$ |
| 2.027 | H | H | H | —OP(O)(OH)(OH) | 1 | CH$_2$ |
| 2.028 | H | H | H | —NHP(O)(OH)(OMe) | 1 | CH$_2$ |
| 2.029 | H | H | H | —NHP(O)(OH)(OH) | 1 | CH$_2$ |
| 2.030 | H | H | H | —NMeP(O)(OH)(OMe) | 1 | CH$_2$ |
| 2.031 | H | H | H | —NMeP(O)(OH)(OH) | 1 | CH$_2$ |
| 2.032 | H | H | H | -tetrazole | 1 | CH$_2$ |
| 2.033 | H | H | H | —S(O)$_2$OH | 2 | CH$_2$CH(NH$_2$) |
| 2.034 | H | H | H | —C(O)OH | 2 | CH$_2$CH(NH$_2$) |
| 2.035 | H | H | H | —C(O)NHCN | 1 | CH$_2$ |
| 2.036 | H | H | H | —OC(O)NHCN | 1 | CH$_2$ |
| 2.037 | H | H | H | —NHC(O)NHCN | 1 | CH$_2$ |
| 2.038 | H | H | H | —NMeC(O)NHCN | 1 | CH$_2$ |
| 2.039 | H | H | H | —S(O)$_2$NHCN | 1 | CH$_2$ |
| 2.040 | H | H | H | —OS(O)$_2$NHCN | 1 | CH$_2$ |
| 2.041 | H | H | H | —NHS(O)$_2$NHCN | 1 | CH$_2$ |
| 2.042 | H | H | H | —NMeS(O)$_2$NHCN | 1 | CH$_2$ |
| 2.043 | H | H | H | —S(O)$_2$NHS(O)$_2$Me | 1 | CH$_2$ |
| 2.044 | H | H | H | —OS(O)$_2$NHS(O)$_2$Me | 1 | CH$_2$ |
| 2.045 | H | H | H | —NHS(O)$_2$NHS(O)$_2$Me | 1 | CH$_2$ |
| 2.046 | H | H | H | —NMeS(O)$_2$NHS(O)$_2$Me | 1 | CH$_2$ |
| 2.047 | H | H | H | —P(O)H(OH) | 1 | CH$_2$ |
| 2.048 | H | H | H | —N(OH)C(O)Me | 1 | CH$_2$ |
| 2.049 | H | H | H | —ONHC(O)Me | 1 | CH$_2$ |

TABLE 3

This table discloses 49 specific compounds of the formula (T-3):

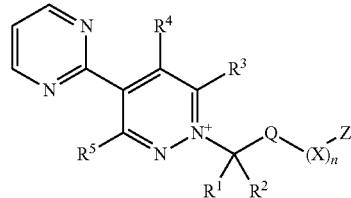
(T-3)

wherein m, Q, $R^3$, $R^4$, $R^5$ and Z are as defined in Table 3,
$R^1$ and $R^2$ are hydrogen and n is 0.

| Compound number | $R^3$ | $R^4$ | $R^5$ | Z | m | Q |
|---|---|---|---|---|---|---|
| 3.001 | H | H | H | —C(O)OH | 2 | $CH_2CH_2$ |
| 3.002 | H | H | H | —C(O)OMe | 2 | $CH_2CH_2$ |
| 3.003 | H | H | H | —C(O)NHOMe | 2 | $CH_2CH_2$ |
| 3.004 | H | H | H | —OC(O)NHOMe | 2 | $CH_2CH_2$ |
| 3.005 | H | H | H | —NHC(O)NHOMe | 2 | $CH_2CH_2$ |
| 3.006 | H | H | H | —NMeC(O)NHOMe | 2 | $CH_2CH_2$ |
| 3.007 | H | H | H | —C(O)NHS(O)$_2$Me | 2 | $CH_2CH_2$ |
| 3.008 | H | H | H | —OC(O)NHS(O)$_2$Me | 2 | $CH_2CH_2$ |
| 3.009 | H | H | H | —NHC(O)NHS(O)$_2$Me | 2 | $CH_2CH_2$ |
| 3.010 | H | H | H | —NMeC(O)NHS(O)$_2$Me | 2 | $CH_2CH_2$ |
| 3.011 | H | H | H | —S(O)$_2$OH | 2 | $CH_2CH_2$ |
| 3.012 | H | H | H | —OS(O)$_2$OH | 2 | $CH_2CH_2$ |
| 3.013 | H | H | H | —NHS(O)$_2$OH | 2 | $CH_2CH_2$ |
| 3.014 | H | H | H | —NMeS(O)$_2$OH | 2 | $CH_2CH_2$ |
| 3.015 | H | H | H | —S(O)OH | 2 | $CH_2CH_2$ |
| 3.016 | H | H | H | —OS(O)OH | 2 | $CH_2CH_2$ |
| 3.017 | H | H | H | —NHS(O)OH | 2 | $CH_2CH_2$ |
| 3.018 | H | H | H | —NMeS(O)OH | 2 | $CH_2CH_2$ |
| 3.019 | H | H | H | —NHS(O)$_2$CF$_3$ | 2 | $CH_2CH_2$ |
| 3.020 | H | H | H | —S(O)$_2$NHC(O)Me | 2 | $CH_2CH_2$ |
| 3.021 | H | H | H | —OS(O)$_2$NHC(O)Me | 2 | $CH_2CH_2$ |
| 3.022 | H | H | H | —NHS(O)$_2$NHC(O)Me | 2 | $CH_2CH_2$ |
| 3.023 | H | H | H | —NMeS(O)$_2$NHC(O)Me | 2 | $CH_2CH_2$ |
| 3.024 | H | H | H | —P(O)(OH)(OMe) | 2 | $CH_2CH_2$ |
| 3.025 | H | H | H | —P(O)(OH)(OH) | 2 | $CH_2CH_2$ |
| 3.026 | H | H | H | —OP(O)(OH)(OMe) | 2 | $CH_2CH_2$ |
| 3.027 | H | H | H | —OP(O)(OH)(OH) | 2 | $CH_2CH_2$ |
| 3.028 | H | H | H | —NHP(O)(OH)(OMe) | 2 | $CH_2CH_2$ |
| 3.029 | H | H | H | —NHP(O)(OH)(OH) | 2 | $CH_2CH_2$ |
| 3.030 | H | H | H | —NMeP(O)(OH)(OMe) | 2 | $CH_2CH_2$ |
| 3.031 | H | H | H | —NMeP(O)(OH)(OH) | 2 | $CH_2CH_2$ |
| 3.032 | H | H | H | -tetrazole | 2 | $CH_2CH_2$ |
| 3.033 | H | H | H | —S(O)$_2$OH | 3 | $CH_2CH_2CH(NH_2)$ |
| 3.034 | H | H | H | —C(O)OH | 3 | $CH_2CH_2CH(NH_2)$ |
| 3.035 | H | H | H | —C(O)NHCN | 2 | $CH_2CH_2$ |
| 3.036 | H | H | H | —OC(O)NHCN | 2 | $CH_2CH_2$ |
| 3.037 | H | H | H | —NHC(O)NHCN | 2 | $CH_2CH_2$ |
| 3.038 | H | H | H | —NMeC(O)NHCN | 2 | $CH_2CH_2$ |
| 3.039 | H | H | H | —S(O)$_2$NHCN | 2 | $CH_2CH_2$ |
| 3.040 | H | H | H | —OS(O)$_2$NHCN | 2 | $CH_2CH_2$ |
| 3.041 | H | H | H | —NHS(O)$_2$NHCN | 2 | $CH_2CH_2$ |
| 3.042 | H | H | H | —NMeS(O)$_2$NHCN | 2 | $CH_2CH_2$ |
| 3.043 | H | H | H | —S(O)$_2$NHS(O)$_2$Me | 2 | $CH_2CH_2$ |
| 3.044 | H | H | H | —OS(O)$_2$NHS(O)$_2$Me | 2 | $CH_2CH_2$ |
| 3.045 | H | H | H | —NHS(O)$_2$NHS(O)$_2$Me | 2 | $CH_2CH_2$ |
| 3.046 | H | H | H | —NMeS(O)$_2$NHS(O)$_2$Me | 2 | $CH_2CH_2$ |
| 3.047 | H | H | H | —P(O)H(OH) | 2 | $CH_2CH_2$ |
| 3.048 | H | H | H | —N(OH)C(O)Me | 2 | $CH_2CH_2$ |
| 3.049 | H | H | H | —ONHC(O)Me | 2 | $CH_2CH_2$ |

Table 4:
This table discloses 53 specific compounds of the formula (T-4):

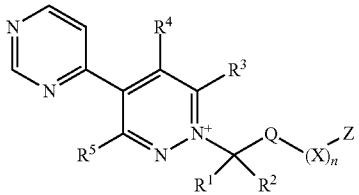
(T-4)

wherein m, Q, R³, R⁴, R⁵ and Z are as defined above in Table 1, R¹ and R² are hydrogen and n is 0.

Table 5:
This table discloses 49 specific compounds of the formula (T-5):

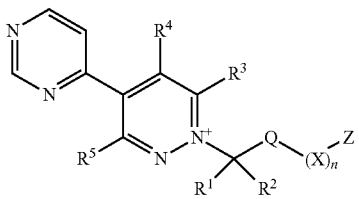
(T-5)

wherein m, Q, R³, R⁴, R⁵ and Z are as defined above in Table 2, R¹ and R² are hydrogen and n is 0.

Table 6:
This table discloses 49 specific compounds of the formula (T-6):

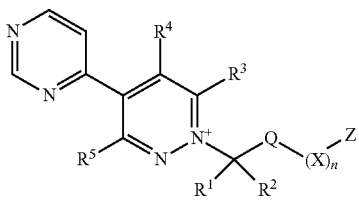
(T-6)

wherein m, Q, R³, R⁴, R⁵ and Z are as defined above in Table 3, R¹ and R² are hydrogen and n is 0.

Table 7:
This table discloses 53 specific compounds of the formula (T-7):

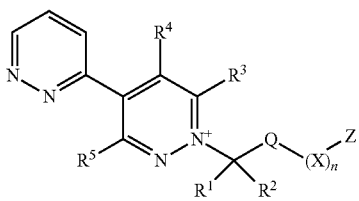
(T-7)

wherein m, Q, R³, R⁴, R⁵ and Z are as defined above in Table 1, R¹ and R² are hydrogen and n is 0.

Table 8:
This table discloses 49 specific compounds of the formula (T-8):

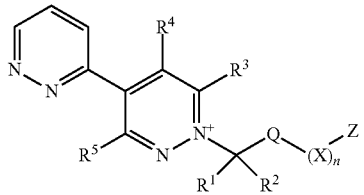
(T-8)

wherein m, Q, R³, R⁴, R⁵ and Z are as defined above in Table 2, R¹ and R² are hydrogen and n is 0.

Table 9:
This table discloses 49 specific compounds of the formula (T-9):

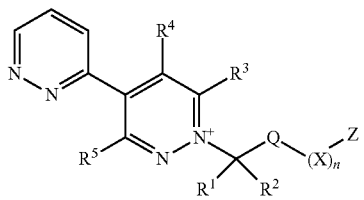
(T-9)

wherein m, Q, R³, R⁴, R⁵ and Z are as defined above in Table 3, R¹ and R² are hydrogen and n is 0.

Table 10:
This table discloses 53 specific compounds of the formula (T-10):

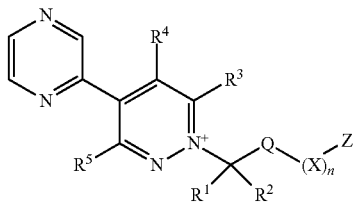
(T-10)

wherein m, Q, R³, R⁴, R⁵ and Z are as defined above in Table 1, R¹ and R² are hydrogen and n is 0.

Table 11:
This table discloses 49 specific compounds of the formula (T-11):

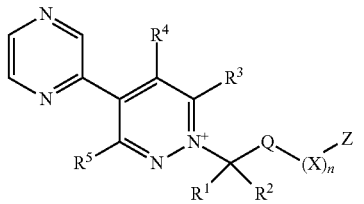
(T-11)

wherein m, Q, R³, R⁴, R⁵ and Z are as defined above in Table 2, R¹ and R² are hydrogen and n is 0.

Table 12:
This table discloses 49 specific compounds of the formula (T-12):

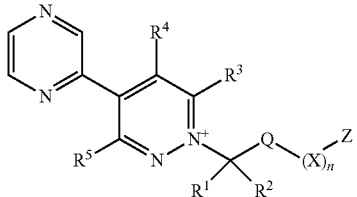
(T-12)

wherein m, Q, $R^3$, $R^4$, $R^5$ and Z are as defined above in Table 3, $R^1$ and $R^2$ are hydrogen and n is 0.

Table 13:
This table discloses 53 specific compounds of the formula (T-13):

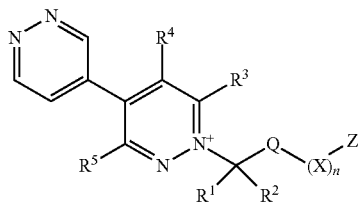
(T-13)

wherein m, Q, $R^3$, $R^4$, $R^5$ and Z are as defined above in Table 1, $R^1$ and $R^2$ are hydrogen and n is 0.

Table 14:
This table discloses 49 specific compounds of the formula (T-14):

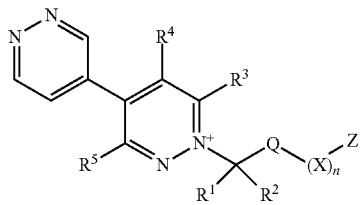
(T-14)

wherein m, Q, $R^3$, $R^4$, $R^5$ and Z are as defined above in Table 2, $R^1$ and $R^2$ are hydrogen and n is 0.

Table 15:
This table discloses 49 specific compounds of the formula (T-15):

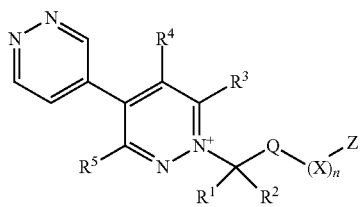
(T-15)

wherein m, Q, $R^3$, $R^4$, $R^5$ and Z are as defined above in Table 3, $R^1$ and $R^2$ are hydrogen and n is 0.

Table 16:
This table discloses 53 specific compounds of the formula (T-16):

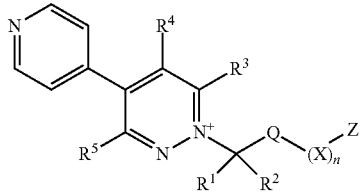
(T-16)

wherein m, Q, $R^3$, $R^4$, $R^5$ and Z are as defined above in Table 1, $R^1$ and $R^2$ are hydrogen and n is 0.

Table 17:
This table discloses 49 specific compounds of the formula (T-17):

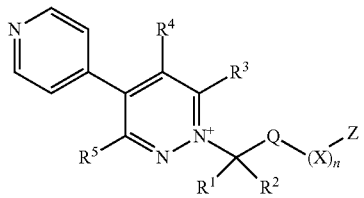
(T-17)

wherein m, Q, $R^3$, $R^4$, $R^5$ and Z are as defined above in Table 2, $R^1$ and $R^2$ are hydrogen and n is 0.

Table 18:
This table discloses 49 specific compounds of the formula (T-18):

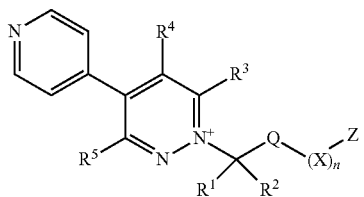
(T-18)

wherein m, Q, $R^3$, $R^4$, $R^5$ and Z are as defined above in Table 3, $R^1$ and $R^2$ are hydrogen and n is 0.

Table 19:
This table discloses 53 specific compounds of the formula (T-19):

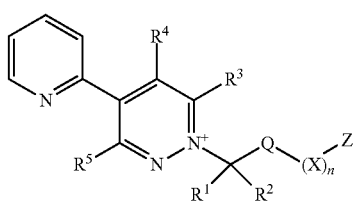
(T-19)

wherein m, Q, $R^3$, $R^4$, $R^5$ and Z are as defined above in Table 1, $R^1$ and $R^2$ are hydrogen and n is 0.

Table 20:

This table discloses 49 specific compounds of the formula (T-20):

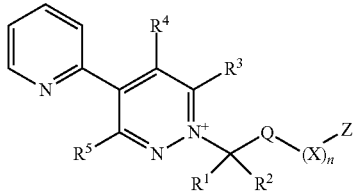
(T-20)

wherein m, Q, $R^3$, $R^4$, $R^5$ and Z are as defined above in Table 2, $R^1$ and $R^2$ are hydrogen and n is 0.

Table 21:

This table discloses 49 specific compounds of the formula (T-21):

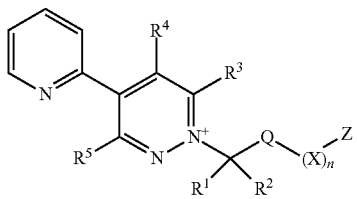
(T-21)

wherein m, Q, $R^3$, $R^4$, $R^5$ and Z are as defined above in Table 3, $R^1$ and $R^2$ are hydrogen and n is 0.

Table 22:

This table discloses 53 specific compounds of the formula (T-22):

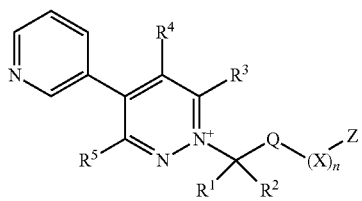
(T-22)

wherein m, Q, $R^3$, $R^4$, $R^5$ and Z are as defined above in Table 1, $R^1$ and $R^2$ are hydrogen and n is 0.

Table 23:

This table discloses 49 specific compounds of the formula (T-23):

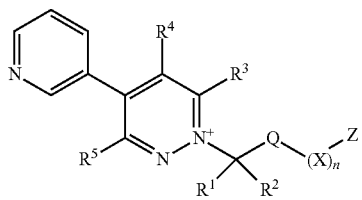
(T-23)

wherein m, Q, $R^3$, $R^4$, $R^5$ and Z are as defined above in Table 2, $R^1$ and $R^2$ are hydrogen and n is 0.

Table 24:

This table discloses 49 specific compounds of the formula (T-24):

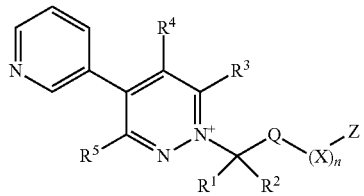
(T-24)

wherein m, Q, $R^3$, $R^4$, $R^5$ and Z are as defined above in Table 3, $R^1$ and $R^2$ are hydrogen and n is 0.

Table 25:

This table discloses 53 specific compounds of the formula (T-25):

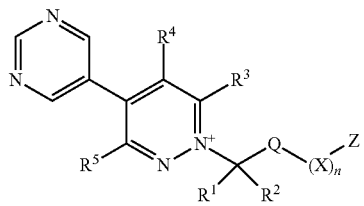
(T-25)

wherein m, Q, $R^3$, $R^4$, $R^5$ and Z are as defined above in Table 1, $R^1$ and $R^2$ are hydrogen and n is 0.

Table 26:

This table discloses 49 specific compounds of the formula (T-26):

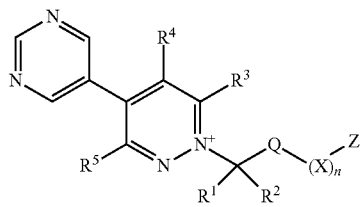
(T-26)

wherein m, Q, $R^3$, $R^4$, $R^5$ and Z are as defined above in Table 2, $R^1$ and $R^2$ are hydrogen and n is 0.

Table 27:

This table discloses 49 specific compounds of the formula (T-27):

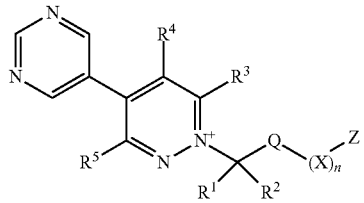
(T-27)

wherein m, Q, $R^3$, $R^4$, $R^5$ and Z are as defined above in Table 3, $R^1$ and $R^2$ are hydrogen and n is 0.

The compounds of the present invention may be prepared according to the following schemes in which the substituents n, m, r, A, Q, X, Z, $R^1$, $R^2$, $R^{1a}$, $R^{2b}$, $R^2$, $R^3$, $R^4$, $R^5$, $R^6$, $R^7$, $R^{7a}$, $R^{7b}$, $R^7$, $R^8$, $R^9$, $R^{10}$, $R^{11}$, $R^{12}$, $R^{13}$, $R^{14}$, $R^{15}$, $R^{15a}$, $R^{16}$, $R^{17}$ and $R^{18}$ are as defined hereinbefore unless explicitly stated otherwise. The compounds of the preceeding Tables 1 to 27 may thus be obtained in an analogous manner.

The compounds of formula (I) may be prepared by the alkylation of compounds of formula (X), wherein $R^3$, $R^4$, $R^5$ and A are as defined for compounds of formula (I), with a suitable alkylating agent of formula (W), wherein $R^1$, $R^2$, Q, X, n and Z are as defined for compounds of formula (I) and LG is a suitable leaving group, for example, halide or pseudohalide such as triflate, mesylate or tosylate, in a suitable solvent at a suitable temperature, as described in reaction scheme 1. Example conditions include stirring a compound of formula (X) with an alkylating agent of formula (W) in a solvent, or mixture of solvents, such as acetone, dichloromethane, dichloroethane, N,N-dimethylformamide, acetonitrile, 1,4-dioxane, water, acetic acid or trifluroacetic acid at a temperature between −78° C. and 150° C. An alkylating agent of formula (W) may include, but is not limited to, bromoacetic acid, methyl bromoacetate, 3-bromopropionoic acid, methyl 3-bromopropionate, 2-bromo-N-methoxyacetamide, sodium 2-bromoethanesulphonate, 2,2-dimethylpropyl 2-(trifluoromethylsulfonyloxy)ethanesulfonate, 2-bromo-N-methanesulfonylacetamide, 3-bromo-N-methanesulfonylpropanamide, dimethoxyphosphorylmethyl trifluoromethanesulfonate, dimethyl 3-bromopropylphosphonate, 3-chloro-2,2-dimethyl-propanoic acid and diethyl 2-bromoethylphosphonate. Such alkylating agents and related compounds are either known in the literature or may be prepared by known literature methods. Compounds of formula (I) which may be described as esters of N-alkyl acids, which include, but are not limited to, esters of carboxylic acids, phosphonic acids, phosphinic acids, sulfonic acids and sulfinic acids, may be subsequently partially or fully hydrolysed by treatment with a suitable reagent, for example, aqueous hydrochloric acid or trimethylsilyl bromide, in a suitable solvent at a suitable temperature between 0° C. and 100° C.

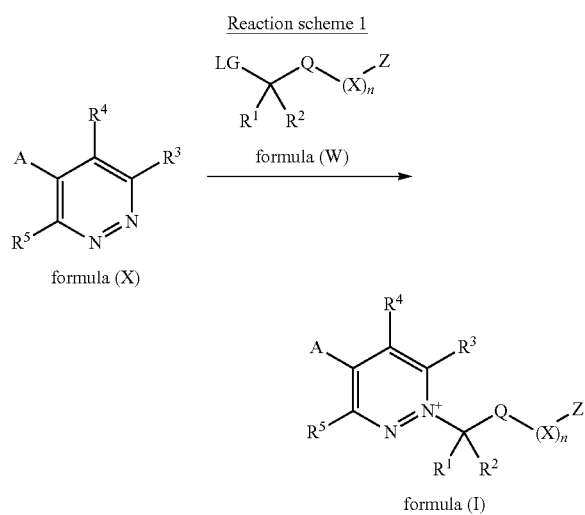

Reaction scheme 1

Additionally, compounds of formula (I) may be prepared by reacting compounds of formula (X), wherein $R^3$, $R^4$, $R^5$ and A are as defined for compounds of formula (I), with a suitably activated electrophilic alkene of formula (B), wherein Z is —S(O)$_2$R$^{10}$, —P(O)(R$^3$)(OR$^{10}$) or —C(O)OR$^{10}$ and $R^1$, $R^2$, $R^{1a}$, $R^{10}$ and $R^{13}$ are as defined for compounds of formula (I), in a suitable solvent at a suitable temperature. Compounds of formula (B) are known in the literature, or may be prepared by known methods. Example reagents include, but are not limited to, acrylic acid, methacrylic acid, crotonic acid, 3,3-dimethylacrylic acid, methyl acrylate, ethene sulfonic acid, isopropyl ethylenesulfonate, 2,2-dimethylpropyl ethenesulfonate and dimethyl vinylphosphonate. The direct products of these reactions, which may be described as esters of N-alkyl acids, which include, but are not limited to, esters of carboxylic acids, phosphonic acids, phosphinic acids, sulfonic acids and sulfinic acids, may be subsequently partially or fully hydrolysed by treament with a suitable reagent in a suitable solvent at a suitable temperature, as described in reaction scheme 2.

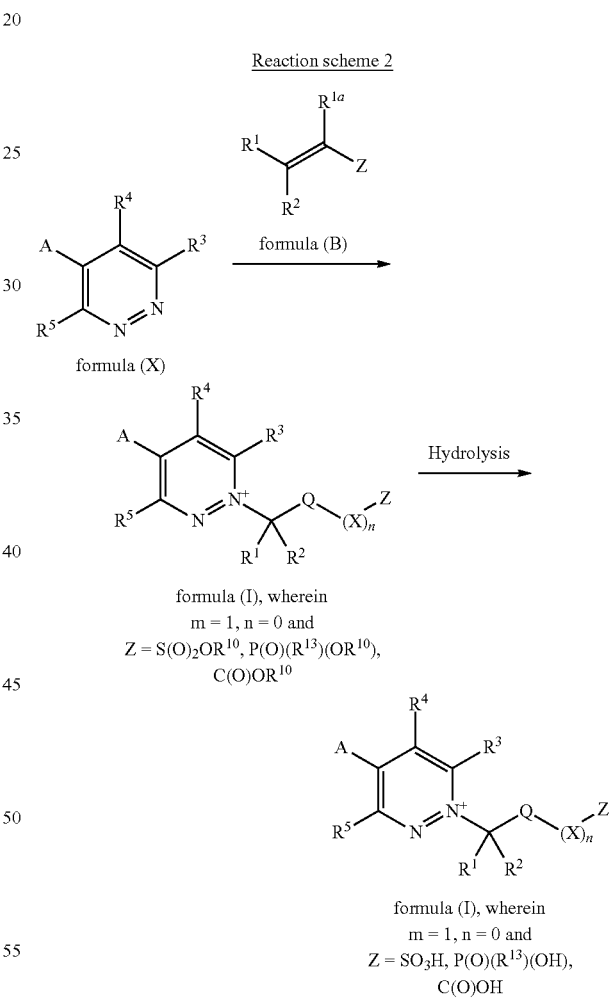

Reaction scheme 2

In a related reaction compounds of formula (I), wherein Q is C(R$^{1a}$R$^{2b}$), m is 1, 2 or 3, n=0 and Z is —S(O)$_2$OH, —OS(O)$_2$OH or —NR$^6$S(O)$_2$H, may be prepared by the reaction of compounds of formula (X), wherein $R^3$, $R^4$, $R^5$ and A are as defined for compounds of formula (I), with a cyclic alkylating agent of formula (E), (F) or (AF), wherein $Y^a$ is C(R$^{1a}$R$^{21}$), O or NR$^6$ and $R^1$, $R^2$, $R^{1a}$ and $R^{2b}$ are as defined for compounds of formula (I), in a suitable solvent at a suitable temperature, as described in reaction scheme 3.

Suitable solvents and suitable temperatures are as previously described. An alkylating agent of formula (E) or (F) may include, but is not limited to, 1,3-propanesultone, 1,4-butanesultone, ethylenesulfate, 1,3-propylene sulfate and 1,2,3-oxathiazolidine 2,2-dioxide. Such alkylating agents and related compounds are either known in the literature or may be prepared by known literature methods.

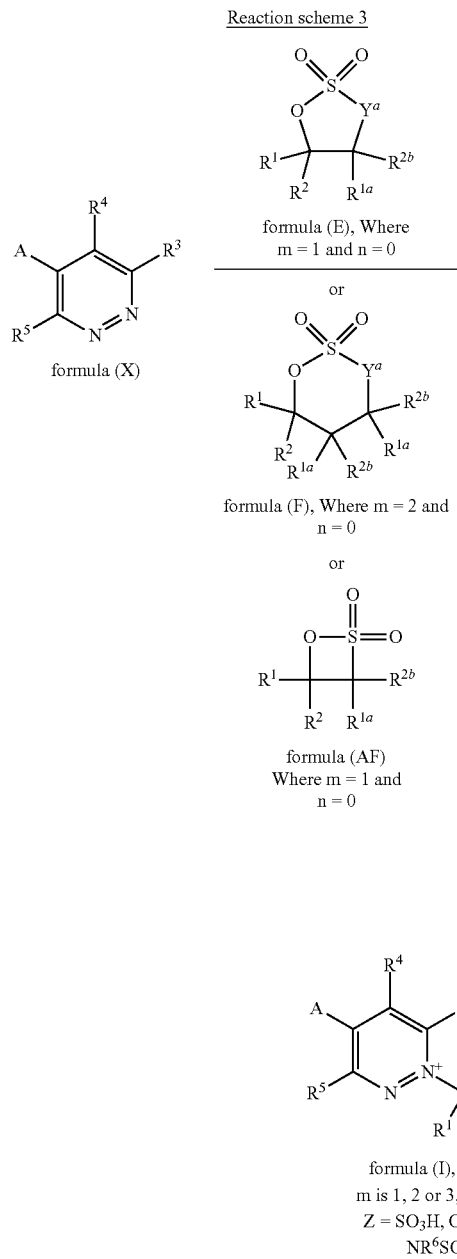

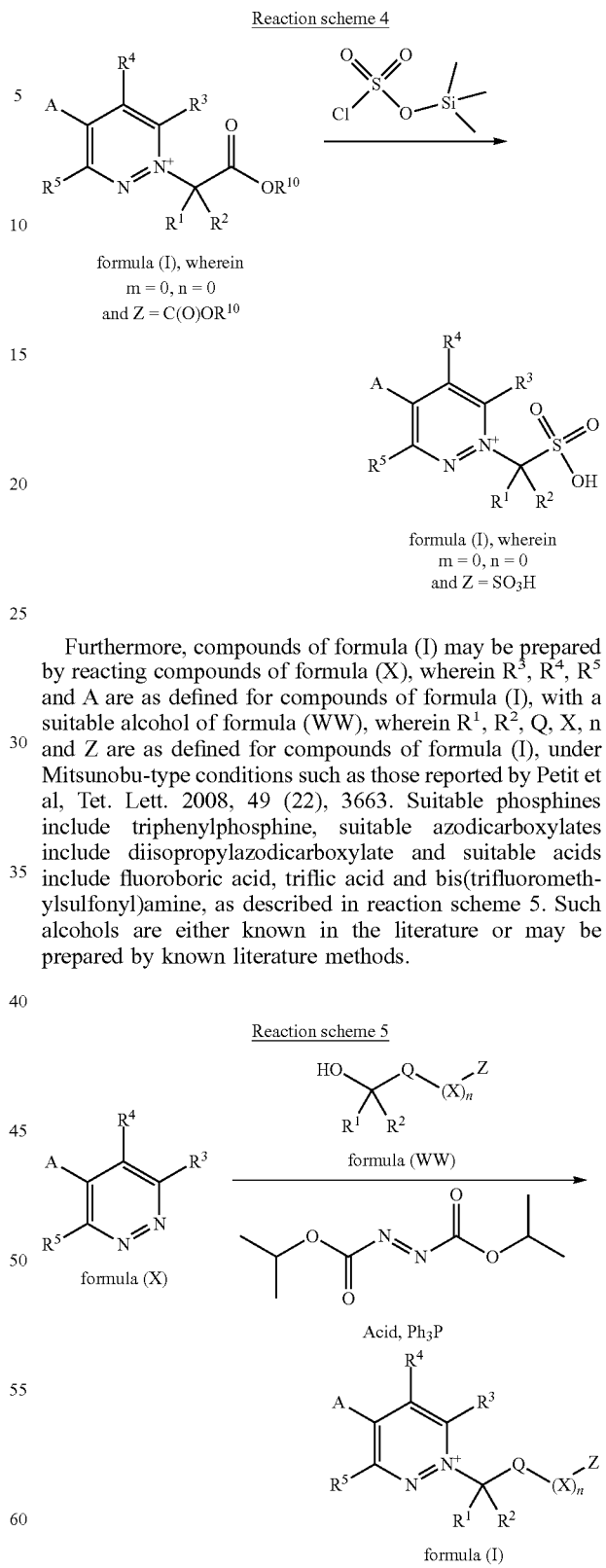

Furthermore, compounds of formula (I) may be prepared by reacting compounds of formula (X), wherein $R^3$, $R^4$, $R^5$ and A are as defined for compounds of formula (I), with a suitable alcohol of formula (WW), wherein $R^1$, $R^2$, Q, X, n and Z are as defined for compounds of formula (I), under Mitsunobu-type conditions such as those reported by Petit et al, Tet. Lett. 2008, 49 (22), 3663. Suitable phosphines include triphenylphosphine, suitable azodicarboxylates include diisopropylazodicarboxylate and suitable acids include fluoroboric acid, triflic acid and bis(trifluoromethylsulfonyl)amine, as described in reaction scheme 5. Such alcohols are either known in the literature or may be prepared by known literature methods.

A compound of formula (I), wherein m is 0, n is 0 and Z is —S(O)$_2$OH, may be prepared from a compound of formula (I), wherein m is 0, n is 0 and Z is C(O)OR$^{10}$, by treatment with trimethylsilylchlorosulfonate in a suitable solvent at a suitable temperature, as described in reaction scheme 4. Preferred conditions include heating the carboxylate precursor in neat trimethylsilylchlorosulfonate at a temperature between 25° C. and 150° C.

Compounds of formula (I) may also be prepared by reacting compounds of formula (C), wherein Q, Z, X, n, $R^1$, $R^2$, $R^3$, $R^4$, $R^5$ and A are as defined for compounds of formula (I), with a hydrazine of formula (D) in a suitable solvent or mixture of solvents, in the presence of a suitable acid at a suitable temperature, between −78° C. and 150° C., as described in reaction scheme 6. Suitable solvents, or mixtures thereof, include, but are not limited to, alcohols, such as methanol, ethanol and isopropanol, water, aqueous hydrochloric acid, aqueous sulfuric acid, acetic acid and trifluoroacetic acid. Hydrazine compounds of formula (D), for example 2,2-dimethylpropyl 2-hydrazinoethanesulfonate, are either known in the literature or may be prepared by known literature procedures.

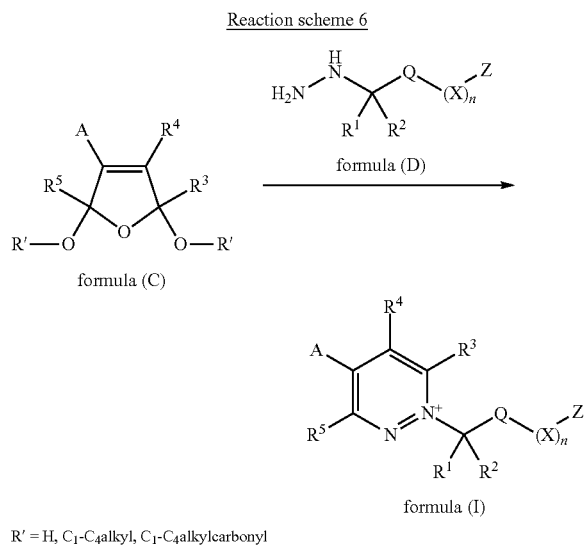

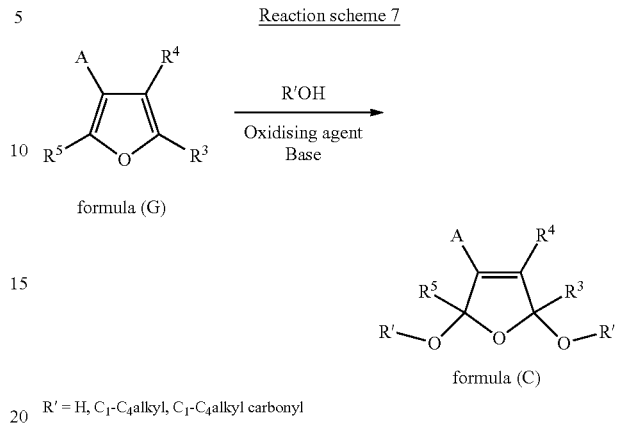

Compounds of formula (C) may be prepared by reacting compounds of formula (G), wherein $R^3$, $R^4$, $R^5$ and A are as defined for compounds of formula (I), with an oxidising agent in a suitable solvent at a suitable temperature, between −78° C. and 150° C., optionally in the presence of a suitable base, as described in reaction scheme 7. Suitable oxidising agents include, but are not limited to, bromine and suitable solvents include, but are not limited to alcohols such as methanol, ethanol and isopropanol. Suitable bases include, but are not limited to, sodium bicarbonate, sodium carbonate, potassium bicarbonate, potassium carbonate and potassium acetate. Similar reactions are known in the literature (for example Hufford, D. L.; Tarbell, D. S.; Koszalka, T. R. J. Amer. Chem. Soc., 1952, 3014). Furans of formula (G) are known in the literature or may be prepared using literature methods. Example methods include, but are not limited to, transition metal cross-couplings such as Stille (for example Farina, V.; Krishnamurthy, V.; Scott, W. J. Organic Reactions, Vol. 50. 1997, and Gazzard, L. et al. J. Med. Chem., 2015, 5053), Suzuki-Miyaura (for example Ando, S.; Matsunaga, H.; Ishizuka, T. J. Org. Chem. 2017, 1266-1272, and Ernst, J. B.; Rakers, L.; Glorius, F. Synthesis, 2017, 260), Negishi (for example Yang, Y.; Oldenhius, N. J.; Buchwald, S. L. Angew. Chem. Int. Ed. 2013, 615, and Braendvang, M.; Gundersen, L. Bioorg. Med. Chem. 2005, 6360), and Kumada (for example Heravi, M. M.; Hajiabbasi, P. Monatsh. Chem., 2012, 1575). The coupling partners may be selected with reference to the specific cross-coupling reaction and target product. Transition metal catalysts, ligands, bases, solvents and temperatures may be selected with reference to the desired cross-coupling and are known in the literature. Cross-coupling reactions using pseudo halogens, including but not limited to, triflates, mesylates, tosylates and anisoles, may also be achieved under related conditions.

In another approach a compound of formula (I), wherein Q, Z, X, n, $R^1$, $R^2$, $R^3$, $R^4$, $R^5$ and A are as defined for compounds of formula (I), may be prepared from a compound of formula (R) and an oxidant, in a suitable solvent at a suitable temperature, as outlined in reaction scheme 8. Example oxidants include, but are not limited to, 2,3-dichloro-5,6-dicyano-1,4-benzoquinone, tetrachloro-p-benzoquinone, potassium permanganate, manganese dioxide, 2,2,6,6-tetramethyl-1-piperidinyloxy and bromine. Related reactions are known in the literature.

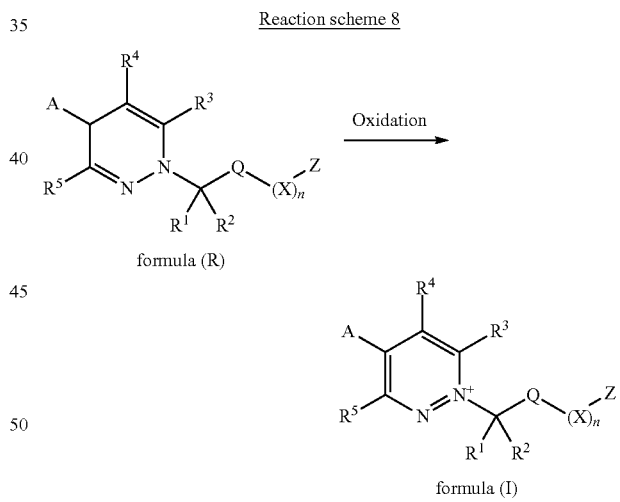

A compound of formula (R), wherein Q, Z, X, n, $R^1$, $R^2$, $R^3$, $R^4$, $R^5$ and A are as defined for compounds of formula (I), may be prepared from a compound of formula (S), wherein Q, Z, X, n, $R^1$, $R^2$, $R^3$, $R^4$ and $R^5$ are as defined for compounds of formula (I), wherein and an organometallic of formula (T), wherein M" includes, but is not limited to, organomagnesium, organolithium, organocopper and organozinc reagents, in a suitable solvent at a suitable temperature, optionally in the presence of an additional transition metal additive, as outlined in reaction scheme 9. Example conditions include treating a compound of formula (S) with a Grignard of formula (T), in the presence of 0.05-100 mol % copper iodide, in a solvent such as tetrahydrofuran at a temperature between −78° C. and 100° C. Organometallics of formula (T) are known in the literature, or may be prepared by known literature methods. Compounds of formula (S) may be prepared by analogous reactions to those for the preparation of compounds of formula (I) from a compound of formula (XX).

Reaction scheme 9

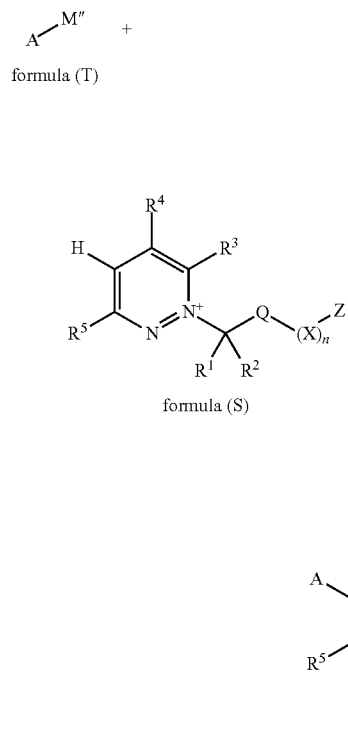

Reaction scheme 10

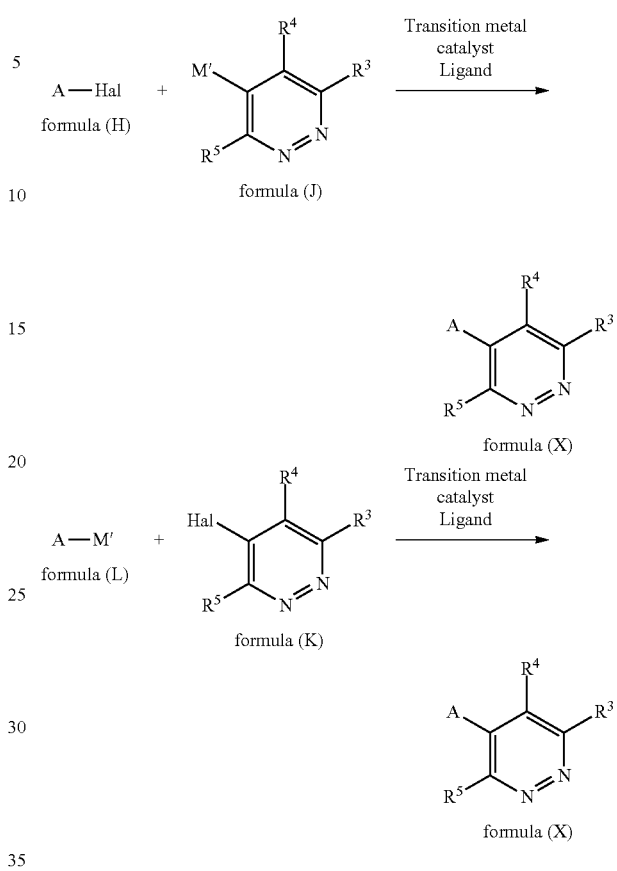

Biaryl pyridazines of formula (X) are known in the literature or may be prepared using literature methods. Example methods include, but are not limited to, the transition metal cross-coupling of compounds of formula (H) and formula (J), or alternatively compounds of formula (K) and formula (L), in which compounds of formula (J) and formula (L), wherein M' is either an organostannane, organoboronic acid or ester, organotrifluoroborate, organomagnesium, organocopper or organozinc, as outlined in reaction scheme 10. Hal is defined as a halogen or pseudo halogen, for example triflate, mesylate and tosylate. Such cross-couplings include Stille (for example Sauer, J.; Heldmann, D. K. Tetrahedron, 1998, 4297), Suzuki-Miyaura (for example Luebbers, T.; Flohr, A.; Jolidon, S.; David-Pierson, P.; Jacobsen, H.; Ozmen, L.; Baumann, K. Bioorg. Med. Chem. Lett., 2011, 6554), Negishi (for example Imahori, T.; Suzawa, K.; Kondo, Y. Heterocycles, 2008, 1057), and Kumada (for example Heravi, M. M.; Hajiabbasi, P. Monatsh. Chem., 2012, 1575). The coupling partners may be selected with reference to the specific cross-coupling reaction and target product. Transition metal catalysts, ligands, bases, solvents and temperatures may be selected with reference to the desired cross-coupling and are known in the literature. Compounds of formula (H), formula (K) and formula (L) are known in the literature, or may be prepared by known literature methods.

An compound of formula (J), wherein M' is either an organostannane, organoboronic acid or ester, organotrifluoroborate, organomagnesium, organocopper or organozinc, may be prepared from a compound of formula (XX), wherein $R^3$, $R^4$ and $R^5$ are as defined for compounds of formula (I), by metallation, as outlined in reaction scheme 11. Similar reactions are known in the literature (for example Ramphal et al, WO2015/153683, Unsinn et al., Organic Letters, 15(5), 1128-1131; 2013, Sadler et al., Organic & Biomolecular Chemistry, 12(37), 7318-7327; 2014. Alternatively, an organometallic of formula (J) may be prepared from compounds of formula (K), wherein $R^3$, $R^4$, $R^5$ are as defined for compounds of formula (I), and Hal is defined as a halogen or pseudo halogen, for example triflate, mesylate and tosylate, as described in scheme 11. Example conditions to prepare an compound of formula (J) wherein M' is an organostannane, include treatment of a compound of formula (K) with lithium tributyl tin in an appropriate solvent at an appropriate temperature (for example see WO 2010/038465). Example conditions to prepare compound of formula (J) wherein M' is an organoboronic acid or ester, include treatment of a compound of formula (K) with bis(pinacolato)diboron, in the presence of an appropriate transition metal catalyst, appropriate ligand, appropriate base, in an appropriate solvent at an appropriate temperature (for example KR 2015135626). Compounds of formula (K) and formula (XX) are either known in the literature or can be prepared by known methods.

Reaction scheme 11

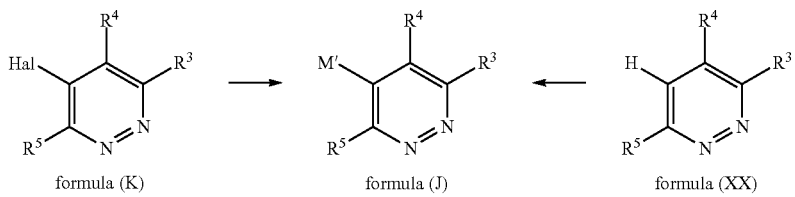

In another approach, an organometallic of formula (J), in which M' is either an organostannane or organoboronic acid or ester, may be prepared from a compound of formula (N) and a compound of formula (O), wherein $R^3$, $R^4$ and $R^5$ are as defined for compounds of formula (I), as outlined in reaction scheme 12. Examples of such a reaction are known in the literature, for example, Helm et al., Org. and Biomed. Chem., 2006, 4 (23), 4278, Sauer et al., Eur. J. Org. Chem., 1998, 12, 2885, and Helm, M. D.; Moore, J. E.; Plant, A.; Harrity, J. P. A., Angew. Chem. Int. Ed., 2005, 3889. Compounds of formula (N) and formula (O) are known in the literature.

Reaction scheme 12

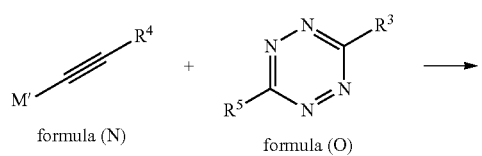

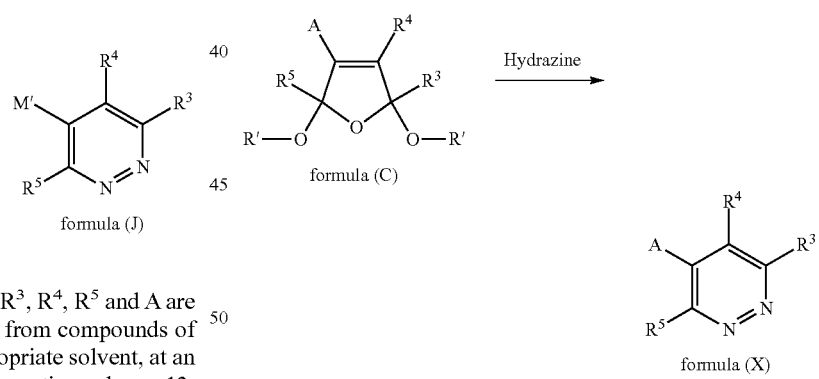

Compounds of formula (X), wherein $R^3$, $R^4$, $R^5$ and A are as previously defined, may be prepared from compounds of formula (P) and formula (O), in an appropriate solvent, at an appropriate temperature, as outlined in reaction scheme 13. Examples of such a reaction are known in the literature, for example, Sauer et al., Eur. J. Org. Chem., 1998, 12, 2885. Compounds of formula (P) are known in the literature, or may be prepared by known methods.

Reaction scheme 13

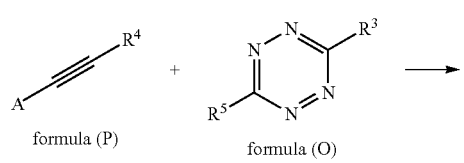

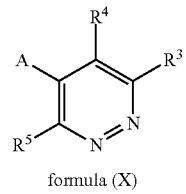

In a further approach a compound of formula (X), wherein $R^3$, $R^4$, $R^5$ and A are as defined for compounds of formula (I), may be prepared from compounds of formula (C) and hydrazine, in an appropriate solvent, at an appropriate temperature, as outlined in reaction scheme 14. This reaction may also optionally be performed in the presence of an acid, for example aqueous sulfuric acid or aqueous hydrochloric acid. Similar reactions are known in the literature (for example DE 102005029094, and Chen, B.; Bohnert, T.; Zhou, X.; Dedon, P. C. Chem. Res. Toxicol., 2004, 1406). Compounds of formula (C) may be prepared as previously outlined.

Reaction scheme 14

R' = H, $C_1$-$C_4$alkyl, $C_1$-$C_4$alkylcarbonyl

The compounds according to the invention can be used as herbicidal agents in unmodified form, but they are generally formulated into compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood N.J. (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, $10^{th}$ Edition, Southern Illinois University, 2010.

The herbicidal compositions generally comprise from 0.1 to 99% by weight, especially from 0.1 to 95% by weight, compounds of Formula (I) and from 1 to 99.9% by weight of a formulation adjuvant which preferably includes from 0 to 25% by weight of a surface-active substance. The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %):

Emulsifiable Concentrates:
active ingredient: 1 to 95%, preferably 60 to 90%
surface-active agent: 1 to 30%, preferably 5 to 20%
liquid carrier: 1 to 80%, preferably 1 to 35%

Dusts:
active ingredient: 0.1 to 10%, preferably 0.1 to 5%
solid carrier: 99.9 to 90%, preferably 99.9 to 99%

Suspension Concentrates:
active ingredient: 5 to 75%, preferably 10 to 50%
water: 94 to 24%, preferably 88 to 30%
surface-active agent: 1 to 40%, preferably 2 to 30%

Wettable Powders:
active ingredient: 0.5 to 90%, preferably 1 to 80%
surface-active agent: 0.5 to 20%, preferably 1 to 15%
solid carrier: 5 to 95%, preferably 15 to 90%

Granules:
active ingredient: 0.1 to 30%, preferably 0.1 to 15%
solid carrier: 99.5 to 70%, preferably 97 to 85%

The composition of the present may further comprise at least one additional pesticide. For example, the compounds according to the invention can also be used in combination with other herbicides or plant growth regulators. In a preferred embodiment the additional pesticide is a herbicide and/or herbicide safener.

Thus, compounds of Formula (I) can be used in combination with one or more other herbicides to provide various herbicidal mixtures. Specific examples of such mixtures include (wherein "I" represents a compound of Formula (I)):—I+acetochlor; I+acifluorfen (including acifluorfen-sodium); I+aclonifen; I+alachlor; I+alloxydim; I+ametryn; I+amicarbazone; I+amidosulfuron; I+aminocyclopyrachlor; I+aminopyralid; I+amitrole; I+asulam; I+atrazine; I+bensulfuron (including bensulfuron-methyl); I+bentazone; I+bicyclopyrone; I+bilanafos; I+bifenox; I+bispyribac-sodium; I+bixlozone; I+bromacil; I+bromoxynil; I+butachlor; I+butafenacil; I+cafenstrole; I+carfentrazone (including carfentrazone-ethyl); cloransulam (including cloransulam-methyl); I+chlorimuron (including chlorimuron-ethyl); I+chlorotoluron; I+cinosulfuron; I+chlorsulfuron; I+cinmethylin; I+clacyfos; I+clethodim; I+clodinafop (including clodinafop-propargyl); I+clomazone; I+clopyralid; I+cyclopyranil; I+cyclopyrimorate; I+cyclosulfamuron; I+cyhalofop (including cyhalofop-butyl); I+2,4-D (including the choline salt and 2-ethylhexyl ester thereof); I+2,4-DB; I+daimuron; I+desmedipham; I+dicamba (including the aluminum, aminopropyl, bis-aminopropylmethyl, choline, dichloroprop, diglycolamine, dimethylamine, dimethylammonium, potassium and sodium salts thereof); I+diclofop-methyl; I+diclosulam; I+diflufenican; I+difenzoquat; I+diflufenican; I+diflufenzopyr; I+dimethachlor; I+dimethenamid-P; I+diquat dibromide; I+diuron; I+esprocarb; I+ethalfluralin; I+ethofumesate; I+fenoxaprop (including fenoxaprop-P-ethyl); I+fenoxasulfone; I+fenquinotrione; I+fentrazamide; I+flazasulfuron; I+florasulam; I+florpyrauxifen; I+fluazifop (including fluazifop-P-butyl); I+flucarbazone (including flucarbazone-sodium); I+flufenacet; I+flumetralin; I+flumetsulam; I+flumioxazin; I+flupyrsulfuron (including flupyrsulfuron-methyl-sodium); I+fluroxypyr (including fluroxypyr-meptyl); I+fluthiacet-methyl; I+fomesafen; I+foramsulfuron; I+glufosinate (including the ammonium salt thereof); I+glyphosate (including the diammonium, isopropylammonium and potassium salts thereof); I+halauxifen (including halauxifen-methyl); I+halosulfuron-methyl; I+haloxyfop (including haloxyfop-methyl); I+hexazinone; I+hydantocidin; I+imazamox; I+imazapic; I+imazapyr; I+imazaquin; I+imazethapyr; I+indaziflam; I+iodosulfuron (including iodosulfuron-methyl-sodium); I+iofensulfuron; I+iofensulfuron-sodium; I+ioxynil; I+ipfencarbazone; I+isoproturon; I+isoxaben; I+isoxaflutole; I+lactofen; I+lancotrione; I+linuron; I+MCPA; I+MCPB; I+mecoprop-P; I+mefenacet; I+mesosulfuron; I+mesosulfuron-methyl; I+mesotrione; I+metamitron; I+metazachlor; I+methiozolin; I+metobromuron; I+metolachlor; I+metosulam; I+metoxuron; I+metribuzin; I+metsulfuron; I+molinate; I+napropamide; I+nicosulfuron; I+norflurazon; I+orthosulfamuron; I+oxadiargyl; I+oxadiazon; I+oxasulfuron; I+oxyfluorfen; I+paraquat dichloride; I+pendimethalin; I+penoxsulam; I+phenmedipham; I+picloram; I+picolinafen; I+pinoxaden; I+pretilachlor; I+primisulfuron-methyl; I+prodiamine; I+prometryn; I+propachlor; I+propanil; I+propaquizafop; I+propham; I+propyrisulfuron, I+propyzamide; I+prosulfocarb; I+prosulfuron; I+pyraclonil; I+pyraflufen (including pyraflufen-ethyl): I+pyrasulfotole; I+pyrazolynate, I+pyrazosulfuron-ethyl; I+pyribenzoxim; I+pyridate; I+pyriftalid; I+pyrimisulfan, I+pyrithiobac-sodium; I+pyroxasulfone; I+pyroxsulam; I+quinclorac; I+quinmerac; I+quizalofop (including quizalofop-P-ethyl and quizalofop-P-tefuryl); I+rimsulfuron; I+saflufenacil; I+sethoxydim; I+simazine; I+S-metolachlor; I+sulcotrione; I+sulfentrazone; I+sulfosulfuron; I+tebuthiuron; I+tefuryltrione; I+tembotrione; I+terbuthylazine; I+terbutryn; I+thiencarbazone; I+thifensulfuron; I+tiafenacil; I+tolpyralate; I+topramezone; I+tralkoxydim; I+triafamone; I+triallate; I+triasulfuron; I+tribenuron (including tribenuron-methyl); I+triclopyr; I+trifloxysulfuron (including trifloxysulfuron-sodium); I+trifludimoxazin; I+trifluralin; I+triflusulfuron; I+tritosulfuron; I+4-hydroxy-1-methoxy-5-methyl-3-[4-(trifluoromethyl)-2-pyridyl]imidazolidin-2-one; I+4-hydroxy-1,5-dimethyl-3-[4-(trifluoromethyl)-2-pyridyl]imidazolidin-2-one; I+5-ethoxy-4-hydroxy-1-methyl-3-[4-(trifluoromethyl)-2-pyridyl]imidazolidin-2-one; I+4-hydroxy-1-methyl-3-[4-(trifluoromethyl)-2-pyridyl]imidazolidin-2-one; I+4-hydroxy-1,5-dimethyl-3-[1-methyl-5-(trifluoromethyl) pyrazol-3-yl]imidazolidin-2-one; I+(4R)$_1$-(5-tert-butylisoxazol-3-yl)-4-ethoxy-5-hydroxy-3-methyl-imidazolidin-2-one; I+3-[2-(3,4-dimethoxyphenyl)-6-methyl-3-oxo-pyridazine-4-carbonyl]bicyclo[3.2.1]octane-2,4-dione; I+2-[2-(3,4-dimethoxyphenyl)-6-methyl-3-oxo-pyridazine-4-carbonyl]-5-methyl-cyclohexane-1,3-dione; I+2-[2-(3,4-dimethoxyphenyl)-6-methyl-3-oxo-pyridazine-4-carbonyl]cyclohexane-1,3-dione; I+2-[2-(3,4-dimethoxyphenyl)-6-methyl-3-oxo-pyridazine-4-carbonyl]-5,5-dimethyl-cyclohexane-1,3-dione; I+6-[2-(3,4-dimethoxyphenyl)-6-methyl-3-oxo-pyridazine-4-carbonyl]-2,2,4,4-tetramethyl-cyclohexane-1,3,5-trione; I+2-[2-(3,4-dimethoxyphenyl)-6-methyl-3-oxo-pyridazine-4-carbonyl]-5-ethyl-cyclohexane-1,3-dione; I+2-[2-(3,4-dimethoxyphenyl)-6-methyl-3-oxo-pyridazine-4-carbonyl]-4,4,6,6-tetramethyl-cyclohexane-1,3-dione; I+2-[6-cyclopropyl-2-(3,4-dimethoxyphenyl)-3-oxo-pyridazine-4-carbonyl]-5-methyl-cyclohexane-1,3-dione; I+3-[6-cyclopropyl-2-(3,4-dimethoxyphenyl)-3-oxo-pyridazine-4-carbonyl]bicyclo[3.2.1]octane-2,4-dione; I+2-[6-cyclopropyl-2-(3,4-dimethoxyphenyl)-3-oxo-pyridazine-4-carbonyl]-5,5-dimethyl-cyclohexane-1,3-dione; I+6-[6-cyclopropyl-2-(3,4-dimethoxyphenyl)-3-oxo-pyridazine-4-carbonyl]-2,2,4,4-tetramethyl-cyclohexane-1,3,5-trione; I+2-[6-cyclopropyl-2-(3,4-dimethoxyphenyl)-3-oxo-pyridazine-4-carbonyl]cyclohexane-1,3-dione; I+4-[2-(3,4-dimethoxyphenyl)-6-methyl-3-oxo-pyridazine-4-carbonyl]-2,2,6,6-tetramethyl-tetrahydropyran-3,5-dione and I+4-[6-cyclopropyl-2-(3,4-dimethoxyphenyl)-3-oxo-pyridazine-4-carbonyl]-2,2,6,6-tetramethyl-tetrahydropyran-3,5-dione.

The mixing partners of the compound of Formula (I) may also be in the form of esters or salts, as mentioned e.g. in The Pesticide Manual, Fourteenth Edition, British Crop Protection Council, 2006.

The compound of Formula (I) can also be used in mixtures with other agrochemicals such as fungicides, nematicides or insecticides, examples of which are given in The Pesticide Manual.

The mixing ratio of the compound of Formula (I) to the mixing partner is preferably from 1:100 to 1000:1.

The mixtures can advantageously be used in the above-mentioned formulations (in which case "active ingredient" relates to the respective mixture of compound of Formula (I) with the mixing partner).

Compounds of Formula (I) of the present invention may also be combined with herbicide safeners. Preferred combinations (wherein "I" represents a compound of Formula (I)) include:—I+benoxacor, I+cloquintocet (including cloquintocet-mexyl); I+cyprosulfamide; I+dichlormid; I+fenchlorazole (including fenchlorazole-ethyl); I+fenclorim; I+fluxofenim; I+furilazole I+isoxadifen (including isoxadifen-ethyl); I+mefenpyr (including mefenpyr-diethyl); I+metcamifen; I+N-(2-methoxybenzoyl)-4-[(methyl-aminocarbonyl)amino] benzenesulfonamide and I+oxabetrinil.

Particularly preferred are mixtures of a compound of Formula (I) with cyprosulfamide, isoxadifen (including isoxadifen-ethyl), cloquintocet (including cloquintocet-mexyl) and/or N-(2-methoxybenzoyl)-4-[(methyl-aminocarbonyl)amino]benzenesulfonamide.

The safeners of the compound of Formula (I) may also be in the form of esters or salts, as mentioned e.g. in The Pesticide Manual, 14$^{th}$ Edition (BCPC), 2006. The reference to cloquintocet-mexyl also applies to a lithium, sodium, potassium, calcium, magnesium, aluminium, iron, ammonium, quaternary ammonium, sulfonium or phosphonium salt thereof as disclosed in WO 02/34048, and the reference to fenchlorazole-ethyl also applies to fenchlorazole, etc.

Preferably the mixing ratio of compound of Formula (I) to safener is from 100:1 to 1:10, especially from 20:1 to 1:1.

The mixtures can advantageously be used in the above-mentioned formulations (in which case "active ingredient" relates to the respective mixture of compound of Formula (I) with the safener).

The compounds of Formula (I) of this invention are useful as herbicides. The present invention therefore further comprises a method for controlling unwanted plants comprising applying to the said plants or a locus comprising them, an effective amount of a compound of the invention or a herbicidal composition containing said compound. 'Controlling' means killing, reducing or retarding growth or preventing or reducing germination. Generally the plants to be controlled are unwanted plants (weeds). 'Locus' means the area in which the plants are growing or will grow.

The rates of application of compounds of Formula (I) may vary within wide limits and depend on the nature of the soil, the method of application (pre-emergence; post-emergence; application to the seed furrow; no tillage application etc.), the crop plant, the weed(s) to be controlled, the prevailing climatic conditions, and other factors governed by the method of application, the time of application and the target crop. The compounds of Formula (I) according to the invention are generally applied at a rate of from 10 to 2000 g/ha, especially from 50 to 1000 g/ha.

The application is generally made by spraying the composition, typically by tractor mounted sprayer for large areas, but other methods such as dusting (for powders), drip or drench can also be used.

Useful plants in which the composition according to the invention can be used include crops such as cereals, for example barley and wheat, cotton, oilseed rape, sunflower, maize, rice, soybeans, sugar beet, sugar cane and turf.

Crop plants can also include trees, such as fruit trees, palm trees, coconut trees or other nuts. Also included are vines such as grapes, fruit bushes, fruit plants and vegetables.

Crops are to be understood as also including those crops which have been rendered tolerant to herbicides or classes of herbicides (e.g. ALS-, GS-, EPSPS-, PPO-, ACCase- and HPPD-inhibitors) by conventional methods of breeding or by genetic engineering. An example of a crop that has been rendered tolerant to imidazolinones, e.g. imazamox, by conventional methods of breeding is Clearfield@summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

Other useful plants include turf grass for example in golf-courses, lawns, parks and roadsides, or grown commercially for sod, and ornamental plants such as flowers or bushes.

Compounds of Formula (I) and compositions of the invention can typically be used to control a wide variety of monocotyledonous and dicotyledonous weed species. Examples of monocotyledonous species that can typically be controlled include *Alopecurus myosuroides, Avena fatua, Brachiaria plantaginea, Bromus tectorum, Cyperus esculentus, Digitaria sanguinalis, Echinochloa crus-galli, Lolium perenne, Lolium multiflorum, Panicum miliaceum, Poa annua, Setaria viridis, Setaria faberi* and *Sorghum bicolor*. Examples of dicotyledonous species that can be controlled include *Abutilon theophrasti, Amaranthus retroflexus, Bidens pilosa, Chenopodium album, Euphorbia heterophylla, Galium aparine, Ipomoea hederacea, Kochia scoparia, Polygonum convolvulus, Sida spinosa, Sinapis arvensis, Solanum nigrum, Stellaria media, Veronica persica* and *Xanthium strumarium*.

Compounds/compositions of the invention are particularly useful in non-selective burn-down applications, and as such may also be used to control volunteer or escape crop plants.

Various aspects and embodiments of the present invention will now be illustrated in more detail by way of example. It will be appreciated that modification of detail may be made without departing from the scope of the invention.

EXAMPLES

The Examples which follow serve to illustrate, but do not limit, the invention.

FORMULATION EXAMPLES

| Wettable powders | a) | b) | c) |
|---|---|---|---|
| active ingredients | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Emulsifiable concentrate | |
|---|---|
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill.

| Extruder granules | |
|---|---|
| Active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
|---|---|
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

| Suspension concentrate | |
|---|---|
| active ingredients | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed.

The obtained capsule suspension is stabilized by adding 0.25 parts of a thickener and 3 parts of a dispersing agent. The capsule suspension formulation contains 28% of the active ingredients. The medium capsule diameter is 8-15 microns.

The resulting formulation is applied to seeds as an aqueous suspension in an apparatus suitable for that purpose.

List of Abbreviations

Boc=tert-butyloxycarbonyl
br=broad
CDCl$_3$=chloroform-d
CD$_3$OD=methanol-d
° C.=degrees Celsius
D$_2$O=water-d
DCM=dichloromethane
d=doublet
dd=double doublet
dt=double triplet
DMSO=dimethylsulfoxide
EtOAc=ethyl acetate
h=hour(s)
HCl=hydrochloric acid
HPLC=high-performance liquid chromatography (description of the apparatus and the methods used for HPLC are given below)
m=multiplet
M=molar
min=minutes
MHz=megahertz
mL=millilitre
mp=melting point
ppm=parts per million
q=quartet
quin=quintet
rt=room temperature
s=singlet
t=triplet
THF=tetrahydrofuran
LC/MS=Liquid Chromatography Mass Spectrometry Preparative Reverse Phase HPLC Method:

Compounds purified by mass directed preparative HPLC using ES+/ES− on a Waters FractionLynx Autopurification system comprising a 2767 injector/collector with a 2545 gradient pump, two 515 isocratic pumps, SFO, 2998 photodiode array (Wavelength range (nm): 210 to 400), 2424 ELSD and QDa mass spectrometer. A Waters Atlantis T3 5 micron 19×10 mm guard column was used with a Waters Atlantis T3 OBD, 5 micron 30×100 mm prep column.

Ionisation method: Electrospray positive and negative: Cone (V) 20.00, Source Temperature (° C.) 120, Cone Gas Flow (L/Hr.) 50

Mass range (Da): positive 100 to 800, negative 115 to 800.

The preparative HPLC was conducted using an 11.4 minute run time (not using at column dilution, bypassed with the column selector), according to the following gradient table:

| Time (mins) | Solvent A (%) | Solvent B (%) | Flow (ml/min) |
|---|---|---|---|
| 0.00 | 100 | 0 | 35 |
| 2.00 | 100 | 0 | 35 |
| 2.01 | 100 | 0 | 35 |
| 7.0 | 90 | 10 | 35 |
| 7.3 | 0 | 100 | 35 |
| 9.2 | 0 | 100 | 35 |
| 9.8 | 99 | 1 | 35 |
| 11.35 | 99 | 1 | 35 |
| 11.40 | 99 | 1 | 35 |

515 pump 0 ml/min Acetonitrile (ACD)
515 pump 1 ml/min 90% Methanol/10% Water (make up pump)
Solvent A: Water with 0.05% Trifluoroacetic Acid
Solvent B: Acetonitrile with 0.05% Trifluoroacetic Acid

PREPARATION EXAMPLES

Example 1: Preparation of 2-(4-pyrimidin-2-ylpyridazin-1-ium-1-yl)ethanesulfonate A1

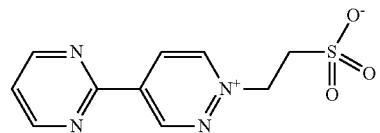 [SMILES: O=S(=O)([O-])CC[n+]1ccc(-c2ncccn2)cn1]

Step 1: Preparation of tributyl(pyridazin-4-yl)stannane

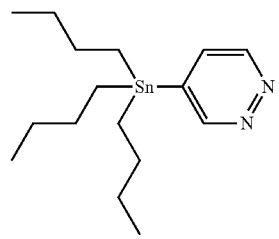 [SMILES: CCC[CH2][Sn]([CH2]CCC)([CH2]CCC)[c]1ccnnc1]

To a solution of lithium diisopropylamide (1M solution in tetrahydrofuran, 125 mL) at −78° C. under nitrogen was added a solution of pyridazine (10 g) and tri-n-butyltin chloride (44.6 g) in THF (100 mL) drop wise. The reaction mixture was stirred at −78° C. for 1 hour. The reaction mixture was warmed to room temperature and quenched with saturated aqueous ammonium chloride (100 mL) and extracted with ethyl acetate (3×150 mL). The organic layer was dried over sodium sulfate, concentrated and purified by chromatography on silica eluting with 30% ethyl acetate in hexanes to afford tributyl(pyridazin-4-yl)stannane as a pale brown liquid.

$^1$H NMR (400 MHz, CDCl$_3$) 9.17 (t, 1H) 9.02 (dd, 1H) 7.54 (dd, 1H) 1.57-1.49 (m, 6H) 1.37-1.29 (m, 6H) 1.19-1.13 (m, 6H) 0.92-0.86 (m, 9H).

Step 2: Preparation of 2-pyridazin-4-ylpyrimidine

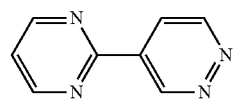 [SMILES: c1cnc(-c2ccnnc2)nc1]

A solution of 2-bromopyrimidine (2.50 g) and tributyl(pyridazin-4-yl)stannane (5.80 g) in tetrahydrofuran (25 mL) was degassed with argon for 20 min. Tetrakis (triphenylphosphine) palladium (0) (1.80 g) was added to the reaction mixture at room temperature and then irradiated in a microwave at 120° C. for 30 minutes. The reaction mixture was poured into water and extracted with ethyl acetate (100 mL). The organic layer was concentrated and purified by chromatography on silica eluting with 80% ethyl acetate in hexanes to give 2-pyridazin-4-ylpyrimidine as a beige solid.

$^1$H NMR (400 MHz, CDCl$_3$) 10.17 (dd, 1H) 9.39 (dd, 1H) 8.92 (d, 2H) 8.43 (dd, 1H) 7.39 (t, 1H).

Step 3: Preparation of 2-(4-pyrimidin-2-ylpyridazin-1-ium-1-yl)ethanesulfonate A1

A mixture of 2-pyridazin-4-ylpyrimidine (0.120 g) and sodium 2-bromoethanesulfonate (0.196 g) was stirred in water (2.3 mL) at 100° C. for 42 hours. The reaction mixture was concentrated and purified by preparative reverse phase HPLC to give 2-(4-pyrimidin-2-ylpyridazin-1-ium-1-yl)ethanesulfonate as a beige solid.

$^1$H NMR (400 MHz, D$_2$O) 10.19 (d, 1H) 9.84 (d, 1H) 9.20 (dd, 1H) 8.99 (d, 2H) 7.64 (t, 1H) 5.27-5.18 (m, 2H) 3.71-3.63 (m, 2H).

Example 2: Preparation of 4-pyridazin-4-ylpyrimidine

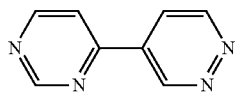 [SMILES: c1cc(-c2ccnnc2)ncn1]

A microwave vial was charged with tributyl(pyridazin-4-yl)stannane (0.387 g), 4-chloropyrimidine (0.100 g), palladium (0) tetrakis(triphenylphosphine) (0.101 g), cesium fluoride (0.265 g), cuprous iodide (0.00665 g) and 1,4-dioxane (4.37 mL) and heated to 140° C. under microwave conditions for 1 hour. The reaction mixture was concentrated and purified by chromatography on silica eluting with a gradient from 0 to 70% acetonitrile in dichloromethane to give 4-pyridazin-4-ylpyrimidine as an orange solid.

$^1$H NMR (400 MHz, CDCl$_3$) 9.90-9.83 (m, 1H) 9.41 (dd, 2H) 8.97 (d, 1H) 8.21-8.13 (m, 1H) 7.89 (dd, 1H).

Example 3: Preparation of methyl 2-(4-pyrimidin-2-ylpyridazin-1-ium-1-yl)acetate bromide A2

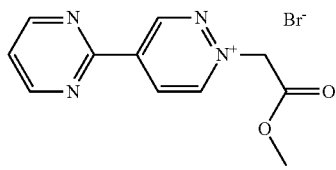 [SMILES: COC(=O)C[n+]1ccc(-c2ncccn2)cn1 ; [Br-]]

Methyl bromoacetate (0.755 g) was added drop wise to a solution of 2-pyridazin-4-ylpyrimidine (0.505 g) in acetone (6.4 mL) and heated at 60° C. for 24 hours. The reaction mixture was concentrated and the residue triturated with dichloromethane. The resulting solid was filtered, washed with acetone and dried to give methyl 2-(4-pyrimidin-2-ylpyridazin-1-ium-1-yl)acetate bromide as a brown solid.

$^1$H NMR (400 MHz, D$_2$O) 10.22 (d, 1H) 9.84 (d, 1H) 9.30 (dd, 1H) 9.01 (d, 2H) 7.66 (t, 1H) 5.84 (s, 2H) 3.79 (s, 3H).

Example 4: Preparation of (4-pyrimidin-2-ylpyridazin-1-ium-1-yl)methanesulfonate A3

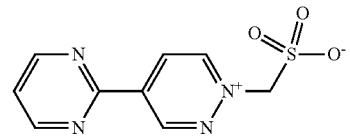 [SMILES: O=S(=O)([O-])C[n+]1ccc(-c2ncccn2)cn1]

Methyl 2-(4-pyrimidin-2-ylpyridazin-1-ium-1-yl)acetate bromide (0.420 g) was stirred in trimethylsilyl chlorosulfonate (4.96 g) at 80° C. for 66 hours. The reaction mixture was carefully quenched with water, concentrated and purified by preparative reverse phase HPLC to give (4-pyrimidin-2-ylpyridazin-1-ium-1-yl)methanesulfonate as a pale brown solid.

$^1$H NMR (400 MHz, D$_2$O) 10.26 (brs, 1H) 9.94 (brd, 1H) 9.27-9.39 (m, 1H) 8.96-9.14 (m, 2H) 7.56-7.73 (m, 1H) 5.97 (s, 2H).

Example 5: Preparation of 3-(4-pyrimidin-2-ylpyridazin-1-ium-1-yl)propane-1-sulfonate A6

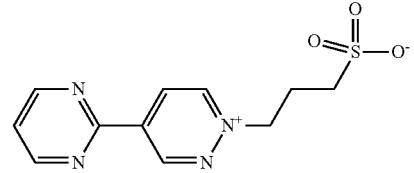 [SMILES: O=S(=O)([O-])CCC[n+]1ccc(-c2ncccn2)cn1]

To a solution of 2-pyridazin-4-ylpyrimidine (0.200 g) in 1,4-dioxane (3.79 mL) was added 1,3-propanesultone (0.189 g). The mixture was stirred at 90° C. for 44 hours. The resulting solid was filtered off and washed with acetone. The solid was purified by preparative reverse phase HPLC to give 3-(4-pyrimidin-2-ylpyridazin-1-ium-1-yl)propane-1-sulfonate.

$^1$H NMR (400 MHz, D$_2$O) 10.18 (d, 1H) 9.80 (d, 1H) 9.19 (dd, 1H) 9.00 (d, 2H) 7.64 (t, 1H) 5.01 (t, 2H) 2.98 (t, 2H) 2.53 (quin, 2H).

Example 6: Preparation of 3-(4-pyrazin-2-ylpyridazin-1-ium-1-yl)propanoic acid 2,2,2-trifluoroacetate A9

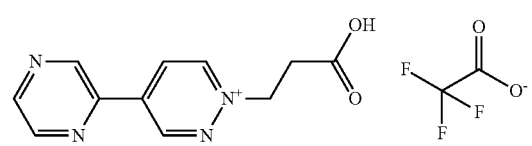 [SMILES: O=C(O)CC[n+]1ccc(-c2cnccn2)cn1 ; O=C([O-])C(F)(F)F]

Step 1: Preparation of 2-pyridazin-4-ylpyrazine

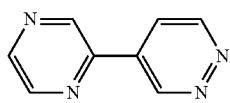 [SMILES: c1cnc(-c2ccnnc2)cn1]

A mixture of tributyl(pyridazin-4-yl)stannane (3.87 g), 2-chloropyrazine (1.00 g), palladium (0) tetrakis(triphenylphosphine) (1.03 g) and 1,4-dioxane (43.7 mL) was heated to 140° C. under microwave conditions for 1 hour. The reaction mixture was concentrated and purified on silica using a gradient of 0% to 50% acetonitrile in dichloromethane to give 2-pyridazin-4-ylpyrazine as an off white solid.

$^1$H NMR (400 MHz, CDCl$_3$) 9.87 (dd, 1H) 9.39 (dd, 1H) 9.19 (d, 1H) 8.81-8.75 (m, 1H) 8.72 (d, 1H) 8.11 (dd, 1H).

Step 2: Preparation of methyl 3-(4-pyrazin-2-ylpyridazin-1-ium-1-yl)propanoate Bromide

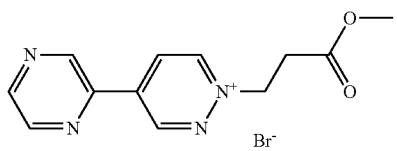

Methyl 3-bromopropanoate (0.518 mL) was added to a solution of 2-pyridazin-4-ylpyrazine (0.250 g) in acetonitrile (15.8 mL). The reaction mixture was heated to 80° C. for 24 hours. The reaction mixture was concentrated and the residue taken up in water and washed with dichloromethane. The aqueous phase was concentrated to give crude methyl 3-(4-pyrazin-2-ylpyridazin-1-ium-1-yl)propanoate bromide (as a 1:1 mixture with 3-(5-pyrazin-2-ylpyridazin-1-ium-1-yl)propanoic acid bromide) as a brown gum, which was used crude in subsequent reactions.

Step 3: Preparation of 3-(4-pyrazin-2-ylpyridazin-1-ium-1-yl)propanoic Acid 2,2,2-trifluoroacetate A9

The crude mixture of methyl 3-(4-pyrazin-2-ylpyridazin-1-ium-1-yl)propanoate bromide (0.515 g) and conc. hydrochloric acid (11.1 mL) was heated to 80° C. for 4 hours. The reaction mixture was cooled and allowed to stand overnight. The reaction mixture was concentrated and purified by preparative reverse phase HPLC to give 3-(4-pyrazin-2-ylpyridazin-1-ium-1-yl)propanoic acid 2,2,2-trifluoroacetate as a brown gum.

$^1$H NMR (400 MHz, CD$_3$OD) 10.28 (d, 1H) 10.00 (d, 1H) 9.62 (d, 1H) 9.28 (dd, 1H) 8.96-8.93 (m, 1H) 8.90 (d, 1H) 5.19-5.12 (t, 2H) 3.28 (t, 2H).

Example 7: Preparation of 2-(4-pyridazin-4-ylpyridazin-1-ium-1-yl)ethanesulfonate A11

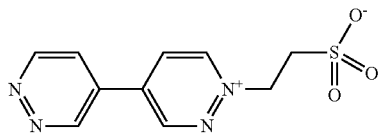 [SMILES: O=S(=O)([O-])CC[n+]1ccc(-c2ccnnc2)cn1]

Step 1: Preparation of 2,2-dimethylpropyl 2-(2-tert-butoxycarbonylhydrazino)ethanesulfonate

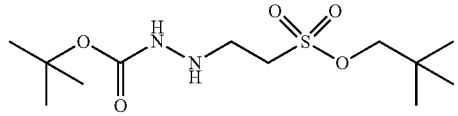 [SMILES: CC(C)(C)COS(=O)(=O)CCNNC(=O)OC(C)(C)C]

Boc-hydrazide (1.00 g) was added to a solution of 2,2-dimethylpropyl ethenesulfonate (1.35 g) in methanol (10.1 mL) and heated to 70° C. for 24 hours. The reaction was concentrated to give 2,2-dimethylpropyl 2-(2-tert-butoxycarbonylhydrazino)ethanesulfonate as a thick yellow liquid.

$^1$H NMR (400 MHz, CDCl$_3$) 3.90 (s, 2H) 3.38-3.30 (m, 4H) 1.50-1.43 (s, 9H) 1.00-0.97 (s, 9H).

Step 2: Preparation of [2-(2,2-dimethylpropoxysulfonyl)ethylamino]ammonium Chloride

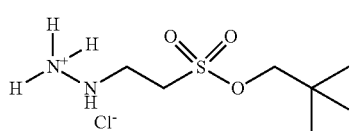

A mixture of 2,2-dimethylpropyl 2-(2-tert-butoxycarbonylhydrazino)ethanesulfonate (1.00 g) and 3M methanolic hydrogen chloride (24.2 mL) was heated to 70° C. for 7 hours. The reaction mixture was concentrated to give [2-(2,2-dimethylpropoxysulfonyl)ethylamino]ammonium chloride as a pink gum that solidified on standing.

$^1$H NMR (400 MHz, CD$_3$OD) 3.95 (s, 2H) 3.59-3.53 (m, 2H) 3.44-3.39 (m, 2H) 1.00 (s, 9H) sample contained ~20% methanol and was used as such.

Step 3: Preparation of 4-(3-furyl)pyridazine

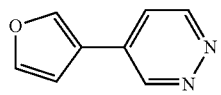

To a mixture of 4-bromopyridazin-1-ium bromide (2.50 g), sodium carbonate (2.2 g), degassed toluene (17.3 mL) and 1,1'-bis(diphenylphosphino)ferrocenepalladium (II) dichloride (0.634 g) was added a solution of 3-furylboronic acid (1.00 g) in ethanol (17.3 mL). The mixture was heated to 80° C. under nitrogen atmosphere for 24 hours. The reaction mixture was filtered through celite and concentrated. The residue was partitioned between water and dichloromethane then extracted with further dichloromethane. The combined organic layers were washed with brine and dried with magnesium sulfate. The concentrated filtrate was purified on silica eluting with a gradient of 0-100% ethyl acetate in iso-hexane to give 4-(3-furyl)pyridazine as a dark red semi-solid.

$^1$H NMR (400 MHz, CD$_3$OD) 9.45 (s, 1H) 9.03-9.16 (m, 1H) 8.36 (s, 1H) 7.86 (dd, 1H) 7.71 (t, 1H) 7.04 (d, 1H).

Step 4: Preparation of 4-(2,5-dimethoxy-2,5-dihydrofuran-3-yl)pyridazine

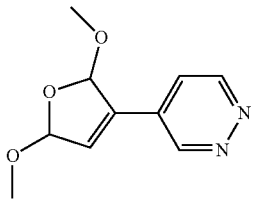

A mixture of 4-(3-furyl)pyridazine (0.025 g) and sodium bicarbonate (0.14 g) in methanol (0.5 mL) was cooled to −10° C. and bromine (0.069 g) was added drop wise. After 30 minutes the reaction was quenched with 1:1 sat. aqueous sodium bicarbonate and 1M aqueous sodium thiosulfate (3 mL). The aqueous layer was extracted with ethyl acetate. The organic layer was concentrated to give crude 4-(2,5-dimethoxy-2,5-dihydrofuran-3-yl)pyridazine.

¹H NMR (400 MHz, CD₃OD) 9.42-9.41 (m, 1H) 9.20-9.19 (m, 1H) 7.85 (dt, 1H) 7.02-6.94 (m, 1H) 6.08-5.77 (m, 2H) 3.46 (d, 3H) 3.42 (d, 3H).

Step 5: Preparation of 2-(4-pyridazin-4-ylpyridazin-1-ium-1-yl)ethanesulfonate A11

A mixture of 4-(2,5-dimethoxy-2,5-dihydrofuran-3-yl)pyridazine (0.500 g) and [2-(2,2-dimethylpropoxysulfonyl)ethylamino]ammonium chloride (0.658 g) was heated in aqueous 3M hydrochloric acid (12 mL) at 60° C. for 2 hours. The reaction mixture was concentrated and purified by preparative reverse phase HPLC to give 2-(4-pyridazin-4-ylpyridazin-1-ium-1-yl)ethanesulfonate as a brown solid.

¹H NMR (400 MHz, D₂O) 9.80-9.97 (m, 2H) 9.62-9.75 (m, 1H) 9.35-9.50 (m, 1H) 8.97 (dd, 1H) 8.19-8.42 (m, 1H) 5.20-5.29 (m 2H) 3.59-3.73 (m 2H).

Example 8: Preparation of 3-(4-pyrazin-2-ylpyridazin-1-ium-1-yl)propanoic Acid Chloride A29

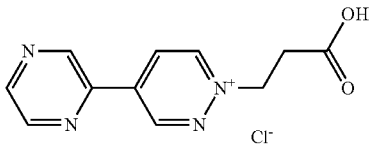 [SMILES: O=C(O)CC[n+]1ccc(-c2cnccn2)cn1 ; [Cl-]]

A column packed with ion exchange resin (5.84 g, Discovery DSC-SCX) was washed with water (3 column volumes). The 3-(4-pyrazin-2-ylpyridazin-1-ium-1-yl)propanoic acid 2,2,2-trifluoroacetate (0.292 g) dissolved in a minimum amount of water was loaded onto the column. The column was first eluted with water (3 column volumes) and then eluted with 2M hydrochloric acid (3 column volumes). The collected washings were concentrated to give 3-(4-pyrazin-2-ylpyridazin-1-ium-1-yl)propanoic acid chloride as a yellow solid.

¹H NMR (400 MHz, D₂O) 10.03 (d, 1H) 9.80 (d, 1H) 9.35 (d, 1H) 9.05 (dd, 1H) 8.87-8.82 (m, 1H) 8.76 (d, 1H) 5.08 (t, 2H) 3.22 (t, 2H).

Example 9: Preparation of Methyl 3-(4-pyrazin-2-ylpyridazin-1-ium-1-yl)propanoate Chloride A30

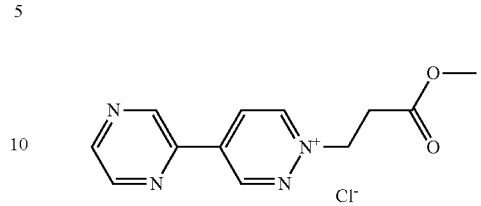

A column packed with ion exchange resin (1.6 g, Discovery DSC-SCX) was washed with methanol (3 column volumes). The 3-(4-pyrazin-2-ylpyridazin-1-ium-1-yl)propanoic acid 2,2,2-trifluoroacetate (0.081 g) dissolved in a minimum amount of methanol was loaded onto the column. The column was first eluted with methanol (3 column volumes) and then eluted with 3M methanolic hydrochloric acid (3 column volumes). The collected washings were concentrated to give methyl 3-(4-pyrazin-2-ylpyridazin-1-ium-1-yl)propanoate chloride as a blue gum.

¹H NMR (400 MHz, CD₃OD) 10.30-10.26 (m, 1H) 10.04-10.00 (m, 1H) 9.66-9.64 (m, 1H) 9.33-9.30 (m, 1H) 8.97-8.93 (m, 1H) 8.91-8.88 (m, 1H) 5.25-5.14 (m, 2H) 3.71-3.68 (m, 3H) 3.35-3.27 (m, 2H).

Example 10: Preparation of Isopropyl 3-(4-pyrimidin-2-ylpyridazin-1-ium-1-yl)propanoate 2,2,2-trifluoroacetate A81

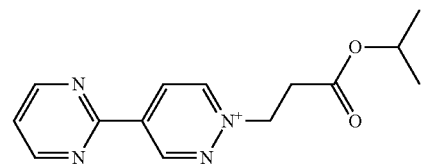

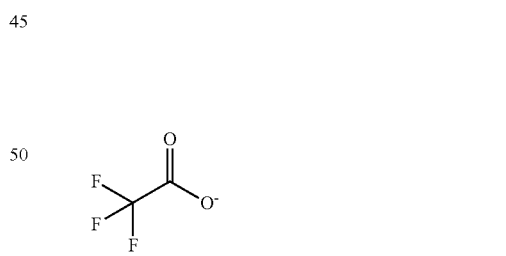

Sodium iodide (0.24 g) and isopropyl 3-chloropropanoate (0.357 g) were added to a solution of 2-pyridazin-4-ylpyrimidine (0.25 g) in acetonitrile (6 mL) and heated at 80° C. for 25 hours. The reaction mixture was concentrated and purified by preparative reverse phase HPLC to give isopropyl 3-(4-pyrimidin-2-ylpyridazin-1-ium-1-yl)propanoate 2,2,2-trifluoroacetate as a brown gum.

¹H NMR (400 MHz, CD₃OD) 10.29-10.43 (m, 1H) 10.02 (d, 1H) 9.36-9.49 (m, 1H) 9.04-9.18 (m, 2H) 7.63-7.76 (m, 1H) 5.10-5.24 (m, 2H) 4.92-5.04 (m, 1H) 3.14-3.41 (m, 2H) 1.12-1.25 (m, 6H).

Example 11: Preparation of 3-(4-pyrimidin-2-ylpyridazin-1-ium-1-yl)propanoic Acid Bromide A107

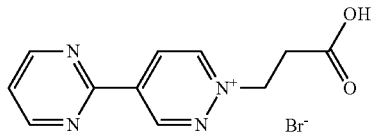 [SMILES: O=C(O)CC[n+]1ccc(-c2ncccn2)cn1 ; [Br-]]

A mixture of methyl 3-(4-pyrimidin-2-ylpyridazin-1-ium-1-yl)propanoate 2,2,2-trifluoroacetate (0.2 g), concentrated hydrogen bromide (1 mL, 48 mass %) and water (5 mL) was heated to 80° C. for 4 hours and left to cool overnight. After a further 4 hours heating at 80° C. the reaction mixture was concentrated and the resulting yellow gum was triturated with acetone to give 3-(4-pyrimidin-2-ylpyridazin-1-ium-1-yl)propanoic acid bromide as a cream solid.

$^1$H NMR (400 MHz, D$_2$O) 10.16 (d, 1H) 9.86 (d, 1H) 9.21-9.15 (m, 1H) 8.99 (d, 2H) 7.64 (t, 1H) 5.11 (t, 2H) 3.24 (t, 2H).

Example 12: Preparation of 1-(4-pyrimidin-2-ylpyridazin-1-ium-1-yl)propane-2-sulfonate A134

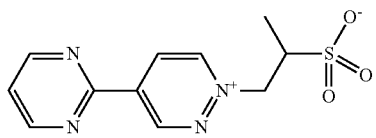 [SMILES: CC(C[n+]1ccc(-c2ncccn2)cn1)S(=O)(=O)[O-]]

Step 1: Preparation of Methyl 2-(2,2-dimethylpropoxysulfonyl)acetate

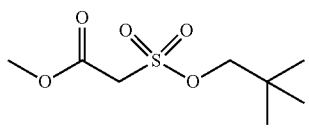

Methyl 2-chlorosulfonylacetate (0.5 g) was added dropwise to a cooled (ice bath) solution of 2,2-dimethylpropan-1-ol (0.306 g) and pyridine (0.284 mL) in dichloromethane (14.5 mL). The reaction mixture was stirred cold for a further 2 hours then partitioned with aqueous sat. ammonium chloride. The aqueous phase was extracted with further dichloromethane (×2). The combined organic extracts were concentrated and passed through a plug of silica eluting with diethyl ether. The filtrate was concentrated to give methyl 2-(2,2-dimethylpropoxysulfonyl)acetate as a yellow liquid.

$^1$H NMR (400 MHz, CDCl$_3$) 4.11 (s, 2H) 4.00 (s, 2H) 3.84 (s, 3H) 1.01 (s, 9H).

Step 2: Preparation of Methyl 2-(2,2-dimethylpropoxysulfonyl)propanoate

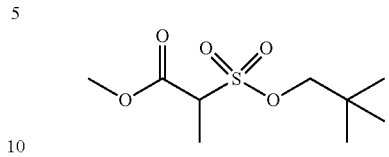

A mixture of sodium hydride (60% in mineral oil, 0.039 g) in tetrahydrofuran (4.46 mL) was cooled (ice bath) to 0° C. under nitrogen atmosphere. To this was added a solution of methyl 2-(2,2-dimethylpropoxysulfonyl)acetate (0.2 g) in tetrahydrofuran (1.78 mL) and stirred at this temperature for 5 minutes. Iodomethane (0.067 mL) was added and the reaction was allowed to warm to room temperature and stirred for 1 hour. The reaction mixture was partitioned between 2M hydrochloric acid and ethyl acetate. The aqueous layer was extracted with further ethyl acetate (×2). The combined organic extracts were dried with magnesium sulfate and concentrated to give methyl 2-(2,2-dimethylpropoxysulfonyl)propanoate as a yellow liquid.

$^1$H NMR (400 MHz, CDCl$_3$) 4.12-4.09 (m, 1H) 3.97 (d, 2H) 3.83 (s, 3H) 1.69 (d, 3H) 0.99 (s, 9H).

Step 3: Preparation of 2,2-dimethylpropyl 1-hydroxypropane-2-sulfonate

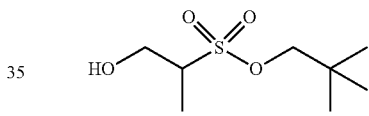

To a cooled (ice bath) solution of methyl 2-(2,2-dimethylpropoxysulfonyl)propanoate (1 g) in dichloromethane (126 mL) was added dropwise, under nitrogen atmosphere, diisobutylaluminum hydride (1M in dichloromethane, 10.5 mL) maintaining the temperature below 5° C. during the addition. The reaction mixture was stirred at 0° C. for 1 hour. Propan-2-ol (12.6 mL) was added and the reaction mixture was stirred at 0° C. for 1 hour and then allowed to warm to room temperature. The reaction mixture was partitioned between 2M aqueous hydrochloric acid and dichloromethane. The organic phase was dried with magnesium sulfate, concentrated and chromatographed on silica using a gradient from 0 to 100% EtOAc in isohexane to give 2,2-dimethylpropyl 1-hydroxypropane-2-sulfonate as a colourless liquid.

$^1$H NMR (400 MHz, CDCl$_3$) 4.03-3.84 (m, 4H) 3.43-3.33 (m, 1H) 2.60-2.52 (m, 1H) 1.45 (d, 3H) 1.00 (s, 9H).

Step 4: Preparation of 1-hydroxypropane-2-sulfonic Acid

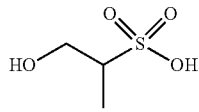

A mixture of 2,2-dimethylpropyl 1-hydroxypropane-2-sulfonate (0.25 g) and 6M aqueous hydrochloric acid (9.51 mL) was heated to 95° C. for 4 hours. The reaction mixture was cooled and concentrated by freeze drying.

$^1$H NMR (400 MHz, D$_2$O) 3.88-3.78 (m, 1H) 3.56-3.47 (m, 1H) 2.98-2.89 (m, 1H) 1.18 (d, 3H).

Step 5: Preparation of 1-(4-pyrimidin-2-ylpyridazin-1-ium-1-yl)propane-2-sulfonate A134

To a cooled (ice bath) solution of 2-pyridazin-4-ylpyrimidine (0.1 g) in dry acetonitrile (6.32 mL) was added 1,1,1-trifluoro-N-(trifluoromethylsulfonyl)methanesulfonamide (0.131 mL) and the reaction mixture was stirred at room temperature for 15 minutes. To this mixture was added triphenylphosphine (0.332 g) and a solution of 1-hydroxypropane-2-sulfonic acid (0.133 g) in acetonitrile (0.5 mL), followed by drop wise addition of diisopropyl azodicarboxylate (0.25 mL). The reaction mixture was heated at 80° C. for 170 hours. The reaction mixture was concentrated and partitioned between water and diethyl ether. The aqueous layer was concentrated and purified by preparative reverse phase HPLC to give 1-(4-pyrimidin-2-ylpyridazin-1-ium-1-yl)propane-2-sulfonate as a white solid.

$^1$H NMR (400 MHz, D$_2$O) 10.20-10.18 (m, 1H) 9.81 (dd, 1H) 9.19 (dd, 1H) 9.00 (d, 2H) 7.65 (t, 1H) 5.10-5.07 (m, 2H) 3.84-3.74 (m, 1H) 1.39 (d, 3H).

Example 13: Preparation of 3-(4-pyrimidin-2-ylpyridazin-1-ium-1-yl)butanoic acid 2,2,2-trifluoroacetate A40

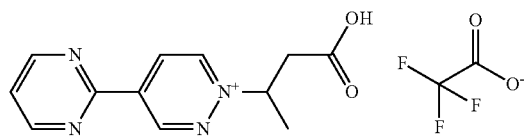 [SMILES: CC(CC(=O)O)[n+]1ccc(-c2ncccn2)cn1 ; O=C([O-])C(F)(F)F]

To a mixture of 2-pyridazin-4-ylpyrimidine (0.5 g) in water (10 mL) was added but-2-enoic acid (0.816 g). The mixture was heated at reflux for 40 hours. The reaction mixture was concentrated and the resulting solid was triturated with tert-butylmethylether and acetone. The solid was purified by preparative reverse phase HPLC to give 3-(4-pyrimidin-2-ylpyridazin-1-ium-1-yl)butanoic acid 2,2,2-trifluoroacetate.

$^1$H NMR (400 MHz, D$_2$O) 10.22 (d, 1H) 9.92 (d, 1H) 9.18-9.26 (m, 1H) 8.99-9.05 (m, 2H) 7.68 (t, 1H) 5.49-5.60 (m, 1H) 3.39 (dd, 1H) 3.10-3.21 (m, 1H) 1.71 (d, 3H).

Example 14: Preparation of 2-(3-methyl-4-pyrimidin-2-yl-pyridazin-1-ium-1-yl)ethanesulfonate

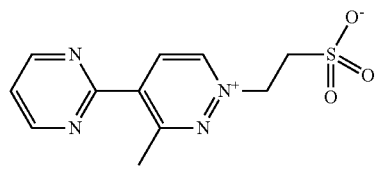 [SMILES: Cc1n[n+](CCS(=O)(=O)[O-])ccc1-c1ncccn1]

Step 1: Preparation of tributyl-(3-chloro-6-methoxypyridazin-4-yl)stannane

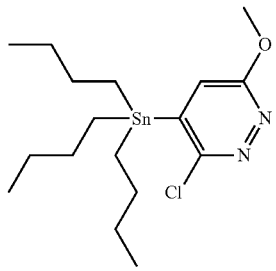 [SMILES: CCC[CH2][Sn]([CH2]CCC)([CH2]CCC)[c]1cc(OC)nnc1Cl]

A solution of lithium diisopropylamide (1M in tetrahydrofuran, 1.7 mL) was cooled to −78° C. To this was added a solution of 3-chloro-6-methoxy-pyridazine (0.2 g) in tetrahydrofuran (2 mL) whilst maintaining the temperature below −70° C. The resulting mixture was stirred at −78° C. for 40 minutes. To this was slowly added tri-n-butyltin chloride (0.47 mL) at −78° C. over a period of 10 minutes, then stirring was continued at −78° C. for 2 hours. The reaction mixture was quenched with water (10 mL) and extracted with ethyl acetate (50 mL). The aqueous layer was extracted with further ethyl acetate (50 mL). The combined organic layers were dried over sodium sulphate, concentrated and chromatographed on silica using a gradient from 0 to 100% ethyl acetate in isohexane to give crude tributyl-(3-chloro-6-methoxy-pyridazin-4-yl)stannane (HPLC retention time 2.07 min) in a 2:1 ratio with the isomer tributyl-(6-chloro-3-methoxy-pyridazin-4-yl)stannane (HPLC retention time 1.79 min).

Step 2: Preparation of 3-chloro-6-methoxy-4-pyrimidin-2-yl-pyridazine

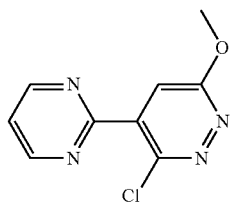

A solution of the crude tributyl-(3-chloro-6-methoxy-pyridazin-4-yl)stannane (15.2 g) in 1,4-dioxane (304 mL) was degassed with nitrogen for 20 minutes. To this was added cuprous iodide (1.02 g), tris(dibenzylideneacetone)dipalladium(0) (1.65 g) and triphenylphosphine (0.763 g) and again degassed for 20 minutes. After the addition of 2-bromopyrimidine (6.13 g) the reaction mixture was heated at reflux for 18 hours. The reaction mixture was cooled, concentrated and chromatographed on silica using a gradient from 0 to 100% ethyl acetate in isohexane to give a mixture of isomers 3-chloro-6-methoxy-4-pyrimidin-2-yl-pyridazine and 6-chloro-3-methoxy-4-pyrimidin-2-yl-pyridazine, as an off-white solid, which was used crude in the next step.

Step 3: Preparation of 6-methoxy-3-methyl-4-pyrimidin-2-yl-pyridazine

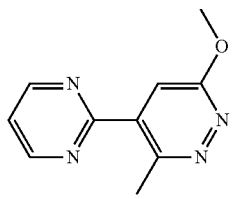

To a solution of crude 3-chloro-6-methoxy-4-pyrimidin-2-yl-pyridazine (1.5 g) in 1,4-dioxane (45 mL), under a nitrogen atmosphere, was added methylboronic acid (1.2 g) and [1,1'-bis(diphenylphosphino)ferrocene]dichloropalladium(II) (0.49 g). The mixture was degassed with nitrogen for 15 minutes then heated to 100° C. Cesium carbonate (4.4 g) was added over 5 minutes and the mixture heated at 100° C. for 3 hours. The reaction mixture was cooled, concentrated and chromatographed on silica using a gradient from 0 to 100% ethyl acetate in isohexane to give 6-methoxy-3-methyl-4-pyrimidin-2-yl-pyridazine.

$^1$H NMR (400 MHz, CDCl$_3$) 8.91 (d, 1H) 8.82-8.99 (m, 1H) 7.52 (s, 1H) 7.37 (t, 1H) 4.17 (s, 3H) 2.88 (s, 3H).

Step 4: Preparation of 6-methyl-5-pyrimidin-2-yl-pyridazin-3-ol

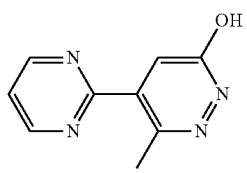

A mixture of 6-methoxy-3-methyl-4-pyrimidin-2-yl-pyridazine (0.5 g) in concentrated hydrogen bromide (10 mL, 48 mass %) was heated at 80° C. for 16 hours. The reaction mixture was cooled, concentrated and azeotroped with toluene (2×30 mL) to give crude 6-methyl-5-pyrimidin-2-yl-pyridazin-3-ol which was used in the next step without further purification.

Step 5: Preparation of 6-chloro-3-methyl-4-pyrimidin-2-yl-pyridazine

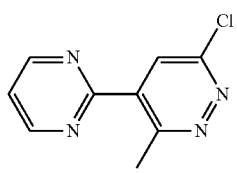

A mixture of 6-methyl-5-pyrimidin-2-yl-pyridazin-3-ol (0.025 g) in phosphorus oxychloride (0.25 mL) was heated at 80° C. for 3 hours. The reaction mixture was concentrated and the residue was diluted with ice cold water (2 mL) and neutralised with sodium bicarbonate solution. The aqueous was extracted with ethyl acetate (2×15 mL). The combined organic layers were dried over sodium sulphate and concentrated to give 6-chloro-3-methyl-4-pyrimidin-2-yl-pyridazine, which was used in the next step without further purification.

$^1$H NMR (400 MHz, CDCl$_3$) 8.94 (d, 2H) 8.13 (s, 1H) 7.41 (t, 1H) 3.03 (s, 3H).

Step 6: Preparation of 3-methyl-4-pyrimidin-2-yl-pyridazine

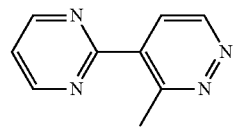

To a solution of 6-chloro-3-methyl-4-pyrimidin-2-yl-pyridazine (0.37 g) in ethanol (15 mL) was added triethylamine (0.24 g) and 10% palladium on carbon (0.035 g). The mixture was hydrogenated under balloon pressure for 1 hour. The reaction mixture was diluted with ethanol (10 mL) and filtered through celite, washing through with further ethanol (2×20 mL). The filtrate was concentrated and chromatographed on silica using a gradient from 0 to 100% ethyl acetate in isohexane to give 3-methyl-4-pyrimidin-2-yl-pyridazine as a white solid.

$^1$H NMR (400 MHz, CDCl$_3$) 9.25 (d, 1H) 8.93 (d, 2H) 8.02 (d, 1H) 7.38 (t, 1H) 3.04 (s, 3H).

Step 7: Preparation of 2-(3-methyl-4-pyrimidin-2-yl-pyridazin-1-ium-1-yl)ethanesulfonate A88

A mixture of 3-methyl-4-pyrimidin-2-yl-pyridazine (0.125 g) and sodium 2-bromoethanesulfonate (0.153 g) in water (2.5 mL) was heated at reflux for 18 hours. The reaction mixture was concentrated and purified by preparative reverse phase HPLC to give 2-(3-methyl-4-pyrimidin-2-yl-pyridazin-1-ium-1-yl)ethanesulfonate, A88.

$^1$H NMR (400 MHz, D$_2$O) 9.76 (d, 1H) 9.69-9.88 (m, 1H) 9.02 (d, 1H) 8.77 (d, 1H) 7.69 (t, 1H) 5.21 (t, 2H) 3.71 (t, 2H) 2.94 (s, 3H).

Example 15: Preparation of 3-bromo-N-methylsulfonyl-propanamide

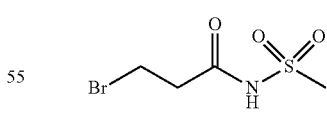

To a solution of methanesulfonamide (0.5 g) in toluene (25.8 mL) was added 3-bromopropionyl chloride (1.77 g) drop wise at room temperature. The reaction mixture was heated at 110° C. for 4 hours. The reaction was cooled in ice and the resulting solid was filtered and washed with cold toluene to give 3-bromo-N-methylsulfonyl-propanamide as a colourless solid.

$^1$H NMR (400 MHz, CDCl$_3$) 8.28 (br s, 1H) 3.62 (t, 2H) 3.34 (s, 3H) 2.94 (t, 2H).

Example 16: Preparation of 2-hydroxy-3-(4-pyrimidin-2-ylpyridazin-1-ium-1-yl)propane-1-sulfonate A143

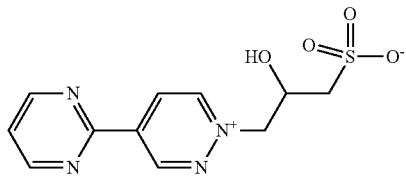 [SMILES: O=S(=O)([O-])CC(O)C[n+]1ccc(-c2ncccn2)cn1]

A mixture of 2-pyridazin-4-ylpyrimidine (0.3 g), water (6 mL) and sodium 3-chloro-2-hydroxy-propane-1-sulfonate (0.45 g) was heated at reflux for 3 days. The reaction mixture was concentrated and the resulting solid was washed with t-butylmethyl ether and acetone. The solid was purified by preparative reverse phase HPLC to give 2-hydroxy-3-(4-pyrimidin-2-ylpyridazin-1-ium-1-yl)propane-1-sulfonate, A143.

$^1$H NMR (400 MHz, D$_2$O) 10.24 (d, 1H) 9.80 (d, 1H) 9.25 (dd, 1H) 9.04 (d, 2H) 7.68 (t, 1H) 5.21 (dd, 1H) 4.93 (dd, 1H) 4.64-4.71 (m, 1H) 3.19-3.36 (m 2H).

Example 17: Preparation of 3-(4-pyrimidin-2-ylpyridazin-1-ium-1-yl)propanoic Acid 2,2,2-trifluoroacetate A125

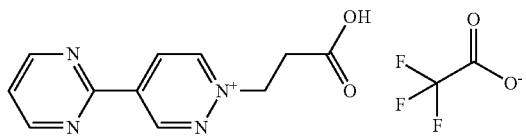 [SMILES: O=C(O)CC[n+]1ccc(-c2ncccn2)cn1 ; O=C([O-])C(F)(F)F]

3-(4-pyrimidin-2-ylpyridazin-1-ium-1-yl)propanoic acid chloride (0.119 g) was stirred in 2,2,2-trifluoroacetic acid (4 mL) at room temperature for two hours. The reaction mixture was concentrated and freeze dried to give 3-(4-pyrimidin-2-ylpyridazin-1-ium-1-yl)propanoic acid 2,2,2-trifluoroacetate, A125, as a pale yellow gum, which solidified on standing.

$^1$H NMR (400 MHz, D$_2$O) 10.18-10.13 (m, 1H) 9.87-9.82 (m, 1H) 9.20-9.14 (m, 1H) 8.98 (d, 2H) 7.63 (s, 1H) 5.10 (s, 2H) 3.24 (t, 2H).

Example 18: Preparation of 3-methyl-3-(4-pyrimidin-2-ylpyridazin-1-ium-1-yl)butanoic Acid 2,2,2-trifluoroacetate A131

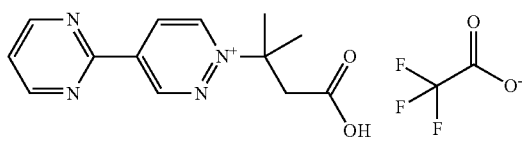 [SMILES: CC(C)(CC(=O)O)[n+]1ccc(-c2ncccn2)cn1 ; O=C([O-])C(F)(F)F]

A mixture of 2-pyridazin-4-ylpyrimidine (1 g), 3,3-dimethylacrylic acid (1.96 g), 2,2,2-trifluoroacetic acid (5 mL) and water (5 mL) was heated at 100° C. under microwave conditions for 18 hours. The reaction mixture was concentrated and the resulting solid was washed with diethyl ether (5×10 mL). The solid was purified by preparative reverse phase HPLC to give 3-methyl-3-(4-pyrimidin-2-ylpyridazin-1-ium-1-yl)butanoic acid 2,2,2-trifluoroacetate, A131.

$^1$H NMR (400 MHz, D$_2$O) 10.18 (m, 1H) 9.97 (m, 1H) 9.21 (m, 1H) 8.98 (m, 2H) 7.61 (m, 1H) 3.36 (s, 2H) 1.94 (s, 6H).

Example 19: Preparation of 5-methylsulfonyl-2-pyridazin-4-yl-pyrimidine

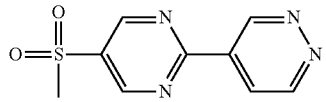 [SMILES: CS(=O)(=O)c1cnc(-c2ccnnc2)nc1]

Step 1: Preparation of 5-chloro-2-pyridazin-4-yl-pyrimidine

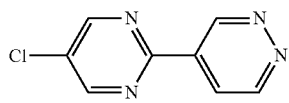

A solution of 2,5-dichloropyrimidine (6 g) in 1,4-dioxane (60 mL) was degassed with nitrogen for 20 minutes. To this was added tributyl(pyridazin-4-yl)stannane (14.87 g), tetrakis(triphenylphosphine)palladium(0) (4.66 g) and the mixture heated at 110° C. for 18 hours. The reaction mixture was poured into water and extracted with ethyl acetate (3×100 mL). The organic layers were concentrated and chromatographed on silica eluting with 75% ethyl acetate in hexanes to give 5-chloro-2-pyridazin-4-yl-pyrimidine as a pinkish solid.

$^1$H NMR (400 MHz, CDCl$_3$) 10.12 (dd, 1H) 9.38 (dd, 1H) 8.86 (s, 2H) 8.38 (dd, 1H)

Step 2: Preparation of 5-methylsulfonyl-2-pyridazin-4-yl-pyrimidine

To a solution of 5-chloro-2-pyridazin-4-yl-pyrimidine (0.8 g) in N,N-dimethylformamide (8 mL) was added sodium methanesulfinate (1 g) and the mixture heated at 100° C. for 18 hours. The reaction mixture was cooled to room temperature and poured into ice cold water (50 mL). The resulting solid was filtered and dried to give 5-methylsulfonyl-2-pyridazin-4-yl-pyrimidine as a white solid.

$^1$H NMR (400 MHz, de-DMSO) 10.01-10.10 (m, 1H) 9.45-9.60 (m, 3H) 8.46-8.55 (m, 1H), 3.48 (s, 3H).

Example 20: Preparation of N,N-dimethyl-2-pyridazin-4-yl-pyrimidin-5-amine

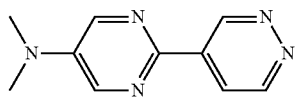

To a mixture of 5-chloro-2-pyridazin-4-yl-pyrimidine (0.035 g) in dimethylamine (40 mass % in water, 1 mL) in a microwave vial was added N,N-diisopropylethylamine (0.16 mL). The mixture was heated under microwave conditions at 150° C. for 6 hours. The reaction mixture was partitioned between ethyl acetate (30 mL) and water (15 mL). The aqueous layer was extracted with further ethyl acetate (30 mL). The organic layers were dried over sodium sulfate and concentrated to give N,N-dimethyl-2-pyridazin-4-yl-pyrimidin-5-amine as a yellow solid.

¹H NMR (400 MHz, CDCl₃) 10.05 (s, 1H) 9.24 (d, 1H) 8.30 (s, 2H) 8.25 (dd, 1H) 3.12 (s, 6H).

Example 21: Preparation of 2-pyridazin-4-ylpyrimidine-5-carbonitrile

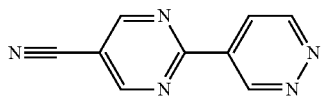

A mixture of 5-chloro-2-pyridazin-4-yl-pyrimidine (2 g), zinc cyanide (0.75 g), zinc (0.068 g), tris(dibenzylideneacetone)dipalladium(0) (0.98 g) and dicyclohexyl-[2-(2,4,6-triisopropylphenyl)phenyl]phosphane (0.99 g) in N,N-dimethylacetamide (16 mL) was heated at 120° C. under nitrogen atmosphere for 12 hours. After cooling, the reaction was partitioned between water and ethyl acetate. The organic layer was dried over sodium sulfate, concentrated and chromatographed on silica eluting with 20-100% ethyl acetate in hexanes to give 2-pyridazin-4-ylpyrimidine-5-carbonitrile as a yellow solid.

¹H NMR (400 MHz, CDCl₃) 10.19-10.20 (m, 1H) 9.50 (d, 1H) 9.19 (s, 2H) 8.47-8.49 (m, 1H).

Example 22: Preparation of 5-cyclopropyl-2-pyridazin-4-yl-pyrimidine

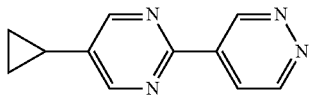 [SMILES: c1cc(-c2ncc(C3CC3)cn2)cnn1]

A mixture of 5-chloro-2-pyridazin-4-yl-pyrimidine (0.05 g), tricyclohexylphosphane (0.007 g), cyclopropylboronic acid (0.045 g), tris(dibenzylideneacetone)dipalladium(0) (0.024 g) and potassium phosphate (0.07 g) in dioxane (0.5 mL) was heated at 120° C. under nitrogen atmosphere for 4 hours. The reaction was concentrated and chromatographed on silica eluting with 60% ethyl acetate in cyclohexane to give 5-cyclopropyl-2-pyridazin-4-yl-pyrimidine as a yellow solid.

¹H NMR (400 MHz, CDCl₃) 10.00-10.21 (m, 1H) 9.27-9.40 (m, 1H) 8.54-8.67 (m, 2H) 8.35-8.46 (m, 1H) 2.14-2.22 (m, 1H) 1.18-1.24 (m, 2H) 0.87-0.93 (m, 2H).

Example 23: Preparation of 1-(2-pyridazin-4-ylpyrimidin-5-yl)ethanone

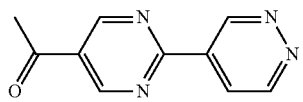

Step 1: Preparation of 5-(1-ethoxyvinyl)-2-pyridazin-4-yl-pyrimidine

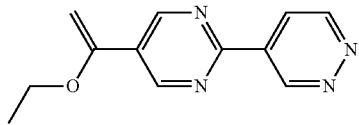

A mixture of 5-chloro-2-pyridazin-4-yl-pyrimidine (1 g), tributyl(1-ethoxyvinyl)stannane (2.062 g), palladium(II)bis(triphenylphosphine) dichloride (0.368 g) in N,N-dimethylformamide (10 mL) was heated at 70° C. for 16 hours. After cooling the reaction was partitioned between water and ethyl acetate. The organic layer was dried over sodium sulfate, concentrated and chromatographed on silica eluting with 20-100% ethyl acetate in hexanes to give 5-(1-ethoxyvinyl)-2-pyridazin-4-yl-pyrimidine as a yellow solid.

¹H NMR (400 MHz, CDCl₃) 10.17 (s, 1H) 9.36-9.47 (m, 1H) 9.09 (s, 2H) 8.87 (s, 1H) 4.83-4.88 (m, 1H) 4.46-4.49 (m, 1H) 3.97-4.04 (m, 2H) 1.45-1.51 (m, 3H).

Step 2: Preparation of 1-(2-pyridazin-4-ylpyrimidin-5-yl)ethanone

A solution of 5-(1-ethoxyvinyl)-2-pyridazin-4-yl-pyrimidine (0.4 g), acetone (4 mL) and 2M aqueous hydrochloric acid (0.88 mL) was heated at 65° C. for 18 hours. After cooling the reaction was partitioned between water and ethyl acetate. The organic layer was washed further with water and brine. The organic layer was dried over sodium sulfate, concentrated and chromatographed on silica eluting with 20-100% ethyl acetate in hexanes to give 1-(2-pyridazin-4-ylpyrimidin-5-yl)ethanone.

¹H NMR (400 MHz, CDCl₃) 10.15 (s, 1H) 9.41 (d, 1H) 8.88 (s, 2H) 8.42-8.44 (m, 1H) 2.10 (s, 3H).

Example 24: Preparation of N,N-dimethyl-2-pyridazin-4-yl-pyrimidine-5-carboxamide

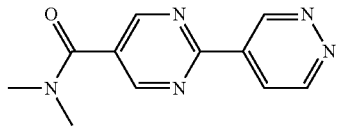 [SMILES: CN(C)C(=O)c1cnc(-c2ccnnc2)nc1]

Step 1: Preparation of methyl 2-pyridazin-4-ylpyrimidine-5-carboxylate

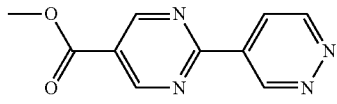 [SMILES: COC(=O)c1cnc(-c2ccnnc2)nc1]

To a solution of 2-pyridazin-4-ylpyrimidine-5-carbonitrile (0.52 g) in methanol (5.2 mL) was added a solution of potassium hydroxide (0.023 g) in water (5.2 mL) at 0° C. After stirring at 0° C. for 90 minutes the reaction mixture was acidified with acetic acid to pH 3. The reaction mixture was concentrated and partitioned between water and ethyl acetate. The aqueous layer was extracted with further ethyl acetate (2×200 mL). The combined organic layers were dried over sodium sulfate and concentrated to give methyl 2-pyridazin-4-ylpyrimidine-5-carboxylate as a brown solid.

¹H NMR (400 MHz, CDCl₃) 10.22 (s, 1H) 9.41-9.46 (m, 3H) 8.50 (dd, 1H) 4.05 (s, 3H).

Step 2: Preparation of N,N-dimethyl-2-pyridazin-4-yl-pyrimidine-5-carboxamide

A mixture of methyl 2-pyridazin-4-ylpyrimidine-5-carboxylate (0.02 g) and N-methylmethanamine (2 mL) in a sealed vial was heated at 85° C. for 2 hours. The reaction mixture was concentrated to give N,N-dimethyl-2-pyridazin-4-yl-pyrimidine-5-carboxamide as a white solid.

¹H NMR (400 MHz, D₂O) 9.82-9.88 (m, 1H) 9.28-9.32 (m, 1H) 8.98 (s, 2H) 8.42-8.44 (m, 1H) 2.98-3.02 (m, 6H).

Example 25: Preparation of N-methyl-2-pyridazin-4-yl-pyrimidine-5-carboxamide

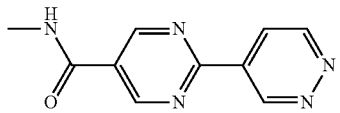

A mixture of methyl 2-pyridazin-4-ylpyrimidine-5-carboxylate (0.02 g) and methylamine in methanol (2M solution, 0.2 mL) in a sealed vial was heated at 100° C. for 2 hours. The reaction mixture was concentrated to give N-methyl-2-pyridazin-4-yl-pyrimidine-5-carboxamide as a brown solid.

¹H NMR (400 MHz, CD₃OD) 10.05-10.20 (m, 1H) 9.40-9.45 (m, 1H) 9.27-9.39 (m, 2H) 8.66 (dd, 1H) 2.99 (s, 3H).

Example 26: Preparation of (2-pyridazin-4-ylpyrimidin-4-yl)methanol

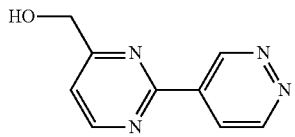 [SMILES: OCc1ccnc(-c2ccnnc2)n1]

Step 1: Preparation of 2-pyridazin-4-ylpyrimidine-4-carbonitrile

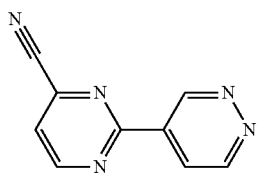 [SMILES: N#Cc1ccnc(-c2ccnnc2)n1]

A solution of 2-chloropyrimidine-4-carbonitrile (4.89 g) in tetrahydrofuran (50 mL) was degassed with nitrogen for 30 minutes. To this was added tributyl(pyridazin-4-yl)stannane (12.9 g) and tetrakis(triphenylphosphine)palladium(0) (4.06 g) and the reaction mixture was heated at 110° C. for 12 hours. After cooling the reaction was partitioned between water and ethyl acetate and extracted with further ethyl acetate (2×200 mL). The combined organic layers were dried over sodium sulfate, concentrated and chromatographed on silica eluting with 20-100% ethyl acetate in hexanes to give 2-pyridazin-4-ylpyrimidine-4-carbonitrile as a brown solid.

¹H NMR (400 MHz, CDCl₃) 10.17 (dd, 1H) 9.46 (dd, 1H) 9.09-9.20 (m, 1H) 8.36-8.53 (m, 1H) 7.72 (d, 1H).

Step 2: Preparation of Methyl 2-pyridazin-4-ylpyrimidine-4-carboxylate

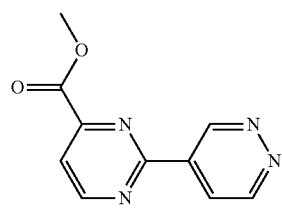 [SMILES: COC(=O)c1ccnc(-c2ccnnc2)n1]

To a solution of 2-pyridazin-4-ylpyrimidine-4-carbonitrile (2.7 g) in methanol (27 mL) was added a solution of potassium hydroxide (0.55 g) in water (27 mL) at 0° C. After stirring at 0° C. for 90 minutes the reaction mixture was acidified with acetic acid to pH 3. The reaction mixture was concentrated and partitioned between water and ethyl acetate. The aqueous layer was extracted with further ethyl acetate (2×200 mL). The combined organic layers were dried over sodium sulfate and concentrated to give methyl 2-pyridazin-4-ylpyrimidine-4-carboxylate as a brown solid.

¹H NMR (400 MHz, CDCl₃) 10.24 (s, 1H) 9.44 (dd, 1H) 9.17 (d, 1H) 8.53 (dd, 1H) 8.06 (d, 1H) 4.11 (s, 3H).

Step 3: Preparation of (2-pyridazin-4-ylpyrimidin-4-yl)methanol

To a solution of methyl 2-pyridazin-4-ylpyrimidine-4-carboxylate (0.05 g) in methanol (0.5 mL) under a nitrogen atmosphere was added sodium borohydride (0.018 g) slowly, keeping the reaction temperature below 20° C. The mixture was stirred for 16 hours at room temperature. The reaction mixture was quenched with water and extracted with ethyl acetate (3×30 mL). The aqueous layer was further extracted with 10% isopropanol in chloroform (100 mL). The combined organic layers were dried over sodium sulfate, concentrated and chromatographed on silica eluting with 20-100% ethyl acetate in hexanes to give (2-pyridazin-4-ylpyrimidin-4-yl)methanol as a yellow solid.

¹H NMR (400 MHz, d₆-DMSO) 10.00 (s, 1H) 9.45 (d, 1H) 9.02 (d, 1H) 8.40-8.44 (m, 1H) 7.68 (d, 1H) 4.70 (d, 2H).

Example 27: Preparation of 2-methyl-1-(4-pyrimidin-2-ylpyridazin-1-ium-1-yl)propane-2-sulfonate A114

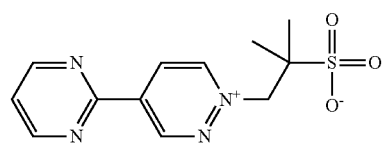 [SMILES: CC(C)(C[n+]1ccc(-c2ncccn2)cn1)S(=O)(=O)[O-]]

Step 1: Preparation of Methyl 2-(2,2-dimethyl-propoxysulfonyl)-2-methyl-propanoate

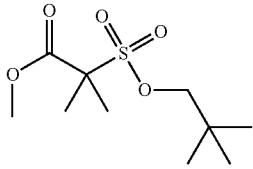 [SMILES: COC(=O)C(C)(C)S(=O)(=O)OCC(C)(C)C]

To sodium hydride (60% in mineral oil, 0.392 g), under a nitrogen atmosphere and cooled in an ice bath, was added tetrahydrofuran (22.3 mL) followed by a solution of methyl 2-(2,2-dimethylpropoxysulfonyl)acetate (1 g) in tetrahydrofuran (8.92 mL). The reaction mixture was stirred at this temperature for 5 minutes and then iodomethane (0.694 mL) was added. The ice bath was removed and the reaction mixture was stirred at room temperature for 1 hour. The reaction mixture was quenched with water and extracted with ethyl acetate (×3). The combined organic layers were dried over sodium sulfate and concentrated to give methyl 2-(2,2-dimethylpropoxysulfonyl)-2-methyl-propanoate as a yellow liquid.
$^1$H NMR (400 MHz, CDCl$_3$) 3.95 (s, 2H) 3.82 (s, 3H) 1.71 (s, 6H) 0.98 (s, 9H).

Step 2: Preparation of 2,2-dimethylpropyl 1-hydroxy-2-methyl-propane-2-sulfonate

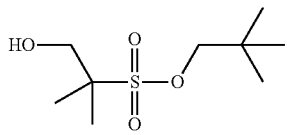

Diisobutylaluminum hydride (1M in dichloromethane, 6.62 mL) was added drop wise to a cooled (ice bath) solution of methyl 2-(2,2-dimethylpropoxysulfonyl)-2-methyl-propanoate (0.668 g) in dichloromethane (79.4 mL) under a nitrogen atmosphere, maintaining the temperature below 5° C. during the addition. The reaction mixture was stirred at 0° C. for 1 hour. Propan-2-ol (7.94 mL) was added to the reaction mixture and stirring continued at 0° C. for a further hour, then it was allowed to warm to room temperature. The reaction mixture was diluted with dichloromethane and washed with 2M aqueous hydrochloric acid. The organic phase was dried over sodium sulfate, concentrated and chromatographed on silica eluting with 0-100% ethyl acetate in hexanes to give 2,2-dimethylpropyl 1-hydroxy-2-methyl-propane-2-sulfonate as a clear colourless liquid.
$^1$H NMR (400 MHz, CDCl$_3$) 3.94 (s, 2H) 3.80 (d, 2H) 2.53 (t, 1H) 1.46 (s, 6H) 1.00 (s, 9H).

Step 3: Preparation of 1-hydroxy-2-methyl-propane-2-sulfonic Acid

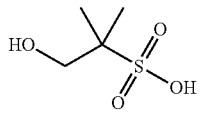

A mixture of 2,2-dimethylpropyl 1-hydroxy-2-methyl-propane-2-sulfonate (0.393 g) and 6M aqueous hydrochloric acid (14.0 mL) was heated to 95° C. for 4 hours. The reaction mixture was cooled and concentrated. The residue was taken up in acetonitrile, dried over magnesium sulfate and concentrated to give 1-hydroxy-2-methyl-propane-2-sulfonic acid as a colourless gum.
$^1$H NMR (400 MHz, D$_2$O) 3.93-3.86 (m, 2H) 1.15-1.08 (m, 6H).

Step 4: Preparation of 2-methyl-1-(trifluoromethyl-sulfonyloxy)propane-2-sulfonate

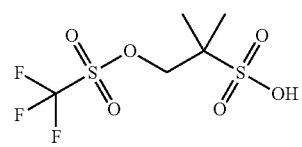 [SMILES: CC(C)(COS(=O)(=O)C(F)(F)F)S(=O)(=O)O]

A mixture of 2,6-dimethylpyridine (0.278 g) and 1-hydroxy-2-methyl-propane-2-sulfonic acid (0.200 g) in dichloromethane (2.33 mL) was cooled to 0° C. in an ice bath. Trifluoromethylsulfonyl trifluoromethanesulfonate (0.403 g) was added dropwise and the reaction mixture was stirred cold for 15 minutes then allowed to warm to room temperature. The reaction mixture was quenched with water and extracted with dichloromethane (×3). The combined organic extracts were dried over magnesium sulfate and concentrated to give 2-methyl-1-(trifluoromethylsulfonyloxy)propane-2-sulfonate as a brown gum.
$^1$H NMR (400 MHz, CDCl$_3$) 4.09 (s, 2H) 1.77 (s, 6H).

Step 5: Preparation of 2-methyl-1-(4-pyrimidin-2-ylpyridazin-1-ium-1-yl)propane-2-sulfonate A114

A mixture of 2-pyridazin-4-ylpyrimidine (0.040 g), 2-methyl-1-(trifluoromethylsulfonyloxy)propane-2-sulfonate (0.072 g) and 1,4-dioxane (2.0 mL) was heated to 90° C. overnight. The reaction mixture was cooled, concentrated and purified by preparative reverse phase HPLC to give 2-methyl-1-(4-pyrimidin-2-ylpyridazin-1-ium-1-yl)propane-2-sulfonate A114 as a white solid.
$^1$H NMR (400 MHz, D$_2$O) 10.17-10.12 (m, 1H) 9.75-9.71 (m, 1H) 9.15 (dd, 1H) 8.97 (d, 2H) 7.61 (t, 1H) 5.04 (s, 2H) 1.37 (s, 6H).

Example 28: Preparation of ethoxy-[2-(4-pyrimidin-2-ylpyridazin-1-ium-1-yl)ethyl]phosphinate A113

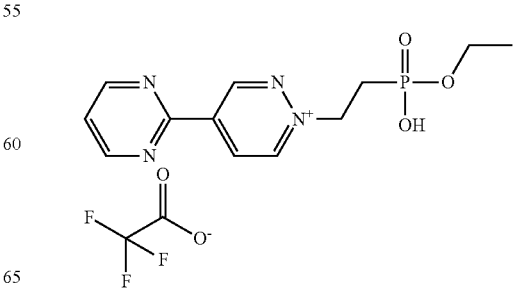

Step 1: Preparation of 1-(2-diethoxyphosphoryl-ethyl)-4-pyrimidin-2-yl-pyridazin-1-ium A124

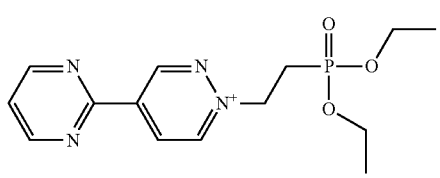

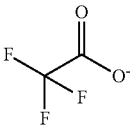

To a mixture of 2-pyridazin-4-ylpyrimidine (0.5 g) in acetonitrile (10 mL) was added 1-bromo-2-diethoxyphosphoryl-ethane (0.929 g). The mixture was heated at reflux for 24 hours. The reaction was concentrated and the residue washed with ethyl acetate and acetone. The residue was purified by preparative reverse phase HPLC (trifluoroacetic acid was present in the eluent) to give 1-(2-diethoxyphosphorylethyl)-4-pyrimidin-2-yl-pyridazin-1-ium, A124.

$^1$H NMR (400 MHz, D$_2$O) 10.26 (d, 1H) 9.89 (d, 1H) 9.27 (dd, 1H) 9.00-9.06 (m, 2H) 7.69 (t, 1H) 5.11-5.23 (m, 2H) 4.03-4.15 (m, 4H) 2.84 (dt, 2H) 1.21 (t, 6H).

Step 2: Preparation of ethoxy-[2-(4-pyrimidin-2-ylpyridazin-1-ium-1-yl)ethyl]phosphinate A113

A mixture of 1-(2-diethoxyphosphorylethyl)-4-pyrimidin-2-yl-pyridazin-1-ium (0.2 g) in 2M aqueous hydrochloric acid (4 mL) was heated at 60° C. for 4 hours. The reaction was concentrated and purified by preparative reverse phase HPLC (trifluoroacetic acid is present in the eluent) to give ethoxy-[2-(4-pyrimidin-2-ylpyridazin-1-ium-1-yl)ethyl]phosphinate, A113.

$^1$H NMR (400 MHz, D$_2$O) 10.22 (d, 1H) 9.86 (d, 1H) 9.23 (dd, 1H) 9.04 (d, 2H) 7.69 (t, 1H) 5.06 (dt, 2H) 3.85 (quin, 2H) 2.44-2.53 (m 2H) 1.13 (t, 3H).

Example 29: Preparation of 3-(4-pyridazin-3-ylpyridazin-1-ium-1-yl)propanoic Acid Chloride A138

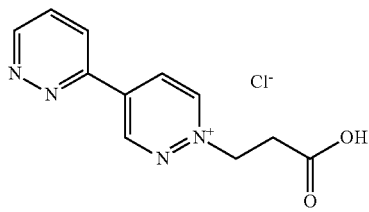 [SMILES: O=C(O)CC[n+]1ccc(-c2cccnn2)cn1 ; [Cl-]]

Step 1: Preparation of 3-pyridazin-4-ylpyridazine

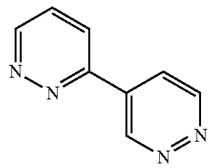 [SMILES: c1cnnc(-c2ccnnc2)c1]

A microwave vial, under nitrogen atmosphere, was charged with tributyl(pyridazin-4-yl)stannane (0.697 g), 3-bromopyridazine (0.25 g), palladium (0) tetrakis(triphenylphosphine) (0.185 g) and 1,4-dioxane (7.86 mL) and heated at 140O0 in the microwave for 1 hour. The reaction mixture was concentrated and purified on silica using a gradient of 0% to 50% acetonitrile in dichloromethane to give 3-pyridazin-4-ylpyridazine as an orange solid.

1 HNMR (400 MHz, CDCl$_3$) 9.94-9.89 (m, 1H) 9.42 (dd, 1H) 9.35 (dd, 1H) 8.24 (dd, 1H) 8.09 (dd, 1H) 7.79-7.72 (m, 1H).

Step 2: Preparation of 3-(4-pyridazin-3-ylpyridazin-1-ium-1-yl)propanoic Acid 2,2,2-trifluoroacetate A182

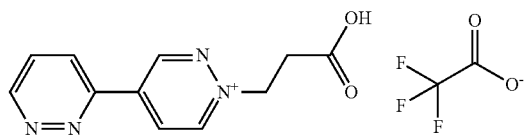 [SMILES: O=C(O)CC[n+]1ccc(-c2cccnn2)cn1 ; O=C([O-])C(F)(F)F]

A mixture of 3-pyridazin-4-ylpyridazine (0.25 g), water (15 mL) and 3-bromopropanoic acid (0.363 g) was heated at 100° C. for 25 hours. The mixture was concentrated and purified by preparative reverse phase HPLC (trifluoroacetic acid is present in the eluent) to give 3-(4-pyridazin-3-ylpyridazin-1-ium-1-yl)propanoic acid 2,2,2-trifluoroacetate, A182.

1H NMR (400 MHz, D$_2$O) 10.11 (d, 1H) 9.88 (d, 1H) 9.32 (dd, 1H) 9.10 (dd, 1H) 8.50 (dd, 1H) 7.99 (dd, 1H) 5.13 (t, 2H) 3.26 (t, 2H) (one C$_{o2}$H proton missing).

Step 3: Preparation of 3-(4-pyridazin-1-ium-3-ylpyridazin-1-ium-1-yl)propanoic Acid Dichloride A234

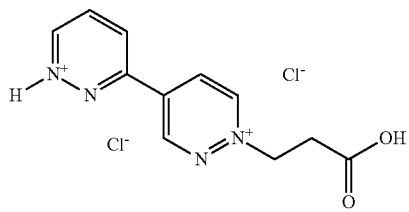 [SMILES: O=C(O)CC[n+]1ccc(-c2ccc[nH+]n2)cn1 ; [Cl-] ; [Cl-]]

A mixture of 3-(4-pyridazin-3-ylpyridazin-1-ium-1-yl) propanoic acid 2,2,2-trifluoroacetate (6.56 g) and 2M aqueous hydrochloric acid (114 mL) was stirred at room temperature for 3 hours. The mixture was concentrated and the residue was taken up in a small amount of water and freeze dried. The resulting glassy yellow solid was stirred in acetone (105 mL) overnight. The solid material was collected by filtration, washed with further acetone and dried under vacuum to give 3-(4-pyridazin-1-ium-3-ylpyridazin-1-ium-1-yl)propanoic acid dichloride, A234, as a beige solid.

1H NMR (400 MHz, D$_2$O) 10.11 (d, 1H) 9.88 (d, 1H) 9.36 (br d, 1H) 9.10 (dd, 1H) 8.48-8.56 (m, 1H) 7.92-8.07 (m, 1H) 4.98-5.20 (m, 2H) 3.18-3.32 (m, 2H) (one CO$_2$H proton missing)

Step 4: Preparation of 3-(4-pyridazin-3-ylpyridazin-1-ium-1-yl)propanoic Acid Chloride A138

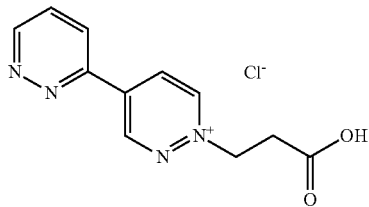 [SMILES: O=C(O)CC[n+]1ccc(-c2cccnn2)cn1 ; [Cl-]]

A mixture of 3-(4-pyridazin-1-ium-3-ylpyridazin-1-ium-1-yl)propanoic acid dichloride (0.541 g) and 2-propanol (10 mL) was heated at 90° C. Water was added drop wise until a clear solution was obtained, this took ~0.8 mL. To this was added further hot 2-propanol (10 mL) and the solution left to cool. Filtered off the precipitate and washed with cold 2-propanol and acetone and dried under vacuum to give 3-(4-pyridazin-3-ylpyridazin-1-ium-1-yl)propanoic acid chloride, A138, as a beige solid.

1H NMR (400 MHz, D$_2$O) 10.11 (d, 1H) 9.87 (d, 1H) 9.32 (dd, 1H) 9.12-9.08 (m, 1H) 8.50 (dd, 1H) 7.99 (dd, 1H) 5.12 (t, 2H) 3.24 (t, 2H) (one C$_{02}$H proton missing)

Example 30: Preparation of 2-(4-pyridazin-1-ium-3-ylpyridazin-1-ium-1-yl)ethanesulfonate Chloride A213

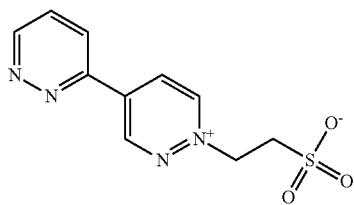

Step 1: Preparation of 2-(4-pyridazin-3-ylpyridazin-1-ium-1-yl)ethanesulfonate A5

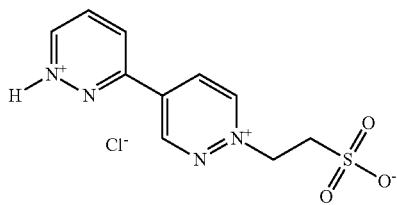 [SMILES: O=S(=O)([O-])CC[n+]1ccc(-c2ccc[nH+]n2)cn1 ; [Cl-]]

A mixture of 3-pyridazin-4-ylpyridazine (0.41 g), sodium 2-bromoethanesulfonic acid (0.656 g) and water (7.78 mL) was heated at 100° C. for 17 hours. The reaction mixture was cooled, filtered through a syringe filter and purified by preparative reverse phase HPLC (trifluoroacetic acid is present in the eluent) to give 2-(4-pyridazin-3-ylpyridazin-1-ium-1-yl)ethanesulfonate as a yellow solid.

1H NMR (400 MHz, D$_2$O) 10.15 (d, 1H) 9.87 (d, 1H) 9.33 (dd, 1H) 9.12 (dd, 1H) 8.52 (dd, 1H) 7.99 (dd, 1H) 5.32-5.19 (m, 2H) 3.73-3.65 (m, 2H)

Step 2: Preparation of 2-(4-pyridazin-1-ium-3-ylpyridazin-1-ium-1-yl)ethanesulfonate Chloride A213

A solution of 2-(4-pyridazin-3-ylpyridazin-1-ium-1-yl)ethanesulfonate (0.2 g) and 2M aqueous hydrochloric acid (5 mL) was stirred at room temperature for 2 hours. The mixture was concentrated and the residue was taken up in a small amount of water and freeze dried to give 2-(4-pyridazin-1-ium-3-ylpyridazin-1-ium-1-yl)ethanesulfonate chloride as a cream glass like solid.

1H NMR (400 MHz, D$_2$O) 10.13 (d, 1H) 9.86 (d, 1H) 9.35 (dd, 1H) 9.11 (dd, 1H) 8.57 (dd, 1H) 8.05 (dd, 1H) 5.27-5.21 (m, 2H) 3.71-3.64 (m, 2H) (one NH proton missing)

Example 31: Preparation of 4-pyridazin-4-ylpyrimidin-2-amine

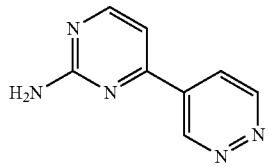 [SMILES: Nc1nccc(-c2ccnnc2)n1]

A microwave vial, under nitrogen atmosphere, was charged with tributyl(pyridazin-4-yl)stannane (3.42 g), 4-pyridazin-4-ylpyrimidin-2-amine (0.727 g), palladium (0) tetrakis(triphenylphosphine) (0.892 g), N,N-diisopropylethylamine (1.35 mL) and 1,4-dioxane (38.6 mL) and heated to 140° C. in the microwave for 1 hour. The reaction mixture was concentrated and purified on silica using a gradient of 0% to 70% acetonitrile in dichloromethane to give 4-pyridazin-4-ylpyrimidin-2-amine as a beige solid.

1H NMR (400 MHz, d$_6$-DMSO) 9.82 (dd, 1H) 9.41 (dd, 1H) 8.47 (d, 1H) 8.22 (dd, 1H) 7.38 (d, 1H) 6.98 (br s, 2H)

Example 32: Preparation of 2-pyridazin-4-ylpyrimidin-4-ol

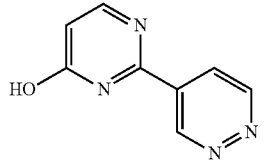 [SMILES: Oc1ccnc(-c2ccnnc2)n1]

To a mixture of 2-pyridazin-4-ylpyrimidin-4-amine (0.1 g) and acetic acid (1 mL) was added a solution of sodium nitrite (0.12 g) in water (1 mL) drop wise at room temperature. The mixture was heated to 90° C. for 30 minutes. The reaction mixture was concentrated and the resulting solid washed with water and t-butylmethylether to give 2-pyridazin-4-ylpyrimidin-4-ol.

1H NMR (400 MHz, d$_6$-DMSO) 12.39-13.52 (m, 1H) 9.82-9.86 (m, 1H) 9.46 (d, 1H) 8.37 (d, 1H) 8.30 (d, 1H) 6.64 (d, 1H)

Example 33: Preparation of 4-methyl-5-pyrimidin-2-yl-pyridazine

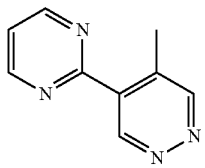

Step 1: Preparation of 2-(5-methyl-1,4-dihydropyridazin-4-yl)pyrimidine

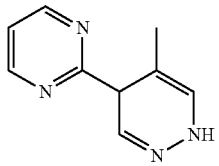

A solution of 2-pyridazin-4-ylpyrimidine (2 g) in tetrahydrofuran (20 mL), under nitrogen atmosphere, was cooled to 0° C. and to this was added methylmagnesium chloride (3M in tetrahydrofuran, 8.4 mL). The reaction mixture was allowed to warm to room temperature and stirred for 16 hours. The reaction mixture was partitioned between aqueous ammonium chloride and ethyl acetate. The organic layer was washed with brine (2×), dried over anhydrous sodium sulfate and concentrated to give crude 2-(5-methyl-1,4-dihydropyridazin-4-yl)pyrimidine, which was used without further purification Step 2: Preparation of 4-methyl-5-pyrimidin-2-yl-pyridazine To a solution of 2-(5-methyl-1,2-dihydropyridazin-4-yl) pyrimidine (1 g) in dichloromethane (20 mL), under nitrogen atmosphere, was added 2,3-dichloro-5,6-dicyano-1,4-benzoquinone (2.61 g) and the mixture stirred at room temperature for 16 hours. The reaction mixture was concentrated and purified on silica using 20% methanol in dichloromethane as eluent. The resulting solid was triturated with ethyl acetate to give 4-methyl-5-pyrimidin-2-yl-pyridazine.

1H NMR (400 MHz, d$_6$-DMSO) 9.54 (m, 1H) 9.28-9.31 (m, 1H) 9.02-9.07 (m, 2H) 7.60-7.68 (m, 1H) 2.62 (s, 3H)

Example 34: Preparation of 3-[4-(5-chloro-6-oxo-1H-pyrimidin-2-yl)pyridazin-1-ium-1-yl]propanoic Acid 2,2,2-trifluoroacetate A161

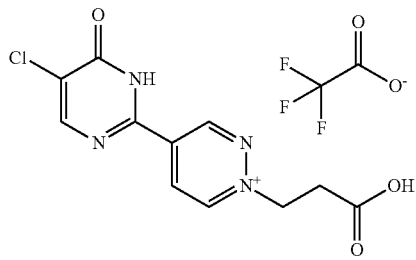 [SMILES: O=C(O)CC[n+]1ccc(-c2ncc(Cl)c(=O)[nH]2)cn1 ; O=C([O-])C(F)(F)F]

Step 1: Preparation of ethyl 3-[4-(5-chloro-4-methoxy-pyrimidin-2-yl)pyridazin-1-ium-1-yl]propanoate

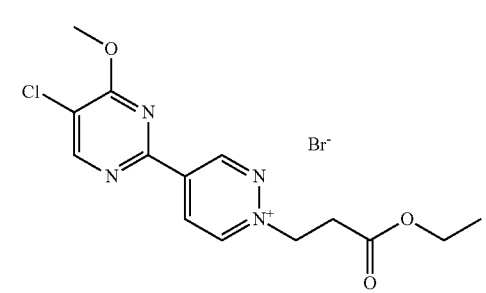 [SMILES: CCOC(=O)CC[n+]1ccc(-c2ncc(Cl)c(OC)n2)cn1 ; [Br-]]

To a mixture of 5-chloro-4-methoxy-2-pyridazin-4-yl-pyrimidine (0.4 g) in acetonitrile (4 mL), under nitrogen atmosphere, was added ethyl 3-bromopropanoate (0.346 mL). The mixture was heated at 60° C. for 48 hours and concentrated to give crude ethyl 3-[4-(5-chloro-4-methoxy-pyrimidin-2-yl)pyridazin-1-ium-1-yl]propanoate bromide, which was used without further purification.

Step 2: Preparation of 3-[4-(5-chloro-6-oxo-1H-pyrimidin-2-yl)pyridazin-1-ium-1-yl]propanoic Acid; 2,22-trifluoroacetate A161

A mixture of ethyl 3-[4-(5-chloro-4-methoxy-pyrimidin-2-yl)pyridazin-1-ium-1-yl]propanoate (0.88 g) and 2M aqueous hydrochloric acid (8.8 mL) was stirred at room temperature overnight. The mixture was concentrated and purified by preparative reverse phase HPLC (trifluoroacetic acid is present in the eluent) to give 3-[4-(5-chloro-6-oxo-1H-pyrimidin-2-yl)pyridazin-1-ium-1-yl]propanoic acid 2,2,2-trifluoroacetate.

1H NMR (400 MHz, D$_2$O) 9.95 (s, 1H) 9.87 (d, 1H) 9.00 (dd, 1H) 8.44 (s, 1H) 5.09 (t, 2H) 3.22 (t, 2H) (one NH proton and one CO$_2$H proton missing)

Example 35: Preparation of 2-methyl-2-(4-pyrimidin-2-ylpyridazin-1-ium-1-yl)propane-1-sulfonate A184

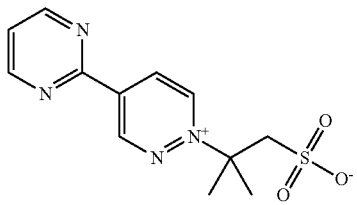 [SMILES: CC(C)(CS(=O)(=O)[O-])[n+]1ccc(-c2ncccn2)cn1]

Step 1: Preparation of 2,2-dimethylpropyl Methanesulfonate

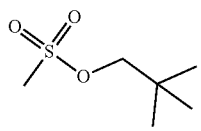

A solution of triethylamine (8.1 mL) and 2,2-dimethyl-propan-1-ol (2.3 g) in dichloromethane (40 mL) was cooled to 0° C. in an ice/acetone bath. To this was added methanesulfonyl chloride (2.2 mL) drop wise. The reaction mixture was stirred cold for 2 hours and washed with aqueous ammonium chloride. The organic layer was concentrated and the residue dissolved in ether. The ether solution was passed through a plug of silica eluting with further ether. Concentration of the ether filtrate gave 2,2-dimethylpropyl methanesulfonate as a light yellow liquid.

1H NMR (400 MHz, CDCl$_3$) 3.90-3.85 (m, 2H) 3.01 (s, 3H) 1.00 (s, 9H)

Step 2: Preparation of 2,2-dimethylpropyl 2-hydroxy-2-methyl-propane-1-sulfonate

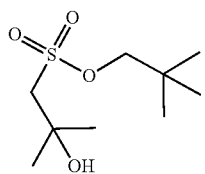

A solution of 2,2-dimethylpropyl methanesulfonate (1.75 g) in tetrahydrofuran (22.1 mL) was cooled to −78° C. under nitrogen atmosphere. To this was added drop wise n-butyllithium (2.5 mol/L in hexane, 5.1 mL). The reaction mixture was gradually warmed to −30° C. over 2 hours and acetone (7.73 mL) was added. The reaction mixture was warmed to room temperature and stirred for a further 1.5 hours. The reaction was quenched with 2M aqueous hydrochloric acid and extracted with ethyl acetate (×3). The combined organic extracts were dried with magnesium sulfate, concentrated and purified on silica using a gradient from 0 to 100% ethyl acetate in iso-hexane to give 2,2-dimethylpropyl 2-hydroxy-2-methyl-propane-1-sulfonate as a colourless liquid.

1H NMR (400 MHz, CDCl$_3$) 3.90 (s, 2H) 3.32 (s, 2H) 2.79 (br s, 1H) 1.44 (s, 6H) 0.99 (s, 9H)

Step 3: Preparation of 2-hydroxy-2-methyl-propane-1-sulfonic Acid

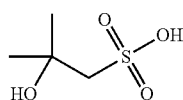

A mixture of 2,2-dimethylpropyl 2-hydroxy-2-methyl-propane-1-sulfonate (1.84 g) and 6M aqueous hydrochloric acid (32.8 mL) was heated at 95° C. for 4 hours. The reaction mixture was cooled to room temperature and freeze dried overnight to give 2-hydroxy-2-methyl-propane-1-sulfonic acid as an off white solid.

1H NMR (400 MHz, D$_2$O) 2.99 (s, 2H) 1.24 (s, 6H) (one OH proton and one SO$_3$H proton missing)

Step 4: Preparation of 2-methyl-2-(4-pyrimidin-2-ylpyridazin-1-ium-1-yl)propane-1-sulfonate A184

A mixture of 2-pyridazin-4-ylpyrimidine (0.507 g) in dry acetonitrile (32.1 mL) was cooled in an ice bath. To this was added 1,1,1-trifluoro-N-(trifluoromethylsulfonyl)methanesulfonamide (0.663 mL) and the reaction mixture stirred at room temperature for 15 minutes. To this was added triphenylphosphine (1.68 g) and a solution of 2-hydroxy-2-methyl-propane-1-sulfonic acid (0.741 g) in dry acetonitrile (0.5 mL) followed by drop wise addition of diisopropyl azodicarboxylate (1.26 mL, 1.30 g). The reaction mixture was then heated at 80° C. for 144 hours. The reaction mixture was partitioned between water and dichloromethane and the aqueous layer purified by preparative reverse phase HPLC (trifluoroacetic acid is present in the eluent) to give 2-methyl-2-(4-pyrimidin-2-ylpyridazin-1-ium-1-yl)propane-1-sulfonate as a yellow solid.

1H NMR (400 MHz, CD$_3$OD) 10.41-10.35 (m, 1H) 10.05-9.99 (m, 1H) 9.31 (dd, 1H) 9.12 (d, 2H) 7.67 (t, 1H) 3.67 (s, 2H) 2.10 (s, 6H)

Example 36: Preparation of 2-(4-pyrimidin-2-ylpyridazin-1-ium-1-yl)propane-1-sulfonate A181

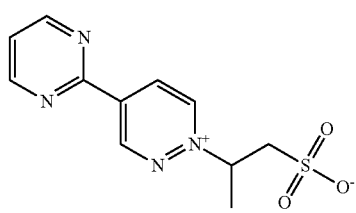 [SMILES: CC(CS(=O)(=O)[O-])[n+]1ccc(-c2ncccn2)cn1]

Step 1: Preparation of 2,2-dimethylpropyl 2-hydroxypropane-1-sulfonate

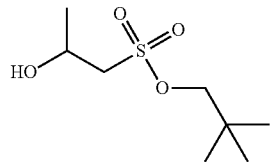

A solution of 2,2-dimethylpropyl methanesulfonate (2 g) in tetrahydrofuran (25 mL) was cooled to −78° C. under nitrogen atmosphere and n-butyllithium (2.5 mol/L in hexane, 5.8 mL) was added drop wise. The reaction mixture was gradually warmed to −30° C. over 1 hour and acetaldehyde (6.8 mL) was added. The reaction mixture was warmed to room temperature and stirred for a further 2.5 hours. The reaction was quenched with 2M aqueous hydrochloric acid and extracted with ethyl acetate (×3). The combined organic extracts were dried with magnesium sulfate, concentrated and purified on silica using a gradient from 0 to 100% ethyl acetate in iso-hexane to give 2,2-dimethylpropyl 2-hydroxypropane-1-sulfonate as a yellow liquid.

1H NMR (400 MHz, CDCl$_3$) 4.47-4.34 (m, 1H) 3.96-3.87 (m, 2H) 3.25-3.17 (m, 2H) 3.01 (br s, 1H) 1.34 (d, 3H) 1.00 (s, 9H)

Step 2: Preparation of 2-hydroxypropane-1-sulfonic Acid

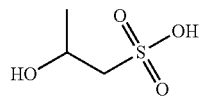

A mixture of 2,2-dimethylpropyl 2-hydroxypropane-1-sulfonate (1.35 g) and 6M aqueous hydrochloric acid (32.8 mL) was heated at 95° C. for 4 hours. The reaction mixture was cooled to room temperature and freeze dried overnight to give 2-hydroxypropane-1-sulfonic acid as a brown solid.

1H NMR (400 MHz, D$_2$O) 4.17-4.06 (m, 1H) 2.99-2.85 (m, 2H) 1.16 (d, 3H) (one OH proton and one SO$_3$H proton missing)

Step 3: Preparation of 2-(trifluoromethylsulfonyloxy)propane-1-sulfonic Acid

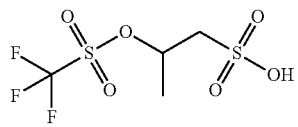

To a mixture of 2-hydroxypropane-1-sulfonic acid (0.2 g) in dichloromethane (2.57 mL) was added 2,6-dimethylpyridine (0.33 mL) and the resulting mixture was cooled to 0° C. To this was added drop wise trifluoromethylsulfonyl trifluoromethanesulfonate (0.264 mL) and stirring continued at this temperature for 15 minutes. Cooling was removed and the reaction mixture was stirred at room temperature for a further hour. The reaction mixture was quenched with water and extracted with dichloromethane (×3). The combined organic extracts were dried with magnesium sulfate and concentrated to give 2-(trifluoromethylsulfonyloxy)propane-1-sulfonic acid as a brown gum, ~50% purity. The product was used immediately in subsequent reactions without further purification.

1H NMR (400 MHz, CDCl$_3$) product peaks only 5.57-5.41 (m, 1H) 4.18-3.98 (m, 1H) 3.58-3.35 (m, 1H) 1.76-1.65 (m, 3H) (one SO$_3$H proton missing)

Step 4: Preparation of 2-(4-pyrimidin-2-ylpyridazin-1-ium-1-yl)propane-1-sulfonate A181

A mixture of 2-pyridazin-4-ylpyrimidine (0.15 g), 2-(trifluoromethylsulfonyloxy)propane-1-sulfonate (0.55 g) and 1,4-dioxane (7.8 mL) was heated at 90° C. for 24 hours. The reaction mixture was partitioned between water and dichloromethane and the aqueous layer purified by preparative reverse phase HPLC (trifluoroacetic acid is present in the eluent) to give 2-(4-pyrimidin-2-ylpyridazin-1-ium-1-yl) propane-1-sulfonate as a yellow solid.

1H NMR (400 MHz, CD$_3$OD) 10.43-10.37 (m, 1H) 9.93 (dd, 1H) 9.34 (dd, 1H) 9.11 (d, 2H) 7.68 (t, 1H) 5.66-5.53 (m, 1H) 3.66 (dd, 1H) 3.43 (dd, 1H) 1.83 (d, 3H)

Example 37: Preparation of 2-(4-pyrimidin-2-ylpyridazin-1-ium-1-yl)ethanol 2,2,2-trifluoroacetate A195

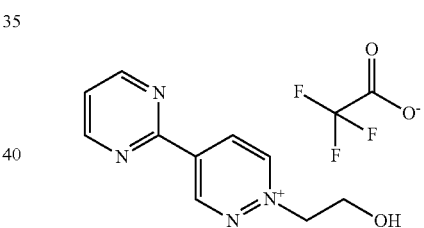

Step 1: Preparation of 2-(4-pyrimidin-2-ylpyridazin-1-ium-1-yl)ethyl Sulfate A194

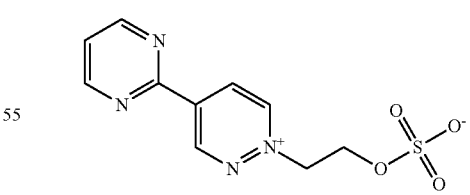

A mixture of 2-pyridazin-4-ylpyrimidine (0.2 g), 1,2-dichloroethane (3.8 mL) and 1,3,2-dioxathiolane 2,2-dioxide (0.198 g) was stirred at room temperature for 22 hours. The resulting precipitate was filtered off and washed with dichloromethane to give a mixture of regio-isomers. This mixture was triturated with water and filtered to give 2-(4-pyrimidin-2-ylpyridazin-1-ium-1-yl)ethyl sulfate as a pale grey solid.

1H NMR (400 MHz, D₂O) 10.28 (d, 1H) 9.87 (d, 1H) 9.29 (dd, 1H) 9.07 (d, 2H) 7.72 (t, 1H) 5.18-5.28 (m, 2H) 4.62-4.72 (m, 2H)

Step 2: Preparation of 2-(4-pyrimidin-2-ylpyridazin-1-ium-1-yl)ethanol 2,2,2-trifluoroacetate A195

A mixture of crude 2-(4-pyrimidin-2-ylpyridazin-1-ium-1-yl)ethyl sulfate (0.25 g, mixture of regio-isomers) and 2M aqueous hydrochloric acid (5 mL) was heated at 80° C. for 12 hours. The reaction mixture was concentrated, washed with cyclohexane and tert-butylmethylether and purified by preparative reverse phase HPLC (trifluoroacetic acid is present in the eluent) to give 2-(4-pyrimidin-2-ylpyridazin-1-ium-1-yl)ethanol 2,2,2-trifluoroacetate.

1H NMR (400 MHz, D₂O) 10.25 (d, 1H) 9.81 (d, 1H) 9.26 (dd, 1H) 9.05 (d, 2H) 7.70 (t, 1H) 4.94-5.08 (m 2H) 4.17-4.22 (m 2H)

Example 38: Preparation of 3-[4-(5-carbamoylpyrazin-2-yl)pyridazin-1-ium-1-yl]propanoic Acid 2,2,2-trifluoroacetate A202

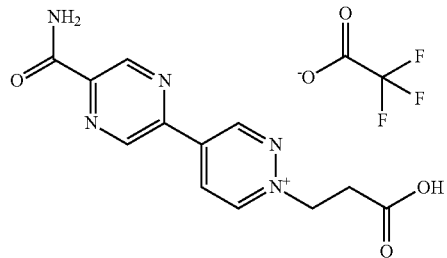

A mixture of ethyl 3-[4-(5-cyanopyrazin-2-yl)pyridazin-1-ium-1-yl]propanoate bromide (0.33 g) and 2M aqueous hydrochloric acid (5 mL) was stirred at room temperature for 40 hours. The reaction mixture was concentrated, washed with cyclohexane and tert-butylmethylether and purified by preparative reverse phase HPLC (trifluoroacetic acid is present in the eluent) to give 3-[4-(5-carbamoylpyrazin-2-yl)pyridazin-1-ium-1-yl]propanoic acid 2,2,2-trifluoroacetate.

1H NMR (400 MHz, D₂O) 10.18 (d, 1H) 9.92 (d, 1H) 9.51 (d, 1H) 9.43 (d, 1H) 9.20 (dd, 1H) 5.18 (t, 2H) 3.31 (t, 2H) (two NH protons and one C₀₂H proton missing)

Example 39: Preparation of [(1S)-1-carboxy-3-(4-pyrimidin-2-ylpyridazin-1-ium-1-yl)propyl]ammonium 2,2,2-trifluoroacetate A201

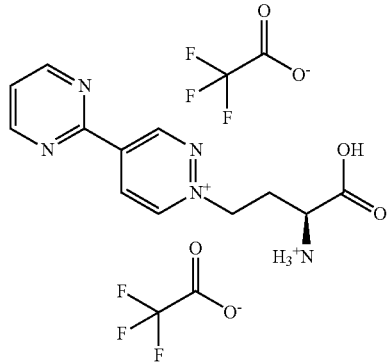

Step 1: Preparation of [(1S)-3-bromo-1-methoxycarbonyt-propyl]ammonium chloride

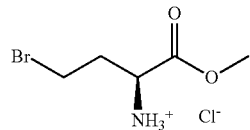

To a mixture of (2S)-2-amino-4-bromo-butanoic acid (0.2 g) in dry methanol (4 mL) at 0° C., under nitrogen atmosphere, was added thionyl chloride (0.392 g) drop wise. The reaction mixture was stirred overnight at room temperature and concentrated to give crude [(1S)-3-bromo-1-methoxycarbonyl-propyl]ammonium chloride as an orange gum, which was used without further purification.

Step 2: Preparation of methyl (2S)-2-(benzyloxycarbonylamino)-4-bromo-butanoate

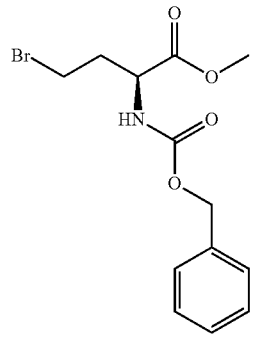 [SMILES: COC(=O)[C@H](CCBr)NC(=O)OCc1ccccc1]

Crude [(1S)-3-bromo-1-methoxycarbonyl-propyl]ammonium chloride was stirred in dichloromethane (4 mL) and a solution of sodium hydrogen carbonate (0.28 g) in water (4 mL) was added. The mixture was cooled to 0° C. and benzyl carbonochloridate (0.225 g) was added. The reaction mass was warmed to room temperature and stirred for 15 hours. The reaction mixture was diluted with water (10 mL) and extracted with dichloromethane (3×20 mL). The combined organic layers were dried over sodium sulfate, concentrated and purified on silica using a gradient from 0 to 100% ethyl acetate in cyclohexane to give methyl (2S)-2-(benzyloxycarbonylamino)-4-bromo-butanoate.

1H NMR (400 MHz, CDCl₃) 7.30-7.40 (m, 5H) 5.37-5.43 (m, 1H) 5.13 (s, 2H) 3.78 (s, 3H) 3.42-3.46 (m, 2H) 2.25-2.49 (m, 2H)

Step 3: Preparation of Methyl (2S)-2-(benzyloxycarbonylamino)-4-(4-pyrimidin-2-ylpyridazin-1-ium-1-yl)butanoate Iodide

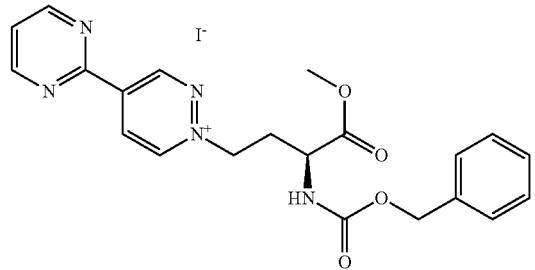 [SMILES: COC(=O)[C@H](CC[n+]1ccc(-c2ncccn2)cn1)NC(=O)OCc1ccccc1 ; [I-]]

To a solution of methyl (2S)-2-(benzyloxycarbonylamino)-4-bromo-butanoate (0.1 g) in dry acetone (2 mL), under nitrogen atmosphere, was added sodium iodide (0.054 g). The reaction mixture was stirred at room temperature overnight. To this was added 2-pyridazin-4-ylpyrimidine (0.048 g) and the mixture heated at reflux for 16 hours. The reaction mixture was concentrated and the crude methyl (2S)-2-(benzyloxycarbonylamino)-4-(4-pyrimidin-2-ylpyridazin-1-ium-1-yl)butanoate iodide was used in the next step without further purification.

Step 4: Preparation of [(1S)-1-carboxy-3-(4-pyrimidin-2-ylpyridazin-1-ium-1-yl)propyl]ammonium 2,2,2-trifluoroacetate A201

A mixture of methyl (2S)-2-(benzyloxycarbonylamino)-4-(4-pyrimidin-2-ylpyridazin-1-ium-1-yl)butanoate iodide (0.5 g) and concentrated hydrochloric acid (4.9 mL) was heated at 80° C. for 30 minutes. The reaction mixture was concentrated, dissolved in water and extracted with ethyl acetate (3×20 mL). The aqueous layer was purified by preparative reverse phase HPLC (trifluoroacetic acid is present in the eluent) to give [(1S)-1-carboxy-3-(4-pyrimidin-2-ylpyridazin-1-ium-1-yl)propyl]ammonium 2,2,2-trifluoroacetate.

1H NMR (400 MHz, $D_2O$) 10.26 (d, 1H) 9.90 (d, 1H) 9.27 (dd, 1H) 9.06 (d, 2H) 7.72 (t, 1H) 5.17 (t, 2H) 4.09 (dd, 1H) 2.76-2.79 (m, 2H) (Three NH protons and one $C_{O2}H$ proton missing)

Example 40: Preparation of [(1R)-1-carboxy-3-(4-pyrimidin-2-ylpyridazin-1-ium-1-yl)propyl]ammonium 2,2,2-trifluoroacetate A207

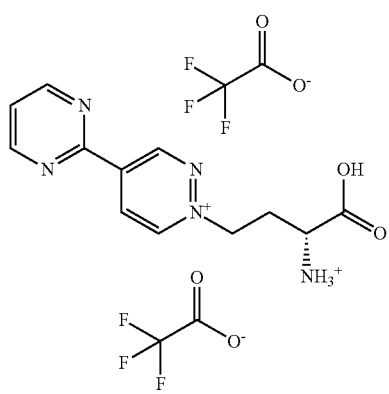 [SMILES: [NH3+][C@H](CC[n+]1ccc(-c2ncccn2)cn1)C(=O)O ; O=C([O-])C(F)(F)F ; O=C([O-])C(F)(F)F]

Step 1: Preparation of [(1R)-3-bromo-1-methoxycarbonyl-propyl]ammonium Chloride

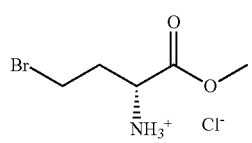

To a mixture of [(1R)-3-bromo-1-carboxy-propyl]ammonium bromide (0.1 g) in dry methanol (2 mL) at 0° C., under nitrogen atmosphere, was added thionyl chloride (0.083 mL) drop wise. The reaction mixture was stirred overnight at room temperature and concentrated to give crude [(1S)-3-bromo-1-methoxycarbonyl-propyl]ammonium chloride as a yellow solid, which was used without further purification.

Step 2: Preparation of [(1R)-1-methoxycarbonyl-3-(4-pyrimidin-2-ylpyridazin-1-ium-1-yl)propyl]ammonium Bromide Chloride

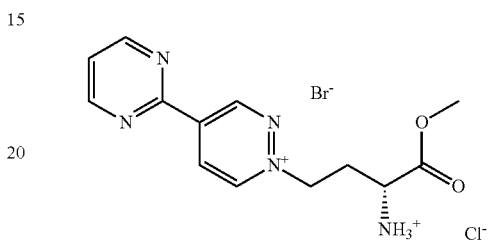

To a mixture of 2-pyridazin-4-ylpyrimidine (0.1 g) in acetonitrile (3.16 mL) was added [(1R)-3-bromo-1-methoxycarbonyl-propyl]ammonium chloride (0.16 g) The mixture was heated at reflux for 12 hours. The reaction mixture was concentrated to give crude [(1R)-1-methoxycarbonyl-3-(4-pyrimidin-2-ylpyridazin-1-ium-1-yl)propyl]ammonium bromide as a dark brown gum, which was used without further purification.

Step 3: Preparation of [(1R)-1-carboxy-3-(4-pyrimidin-2-ylpyridazin-1-ium-1-yl)propyl]ammonium 2,2,2-trifluoroacetate A207

A mixture of [(1R)-1-methoxycarbonyl-3-(4-pyrimidin-2-ylpyridazin-1-ium-1-yl)propyl]ammonium bromide (0.5 g) and 2M aqueous hydrochloric acid (7.29 mL) was heated at 80° C. for 2 hours. The reaction mixture was concentrated and purified by preparative reverse phase HPLC (trifluoroacetic acid is present in the eluent) to give [(1R)-1-carboxy-3-(4-pyrimidin-2-ylpyridazin-1-ium-1-yl)propyl]ammonium 2,2,2-trifluoroacetate.

1H NMR (400 MHz, $D_2O$) 10.22 (s, 1H) 9.87 (d, 1H) 9.24 (d, 1H) 8.99-9.04 (m, 2H) 7.66 (t, 1H) 5.16 (t, 2H) 4.17 (dd, 1H) 2.69-2.85 (m, 2H) (Three NH protons and one $C_{o2}H$ proton missing)

Example 41: Preparation of hydroxy-[(4-pyrimidin-2-ylpyridazin-1-ium-1-yl)methyl]phosphinate A205

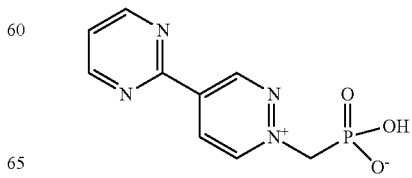

Step 1: Preparation of 1-(diethoxyphosphorylmethyl)-4-pyrimidin-2-yl-pyridazin-1-ium 2,2,2-trifluoroacetate A230

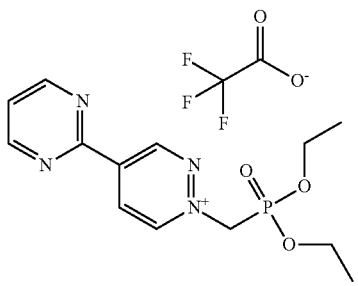 [SMILES: CCOP(=O)(C[n+]1ccc(-c2ncccn2)cn1)OCC ; O=C([O-])C(F)(F)F]

To a solution of diethoxyphosphorylmethanol (0.2 g) in dichloromethane (3.57 mL) at −78° C., under nitrogen atmosphere, was added N,N-diisopropylethylamine (0.244 mL) followed by trifluoromethylsulfonyl trifluoromethanesulfonate (0.24 mL). The reaction was warmed slowly to 0° C. over 2 hours. To this mixture was added a solution of 2-pyridazin-4-ylpyrimidine (0.188 g) in dichloromethane (3.57 mL) and the reaction was stirred at room temperature for 2 hours. The reaction mixture was quenched with water, diluted with ethanol, concentrated and purified by preparative reverse phase HPLC (trifluoroacetic acid is present in the eluent) to give 1-(diethoxyphosphorylmethyl)-4-pyrimidin-2-yl-pyridazin-1-ium 2,2,2-trifluoroacetate as a brown gum.

1H NMR (400 MHz, d$_6$-DMSO) 10.39-10.35 (m, 1H) 10.01 (d, 1H) 9.47 (dd, 1H) 9.22 (d, 2H) 7.84 (t, 1H) 5.78 (d, 2H) 4.24-4.13 (m, 4H) 1.27 (t, 6H)

Step 2: Preparation of hydroxy-[(4-pyrimidin-2-ylpyridazin-1-ium-1-yl)methyl]phosphinate A205

To a mixture of 1-(diethoxyphosphorylmethyl)-4-pyrimidin-2-yl-pyridazin-1-ium 2,2,2-trifluoroacetate (0.17 g) in dry acetonitrile (7.42 mL) at room temperature, under nitrogen atmosphere, was added bromo(trimethyl)silane (0.049 mL). After stirring overnight further bromo(trimethyl)silane (0.049 mL) was added After stirring overnight again a final portion of bromo(trimethyl)silane (0.049 mL) was added. After stirring overnight the reaction mixture was quenched with water and purified by preparative reverse phase HPLC (trifluoroacetic acid is present in the eluent) to give hydroxy-[(4-pyrimidin-2-ylpyridazin-1-ium-1-yl)methyl]phosphinate as an off white solid.

1H NMR (400 MHz, D$_2$O) 10.16-10.13 (m, 1H) 9.72-9.68 (m, 1H) 9.20 (dd, 1H) 8.99 (d, 2H) 7.64 (t, 1H) 5.11 (d, 2H) (one OH proton missing)

Example 42: Preparation of [(1S)-1-carboxy-2-(4-pyrimidin-2-ylpyridazin-1-ium-1-yl)ethyl]ammonium 2,2,2-trifluoroacetate A208

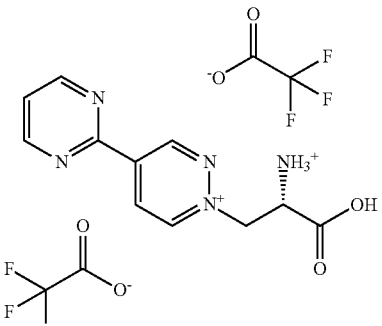

Step 1: Preparation of (2S)-2-(tert-butoxycarbonylamino)-3-(4-pyrimidin-2-ylpyridazin-1-ium-1-yl)propanoate

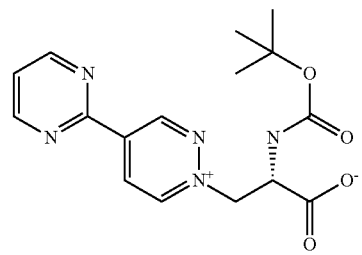 [SMILES: CC(C)(C)OC(=O)N[C@@H](C[n+]1ccc(-c2ncccn2)cn1)C(=O)[O-]]

To a mixture of 2-pyridazin-4-ylpyrimidine (0.05 g) in dry acetonitrile (1 mL) was added tert-butyl N-[(3S)-2-oxooxetan-3-yl]carbamate (0.071 g) and the reaction mixture was stirred at room temperature for 48 hours. Concentration of the reaction mixture gave crude (2S)-2-(tert-butoxycarbonylamino)-3-(4-pyrimidin-2-ylpyridazin-1-ium-1-yl)propanoate, which was used without further purification.

Step 2: Preparation of [(1S)-1-carboxy-2-(4-pyrimidin-2-ylpyridazin-1-ium-1-yl)ethyl]ammonium 2,2,2-trifluoroacetate A208

A mixture of (2S)-2-(tert-butoxycarbonylamino)-3-(4-pyrimidin-2-ylpyridazin-1-ium-1-yl)propanoate (0.4 g) and 2M aqueous hydrochloric acid (10 mL) was stirred at room temperature for 18 hours. The reaction mixture was concentrated and purified by preparative reverse phase HPLC (trifluoroacetic acid is present in the eluent) to give [(1S)-1-carboxy-2-(4-pyrimidin-2-ylpyridazin-1-ium-1-yl)ethyl]ammonium 2,2,2-trifluoroacetate.

1H NMR (400 MHz, D$_2$O) 10.26 (s, 1H) 9.94 (d, 1H) 9.31-9.34 (m, 1H) 9.04 (dd, 2H) 7.69 (t, 1H) 5.48 (d, 2H) 4.75 (t, 1H) (Three NH protons and one CO2H proton missing)

Example 43: Preparation of N-methyl-2-pyridazin-4-yl-pyrimidine-5-sulfonamide

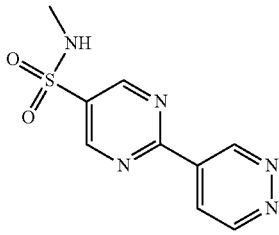 [SMILES: CNS(=O)(=O)c1cnc(-c2ccnnc2)nc1]

Step 1: Preparation of 2-chloro-N-methyl-pyrimidine-5-sulfonamide

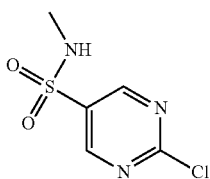

Cooled a solution of 2-chloropyrimidine-5-sulfonyl chloride (0.05 g) in tetrahydrofuran (1 mL) at −78° C., under nitrogen atmosphere, and added methanamine (2M in tetrahydrofuran, 0.117 mL) followed by N,N-diisopropylethylamine (0.065 mL). The reaction was stirred for 20 minutes and quenched with ice cold water (20 mL) and extracted with ethyl acetate (3×20 mL). The combined organic layers were concentrated to give crude 2-chloro-N-methyl-pyrimidine-5-sulfonamide.

1H NMR (400 MHz, d$_6$-DMSO) 9.10 (s, 2H) 7.96-8.00 (m, 1H) 2.54 (d, 3H)

Step 2: Preparation of N-methyl-2-pyridazin-4-yl-pyrimidine-5-sulfonamide

A microwave vial, under nitrogen atmosphere, was charged with tributyl(pyridazin-4-yl)stannane (0.64 g), 2-chloro-N-methyl-pyrimidine-5-sulfonamide (0.3 g), palladium (0) tetrakis(triphenylphosphine) (0.167 g) and 1,4-dioxane (4.5 mL) and heated at 130° C. in the microwave for 30 minutes. The reaction mixture was concentrated and triturated with tert-butylmethylether to give N-methyl-2-pyridazin-4-yl-pyrimidine-5-sulfonamide as a black solid.

1H NMR (400 MHz, d$_6$-DMSO) 10.03-10.04 (m, 1H) 9.53-9.54 (m, 1H) 9.35 (s, 2H) 8.49-8.51 (m, 1H) 8.04-8.05 (m, 1H) 2.58 (d, 3H)

Example 44: Preparation of 2-(6-methyl-4-pyrimidin-2-yl-pyridazin-1-ium-1-yl)ethanesulfonate A212

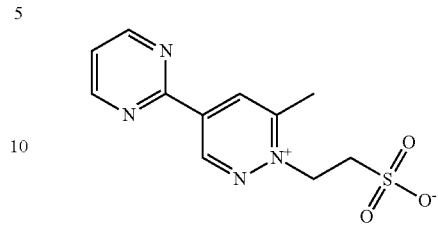

Step 1: Preparation of 3-methyl-5-pyrimidin-2-yl-1H-pyridazin-6-one

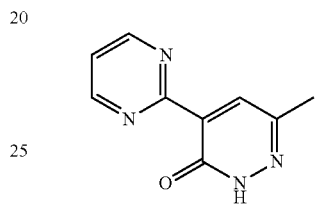

To a mixture of 5-bromo-3-methyl-1H-pyridazin-6-one (0.1 g) in degassed 1,4-dioxane (2 mL), under nitrogen atmosphere, was added tributyl(pyrimidin-2-yl)stannane (0.234 g), dichloropalladium triphenylphosphane (0.038 g) and cuprous iodide (0.02 g) and the mixture heated at 130° C. for 2 hours. The reaction mixture was diluted with 1,4-dioxane, filtered, using a syringe filter, to remove insoluble material and purified on silica using a gradient from 0 to 10% methanol in dichloromethane to give 3-methyl-5-pyrimidin-2-yl-1H-pyridazin-6-one as a white solid.

1H NMR (400 MHz, d$_6$-DMSO) 12.90-13.20 (br s, 1H) 8.92-8.93 (m, 2H) 7.68 (s, 1H) 7.53-7.54 (m, 1H) 2.31 (s, 3H)

Step 2: Preparation of 3-chloro-6-methyl-4-pyrimidin-2-yl-pyridazine

A mixture of 3-methyl-5-pyrimidin-2-yl-1H-pyridazin-6-one (1.93 g) and phosphorus oxychloride (1.93 mL) was heated at 100° C. for 3 hours. After cooling, the reaction mixture was concentrated, poured onto ice and basified with a cold aqueous sodium bicarbonate solution to pH 8. The aqueous was extracted with ethyl acetate (2×150 mL). The combined organic layers were washed with water (2×40 mL), dried over sodium sulphate and concentrated to give 3-chloro-6-methyl-4-pyrimidin-2-yl-pyridazine.

1H NMR (400 MHz, CDCl$_3$) 8.94-8.95 (m 2H) 7.78 (s, 1H) 7.42-7.44 (m, 1H) 2.80 (s, 3H)

Step 3: Preparation of 3-methyl-5-pyrimidin-2-yl-pyridazine

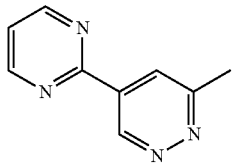

Triethylamine (1.32 mL) was added to a solution of 3-chloro-6-methyl-4-pyrimidin-2-yl-pyridazine (1.5 g) in a mixture of ethanol (40 mL) and ethyl acetate (10 mL). This mixture was degassed with nitrogen and 10% palladium on carbon (0.2 g) was added. This mixture was hydrogenated under a balloon atmosphere of hydrogen for 1 hour at room temperature. Further catalyst (0.2 g) was added and hydrogenation continued for an additional 3 hours. The reaction mixture was diluted with ethanol (50 mL) and filtered through Celite, washing with ethanol (2×40 mL). The filtrate was concentrated and purified on silica using a gradient from 0 to 10% methanol in dichloromethane to give 3-methyl-5-pyrimidin-2-yl-pyridazine as a white solid.

1H NMR (400 MHz, CDCl$_3$) 9.97 (d, 1H) 8.89 (d, 2H) 8.27 (d, 1H) 7.35-7.38 (m, 1H) 2.82 (s, 3H)

Step 4: Preparation of 2-(6-methyl-4-pyrimidin-2-yl-pyridazin-1-ium-1-yl)ethanesulfonate A212

A mixture of 3-methyl-5-pyrimidin-2-yl-pyridazine (0.8 g) and sodium 2-bromoethanesulfonate (1.078 g) in water (16 mL) was heated at 120° C. for 24 hours. The reaction mixture was concentrated, washed with tert-butylmethylether and purified by preparative reverse phase HPLC (trifluoroacetic acid is present in the eluent) to give 2-(6-methyl-4-pyrimidin-2-yl-pyridazin-1-ium-1-yl)ethanesulfonate.

1H NMR (400 MHz, D$_2$O) 10.00 (d, 1H) 9.08 (d, 1H) 9.00 (d, 2H) 7.65 (t, 1H) 5.16 (t, 2H) 3.68 (t, 2H) 3.12 (s, 3H)

Example 45: Preparation of dimethylsulfamoyl-[2-(4-pyrimidin-2-ylpyridazin-1-ium-1-yl)acetyl]azanide A214

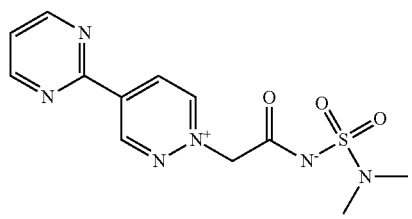 [SMILES: CN(C)S(=O)(=O)[N-]C(=O)C[n+]1ccc(-c2ncccn2)cn1]

Step 1: Preparation of 2-bromo-N-(dimethylsulfamoyl)acetamide

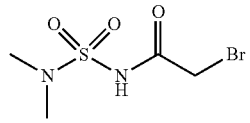

To a solution of dimethylsulfamide (0.5 g) and 4-(dimethylamino)pyridine (0.541 g) in dichloromethane (19.9 mL) at 0° C. was added bromoacetyl bromide (0.903 g) drop wise. The reaction was slowly warmed to room temperature and stirred for 24 hours. The reaction was partitioned with 0.5M aqueous hydrochloric acid. The organic layer was dried over magnesium sulfate and concentrated to give crude 2-bromo-N-(dimethylsulfamoyl)acetamide as a pale yellow oil. The product was used without further purification.

Step 2: Preparation of dimethylsulfamoyl-[2-(4-pyrimidin-2-ylpyridazin-1-ium-1-yl)acetyl]azanide A214

To a solution of 2-pyridazin-4-ylpyrimidine (0.15 g) in acetonitrile (10 mL) was added 2-bromo-N-(dimethylsulfamoyl)acetamide (0.21 g) and the mixture heated at 80° C. for 16 hours. The resulting precipitate was filtered, washed with acetonitrile (2×20 mL) to give dimethylsulfamoyl-[2-(4-pyrimidin-2-ylpyridazin-1-ium-1-yl)acetyl]azanide as a light green solid.

1H NMR (400 MHz, d$_6$-DMSO) 10.36 (s, 1H) 10.06-10.10 (m, 1H) 9.56-9.62 (m, 1H) 9.18-9.22 (m, 2H) 7.82-7.86 (m, 1H) 5.88-5.94 (m, 2H) 2.80-2.86 (m, 6H)

Example 46: Preparation of N-(2-bromoethyl)-1,1,1-trifluoro-methanesulfonamide

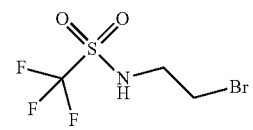

A mixture of 2-bromoethanamine bromide (1 g) and N,N-diisopropylethylamine (1.42 g) was stirred in dichloromethane (24.5 mL) at 0° C. until the reaction became homogeneous. Trifluoromethanesulfonic anhydride (1.55 g) was added drop wise and stirred at 0° C. for 3 hours. The reaction mixture was concentrated and partitioned between 1M aqueous hydrochloric acid and diethyl ether. The organic layer was washed with water, 1M aqueous hydrochloric acid and brine, dried over magnesium sulfate and concentrated to afford N-(2-bromoethyl)-1,1,1-trifluoro-methanesulfonamide as a pale yellow oil.

1H NMR (400 MHz, CDCl$_3$) 5.44 (br. s., 1H) 3.71 (q, 2H) 3.53 (t, 2H).

Example 47: Preparation of 2-bromo-N-methoxy-acetamide

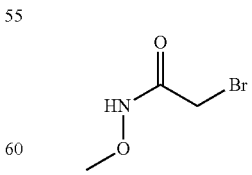

To a suspension of methoxyamine hydrochloride (0.248 g) and N,N-diisopropylethylamine (2.29 mL) in tetrahydrofuran (10 mL) at 0° C. was added 2-bromoacetyl bromide (0.5 g) drop wise. The reaction mixture was warmed to room temperature and stirred for 2 hours. The reaction mixture was concentrated and purified on silica using 2:1 iso-hexane: ethyl acetate to give 2-bromo-N-methoxy-acetamide as a pale yellow liquid.

1H NMR (400 MHz, CDCl₃) 4.48 (s, 2H) 4.24-4.28 (m, 1H) 3.88-3.92 (m 3H)

Example 48: Preparation of 3-bromo-N-cyano-propanamide

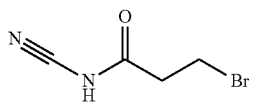

To a stirred solution of cyanamide (0.5 g) in water (10 mL) and tetrahydrofuran (10 mL) at 0° C. was added sodium hydroxide (1.427 g). After 10 minutes at 0° C. a solution of 3-bromopropanoyl chloride (1.27 mL) in tetrahydrofuran (5 mL) was added drop wise. The resulting reaction mixture was stirred at room temperature for 3 hours. Water was added and the mixture was extracted with dichloromethane (2×75 mL). The combined organic layers were dried over sodium sulfate and concentrated to give 3-bromo-N-cyano-propanamide as a light yellow liquid.

1H NMR (400 MHz, d6-DMSO) 12.40 (br s, 1H) 3.54-3.70 (m, 2H) 2.80-2.94 (m, 2H)

Example 49: Preparation of [(1S)-1-carboxy-4-(4-pyrimidin-2-ylpyridazin-1-ium-1-yl)butyl]ammonium Dichloride A211

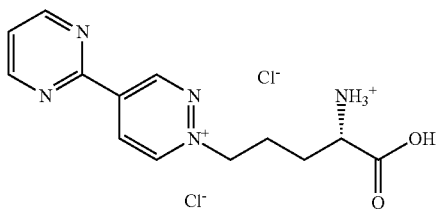 [SMILES: [NH3+][C@@H](CCC[n+]1ccc(-c2ncccn2)cn1)C(=O)O ; [Cl-] ; [Cl-]]

Step 1: Preparation of dimethyl (2S)-2-[bis(tert-butoxycarbonyl)amino]pentanedioate

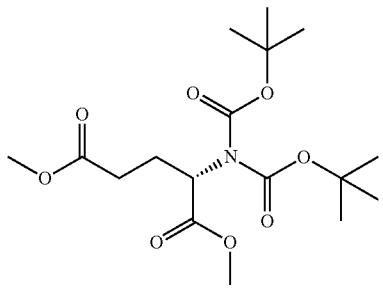 [SMILES: COC(=O)CC[C@@H](C(=O)OC)N(C(=O)OC(C)(C)C)C(=O)OC(C)(C)C]

To a solution of dimethyl (2S)-2-(tert-butoxycarbonylamino)pentanedioate (0.3 g) in acetonitrile (6 mL), under nitrogen atmosphere, was added 4-dimethylaminopyridine (0.028 g). The mixture was cooled to 0° C. and di-tert-butyl dicarbonate (0.264 g) was added. The reaction was allowed to warm to room temperature and stirred for 18 hours. The reaction mixture was partitioned between water and ethyl acetate (80 mL) and extracted with further ethyl acetate (80 mL). The combined organic layers were washed with 10% aqueous citric acid, followed by saturated sodium bicarbonate solution and brine. The combined organic layers were dried over sodium sulfate, concentrated and purified on silica using ethyl acetate in cyclohexane to give dimethyl (2S)-2-[bis(tert-butoxycarbonyl)amino]pentanedioate as a colourless gum.

1H NMR (400 MHz, CDCl₃) 4.95 (dd, 1H) 3.73 (s, 3H) 3.68 (s, 3H) 2.36-2.54 (m 3H) 2.15-2.23 (m, 1H) 1.50 (s, 18H)

Step 2: Preparation of Methyl (2S)-2-[bis(tert-butoxycarbonyl)amino]-5-oxo-pentanoate

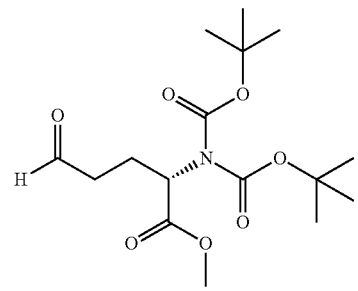 [SMILES: COC(=O)[C@H](CCC=O)N(C(=O)OC(C)(C)C)C(=O)OC(C)(C)C]

Cooled a solution of dimethyl (2S)-2-[bis(tert-butoxycarbonyl)amino]pentanedioate (0.28 g) in diethyl ether (5.6 mL), under nitrogen atmosphere, to −78° C. and added slowly diisobutylaluminum hydride (1M in Toluene, 0.82 mL). The reaction was stirred at −78° C. for 10 minutes, then quenched with water (0.094 mL) and stirred for a further 30 minutes. After warming to room temperature solid sodium sulfate was added. The mixture was filtered through Celite, washed with tert-butylmethylether and the filtrate concentrated to give methyl (2S)-2-[bis(tert-butoxycarbonyl)amino]-5-oxo-pentanoate.

1H NMR (400 MHz, CDCl₃) 9.78 (s, 1H) 4.90 (dd, 1H) 3.73 (m, 3H) 2.45-2.66 (m, 3H) 2.11-2.28 (m, 1H) 1.42-1.63 (m, 18H)

Step 3: Preparation of Methyl (2S)-2-[bis(tert-butoxycarbonyl)amino]-5-hydroxy-pentanoate

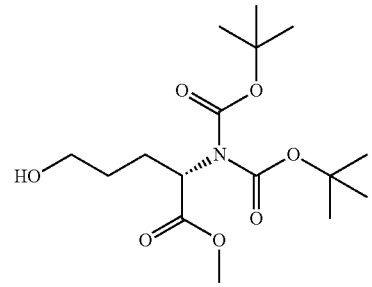 [SMILES: COC(=O)[C@H](CCCBr)N(C(=O)OC(C)(C)C)C(=O)OC(C)(C)C]

Cooled a solution of methyl (2S)-2-[bis(tert-butoxycarbonyl)amino]-5-oxo-pentanoate (0.2 g) in dry methanol (4 mL), under nitrogen atmosphere, to 0° C. and added sodium borohydride (0.025 g) portion wise and stirred for 2 hours. The reaction mixture was concentrated and purified on silica using ethyl acetate in cyclohexane to give methyl (2S)-2-[bis(tert-butoxycarbonyl)amino]-5-hydroxy-pentanoate as a colourless gum.

1H NMR (400 MHz, CDCl$_3$) 4.90 (dd, 1H) 3.74-3.67 (m, 5H) 2.30-2.20 (m, 1H) 1.99-1.89 (m, 1H) 1.68-1.41 (s, 20H) (one OH proton missing)

Step 4: Preparation of methyl (2S)-2-[bis(tert-butoxycarbonyl)amino]-5-bromo-pentanoate

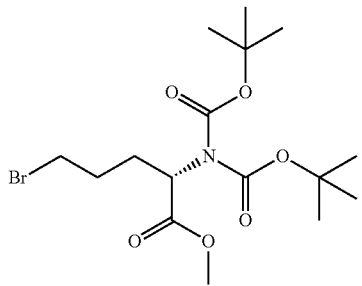

Cooled a solution of methyl (2S)-2-[bis(tert-butoxycarbonyl)amino]-5-hydroxy-pentanoate (4 g) in dry tetrahydrofuran (40 mL) to 0° C. and added carbon tetrabromide (5.728 g). To this was added drop wise a solution of triphenylphosphine (4.576 g) in tetrahydrofuran (40 mL). The reaction was allowed to warm to room temperature and stirred for 24 hours. The reaction mixture was concentrated and purified on silica using ethyl acetate in cyclohexane to give methyl (2S)-2-[bis(tert-butoxycarbonyl)amino]-5-bromo-pentanoate.

1H NMR (400 MHz, CDCl$_3$) 4.88 (dd, 1H) 3.73 (s, 3H) 3.38-3.50 (m, 2H) 2.24-2.27 (m, 1H) 1.85-2.12 (m, 3H) 1.51 (s, 18H)

Step 5: Preparation of [(1S)-1-methoxycarbonyl-4-(4-pyrimidin-2-ylpyridazin-1-ium-1-yl)butyl]ammonium 2,2,2-trifluoroacetate

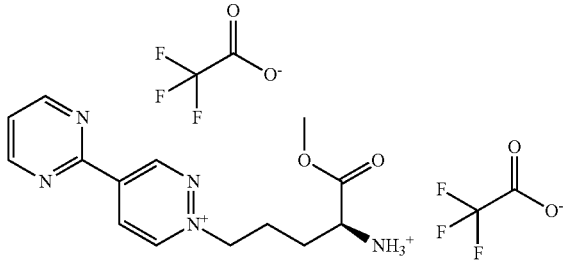 [SMILES: COC(=O)[C@@H]([NH3+])CCC[n+]1ccc(-c2ncccn2)cn1 ; O=C([O-])C(F)(F)F ; O=C([O-])C(F)(F)F]

To a mixture of 2-pyridazin-4-ylpyrimidine (0.4 g) in acetonitrile (12.6 mL) was added methyl (2S)-2-[bis(tert-butoxycarbonyl)amino]-5-bromo-pentanoate (1.141 g) and the reaction mixture was heated at reflux for 12 hours. The reaction mixture was concentrated and purified by preparative reverse phase HPLC (trifluoroacetic acid is present in the eluent which led to the loss of the BOC-protecting groups) to give [(1S)-1-methoxycarbonyl-4-(4-pyrimidin-2-ylpyridazin-1-ium-1-yl)butyl]ammonium 2,2,2-trifluoroacetate.

1H NMR (400 MHz, D$_2$O) 10.22 (d, 1H) 9.80-9.86 (m, 1H) 9.20-9.27 (m, 1H) 8.99-9.06 (m, 2H) 7.66-7.73 (m, 1H) 4.90-5.01 (m, 2H) 4.20 (t, 1H) 3.76-3.84 (m, 3H) 2.20-2.40 (m, 2H) 1.97-2.18 (m, 2H) (NH protons are missing)

Step 6: Preparation of [(1S)-1-carboxy-4-(4-pyrimidin-2-ylpyridazin-1-ium-1-yl)butyl]ammonium dichloride A211

A mixture of [(1S)-1-methoxycarbonyl-4-(4-pyrimidin-2-ylpyridazin-1-ium-1-yl)butyl]ammonium; 2,2,2-trifluoroacetate (0.1 g) and 4M aqueous hydrochloric acid (0.78 mL) was heated at 60° C. for 14 hours. The reaction mixture was concentrated to give [(1S)-1-carboxy-4-(4-pyrimidin-2-ylpyridazin-1-ium-1-yl)butyl]ammonium dichloride.

1H NMR (400 MHz, D$_2$O) 10.24 (dd, 1H) 9.87 (dd, 1H) 9.27 (dd, 1H) 9.06 (d, 2H) 7.72 (t, 1H) 4.99 (t, 2H) 4.08 (t, 1H) 2.23-2.44 (m, 2H) 2.00-2.16 (m, 2H) (three NH protons and one C$_{O2}$H proton missing)

Example 50: Preparation of 3-(4-pyrimidin-2-ylpyridazin-1-ium-1-yl)propanoic Acid Chloride A26

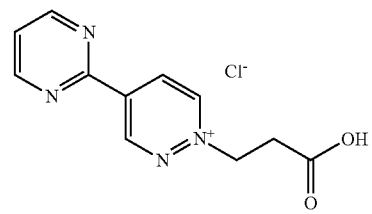 [SMILES: O=C(O)CC[n+]1ccc(-c2ncccn2)cn1 ; [Cl-]]

Step 1: Preparation of methyl 3-(4-pyrimidin-2-ylpyridazin-1-ium-1-yl)propanoate 2,2,2-trifluoroacetate A54

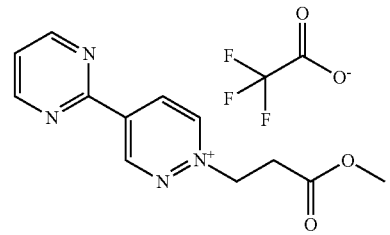 [SMILES: COC(=O)CC[n+]1ccc(-c2ncccn2)cn1 ; O=C([O-])C(F)(F)F]

A mixture of methyl 3-bromopropanoate (1.58 g), 2-pyridazin-4-ylpyrimidine (0.5 g) in acetonitrile (31.6 mL) was heated at 80° C. for 24 hours. The reaction mixture was cooled, concentrated and partitioned between water (10 mL) and dichloromethane (20 mL). The aqueous layer was purified by preparative reverse phase HPLC (trifluoroacetic acid is present in the eluent) to give methyl 3-(4-pyrimidin-2-ylpyridazin-1-ium-1-yl)propanoate 2,2,2-trifluoroacetate as an orange gum.

$^1$H NMR (400 MHz, D$_2$O) 10.15 (d, 1H) 9.85 (d, 1H) 9.18 (dd, 1H) 8.98 (d, 2H) 7.63 (t, 1H) 5.12 (t, 2H) 3.59 (s, 3H) 3.25 (t, 2H)

$^1$H NMR (400 MHz, CD$_3$OD) 10.43-10.32 (m, 1H) 10.04 (d, 1H) 9.43 (dd, 1H) 9.12 (d, 2H) 7.65 (t, 1H) 5.18 (t, 2H) 3.70 (s, 3H) 3.36-3.27 (m, 2H)

Step 2: 3-(4-pyrimidin-2-ylpyridazin-1-ium-1-yl)propanoic Acid Chloride A26

A mixture of methyl 3-(4-pyrimidin-2-ylpyridazin-1-ium-1-yl)propanoate; 2,2,2-trifluoroacetate (0.392 g) and conc. hydrochloric acid (7.66 mL) was heated at 80° C. for 3 hours. The reaction mixture was cooled, concentrated and triturated with acetone to give 3-(4-pyrimidin-2-ylpyridazin-1-ium-1-yl)propanoic acid chloride as a beige solid.

¹H NMR (400 MHz, D₂O) 10.16 (d, 1H) 9.85 (d, 1H) 9.18 (dd, 1H) 8.99 (d, 2H) 7.64 (t, 1H) 5.11 (t, 2H) 3.24 (t, 2H) (one C₀₂H proton missing)

¹H NMR (400 MHz, CD₃OD) 10.43-10.32 (m, 1H) 10.02 (d, 1H) 9.36 (dd, 1H) 9.09 (d, 2H) 7.68 (t, 1H) 5.16 (t, 2H) 3.29-3.21 (m, 2H) (one C₀₂H proton missing)

Example 51: Preparation of methoxy-[(4-pyrimidin-2-ylpyridazin-1-ium-1-yl)methyl]phosphinate A245

Step 1: Preparation of Dimethoxyphosphorylmethyl Trifluoromethanesulfonate

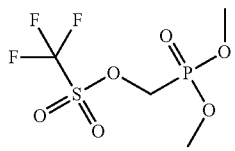

A solution of dimethoxyphosphorylmethanol (1 g) in dichloromethane (20 mL) was cooled to −78° C. and 2,6-Lutidine (1.32 mL) followed by trifluoromethylsulfonyl trifluoromethanesulfonate (1.91 g) was added. The resulting reaction mixture was allowed to warm to room temperature and stirred for 1 hour. The reaction mixture was poured into water and extracted with dichloromethane (50 mL). The organic layer was washed with 1M aqueous hydrochloric acid (50 mL), dried over anhydrous sodium sulfate and concentrated to give dimethoxyphosphorylmethyl trifluoromethanesulfonate as a pale yellow liquid.

1H NMR (400 MHz, d₆-DMSO) 4.82 (d, 2H) 3.78 (s, 3H) 3.74 (s, 3H)

Step 2: Preparation of 1-(dimethoxyphosphorylmethyl)-4-pyrimidin-2-yl-pyridazin-1-ium trifluoromethanesulfonate A238

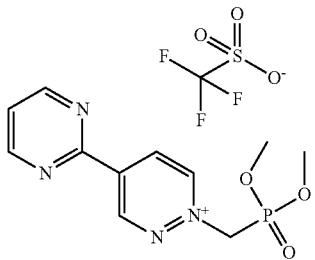 [SMILES: COP(=O)(C[n+]1ccc(-c2ncccn2)cn1)OC ; O=S(=O)([O-])C(F)(F)F]

To a stirred solution of 2-pyridazin-4-ylpyrimidine (0.6 g) in acetonitrile (15 mL) was added dimethoxyphosphorylmethyl trifluoromethanesulfonate (1.549 g) at room temperature. The resulting reaction mixture was stirred at room temperature for 16 hours. The reaction mixture was concentrated and the obtained residue was partitioned between water (75 mL) and dichloromethane (75 mL). The aqueous layer was washed with further dichloromethane (75 mL), concentrated and purified by Reverse Phase chromatography using 100% water (note: no added trifluoroacetic acid) to give 1-(dimethoxyphosphorylmethyl)-4-pyrimidin-2-yl-pyridazin-1-ium trifluoromethanesulfonate as a brown liquid 1H NMR (400 MHz, D₂O) 10.37 (d, 1H) 10.00 (d, 1H) 9.48-9.42 (m, 1H) 9.23-9.20 (m, 2H) 7.83 (t, 1H) 5.82 (d, 2H) 3.83 (s, 3H) 3.82-3.78 (m, 3H)

Step 3: Preparation of methoxy-[(4-pyrimidin-2-ylpyridazin-1-ium-1-yl)methyl]phosphinate A245

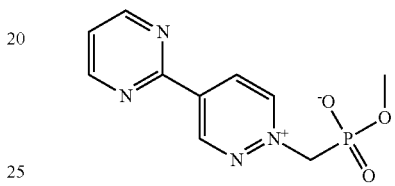

To a stirred solution of 1-(dimethoxyphosphorymethyl)-4-pyrimidin-2-yl-pyridazin-1-ium trifluoromethanesulfonate (0.1 g) in dichloromethane (10 mL) was added bromotrimethylsilane (0.097 mL) at room temperature. The reaction mixture was stirred at room temperature for 2 hours. The reaction was concentrated and the residue was dissolved in water (25 mL) and washed with dichloromethane (2×25 mL). The aqueous layer was concentrated and purified by preparative reverse phase HPLC (trifluoroacetic acid is present in the eluent) to give methoxy-[(4-pyrimidin-2-ylpyridazin-1-ium-1-yl)methyl]phosphinate as a light brown solid.

1H NMR (400 MHz, D₂O) 10.19-10.15 (m, 1H) 9.73-9.69 (m, 1H) 9.25-9.20 (m, 1H) 9.01 (d, 2H) 7.68-7.62 (m, 1H) 5.19 (d, 2H) 3.61 (d, 3H)

Additional compounds in Table A (below) were prepared by analogues procedures, from appropriate starting materials. The skilled person would understand that the compounds of Formula (I) may exist as an agronomically acceptable salt, a zwitterion or an agronomically acceptable salt of a zwitterion as described hereinbefore. Where mentioned the specific counterion is not considered to be limiting, and the compound of Formula (I) may be formed with any suitable counter ion.

NMR spectra contained herein were recorded on either a 400 MHz Bruker AVANCE III HD equipped with a Bruker SMART probe unless otherwise stated. Chemical shifts are expressed as ppm downfield from TMS, with an internal reference of either TMS or the residual solvent signals. The following multiplicities are used to describe the peaks: s=singlet, d=doublet, t=triplet, dd=double doublet, dt=double triplet, q=quartet, quin=quintet, m=multiplet. Additionally br. is used to describe a broad signal and app. is used to describe and apparent multiplicity.

Additional compounds in Table A were prepared by analogous procedures, from appropriate starting materials.

TABLE A

Physical Data for Compounds of the Invention

| Compound Number | Structure | $^1$H NMR |
|---|---|---|
| A1 | 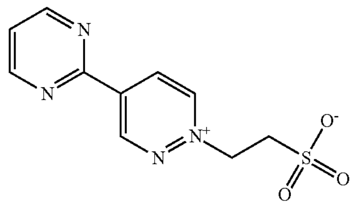 [SMILES: O=S(=O)([O-])CC[n+]1ccc(-c2ncccn2)cn1] | (400 MHz, D$_2$O) 10.19 (d, 1H) 9.84 (d, 1H) 9.20 (dd, 1H) 8.99 (d, 2H) 7.64 (t, 1H) 5.27-5.18 (m, 2H) 3.71-3.63 (m, 2H) |
| A2 | 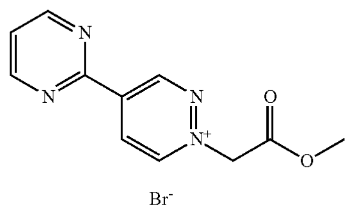 [SMILES: COC(=O)C[n+]1ccc(-c2ncccn2)cn1 ; [Br-]] | (400 MHz, D$_2$O) 10.22 (d, 1H) 9.84 (d, 1H) 9.30 (dd, 1H) 9.01 (d, 2H) 7.66 (t, 1H) 5.84 (s, 2H) 3.79 (s, 3H) |
| A3 | 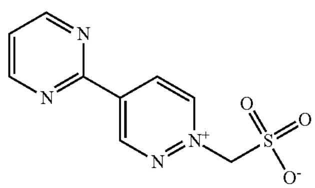 [SMILES: O=S(=O)([O-])C[n+]1ccc(-c2ncccn2)cn1] | (400 MHz, D$_2$O) 10.26 (brs, 1H) 9.94 (br d, 1H) 9.27-9.39 (m, 1H) 8.96-9.14 (m, 2H) 7.56-7.73 (m, 1H) 5.97 (s, 2H) |
| A4 | 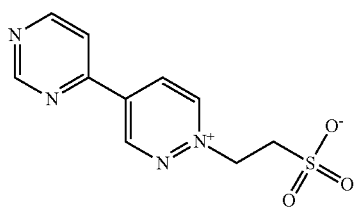 [SMILES: O=S(=O)([O-])CC[n+]1ccc(-c2ccncn2)cn1] | (400 MHz, D$_2$O) 10.09 (d, 1H) 9.87 (d, 1H) 9.35 (d, 1H) 9.12 (dd, 1H) 9.04 (d, 1H) 8.29 (dd, 1H) 5.24 (t, 2H) 3.67 (t, 2H) |
| A5 | 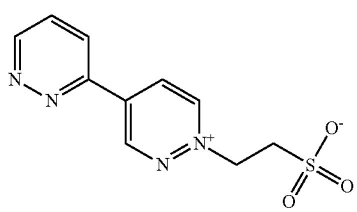 [SMILES: O=S(=O)([O-])CC[n+]1ccc(-c2cccnn2)cn1] | (400 MHz, D$_2$O) 10.15 (d, 1H) 9.87 (d, 1H) 9.33 (dd, 1H) 9.12 (dd, 1H) 8.52 (dd, 1H) 7.99 (dd, 1H) 5.32-5.19 (m, 2H) 3.73-3.65 (m, 2H) |
| A6 | 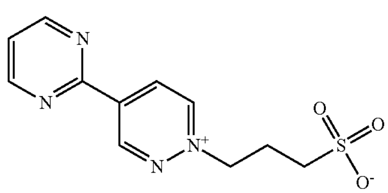 [SMILES: O=S(=O)([O-])CCC[n+]1ccc(-c2ncccn2)cn1] | (400 MHz, D$_2$O) 10.18 (d, 1H) 9.80 (d, 1H) 9.19 (dd, 1H) 9.00 (d, 2H) 7.64 (t, 1H) 5.01 (t, 2H) 2.98 (t, 2H) 2.53 (quin, 2H) |
| A7 | 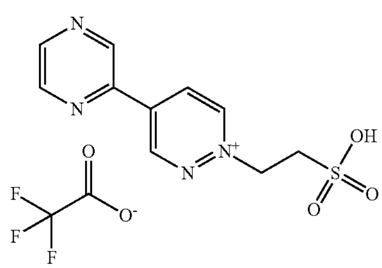 [SMILES: O=C([O-])C(F)(F)F ; O=S(=O)(O)CC[n+]1ccc(-c2cnccn2)cn1] | (400 MHz, D$_2$O) 10.08 (d, 1H) 9.79 (d, 1H) 9.39 (d, 1H) 9.08 (dd, 1H) 8.89-8.83 (m, 1H) 8.78 (d, 1H) 5.24-5.16 (t, 2H) 3.65 (t, 2H) |

TABLE A-continued

Physical Data for Compounds of the Invention

| Compound Number | Structure | ¹H NMR |
|---|---|---|
| A8 | 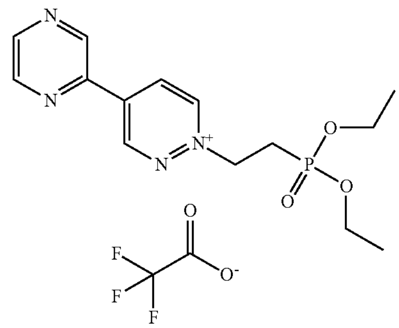 [SMILES: CCOP(=O)(CC[n+]1ccc(-c2cnccn2)cn1)OCC ; O=C([O-])C(F)(F)F] | (400 MHz, CD₃OD) 10.32 (d, 1H) 10.02 (d, 1H) 9.65 (d, 1H) 9.34 (dd, 1H) 8.98-8.94 (m, 1H) 8.92-8.89 (m, 1H) 5.22-5.12 (m, 2H) 4.22-4.11 (m, 4H) 2.87-2.76 (m, 2H) 1.38-1.31 (m, 6H) |
| A9 | 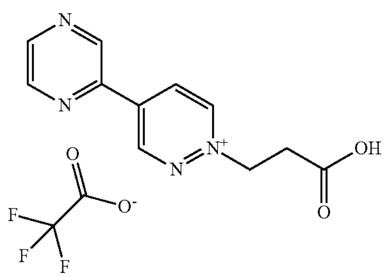 [SMILES: O=C([O-])C(F)(F)F ; O=C(O)CC[n+]1ccc(-c2cnccn2)cn1] | (400 MHz, CD₃OD) 10.28 (d, 1H) 10.00 (d, 1H) 9.62 (d, 1H) 9.28 (dd, 1H) 8.96-8.93 (m, 1H) 8.90 (d, 1H) 5.19-5.12 (t, 2H) 3.28 (t, 2H) (one CO₂H proton missing) |
| A10 | 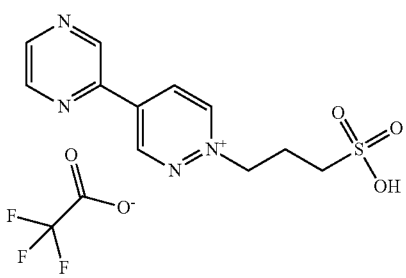 [SMILES: O=C([O-])C(F)(F)F ; O=S(=O)(O)CCC[n+]1ccc(-c2cnccn2)cn1] | (400 MHz, CD₃OD) 10.27 (d, 1H) 9.93 (d, 1H) 9.63 (d, 1H) 9.28 (dd, 1H) 8.96-8.92 (m, 1H) 8.88 (d, 1H) 5.11 (t, 2H) 2.95 (t, 2H) 2.62 (quin, 2H) |
| A11 | 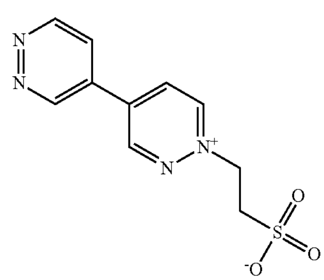 | (400 MHz, D₂O) 9.80-9.97 (m, 2H) 9.62-9.75 (m, 1H) 9.35-9.50 (m, 1H) 8.97 (dd, 1H) 8.19-8.42 (m, 1H) 5.20-5.29 (m, 2H) 3.59-3.73 (m, 2H) |
| A12 | 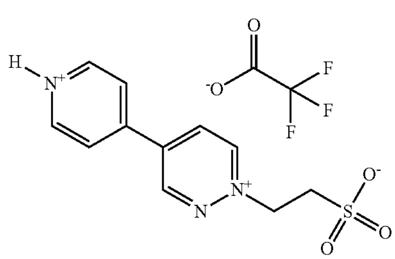 | (400 MHz, D₂O) 9.86-9.95 (m, 2H) 8.90-9.00 (m, 3H) 8.35 (brd, 2H) 5.27 (t, 2H) 3.69 (t, 2H) (one NH proton missing) |

TABLE A-continued

Physical Data for Compounds of the Invention

| Compound Number | Structure | ¹H NMR |
|---|---|---|
| A13 | 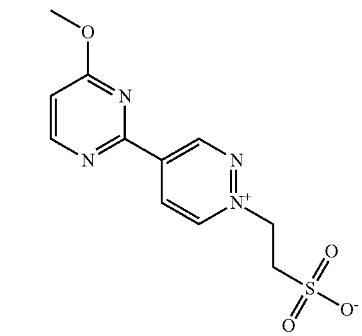 [SMILES: COc1ccnc(-c2cc[n+](CCS(=O)(=O)[O-])nc2)n1] | (400 MHz, D$_2$O) 10.28 (s, 1H) 9.88 (d, 1H) 9.27 (d, 1H) 8.71 (d, 1H) 7.10 (d, 1H) 5.29 (t, 2H) 4.13 (s, 3H) 3.74 (t, 2H) |
| A14 | 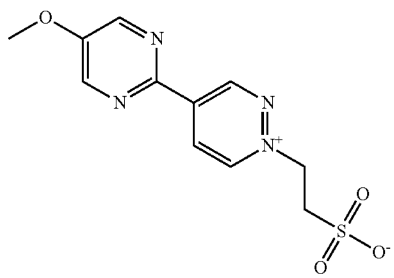 [SMILES: COc1cnc(-c2cc[n+](CCS(=O)(=O)[O-])nc2)nc1] | (400 MHz, D$_2$O) 10.19 (s, 1H) 9.78 (d, 1H) 9.14 (d, 1H) 8.74 (s, 2H) 5.24 (t, 2H) 4.06 (s, 3H) 3.71 (t, 2H) |
| A15 | 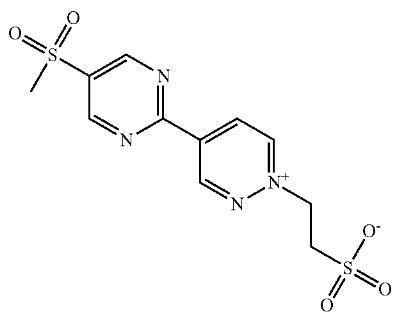 [SMILES: CS(=O)(=O)c1cnc(-c2cc[n+](CCS(=O)(=O)[O-])nc2)nc1] | (400 MHz, D$_2$O) 10.39 (s, 1H) 10.01 (s, 1H) 9.57 (s, 2H) 9.44 (s, 1H) 5.23-5.50 (m, 2H) 3.70-3.85 (m, 2H) 3.45 (s, 3H) |
| A16 | 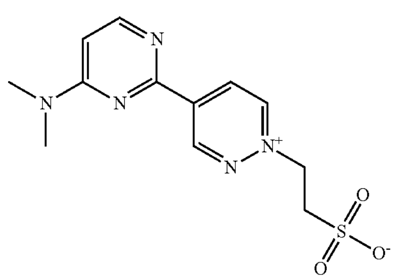 [SMILES: CN(C)c1ccnc(-c2cc[n+](CCS(=O)(=O)[O-])nc2)n1] | (400 MHz, D$_2$O) 10.17 (d, 1H) 10.03 (d, 1H) 9.20 (dd, 1H) 8.23 (d, 1H) 6.99 (d, 1H) 5.35 (m, 2H) 3.74 (m, 2H) 3.35 (s, 6H) |
| A17 | 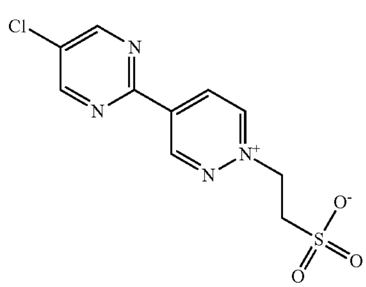 [SMILES: O=S(=O)([O-])CC[n+]1ccc(-c2ncc(Cl)cn2)cn1] | (400 MHz, D$_2$O) 10.24 (d, 1H) 9.86 (d, 1H) 9.24 (dd, 1H) 9.05 (s, 2H) 5.26 (t, 2H) 3.70 (t, 2H) |

TABLE A-continued

Physical Data for Compounds of the Invention

| Compound Number | Structure | ¹H NMR |
|---|---|---|
| A18 | 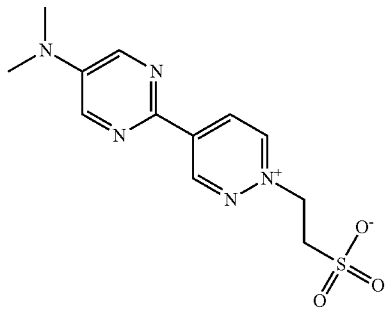 [SMILES: CN(C)c1cnc(-c2cc[n+](CCS(=O)(=O)[O-])nc2)nc1] | (400 MHz, D$_2$O) 9.98 (d, 1H) 9.45 (d, 1H) 8.81 (dd, 1H) 8.37 (s, 2H) 5.06 (t, 2H) 3.56 (t, 2H) 3.12 (s, 6H) |
| A19 | 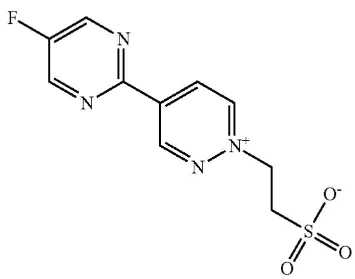 [SMILES: O=S(=O)([O-])CC[n+]1ccc(-c2ncc(F)cn2)cn1] | (400 MHz, D$_2$O) 10.22 (d, 1H) 9.85 (d, 1H) 9.22 (dd, 1H) 8.96 (s, 2H) 5.25 (t, 2H) 3.69 (t, 2H) |
| A20 | 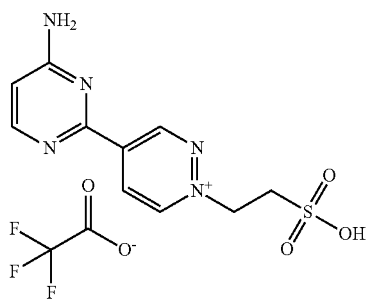 [SMILES: Nc1ccnc(-c2cc[n+](CCS(=O)(=O)O)nc2)n1 ; O=C([O-])C(F)(F)F] | (400 MHz, D$_2$O) 10.11 (d, 1H) 9.96 (d, 1H) 9.13 (dd, 1H) 8.29 (d, 1H) 6.83 (d, 1H) 5.31 (m, 2H) 3.73 (m, 2H) (Two NH$_2$ protons and one SO$_3$H proton missing) |
| A21 | 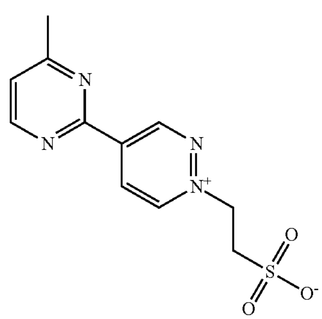 [SMILES: Cc1ccnc(-c2cc[n+](CCS(=O)(=O)[O-])nc2)n1] | (400 MHz, D$_2$O) 10.24 (s, 1H) 9.90 (d, 1H) 9.24 (d, 1H) 8.86 (d, 1H) 7.57 (d, 1H) 5.31 (t, 2H) 3.74 (t, 2H) 2.66 (s, 3H) |
| A22 | 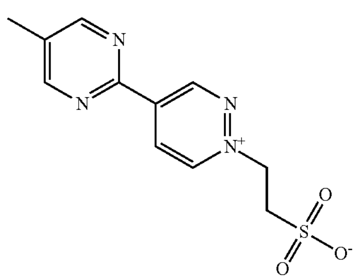 [SMILES: Cc1cnc(-c2cc[n+](CCS(=O)(=O)[O-])nc2)nc1] | (400 MHz, D$_2$O) 10.22 (d, 1H) 9.86 (d, 1H) 9.21 (dd, 1H) 8.90 (s, 2H) 5.25-5.31 (m, 2H) 3.69-3.77 (m, 2H) 2.44 (s, 3H) |

TABLE A-continued

Physical Data for Compounds of the Invention

| Compound Number | Structure | $^1$H NMR |
|---|---|---|
| A23 | 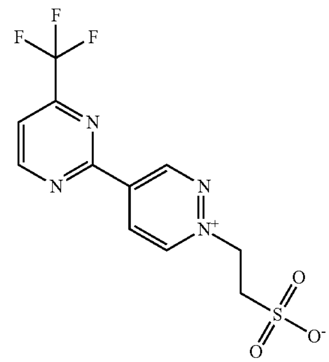 [SMILES: O=S(=O)([O-])CC[n+]1ccc(-c2nccc(C(F)(F)F)n2)cn1] | (400 MHz, D$_2$O) 10.30 (s, 1H) 9.90 (d, 1H) 9.32 (d, 1H) 9.29 (d, 1H) 8.04 (d, 1H) 5.25 (t, 2H) 3.68 (t, 2H) |
| A24 | 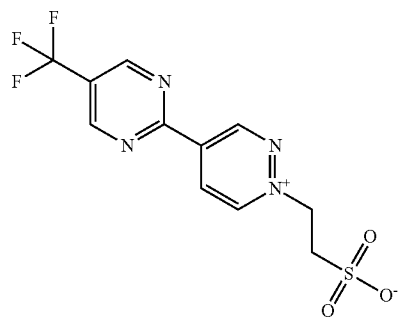 [SMILES: O=S(=O)([O-])CC[n+]1ccc(-c2ncc(C(F)(F)F)cn2)cn1] | (400 MHz, D$_2$O) 10.31 (d, 1H) 9.94 (d, 1H) 9.33-9.38 (m, 3H) 5.26-5.31 (m, 2H) 3.69-3.73 (m, 2H) |
| A25 | 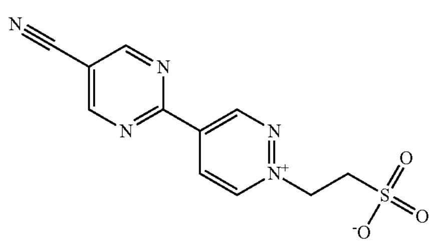 | (400 MHz, D$_2$O) 10.35 (d, 1H) 9.97 (m, 1H) 9.45 (m, 2H) 9.36 (m, 1H) 5.30-5.36 (m, 2H) 3.73 (m, 2H) |
| A26 | 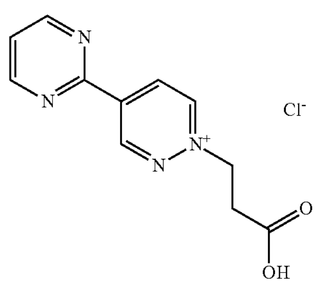 [SMILES: O=C(O)CC[n+]1ccc(-c2ncccn2)cn1 ; [Cl-]] | (400 MHz, D$_2$O) 10.16 (d, 1H) 9.85 (d, 1H) 9.18 (dd, 1H) 8.99 (d, 2H) 7.64 (t, 1H) 5.11 (t, 2H) 3.24 (t, 2H) (one CO$_2$H proton missing) |
| A27 | 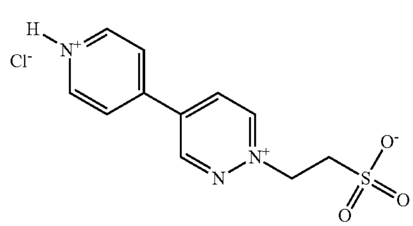 [SMILES: [Cl-] ; O=S(=O)([O-])CC[n+]1ccc(-c2cc[nH+]cc2)cn1] | (400 MHz, D$_2$O) 9.87-9.97 (m, 2H) 8.92-9.07 (m, 3H) 8.44-8.53 (m, 2H) 5.27 (t, 2H) 3.68 (dd, 2H) (one NH proton missing) |

TABLE A-continued

Physical Data for Compounds of the Invention

| Compound Number | Structure | $^1$H NMR |
|---|---|---|
| A28 | 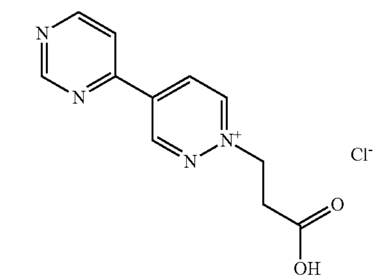 [SMILES: O=C(O)CC[n+]1ccc(-c2ccncn2)cn1 ; [Cl-]] | (400 MHz, CD$_3$OD) 10.32 (d, 1H) 10.13 (d, 1H) 9.56 (s, 1H) 9.42-9.35 (m, 1H) 9.23 (d, 1H) 8.61 (d, 1H) 5.21 (t, 2H) 3.32-3.27 (m, 2H) (one CO$_2$H proton missing) |
| A29 | 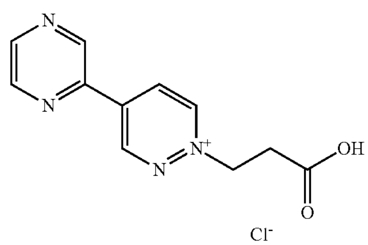 [SMILES: O=C(O)CC[n+]1ccc(-c2cnccn2)cn1 ; [Cl-]] | (400 MHz, D$_2$O) 10.03 (d, 1H) 9.80 (d, 1H) 9.35 (d, 1H) 9.05 (dd, 1H) 8.87-8.82 (m, 1H) 8.76 (d, 1H) 5.08 (t, 2H) 3.22 (t, 2H) (one CO$_2$H proton missing) |
| A30 | 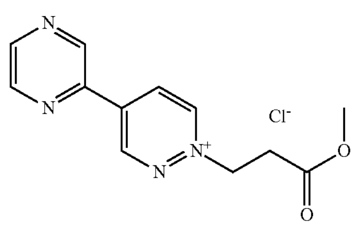 [SMILES: COC(=O)CC[n+]1ccc(-c2cnccn2)cn1 ; [Cl-]] | (400 MHz, CD$_3$OD) 10.30-10.26 (m, 1H) 10.04-10.00 (m, 1H) 9.66-9.64 (m, 1H) 9.33-9.30 (m, 1H) 8.97-8.93 (m, 1H) 8.91-8.88 (m, 1H) 5.25-5.14 (m, 2H) 3.71-3.68 (m, 3H) 3.35-3.27 (m, 2H) |
| A31 | 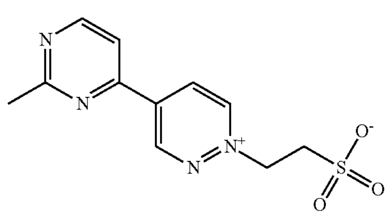 [SMILES: Cc1nccc(-c2cc[n+](CCS(=O)(=O)[O-])nc2)n1] | (400 MHz, D$_2$O) 10.07 (d, 1H) 9.87 (d, 1H) 9.10 (dd, 1H) 8.95 (d, 1H) 8.13 (d, 1H) 5.24 (t, 2H) 3.67 (t, 2H) 2.78 (s, 3H) |
| A32 | 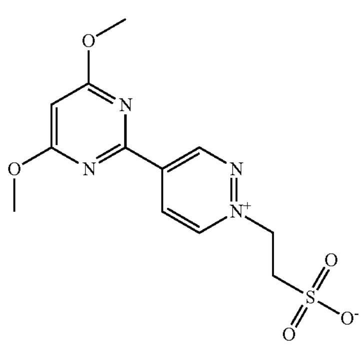 [SMILES: COc1cc(OC)nc(-c2cc[n+](CCS(=O)(=O)[O-])nc2)n1] | (400 MHz, D$_2$O) 10.26 (s, 1H) 9.86 (d, 1H) 9.26 (dd, 1H) 6.42 (s, 1H) 5.28 (t, 2H) 4.06 (s, 6H) 3.74 (t, 2H) |

TABLE A-continued

Physical Data for Compounds of the Invention

| Compound Number | Structure | ¹H NMR |
|---|---|---|
| A33 | 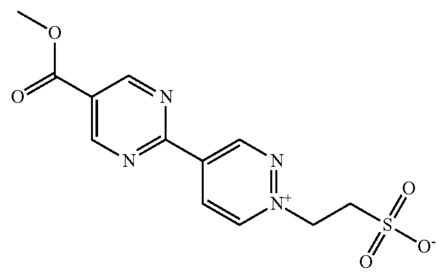 [SMILES: COC(=O)c1cnc(-c2cc[n+](CCS(=O)(=O)[O-])nc2)nc1] | (400 MHz, D$_2$O) 10.34 (d, 1H) 9.96 (d, 1H) 9.54 (s, 2H) 9.37 (m, 1H) 5.25 (m, 2H) 4.02 (s, 3H) 3.70 (m, 2H) |
| A34 | 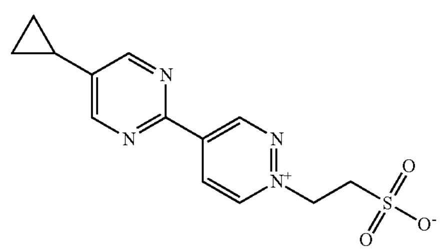 [SMILES: O=S(=O)([O-])CC[n+]1ccc(-c2ncc(C3CC3)cn2)cn1] | (400 MHz, D$_2$O) 10.20 (m, 1H) 9.80 (m, 1H) 9.10 (m, 1H) 8.76 (s, 2H) 5.30 (m, 2H) 3.70 (m, 2H) 2.10 (m, 1H) 1.20 (m, 2H) 0.95 (m, 2H) |
| A35 | 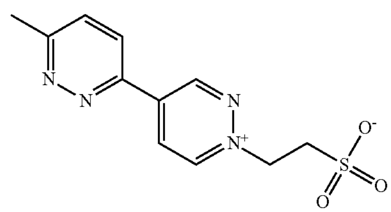 [SMILES: Cc1ccc(-c2cc[n+](CCS(=O)(=O)[O-])nc2)nn1] | (400 MHz, D$_2$O) 10.12 (d, 1H) 9.83 (d, 1H) 9.08 (dd, 1H) 8.42 (d, 1H) 7.89 (d, 1H) 5.28-5.19 (m, 2H) 3.71-3.64 (m, 2H) 2.74 (s, 3H) |
| A36 | 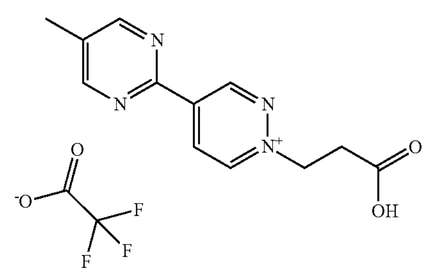 | (400 MHz, D$_2$O) 10.15 (s, 1H) 9.84 (d, 1H) 9.15 (dd, 1H) 8.86 (s, 2H) 5.13 (t, 2H) 3.27 (t, 2H) 2.40 (s, 3H) (one CO$_2$H proton missing) |
| A37 | 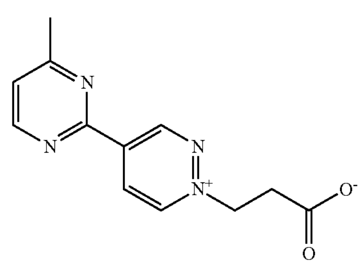 [SMILES: Cc1ccnc(-c2cc[n+](CCC(=O)[O-])nc2)n1] | (400 MHz, D$_2$O) 10.20 (d, 1H) 9.91 (d, 1H) 9.22 (dd, 1H) 8.86 (d, 1H) 7.58 (d, 1H) 5.18 (t, 2H) 3.31 (t, 2H) 2.66 (s, 3H) |
| A38 | 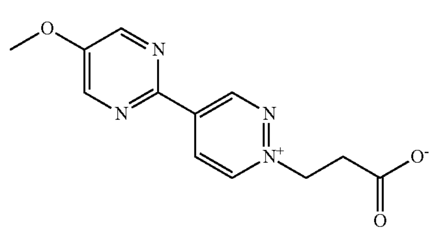 [SMILES: COc1cnc(-c2cc[n+](CCC(=O)[O-])nc2)nc1] | (400 MHz, D$_2$O) 10.15 (d, 1H) 9.79 (d, 1H) 9.12 (dd, 1H) 8.73 (s, 2H) 5.12 (t, 2H) 4.06 (s, 3H) 3.29 (t, 2H) |

TABLE A-continued

Physical Data for Compounds of the Invention

| Compound Number | Structure | ¹H NMR |
|---|---|---|
| A39 | 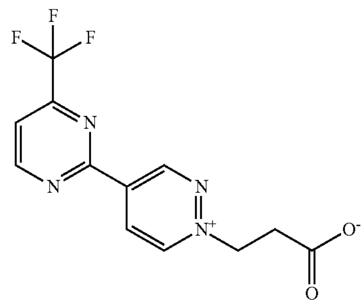 [SMILES: O=C([O-])CC[n+]1ccc(-c2nccc(C(F)(F)F)n2)cn1] | (400 MHz, D$_2$O) 10.32 (d, 1H) 9.96 (d, 1H) 9.32-9.38 (m, 2H) 8.10 (d, 1H) 5.19 (t, 2H) 3.30 (t, 2H) |
| A40 | 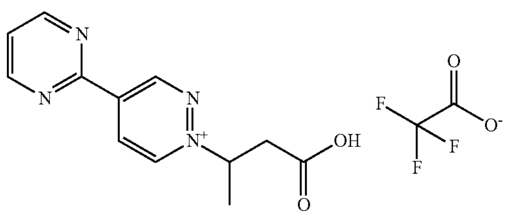 [SMILES: CC(CC(=O)O)[n+]1ccc(-c2ncccn2)cn1 ; O=C([O-])C(F)(F)F] | (400 MHz, D$_2$O) 10.22 (d, 1H) 9.92 (d, 1H) 9.18-9.26 (m, 1H) 8.99-9.05 (m, 2H) 7.68 (t, 1H) 5.49-5.60 (m, 1H) 3.39 (dd, 1H) 3.10-3.21 (m, 1H) 1.71 (d, 3H) (One CO$_2$H proton missing) |
| A41 | 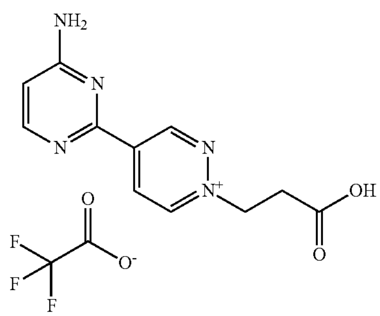 [SMILES: O=C([O-])C(F)(F)F ; Nc1ccnc(-c2cc[n+](CCC(=O)O)nc2)n1] | (400 MHz, D$_2$O) 10.06 (s, 1H) 10.00 (d, 1H) 9.13 (dd, 1H) 8.28 (d, 1H) 6.85 (d, 1H) 5.20 (t, 2H) 3.31 (t, 2H) (Two NH$_2$ protons and one CO$_2$H proton missing) |
| A42 | 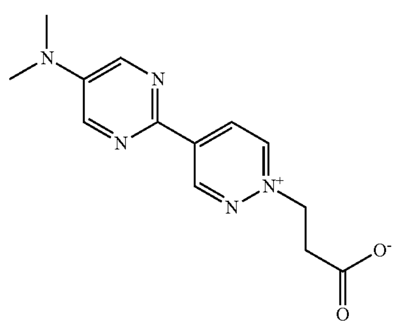 [SMILES: CN(C)c1cnc(-c2cc[n+](CCC(=O)[O-])nc2)nc1] | (400 MHz, D$_2$O) 9.93 (d, 1H) 9.53 (d, 1H) 8.80 (dd, 1H) 8.35 (s, 2H) 5.01 (t, 2H) 3.23 (t, 2H) 3.14 (s, 6H) |
| A43 | 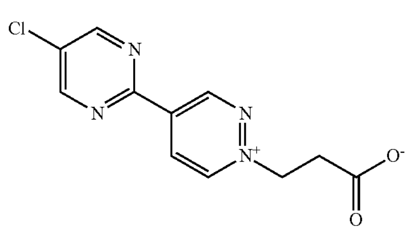 [SMILES: O=C([O-])CC[n+]1ccc(-c2ncc(Cl)cn2)cn1] | (400 MHz, D$_2$O) 10.18 (s, 1H) 9.86 (brd, 1H) 9.21 (dd, 1H) 9.03 (s, 2H) 5.12 (t, 2H) 3.25 (t, 2H) |

TABLE A-continued

Physical Data for Compounds of the Invention

| Compound Number | Structure | ¹H NMR |
|---|---|---|
| A44 | 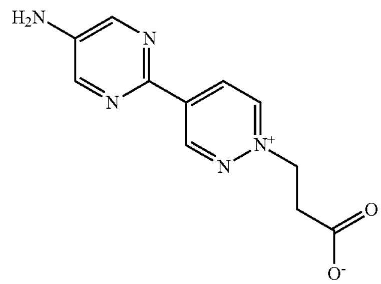 [SMILES: Nc1cnc(-c2cc[n+](CCC(=O)[O-])nc2)nc1] | (400 MHz, D₂O) 9.98 (br s, 1H) 9.60 (br d, 1H) 8.88 (br d, 1H) 8.37 (s, 2H) 5.03 (br t, 2H) 3.20 (br t, 2H) (Two NH₂ protons missing) |
| A45 | 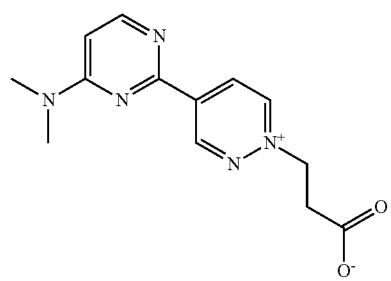 [SMILES: CN(C)c1ccnc(-c2cc[n+](CCC(=O)[O-])nc2)n1] | (400 MHz, D₂O) 10.07 (s, 1H) 9.83 (d, 1H) 9.07 (dd, 1H) 8.15 (d, 1H) 6.76 (d, 1H) 5.10 (t, 2H) 3.20 (t, 2H) 3.16 (s, 6H) |
| A46 | 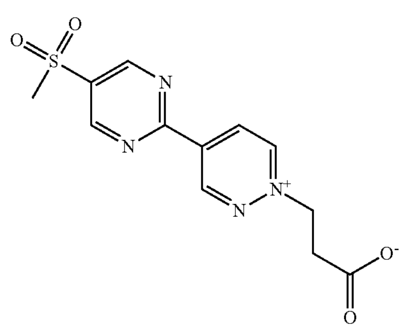 [SMILES: CS(=O)(=O)c1cnc(-c2cc[n+](CCC(=O)[O-])nc2)nc1] | (400 MHz, D₂O) 10.33 (d, 1H) 10.00 (d, 1H) 9.54 (s, 2H) 9.40 (dd, 1H) 5.20 (t, 2H) 3.43 (s, 3H) 3.32 (t, 2H) |
| A47 | 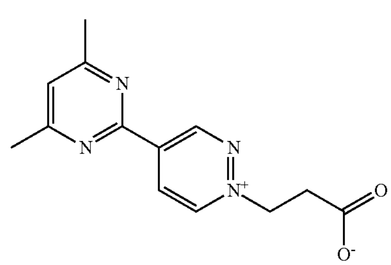 [SMILES: Cc1cc(C)nc(-c2cc[n+](CCC(=O)[O-])nc2)n1] | (400 MHz, D₂O) 10.09 (d, 1H) 9.81 (d, 1H) 9.10 (m, 1H) 7.37 (s, 1H) 5.08 (t, 2H) 3.21 (t, 2H) 2.51 (s, 6H) |
| A48 | 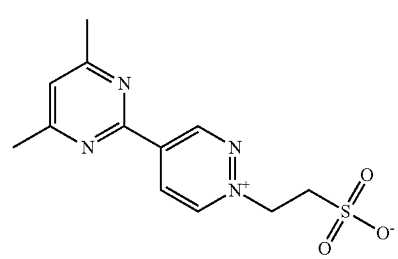 [SMILES: Cc1cc(C)nc(-c2cc[n+](CCS(=O)(=O)[O-])nc2)n1] | (400 MHz, D₂O) 10.13 (s, 1H) 9.80 (d, 1H) 9.12 (dd, 1H) 7.27-7.42 (m, 1H) 5.21 (t, 2H) 3.66 (t, 2H) 2.52 (s, 6H) |

TABLE A-continued

Physical Data for Compounds of the Invention

| Compound Number | Structure | ¹H NMR |
|---|---|---|
| A49 | 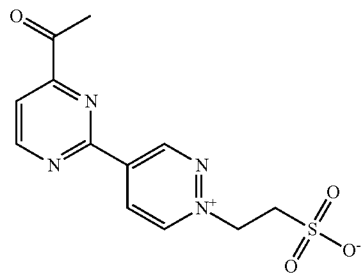 [SMILES: CC(=O)c1ccnc(-c2cc[n+](CCS(=O)(=O)[O-])nc2)n1] | (400 MHz, D$_2$O) 10.39 (d, 1H) 9.92 (d, 1H) 9.39-9.46 (m, 1H) 9.27 (d, 1H) 8.10 (d, 1H) 5.30 (t, 2H) 3.73 (t, 2H) 2.82 (s, 3H) |
| A50 | 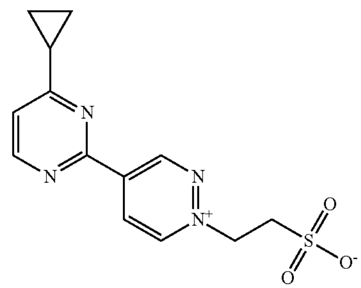 [SMILES: O=S(=O)([O-])CC[n+]1ccc(-c2nccc(C3CC3)n2)cn1] | (400 MHz, D$_2$O) 10.18 (m, 1H) 9.8 (m, 1H) 9.18 (m, 1H) 8.7 (m, 1H) 7.46 (m, 1H) 5.24 (m, 2H) 3.7 (m, 2H) 2.2 (m, 1H) 1.2 (m, 4H) (one OH proton missing) |
| A51 | 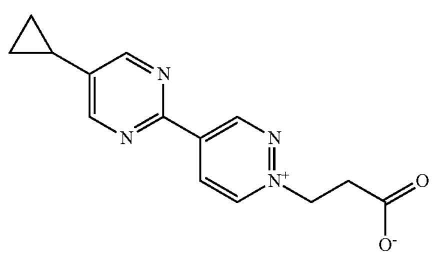 [SMILES: O=C([O-])CC[n+]1ccc(-c2ncc(C3CC3)cn2)cn1] | (400 MHz, D$_2$O) 10.10 (m, 1H) 9.80 (m, 1H) 9.10 (m, 1H) 8.60 (m, 2H) 5.10 (m, 2H) 3.20 (m, 2H) 1.90 (m, 1H) 1.10 (m, 2H) 0.85 (m, 2H) |
| A52 | 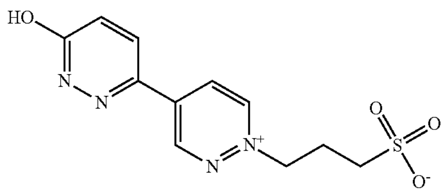 [SMILES: O=S(=O)([O-])CCC[n+]1ccc(-c2ccc(O)nn2)cn1] | (400 MHz, D$_2$O) 9.91 (d, 1H) 9.67 (d, 1H) 8.83 (dd, 1H) 8.22 (d, 1H) 7.19 (d, 1H) 4.93 (t, 2H) 2.95 (t, 2H) 2.49 (quin, 2H) |
| A53 | 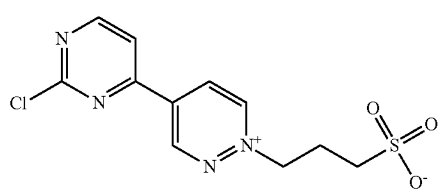 [SMILES: O=S(=O)([O-])CCC[n+]1ccc(-c2ccnc(Cl)n2)cn1] | (400 MHz, D$_2$O) 10.05 (d, 1H) 9.84 (d, 1H) 9.11 (dd, 1H) 8.93 (d, 1H) 8.23 (d, 1H) 5.01 (t, 2H) 2.96 (t, 2H) 2.51 (quin, 2H) |
| A54 | 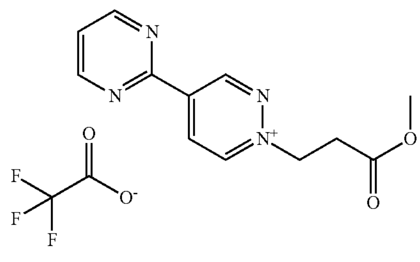 [SMILES: O=C([O-])C(F)(F)F ; COC(=O)CC[n+]1ccc(-c2ncccn2)cn1] | (400 MHz, D$_2$O) 10.15 (d, 1H) 9.85 (d, 1H) 9.18 (dd, 1H) 8.98 (d, 2H) 7.63 (t, 1H) 5.12 (t, 2H) 3.59 (s, 3H) 3.25 (t, 2H) |

TABLE A-continued

Physical Data for Compounds of the Invention

| Compound Number | Structure | ¹H NMR |
|---|---|---|
| A55 | 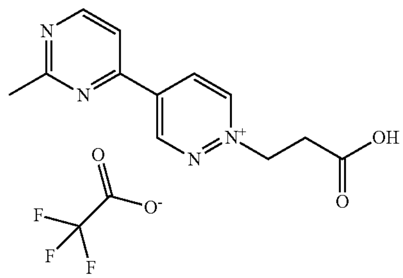 [SMILES: Cc1nccc(-c2cc[n+](CCC(=O)O)nc2)n1 ; O=C([O-])C(F)(F)F] | (400 MHz, CD₃OD) 10.26 (d, 1H) 10.05 (d, 1H) 9.30 (dd, 1H) 9.03 (d, 1H) 8.24 (d, 1H) 5.17 (t, 2H) 3.26 (t, 2H) 2.85 (s, 3H) |
| A56 | 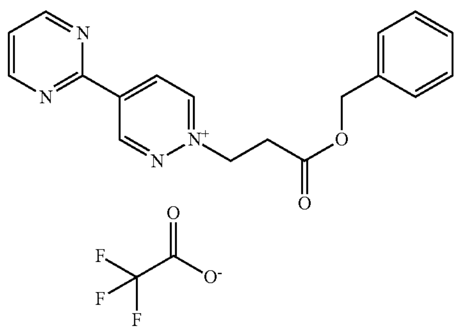 [SMILES: O=C(CC[n+]1ccc(-c2ncccn2)cn1)OCc1ccccc1 ; O=C([O-])C(F)(F)F] | (400 MHz, CD₃OD) 10.21-10.34 (m, 1H) 9.97 (d, 1H) 9.25-9.35 (m, 1H) 9.10-9.15 (m, 2H) 7.60-7.76 (m, 1H) 7.16-7.34 (m, 5H) 5.16-5.24 (m, 2H) 5.05-5.15 (m, 2H) 3.31-3.39 (m, 2H) |
| A57 | 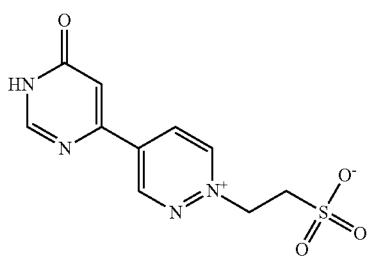 [SMILES: O=c1cc(-c2cc[n+](CCS(=O)(=O)[O-])nc2)nc[nH]1] | (400 MHz, D₂O) 9.94 (d, 1H) 9.81 (d, 1H) 8.97 (dd, 1H) 8.43 (d, 1H) 7.36 (d, 1H) 5.22 (t, 2H) 3.66 (t, 2H) (one NH proton missing) |
| A58 | 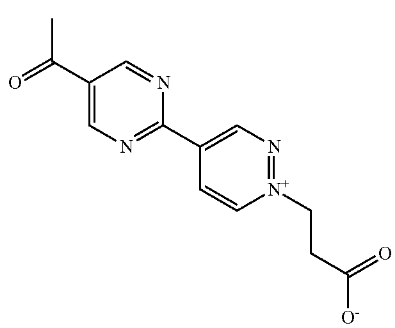 [SMILES: CC(=O)c1cnc(-c2cc[n+](CCC(=O)[O-])nc2)nc1] | (400 MHz, D₂O) 10.29 (m, 1H) 9.91 (m, 1H) 9.49 (s, 2H) 9.31 (m, 1H) 5.14 (m, 2H) 3.26 (m, 2H) 2.74 (s, 3H) |

TABLE A-continued

Physical Data for Compounds of the Invention

| Compound Number | Structure | ¹H NMR |
|---|---|---|
| A59 | 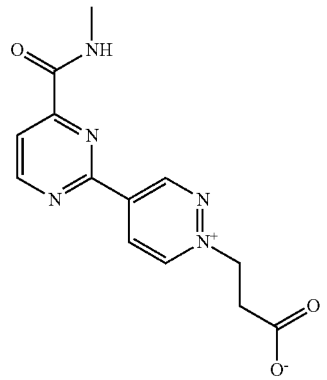 [SMILES: CNC(=O)c1ccnc(-c2cc[n+](CCC(=O)[O-])nc2)n1] | (400 MHz, D₂O) 10.26-10.42 (m, 1H) 9.94 (d, 1H) 9.33-9.49 (m, 1H) 9.23-9.31 (m, 1H) 8.06-8.27 (m, 1H) 8.19 (s, 1H) 5.17 (t, 2H) 3.28 (t, 2H) 3.01 (s, 3H) |
| A60 | 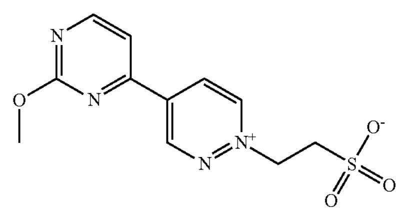 [SMILES: COc1nccc(-c2cc[n+](CCS(=O)(=O)[O-])nc2)n1] | (400 MHz, CD₃OD) 10.28-10.21 (m, 1H) 9.99 (d, 1H) 9.26 (dd, 1H) 8.93 (d, 1H) 8.04 (d, 1H) 5.27 (t, 2H) 4.16 (s, 3H) 3.59 (t, 2H) |
| A61 | 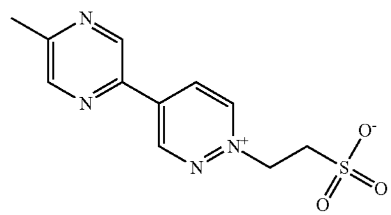 [SMILES: Cc1cnc(-c2cc[n+](CCS(=O)(=O)[O-])nc2)cn1] | (400 MHz, CD₃OD) 10.26-10.22 (m, 1H) 9.87 (d, 1H) 9.49-9.47 (m, 1H) 9.20 (dd, 1H) 8.85-8.82 (m, 1H) 5.24 (t, 2H) 3.58 (t, 2H) 2.71 (s, 3H) |
| A62 | 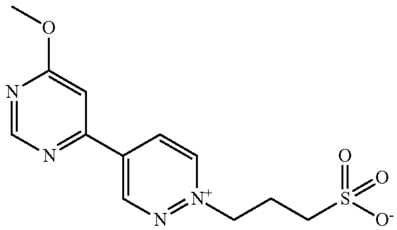 [SMILES: COc1cc(-c2cc[n+](CCCS(=O)(=O)[O-])nc2)ncn1] | (400 MHz, CD₃OD) 10.24-10.20 (m, 1H) 9.93 (d, 1H) 9.24 (dd, 1H) 9.02 (d, 1H) 7.89 (d, 1H) 5.11 (t, 2H) 4.11 (s, 3H) 2.93 (t, 2H) 2.61 (quin, 2H) |
| A63 | 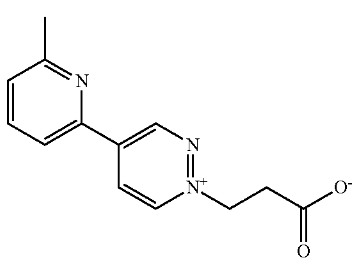 [SMILES: Cc1cccc(-c2cc[n+](CCC(=O)[O-])nc2)n1] | (400 MHz, D₂O) 9.89 (br s, 1H) 9.69 (br d, 1H) 8.82-8.98 (m, 1H) 7.83-8.03 (m, 2H) 7.49 (br d, 1H) 5.02 (br t, 2H) 3.19 (br t, 2H) 2.55 (s, 3H) |
| A64 | 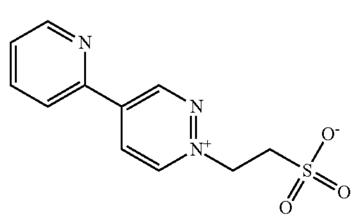 [SMILES: O=S(=O)([O-])CC[n+]1ccc(-c2ccccn2)cn1] | (400 MHz, D₂O) 10.03 (d, 1H) 9.78 (d, 1H) 8.99 (dd, 1H) 8.82 (d, 1H) 8.29 (d, 1H) 8.13 (t, 1H) 7.70 (dd, 1H) 5.24 (t, 2H) 3.71 (t, 2H) |

TABLE A-continued
Physical Data for Compounds of the Invention
| Compound Number | Structure | ¹H NMR |
|---|---|---|
| A65 | 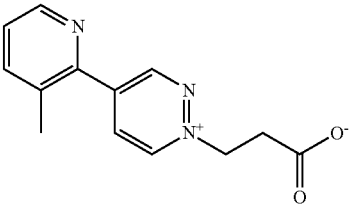 [SMILES: Cc1cccnc1-c1cc[n+](CCC(=O)[O-])nc1] | (400 MHz, D$_2$O) 9.82 (d, 1H) 9.68 (m, 1H) 8.73-8.74 (m, 1H) 8.56-8.57 (m, 1H) 7.91-7.93 (m, 1H) 7.54-7.56 (m, 1H) 5.13 (t, 2H) 3.27 (t, 2H) 2.45 (s, 3H) |
| A66 | 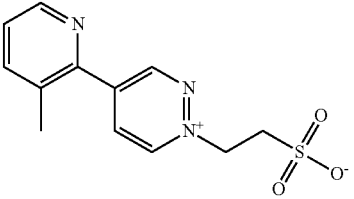 [SMILES: Cc1cccnc1-c1cc[n+](CCS(=O)(=O)[O-])nc1] | (400 MHz, D$_2$O) 9.80 (d, 1H) 9.71 (d, 1H) 8.75 (dd, 1H) 8.52-8.58 (m, 1H) 7.85-7.94 (m, 1H) 7.53 (dd, 1H) 5.21-5.30 (m, 2H) 3.66-3.75 (m, 2H) 2.44 (s, 3H) |
| A67 | 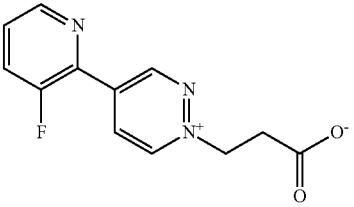 | (400 MHz, D$_2$O) 9.91 (d, 1H) 9.72 (d, 1H) 8.91 (dd, 1H) 8.55 (dt, 1H) 7.74-7.82 (m, 1H) 7.61-7.67 (m, 1H) 5.00-5.05 (m, 2H) 3.18 (t, 2H) |
| A68 | 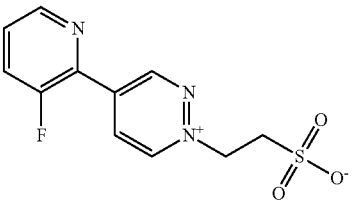 | (400 MHz, D$_2$O) 10.05-10.10 (d, 1H) 9.80 (d, 1H) 8.02 (m, 1H) 8.60-8.69 (m, 1H) 7.83-7.93 (m, 1H) 7.67-7.79 (m, 1H) 5.15-5.35 (m, 2H) 3.69-3.73 (m, 2H) |
| A69 | 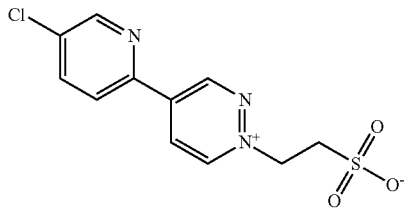 [SMILES: O=S(=O)([O-])CC[n+]1ccc(-c2ccc(Cl)cn2)cn1] | (400 MHz, D$_2$O) 10.03 (d, 1H) 9.74 (d, 1H) 8.98 (dd, 1H) 8.80 (d, 1H) 8.25 (d, 1H) 8.11 (dd, 1H) 5.17-5.24 (m, 2H) 3.65-3.72 (m, 2H) |
| A70 | 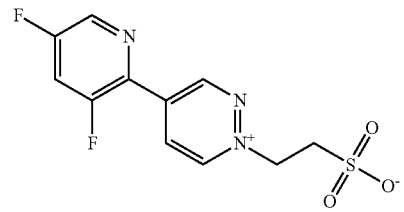 [SMILES: O=S(=O)([O-])CC[n+]1ccc(-c2ncc(F)cc2F)cn1] | (400 MHz, D$_2$O) 10.03 (d, 1H) 9.77 (d, 1H) 8.99 (dd, 1H) 8.63 (d, 1H) 7.77 (dd, 1H) 5.19-5.29 (m, 2H) 3.66-3.72 (m, 2H) |
| A71 | 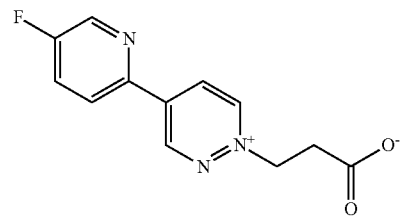 [SMILES: O=C([O-])CC[n+]1ccc(-c2ccc(F)cn2)cn1] | (400 MHz, D$_2$O) 9.99 (d, 1H) 9.75 (d, 1H) 8.94 (dd, 1H) 8.70 (d, 1H) 8.34 (dd, 1H) 7.67-7.90 (m, 1H) 5.09 (t, 2H) 3.24 (t, 2H) |

TABLE A-continued

Physical Data for Compounds of the Invention

| Compound Number | Structure | ¹H NMR |
|---|---|---|
| A72 | 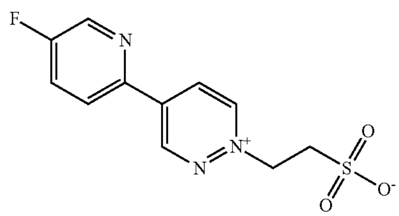 [SMILES: O=S(=O)([O-])CC[n+]1ccc(-c2ccc(F)cn2)cn1] | (400 MHz, D$_2$O) 10.01 (d, 1H) 9.72 (d, 1H) 8.94 (dd, 1H) 8.69 (d, 1H) 8.34 (dd, 1H) 7.74-7.89 (m, 1H) 5.19 (t, 2H) 3.67 (t, 2H) |
| A73 | 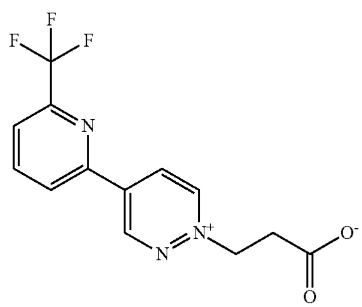 [SMILES: O=C([O-])CC[n+]1ccc(-c2cccc(C(F)(F)F)n2)cn1] | (400 MHz, D$_2$O) 10.11 (d, 1H) 9.83 (d, 1H) 9.08 (dd, 1H) 8.46 (d, 1H) 8.29 (t, 1H) 8.06 (d, 1H) 5.11 (t, 2H) 3.25 (t, 2H) |
| A74 | 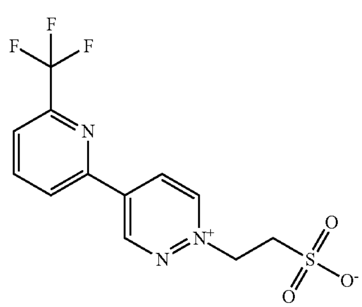 [SMILES: O=S(=O)([O-])CC[n+]1ccc(-c2cccc(C(F)(F)F)n2)cn1] | (400 MHz, D$_2$O) 10.15 (d, 1H) 9.81 (d, 1H) 9.10 (dd, 1H) 8.48 (d, 1H) 8.28 (t, 1H) 8.06 (d, 1H) 5.24 (t, 2H) 3.7 (t, 2H) |
| A75 | 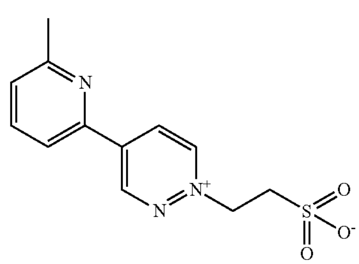 [SMILES: Cc1cccc(-c2cc[n+](CCS(=O)(=O)[O-])nc2)n1] | (400 MHz, D$_2$O) 9.91 (d, 1H) 9.67 (d, 1H) 8.87 (dd, 1H) 7.95-8.03 (m, 1H) 7.85-7.94 (m, 1H) 7.48 (d, 1H) 5.14 (t, 2H) 3.61 (t, 2H) 2.54 (s, 3H) |
| A76 | 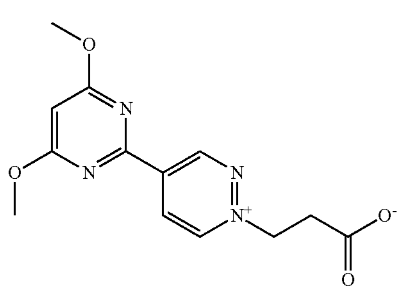 [SMILES: COc1cc(OC)nc(-c2cc[n+](CCC(=O)[O-])nc2)n1] | (400 MHz, D$_2$O) 10.21 (s, 1H) 9.85 (d, 1H) 9.22 (dd, 1H) 6.41 (s, 1H) 5.14 (t, 2H) 4.04 (s, 6H) 3.28 (t, 2H) |

TABLE A-continued

Physical Data for Compounds of the Invention

| Compound Number | Structure | ¹H NMR |
|---|---|---|
| A77 | 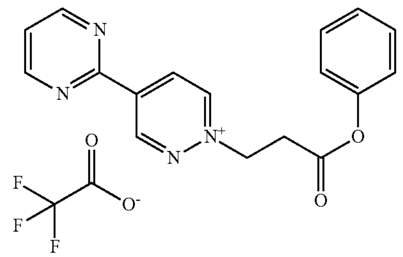 [SMILES: O=C([O-])C(F)(F)F ; O=C(CC[n+]1ccc(-c2ncccn2)cn1)Oc1ccccc1] | (400 MHz, CD₃OD) 10.35-10.47 (m, 1H) 10.05 (d, 1H) 9.37-9.44 (m, 1H) 9.08-9.15 (m, 2H) 7.65-7.78 (m, 1H) 7.32-7.43 (m, 2H) 7.18-7.27 (m, 1H) 7.03-7.15 (m, 2H) 5.30 (t, 2H) 3.58 (t, 2H) |
| A78 | 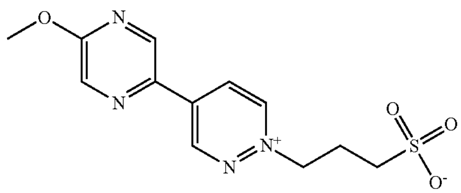 [SMILES: COc1cnc(-c2cc[n+](CCCS(=O)(=O)[O-])nc2)cn1] | (400 MHz, D₂O) 9.98-9.93 (m, 1H) 9.58 (d, 1H) 8.98 (d, 1H) 8.89 (dd, 1H) 8.42 (d, 1H) 4.91 (t, 2H) 4.01 (s, 3H) 2.95 (t, 2H) 2.48 (quin, 2H) |
| A79 | 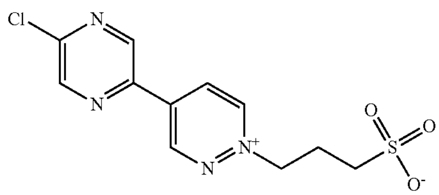 [SMILES: O=S(=O)([O-])CCC[n+]1ccc(-c2cnc(Cl)cn2)cn1] | (400 MHz, D₂O) 10.06-10.04 (m, 1H) 9.76-9.72 (m, 1H) 9.21 (d, 1H) 9.05 (dd, 1H) 8.88 (d, 1H) 4.97 (t, 2H) 2.96 (t, 2H) 2.51 (quin, 2H) |
| A80 | 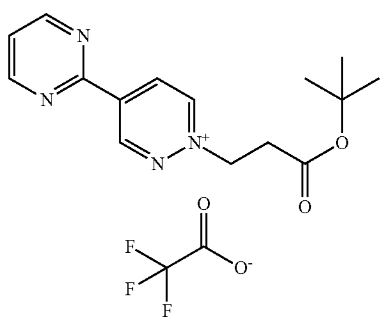 [SMILES: CC(C)(C)OC(=O)CC[n+]1ccc(-c2ncccn2)cn1 ; O=C([O-])C(F)(F)F] | (400 MHz, D₂O) 10.28-10.42 (m, 1H) 9.93-10.10 (m, 1H) 9.37-9.45 (m, 1H) 9.12 (d, 2H) 7.70 (t, 1H) 5.06-5.20 (m, 2H) 3.21 (t, 2H) 1.40-1.46 (m, 9H) |
| A81 | 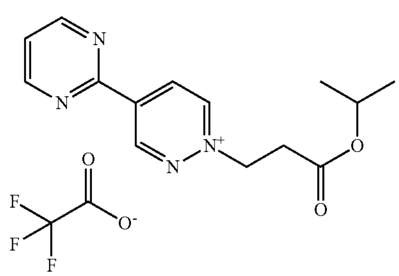 [SMILES: O=C([O-])C(F)(F)F ; CC(C)OC(=O)CC[n+]1ccc(-c2ncccn2)cn1] | (400 MHz, CD₃OD) 10.29-10.43 (m, 1H) 10.02 (d, 1H) 9.36-9.49 (m, 1H) 9.04-9.18 (m, 2H) 7.63-7.76 (m, 1H) 5.10-5.24 (m, 2H) 4.92-5.04 (m, 1H) 3.14-3.41 (m, 2H) 1.12-1.25 (m, 6H) |
| A82 | 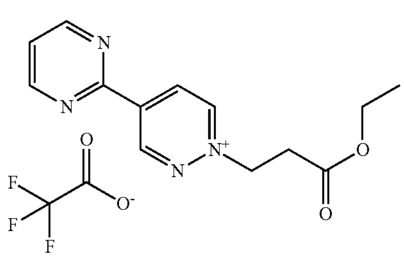 [SMILES: O=C([O-])C(F)(F)F ; CCOC(=O)CC[n+]1ccc(-c2ncccn2)cn1] | (400 MHz, D₂O) 10.07-10.18 (m, 1H) 9.77-9.90 (m, 1H) 9.12-9.23 (m, 1H) 8.96 (d, 2H) 7.52-7.70 (m, 1H) 5.04-5.17 (m, 2H) 4.03 (q, 2H) 3.14-3.30 (m, 2H) 1.01-1.13 (m, 3H) |

TABLE A-continued

Physical Data for Compounds of the Invention

| Compound Number | Structure | ¹H NMR |
|---|---|---|
| A83 | 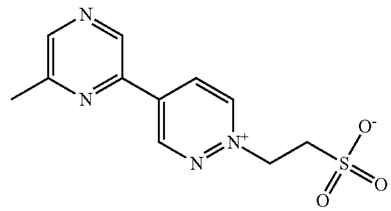 [SMILES: Cc1cncc(-c2cc[n+](CCS(=O)(=O)[O-])nc2)n1] | (400 MHz, D$_2$O) 10.09-10.03 (m, 1H) 9.80-9.76 (m, 1H) 9.15 (s, 1H) 9.04 (dd, 1H) 8.66 (s, 1H) 5.20 (t, 2H) 3.65 (t, 2H) 2.62 (s, 3H) |
| A84 | 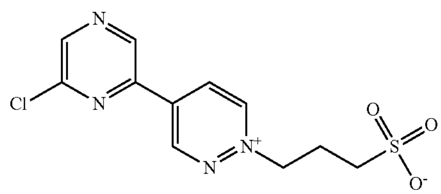 [SMILES: O=S(=O)([O-])CCC[n+]1ccc(-c2cncc(Cl)n2)cn1] | (400 MHz, D$_2$O) 10.08-10.04 (m, 1H) 9.78 (d, 1H) 9.32 (s, 1H) 9.08 (dd, 1H) 8.82 (s, 1H) 4.99 (t, 2H) 2.96 (t, 2H) 2.57-2.46 (m, 2H) |
| A85 | 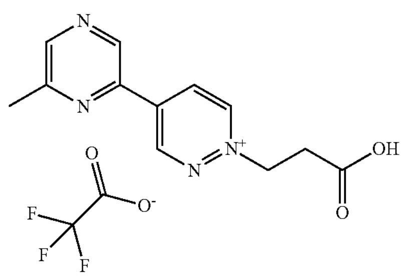 [SMILES: Cc1cncc(-c2cc[n+](CCC(=O)O)nc2)n1 ; O=C([O-])C(F)(F)F] | (400 MHz, CD$_3$OD) 10.29-10.24 (m, 1H) 10.02-9.95 (m, 1H) 9.41 (s, 1H) 9.29-9.25 (m, 1H) 8.79 (s, 1H) 5.16 (t, 2H) 3.30-3.23 (m, 2H) 2.73 (s, 3H) (one CO$_2$H proton missing) |
| A86 | 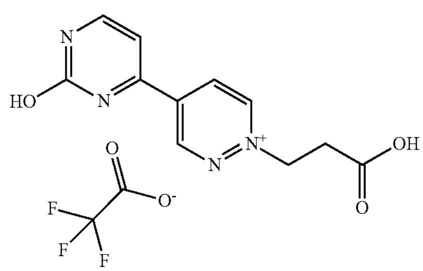 [SMILES: O=C(O)CC[n+]1ccc(-c2ccnc(O)n2)cn1 ; O=C([O-])C(F)(F)F] | (400 MHz, CD$_3$OD) 10.16-10.12 (m, 1H) 10.09 (d, 1H) 9.22 (dd, 1H) 8.36 (d, 1H) 7.44 (d, 1H) 5.18 (t, 2H) 3.27 (t, 2H) (one CO$_2$H proton and one OH proton missing) |
| A87 | 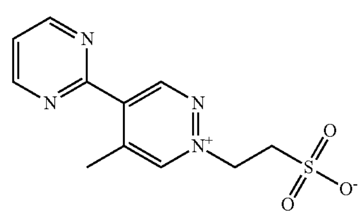 [SMILES: Cc1c[n+](CCS(=O)(=O)[O-])ncc1-c1ncccn1] | (400 MHz, D$_2$O) 9.83-9.86 (m, 1H) 9.62-9.75 (m, 1H) 9.01-9.04 (m, 2H) 7.40-7.83 (m, 1H) 5.18-5.25 (m, 2H) 3.57-3.80 (m, 2H) 2.64-2.87 (m, 3H) |
| A88 | 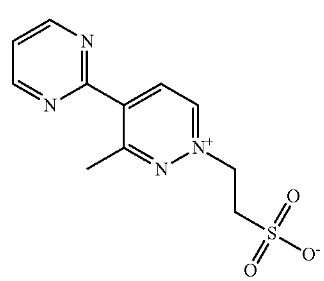 [SMILES: Cc1n[n+](CCS(=O)(=O)[O-])ccc1-c1ncccn1] | (400 MHz, D$_2$O) 9.76 (d, 1H) 9.69-9.88 (m, 1H) 9.02 (d, 1H) 8.77 (d, 1H) 7.69 (t, 1H) 5.21 (t, 2H) 3.71 (t, 2H) 2.94 (s, 3H) |

TABLE A-continued

Physical Data for Compounds of the Invention

| Compound Number | Structure | $^1$H NMR |
|---|---|---|
| A89 | 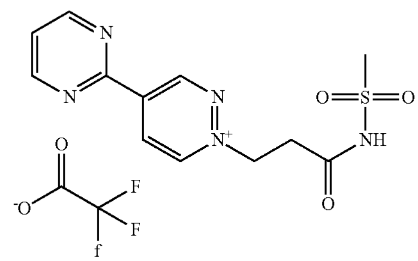 | (400 MHz, D$_2$O) 10.22 (d, 1H) 9.93 (d, 1H) 9.25 (dd, 1H) 9.05 (d, 2H) 7.70 (t, 1H) 5.22 (t, 2H) 3.30-3.40 (m, 2H) 3.27 (s, 3H) (one NH proton missing) |
| A90 | 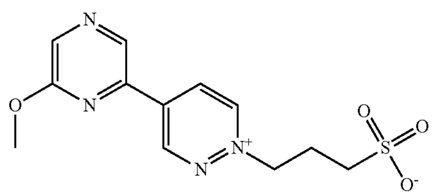 [SMILES: COc1cncc(-c2cc[n+](CCCS(=O)(=O)[O-])nc2)n1] | (400 MHz, D$_2$O) 10.10-10.04 (m, 1H) 9.67 (d, 1H) 9.05 (dd, 1H) 8.91 (s, 1H) 8.34 (s, 1H) 4.94 (t, 2H) 4.01 (s, 3H) 2.97-2.90 (m, 2H) 2.54-2.44 (m, 2H) |
| A91 | 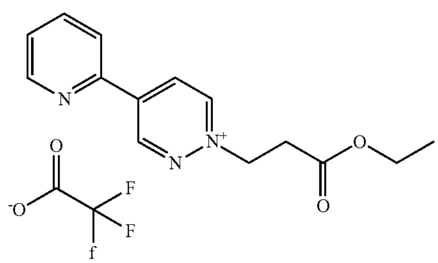 | (400 MHz, D$_2$O) 9.98 (m, 1H) 9.78 (m, 1H) 8.98 (m, 1H) 8.76 (s, 1H) 8.24 (m, 1H) 8.10 (m, 1H) 7.68 (m, 1H) 5.12 (m, 2H) 4.10 (m, 2H) 3.26 (m, 2H) 1.14 (m, 3H) |
| A92 | 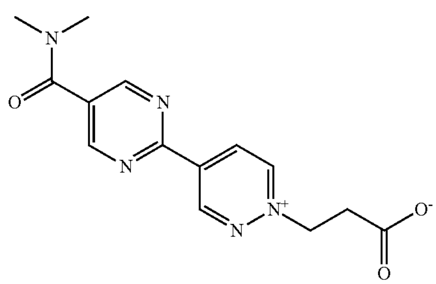 [SMILES: CN(C)C(=O)c1cnc(-c2cc[n+](CCC(=O)[O-])nc2)nc1] | (400 MHz, D$_2$O) 10.23 (m, 1H) 9.89 (m, 1H) 9.25 (m, 1H) 9.12 (s, 2H) 5.16 (m, 2H) 3.26 (m, 2H) 3.08 (s, 3H) 3.02 (s, 3H) |
| A93 | 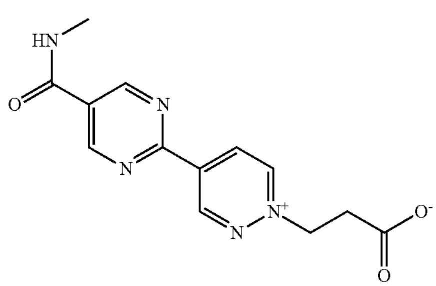 [SMILES: CNC(=O)c1cnc(-c2cc[n+](CCC(=O)[O-])nc2)nc1] | (400 MHz, D$_2$O) 10.27 (m, 1H) 9.94 (m, 1H) 9.33 (s, 3H) 5.18 (m, 2H) 3.26 (m, 2H) 2.94 (m, 3H) (one NH proton missing) |

TABLE A-continued

Physical Data for Compounds of the Invention

| Compound Number | Structure | ¹H NMR |
|---|---|---|
| A94 | 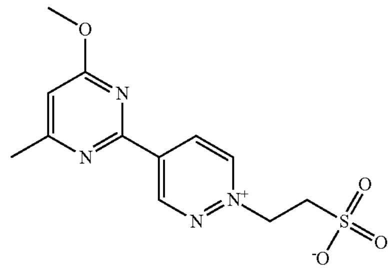 | (400 MHz, D$_2$O) 10.22 (d, 1H) 9.84 (d, 1H) 9.21 (d, 1H) 6.91 (s, 1H) 5.25 (t, 2H) 4.05 (s, 3H) 3.70 (t, 2H) 2.52 (s, 3H) |
| A95 | 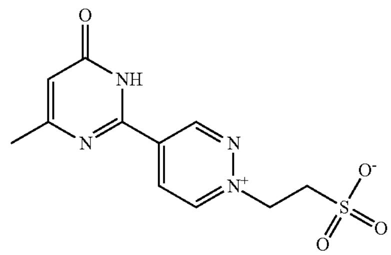 [SMILES: Cc1cc(=O)[nH]c(-c2cc[n+](CCS(=O)(=O)[O-])nc2)n1] | (400 MHz, D$_2$O) 9.89-9.98 (m, 1H) 9.83 (d, 1H) 8.97 (dd, 1H) 6.49 (s, 1H) 5.18 (t, 2H) 3.60 (t, 2H) 2.33 (s, 3H) (one NH proton missing) |
| A96 | 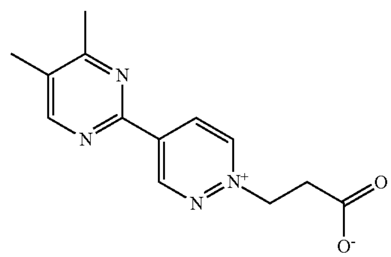 [SMILES: Cc1cnc(-c2cc[n+](CCC(=O)[O-])nc2)nc1C] | (400 MHz, D$_2$O) 10.06 (d, 1H) 9.65-9.77 (m, 1H) 9.00-9.09 (m, 1H) 8.48-8.63 (m, 1H) 5.02 (t, 2H) 3.15 (t, 2H) 2.49 (s, 3H) 2.26 (s, 3H) |
| A97 | 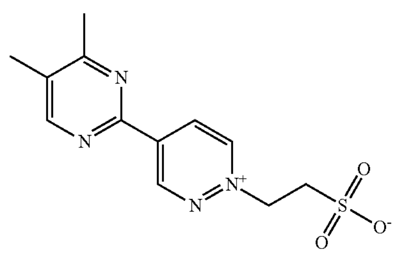 [SMILES: Cc1cnc(-c2cc[n+](CCS(=O)(=O)[O-])nc2)nc1C] | (400 MHz, D$_2$O) 10.10 (d, 1H) 9.73 (d, 1H) 9.07 (dd, 1H) 8.57 (s, 1H) 5.13-5.18 (m, 2H) 3.58-3.64 (m, 2H) 2.49 (s, 3H) 2.26 (s, 3H) |
| A98 | 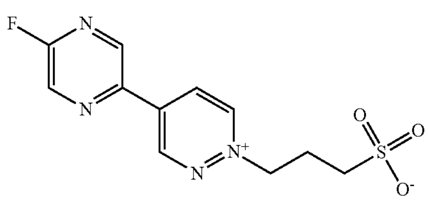 [SMILES: O=S(=O)([O-])CCC[n+]1ccc(-c2cnc(F)cn2)cn1] | (400 MHz, D$_2$O) 10.06-10.03 (m, 1H) 9.75-9.71 (m, 1H) 9.12-9.09 (m, 1H) 9.04 (dd, 1H) 8.74 (dd, 1H) 4.97 (t, 2H) 3.00-2.94 (m, 2H) 2.56-2.47 (m, 2H) |
| A99 | 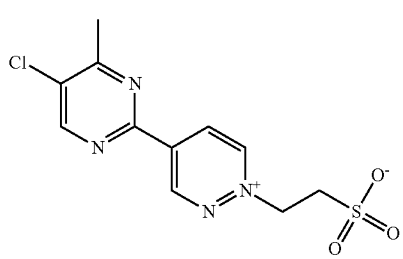 [SMILES: Cc1nc(-c2cc[n+](CCS(=O)(=O)[O-])nc2)ncc1Cl] | (400 MHz, D$_2$O) 10.23 (d, 1H) 9.85 (d, 1H) 9.22 (dd, 1H) 8.89 (s, 1H) 5.25 (m, 2H) 3.70 (m, 2H) 2.70 (s, 3H) |

TABLE A-continued
Physical Data for Compounds of the Invention
| Compound Number | Structure | ¹H NMR |
|---|---|---|
| A100 | 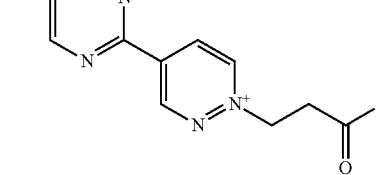 | (400 MHz, D$_2$O) 10.53 (br s, 1H) 9.58 (br s, 1H) 9.16 (br s, 1H) 8.85-8.92 (m, 1H) 5.15-5.22 (m, 2H) 3.23 (br s, 2H) 2.69 (s, 3H) |
| A101 | 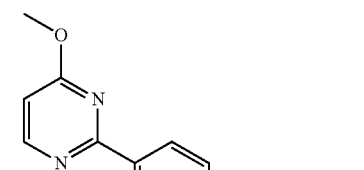 | (400 MHz, D$_2$O) 10.20 (d, 1H) 9.85 (d, 1H) 9.21 (dd, 1H) 8.66 (d, 1H) 7.05 (d, 1H) 5.13 (t, 2H) 4.08 (s, 3H) 3.26 (t, 2H) |
| A102 | 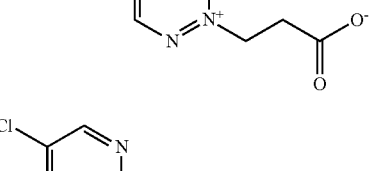 | (400 MHz, D$_2$O) 9.65-9.81 (m, 2H) 8.67-8.77 (m, 1H) 8.53-8.61 (m, 1H) 7.91-8.00 (m, 1H) 4.95-5.10 (m, 2H) 2.98-3.02 (m, 2H) 2.54-2.56 (m, 2H) 2.43-2.45 (m, 3H) |
| A103 | 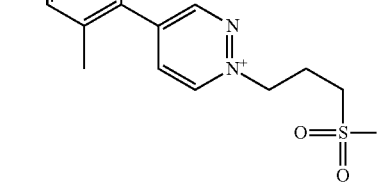 | (400 MHz, D$_2$O) 9.77 (d, 1H) 9.68 (s, 1H) 8.72 (d, 1H) 8.54 (s, 1H) 7.92 (s, 1H) 5.22 (t, 2H) 3.67 (t, 2H) 2.42 (s, 3H) |
| A104 | 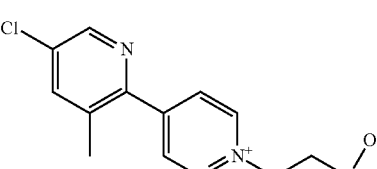 | (400 MHz, D$_2$O) 9.77-9.85 (m, 1H) 9.72 (br s, 1H) 8.74 (br s, 1H) 8.52-8.59 (m, 1H) 7.73 (br s, 1H) 5.26 (br s, 2H) 3.71 (br s, 2H) 2.49 (br s, 3H) |
| A105 | 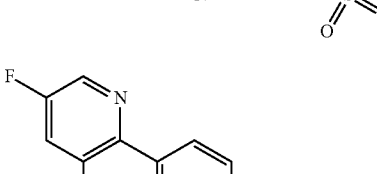 | (400 MHz, D$_2$O) 10.19 (d, 1H) 9.83 (d, 1H) 9.19 (dd, 1H) 6.92 (s, 1H) 5.11 (s, 2H) 4.05 (s, 3H) 3.22 (t, 2H) 2.52 (s, 3H) |

TABLE A-continued

Physical Data for Compounds of the Invention

| Compound Number | Structure | ¹H NMR |
|---|---|---|
| A106 | 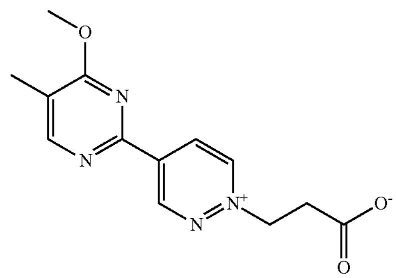 [SMILES: COc1nc(-c2cc[n+](CCC(=O)[O-])nc2)ncc1C] | (400 MHz, D$_2$O) 10.40-10.51 (m, 1H) 9.48-9.65 (m, 1H) 8.99-9.23 (m, 1H) 8.36-8.54 (m, 1H) 5.13-5.30 (m, 2H) 3.97-4.21 (m, 3H) 3.17-3.37 (m, 2H) 2.14-2.25 (m, 3H) |
| A107 | 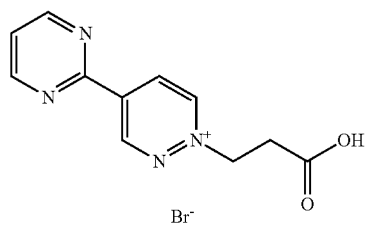 [SMILES: O=C(O)CC[n+]1ccc(-c2ncccn2)cn1 ; [Br-]] | (400 MHz, D$_2$O) 10.16 (d, 1H) 9.86 (d, 1H) 9.21-9.15 (m, 1H) 8.99 (d, 2H) 7.64 (t, 1H) 5.11 (t, 2H) 3.24 (t, 2H) (one CO$_2$H proton missing) |
| A108 | 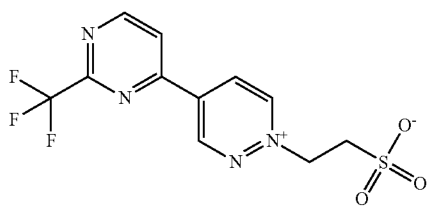 [SMILES: O=S(=O)([O-])CC[n+]1ccc(-c2ccnc(C(F)(F)F)n2)cn1] | (400 MHz, D$_2$O) 10.21-10.16 (m, 1H) 9.92 (d, 1H) 9.25-9.20 (m, 2H) 8.51 (d, 1H) 5.26 (t, 2H) 3.68 (t, 2H) |
| A109 | 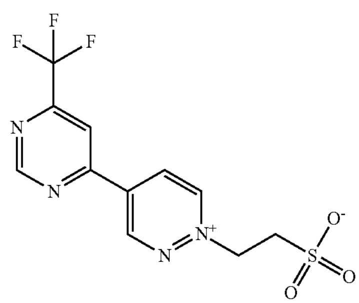 [SMILES: O=S(=O)([O-])CC[n+]1ccc(-c2cc(C(F)(F)F)ncn2)cn1] | (400 MHz, D$_2$O) 10.20-10.14 (m, 1H) 9.93 (d, 1H) 9.56-9.53 (m, 1H) 9.21 (dd, 1H) 8.79-8.74 (m, 1H) 5.25 (t, 2H) 3.67 (t, 2H) |
| A110 | 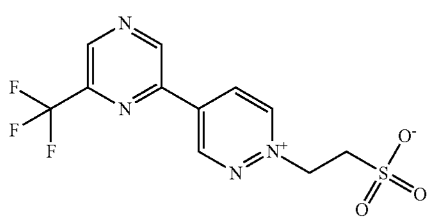 [SMILES: O=S(=O)([O-])CC[n+]1ccc(-c2cncc(C(F)(F)F)n2)cn1] | (400 MHz, D$_2$O) 10.19-10.16 (m, 1H) 9.87 (d, 1H) 9.65 (s, 1H) 9.22 (s, 1H) 9.19 (dd, 1H) 5.23 (t, 2H) 3.66 (t, 2H) |
| A111 | 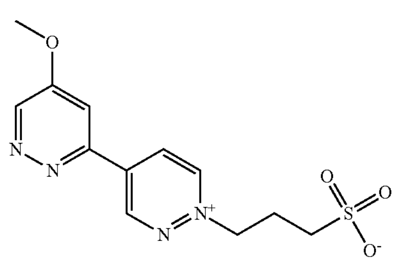 [SMILES: COc1cnnc(-c2cc[n+](CCCS(=O)(=O)[O-])nc2)c1] | (400 MHz, D$_2$O) 10.08-10.04 (m, 1H), 9.84-9.79 (m, 1H) 9.06 (dd, 1H) 9.01 (d, 1H) 7.95 (d, 1H) 5.01 (t, 2H) 4.01 (s, 3H) 3.01-2.95 (m, 2H) 2.58-2.49 (m, 2H) |

TABLE A-continued

Physical Data for Compounds of the Invention

| Compound Number | Structure | ¹H NMR |
|---|---|---|
| A112 | 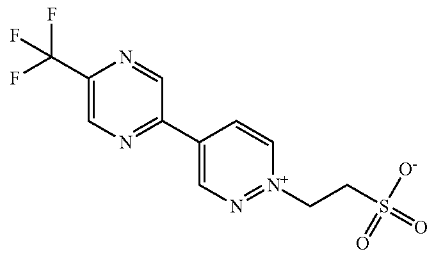 [SMILES: O=S(=O)([O-])CC[n+]1ccc(-c2cnc(C(F)(F)F)cn2)cn1] | (400 MHz, D₂O) 10.18-10.15 (m, 1H) 9.90-9.85 (m, 1H) 9.56-9.53 (m, 1H) 9.30-9.27 (m, 1H) 9.19 (dd, 1H) 5.23 (t, 2H) 3.67 (t, 2H) |
| A113 | 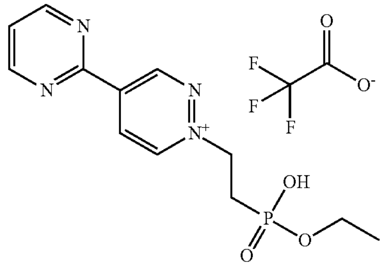 [SMILES: CCOP(=O)(O)CC[n+]1ccc(-c2ncccn2)cn1 ; O=C([O-])C(F)(F)F] | (400 MHz, D₂O) 10.22 (d, 1H) 9.86 (d, 1H) 9.23 (dd, 1H) 9.04 (d, 2H) 7.69 (t, 1H) 5.06 (dt, 2H) 3.85 (quin, 2H) 2.44-2.53 (m, 2H) 1.13 (t, 3H) (one OH proton missing) |
| A114 | 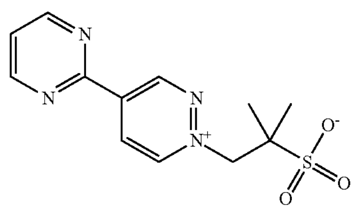 [SMILES: CC(C)(C[n+]1ccc(-c2ncccn2)cn1)S(=O)(=O)[O-]] | (400 MHz, D₂O) 10.17-10.12 (m, 1H) 9.75-9.71 (m, 1H) 9.15 (dd, 1H) 8.97 (d, 2H) 7.61 (t, 1H) 5.04 (s, 2H) 1.37 (s, 6H) |
| A115 | 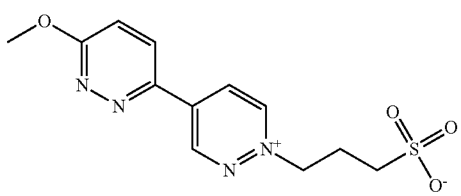 [SMILES: COc1ccc(-c2cc[n+](CCCS(=O)(=O)[O-])nc2)nn1] | (400 MHz, D₂O) 10.00-10.13 (m, 1H) 9.67-9.78 (m, 1H) 8.93-9.06 (m, 1H) 8.30-8.44 (m, 1H) 7.40 (d, 1H) 4.98 (t, 2H) 4.11 (s, 3H) 2.97 (t, 2H) 2.52 (quin, 2H) |
| A116 | 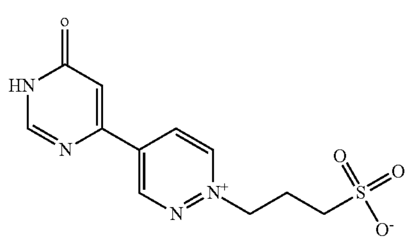 | (400 MHz, D₂O) 9.86-9.98 (m, 1H) 9.72-9.81 (m, 1H) 8.96 (dd, 1H) 8.34-8.48 (m, 1H) 7.35 (d, 1H) 4.86-5.10 (m, 2H) 2.84-3.05 (m, 2H) 2.43 (s, 2H) (one NH proton missing) |
| A117 | 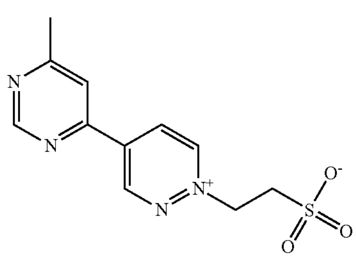 [SMILES: Cc1cc(-c2cc[n+](CCS(=O)(=O)[O-])nc2)ncn1] | (400 MHz, D₂O) 9.98-10.10 (m, 1H) 9.85 (d, 1H) 9.13-9.22 (m, 1H) 9.06 (dd, 1H) 8.12-8.24 (m, 1H) 5.16-5.31 (m, 2H) 3.58-3.73 (m, 2H) 2.57-2.69 (m, 3H) |

TABLE A-continued

Physical Data for Compounds of the Invention

| Compound Number | Structure | $^1$H NMR |
|---|---|---|
| A118 | 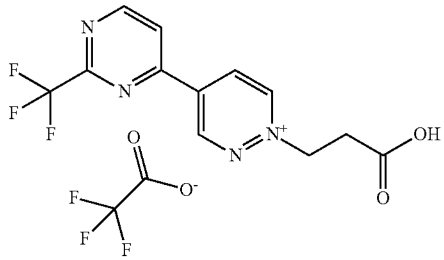 [SMILES: O=C(O)CC[n+]1ccc(-c2ccnc(C(F)(F)F)n2)cn1 ; O=C([O-])C(F)(F)F] | (400 MHz, CD$_3$OD) 10.28 (d, 1H) 10.14 (d, 1H) 9.40-9.32 (m, 2H) 8.67 (d, 1H) 5.21 (t, 2H) 3.34-3.26 (m, 2H) (one CO$_2$H proton missing) |
| A119 | 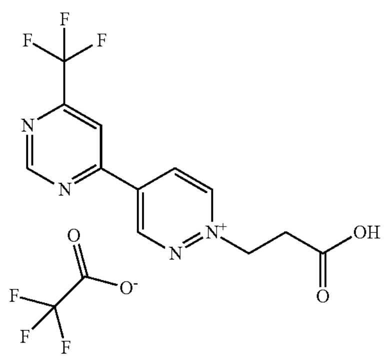 [SMILES: O=C([O-])C(F)(F)F ; O=C(O)CC[n+]1ccc(-c2cc(C(F)(F)F)ncn2)cn1] | (400 MHz, CD$_3$OD) 10.39-10.33 (m, 1H) 10.14 (d, 1H) 9.71-9.68 (m, 1H) 9.44 (dd, 1H) 8.93 (d, 1H) 5.20 (t, 2H) 3.35-3.24 (m, 2H) (one CO$_2$H proton missing) |
| A120 | 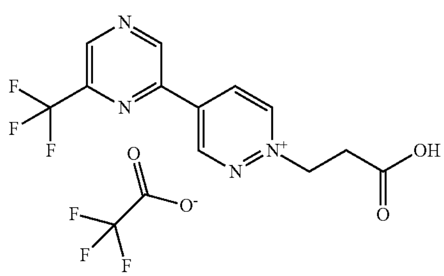 [SMILES: O=C(O)CC[n+]1ccc(-c2cncc(C(F)(F)F)n2)cn1 ; O=C([O-])C(F)(F)F] | 400 MHz, CD$_3$OD) 10.31-10.23 (m, 1H) 10.08 (d, 1H) 9.89 (s, 1H) 9.38-9.31 (m, 2H) 5.19 (t, 2H) 3.34-3.26 (m, 2H) (one CO$_2$H proton missing) |
| A121 | 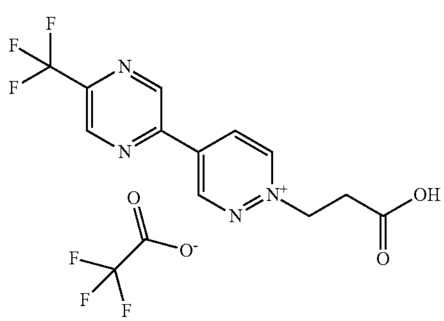 [SMILES: O=C(O)CC[n+]1ccc(-c2cnc(C(F)(F)F)cn2)cn1 ; O=C([O-])C(F)(F)F] | (400 MHz, CD$_3$OD) 10.35-10.28 (m, 1H) 10.09 (d, 1H) 9.77 (d, 1H) 9.40-9.34 (m, 2H) 5.19 (t, 2H) 3.34-3.23 (m, 2H) (one CO$_2$H proton missing) |
| A122 | 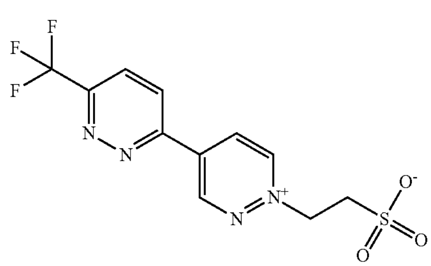 [SMILES: O=S(=O)([O-])CC[n+]1ccc(-c2ccc(C(F)(F)F)nn2)cn1] | (400 MHz, D$_2$O) 10.24-10.20 (m, 1H) 9.91 (d, 1H) 9.20 (dd, 1H) 8.76 (d, 1H) 8.40 (d, 1H) 5.26 (t, 2H) 3.68 (t, 2H) |

TABLE A-continued

Physical Data for Compounds of the Invention

| Compound Number | Structure | $^1$H NMR |
|---|---|---|
| A123 | 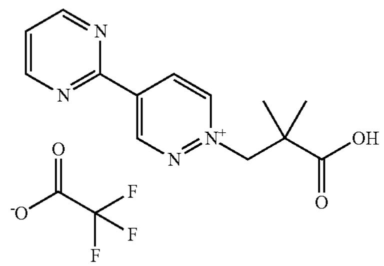 | (400 MHz, D$_2$O) 10.16 (d, 1H) 9.79 (d, 1H) 9.20 (dd, 1H) 9.00 (d, 2H) 7.64 (t, 1H) 5.04 (s, 2H) 1.25 (s, 6H) (one CO$_2$H proton missing) |
| A124 | 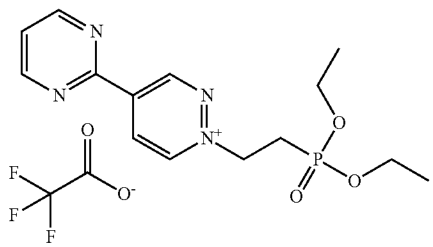 [SMILES: O=C([O-])C(F)(F)F ; CCOP(=O)(CC[n+]1ccc(-c2ncccn2)cn1)OCC] | (400 MHz, D$_2$O) 10.26 (d, 1H) 9.89 (d, 1H) 9.27 (dd, 1H) 9.00-9.06 (m, 2H) 7.69 (t, 1H) 5.11-5.23 (m, 2H) 4.03-4.15 (m, 4H) 2.84 (dt, 2H) 1.21 (t, 6H) |
| A125 | 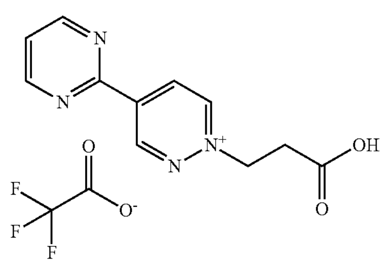 [SMILES: O=C([O-])C(F)(F)F ; O=C(O)CC[n+]1ccc(-c2ncccn2)cn1] | (400 MHz, D$_2$O) 10.18-10.13 (m, 1H) 9.87-9.82 (m, 1H) 9.20-9.14 (m, 1H) 8.98 (d, 2H) 7.63 (s, 1H) 5.10 (s, 2H) 3.24 (t, 2H) (one CO$_2$H proton missing) |
| A126 | 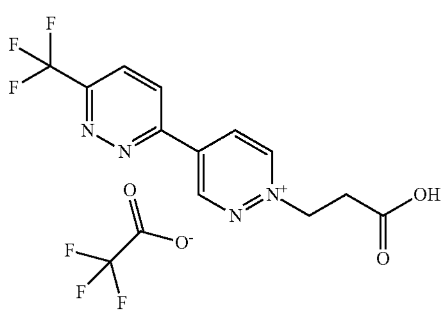 [SMILES: O=C(O)CC[n+]1ccc(-c2ccc(C(F)(F)F)nn2)cn1 ; O=C([O-])C(F)(F)F] | (400 MHz, CD$_3$OD) 10.39 (d, 1H) 10.15 (d, 1H) 9.40 (dd, 1H) 8.89 (d, 1H) 8.45 (d, 1H) 5.22 (t, 2H) 3.34-3.25 (m, 2H) (one CO$_2$H proton missing) |
| A127 | 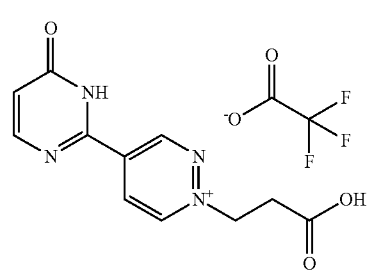 | (400 MHz, D$_2$O) 9.99 (d, 1H) 9.91 (d, 1H) 9.04 (d, 1H) 8.34 (d, 1H) 6.74 (d, 1H) 5.13 (t, 2H) 3.24 (t, 2H) (One NH proton and one CO$_2$H proton missing) |

TABLE A-continued

Physical Data for Compounds of the Invention

| Compound Number | Structure | $^1$H NMR |
|---|---|---|
| A128 | 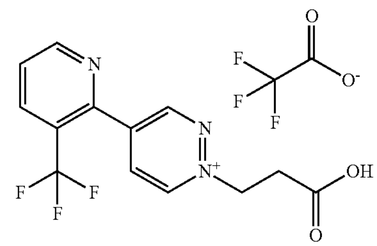 [SMILES: O=C(O)CC[n+]1ccc(-c2ncccc2C(F)(F)F)cn1 ; O=C([O-])C(F)(F)F] | (400 MHz, D$_2$O) 9.99 (s, 1H) 9.62 (d, 1H) 8.88 (d, 1H) 8.71 (dd, 1H) 8.37 (d, 1H) 7.79 (dd, 1H) 5.14 (t, 2H) 3.25 (t, 2H) (one CO$_2$H proton missing) |
| A129 | 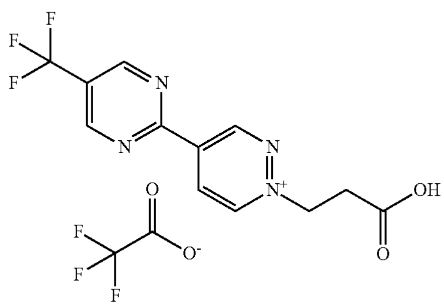 [SMILES: O=C(O)CC[n+]1ccc(-c2ncc(C(F)(F)F)cn2)cn1 ; O=C([O-])C(F)(F)F] | (400 MHz, D$_2$O) 10.29 (d, 1H) 9.95-10.00 (m, 1H) 9.32-9.41 (m, 3H) 5.18 (t, 2H) 3.25-3.35 (m, 2H) (one CO$_2$H proton missing) |
| A130 | 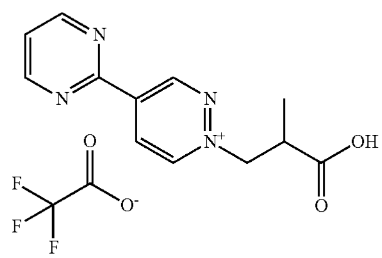 [SMILES: O=C([O-])C(F)(F)F ; CC(C[n+]1ccc(-c2ncccn2)cn1)C(=O)O] | (400 MHz, D$_2$O) 10.16-10.25 (m, 1H) 9.81-9.89 (m, 1H) 9.19-9.27 (m, 1H) 8.97-9.09 (m, 2H) 7.63-7.74 (m, 1H) 5.08-5.20 (m, 1H) 4.92-5.01 (m, 1H) 3.35-3.47 (m, 1H) 1.31 (d, 3H) (one CO$_2$H proton missing) |
| A131 | 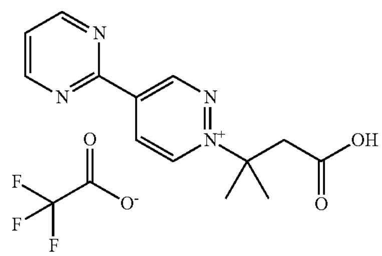 [SMILES: O=C([O-])C(F)(F)F ; CC(C)(CC(=O)O)[n+]1ccc(-c2ncccn2)cn1] | (400 MHz, D$_2$O) 10.18 (m, 1H) 9.97 (m, 1H) 9.21 (m, 1H) 8.98 (m, 2H) 7.61 (m, 1H) 3.36 (s, 2H) 1.94 (s, 6H) (one CO$_2$H proton missing) |
| A132 | 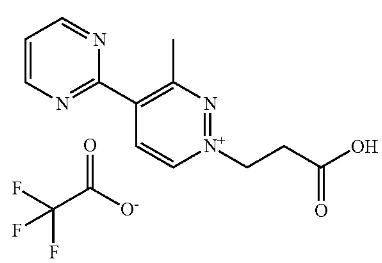 [SMILES: O=C([O-])C(F)(F)F ; Cc1n[n+](CCC(=O)O)ccc1-c1ncccn1] | (400 MHz, D$_2$O) 9.72 (d, 1H) 8.98 (d, 1H) 8.66-8.74 (m, 1H) 8.71 (d, 1H) 7.65 (t, 1H) 5.06 (t, 2H) 3.21 (t, 2H) 2.87 (s, 3H) (one CO$_2$H proton missing) |

TABLE A-continued

Physical Data for Compounds of the Invention

| Compound Number | Structure | $^1$H NMR |
|---|---|---|
| A133 | 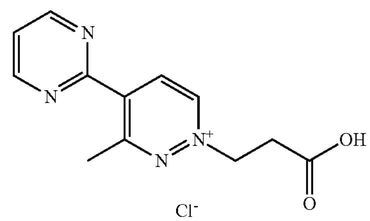 [SMILES: Cc1n[n+](CCC(=O)O)ccc1-c1ncccn1 ; [Cl-]] | (400 MHz, D$_2$O) 9.72 (d, 1H) 8.98 (d, 1H) 8.66-8.74 (m, 1H) 8.71 (d, 1H) 7.65 (t, 1H) 5.06 (t, 2H) 3.21 (t, 2H) 2.87 (s, 3H) (one CO$_2$H proton missing) |
| A134 | 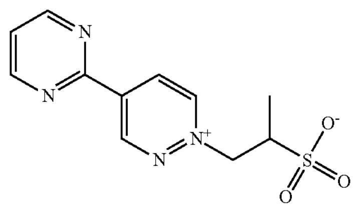 [SMILES: CC(C[n+]1ccc(-c2ncccn2)cn1)S(=O)(=O)[O-]] | (400 MHz, D$_2$O) 10.20-10.18 (m, 1H) 9.81 (dd, 1H) 9.19 (dd, 1H) 9.00 (d, 2H), 7.65 (t, 1H) 5.10-5.07 (m, 2H) 3.84-3.74 (m, 1H) 1.39 (d, 3H) |
| A135 | 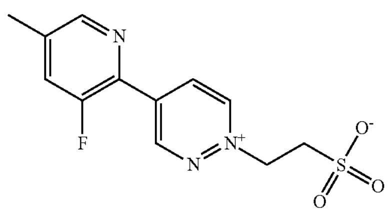 [SMILES: Cc1cnc(-c2cc[n+](CCS(=O)(=O)[O-])nc2)c(F)c1] | (400 MHz, D$_2$O) 10.00 (d, 1H) 9.73 (d, 1H) 8.96 (d, 1H) 8.50 (s, 1H) 7.69 (d, 1H) 5.18-5.23 (m, 2H) 3.66-3.71 (m, 2H) 2.45 (s, 3H) |
| A136 | 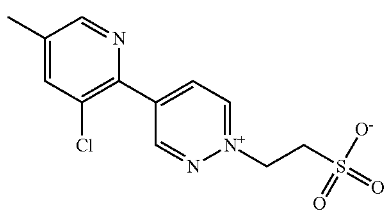 [SMILES: Cc1cnc(-c2cc[n+](CCS(=O)(=O)[O-])nc2)c(Cl)c1] | (400 MHz, D$_2$O) 9.85 (s, 1H) 9.80 (d, 1H) 8.95 (dd, 1H) 8.52 (s, 1H) 7.95 (s, 1H) 5.24 (t, 2H) 3.67-3.72 (m, 2H) 2.40 (s, |
| A137 | 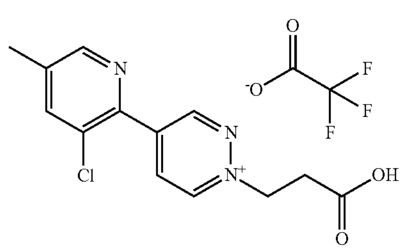 | (400 MHz, D$_2$O) 9.78-9.89 (m, 1H) 8.96 (dd, 1H) 8.87-9.00 (m, 1H) 8.53 (d, 1H) 7.96 (d, 1H) 5.14 (t, 2H) 3.28 (t, 2H) 2.41 (s, 3H) (one CO$_2$H proton missing) |
| A138 | 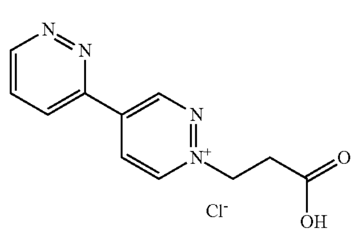 [SMILES: O=C(O)CC[n+]1ccc(-c2cccnn2)cn1 ; [Cl-]] | (400 MHz, D$_2$O) 10.11 (d, 1H) 9.87 (d, 1H) 9.32 (dd, 1H) 9.12-9.08 (m, 1H) 8.50 (dd, 1H) 7.99 (dd, 1H) 5.12 (t, 2H) 3.24 (t, 2H) (one CO$_2$H proton missing) |

TABLE A-continued

Physical Data for Compounds of the Invention

| Compound Number | Structure | ¹H NMR |
|---|---|---|
| A139 | 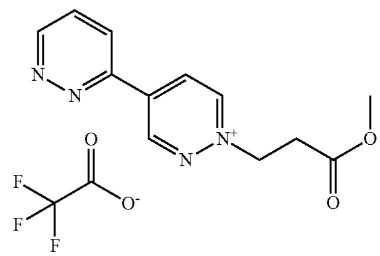 [SMILES: O=C([O-])C(F)(F)F ; COC(=O)CC[n+]1ccc(-c2cccnn2)cn1] | (400 MHz, D$_2$O) 10.05-10.15 (m, 1H) 9.84-9.94 (m, 1H) 9.28-9.39 (m, 1H) 9.05-9.14 (m, 1H) 8.41-8.56 (m, 1H) 7.90-8.06 (m, 1H) 5.07-5.21 (m, 2H) 3.56-3.67 (m, 3H) 3.22-3.34 (m, 2H) |
| A140 | 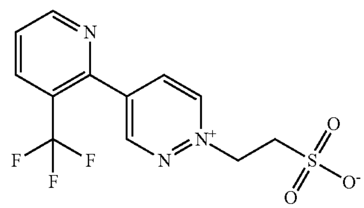 [SMILES: O=S(=O)([O-])CC[n+]1ccc(-c2ncccc2C(F)(F)F)cn1] | (400 MHz, D$_2$O) 9.86 (d, 1H) 9.62 (d, 1H) 8.85 (d, 1H) 8.70 (m, 1H) 8.35 (d, 1H) 7.77 (m, 1H) 5.24 (m, 2H) 3.65 (m, 2H) |
| A141 | 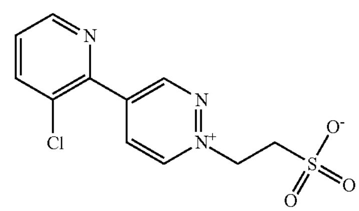 [SMILES: O=S(=O)([O-])CC[n+]1ccc(-c2ncccc2Cl)cn1] | (400 MHz, D$_2$O) 9.83-9.92 (m, 2H) 8.98 (d, 1H) 8.68 (d, 1H) 8.12 (d, 1H) 7.59-7.66 (m, 1H) 5.27 (t, 2H) 3.71 (t, 2H) |
| A142 | 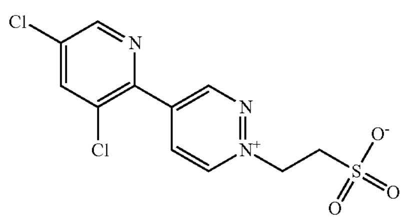 [SMILES: O=S(=O)([O-])CC[n+]1ccc(-c2ncc(Cl)cc2Cl)cn1] | (400 MHz, D$_2$O) 9.87 (d, 1H) 9.83 (d, 1H) 8.99 (dd, 1H) 8.71 (d, 1H) 8.23 (d, 1H) 5.25 (t, 2H) 3.70 (t, 2H) |
| A143 | 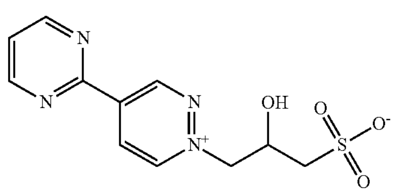 [SMILES: O=S(=O)([O-])CC(O)C[n+]1ccc(-c2ncccn2)cn1] | (400 MHz, D$_2$O) 10.24 (d, 1H) 9.80 (d, 1H) 9.25 (dd, 1H) 9.04 (d, 2H) 7.68 (t, 1H) 5.21 (dd, 1H) 4.93 (dd, 1H) 4.64-4.71 (m, 1H) 3.19-3.36 (m, 2H) (one OH proton missing) |
| A144 | 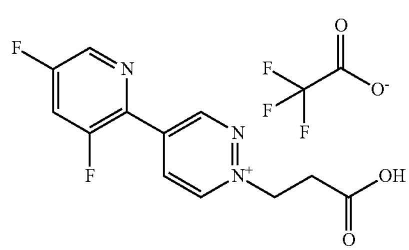 [SMILES: O=C(O)CC[n+]1ccc(-c2ncc(F)cc2F)cn1 ; O=C([O-])C(F)(F)F] | (400 MHz, D$_2$O) 9.95 (d, 1H) 9.74 (d, 1H) 8.93 (dd, 1H) 8.58 (d, 1H) 7.67-7.83 (m, 1H) 5.06 (t, 2H) 3.26 (t, 2H) (one CO$_2$H proton missing) |

TABLE A-continued

Physical Data for Compounds of the Invention

| Compound Number | Structure | $^1$H NMR |
|---|---|---|
| A145 | 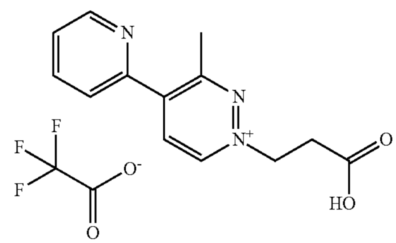 [SMILES: O=C([O-])C(F)(F)F ; Cc1n[n+](CCC(=O)O)ccc1-c1ccccn1] | (400 MHz, D$_2$O) 9.68 (d, 1H) 8.73 (d, 1H) 8.49 (d, 1H) 8.09 (td, 1H) 7.80 (d, 1H) 7.65 (dd, 1H) 5.07 (t, 2H) 3.26 (t, 2H) 2.77 (s, 3H) (one CO$_2$H proton missing) |
| A146 | 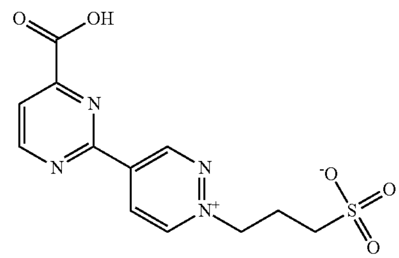 | (400 MHz, D$_2$O) 10.23-10.33 (d, 1H) 9.81 (d, 1H) 9.30 (dd, 1H) 9.15 (d, 1H) 8.06 (d, 1H) 5.01 (t, 2H) 2.97 (t, 2H) 2.52 (m, 2H) (one CO$_2$H proton missing) |
| A147 | 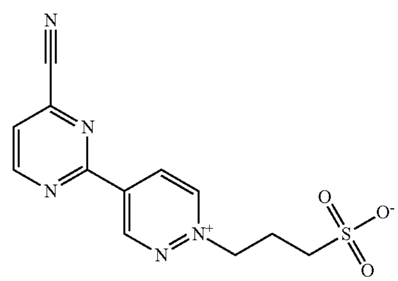 [SMILES: N#Cc1ccnc(-c2cc[n+](CCCS(=O)(=O)[O-])nc2)n1] | (400 MHz, D$_2$O) 10.23 (d, 1H) 9.85 (d, 1H) 9.25 (m, 2H) 8.06 (d, 1H) 5.02 (t, 2H) 2.98 (t, 2H) 2.53 (t, 2H) |
| A148 | 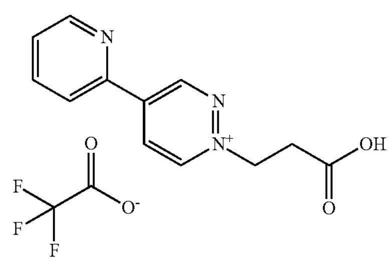 [SMILES: O=C([O-])C(F)(F)F ; O=C(O)CC[n+]1ccc(-c2ccccn2)cn1] | (400 MHz, D$_2$O) 9.99 (s, 1H) 9.77 (d, 1H) 8.96 (dd, 1H) 8.80 (d, 1H) 8.25 (d, 1H) 8.06-8.12 (m, 1H) 7.68 (t, 1H) 5.10 (t, 2H) 3.25 (t, 2H) (one CO$_2$H proton missing) |
| A149 | 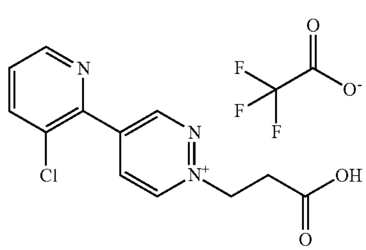 [SMILES: O=C(O)CC[n+]1ccc(-c2ncccc2Cl)cn1 ; O=C([O-])C(F)(F)F] | (400 MHz, D$_2$O) 9.78-9.88 (m, 2H) 8.95 (dd, 1H) 8.66 (d, 1H) 8.10 (d, 1H) 7.56-7.65 (m, 1H) 5.12 (t, 2H) 3.23 (t, 2H) (one CO$_2$H proton missing) |
| A150 | 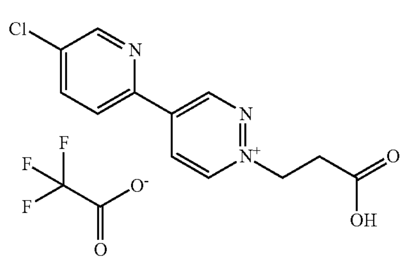 [SMILES: O=C(O)CC[n+]1ccc(-c2ccc(Cl)cn2)cn1 ; O=C([O-])C(F)(F)F] | (400 MHz, D$_2$O) 9.99 (d, 1H) 9.75 (d, 1H) 8.96 (dd, 1H) 8.80 (d, 1H) 8.24 (d, 1H) 8.10 (dd, 1H) 5.09 (t, 2H) 3.25 (t, 2H) (one CO$_2$H proton missing) |

TABLE A-continued

Physical Data for Compounds of the Invention

| Compound Number | Structure | $^1$H NMR |
|---|---|---|
| A151 | 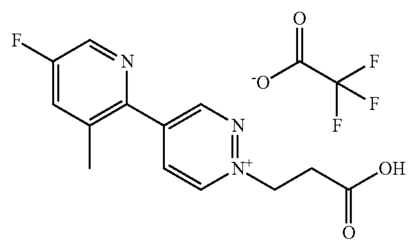 | (400 MHz, D$_2$O) 9.80 (d, 1H) 9.68 (s, 1H) 8.72 (d, 1H) 8.46-8.54 (m, 1H) 7.71 (d, 1H) 5.12 (t, 2H) 3.26 (t, 2H) 2.48 (s, 3H) (one CO$_2$H proton missing) |
| A152 | 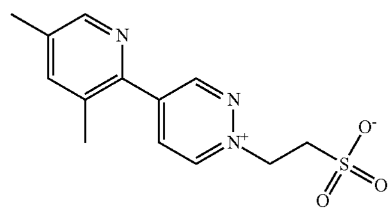 [SMILES: Cc1cnc(-c2cc[n+](CCS(=O)(=O)[O-])nc2)c(C)c1] | (400 MHz, D$_2$O) 9.75 (d, 1H) 9.69 (d, 1H) 8.70 (dd, 1H) 8.42 (s, 1H) 7.74 (s, 1H) 5.23 (t, 2H) 3.69 (t, 2H) 2.42 (s, 3H) 2.36 (s, 3H) |
| A153 | 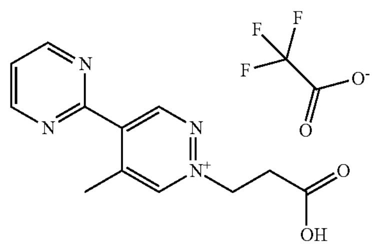 [SMILES: Cc1c[n+](CCC(=O)O)ncc1-c1ncccn1 ; O=C([O-])C(F)(F)F] | (400 MHz, D$_2$O) 9.84 (s, 1H) 9.64-9.69 (m, 1H) 8.99-9.05 (m, 1H) 9.02 (d, 1H) 7.67 (t, 1H) 5.09 (t, 2H) 3.26 (t, 2H) 2.78 (s, 3H) |
| A154 | 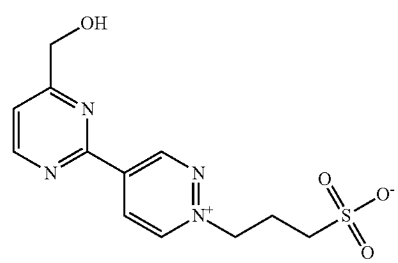 [SMILES: O=S(=O)([O-])CCC[n+]1ccc(-c2nccc(CO)n2)cn1] | (400 MHz, D$_2$O) 10.25 (s, 1H) 9.84 (d, 1H) 9.26 (d, 1H) 8.97 (d, 1H) 7.72 (d, 1H) 5.05 (t, 2H) 4.86 (s, 2H) 3.02 (t, 2H) 2.59 (t, 2H) (one OH proton missing) |
| A155 | 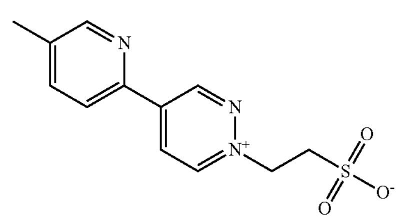 [SMILES: Cc1ccc(-c2cc[n+](CCS(=O)(=O)[O-])nc2)nc1] | (400 MHz, D$_2$O) 9.96 (d, 1H) 9.69 (d, 1H) 8.90 (dd, 1H) 8.62 (s, 1H) 8.14 (d, 1H) 7.89 (dd, 1H) 5.19 (t, 2H) 3.67 (t, 2H) 2.40 (s, 3H) |
| A156 | 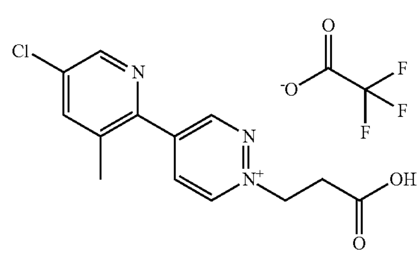 | (400 MHz, D$_2$O) 9.81 (d, 1H) 9.68 (d, 1H) 8.73 (dd, 1H) 8.57 (d, 1H) 7.95 (d, 1H) 5.12 (t, 2H) 3.26 (t, 2H) 2.44 (s, 3H) (one CO$_2$H proton missing) |

TABLE A-continued

Physical Data for Compounds of the Invention

| Compound Number | Structure | ¹H NMR |
|---|---|---|
| A157 | 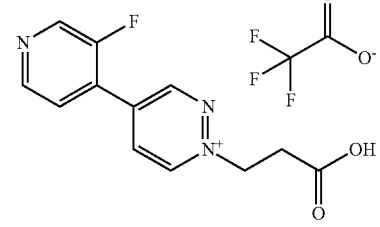 | (400 MHz, D₂O) 9.86 (d, 1H) 9.81 (d, 1H) 8.90 (dd, 1H) 8.73 (d, 1H) 8.63 (d, 1H) 7.89 (t, 1H) 5.16 (br t, 2H) 3.29 ppm (t, 2H) (one CO₂H proton missing) |
| A158 | 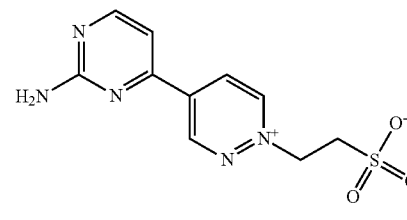 | (400 MHz, D₂O) 10.04-9.99 (m, 1H) 9.87 (d, 1H) 9.07 (dd, 1H) 8.51 (d, 1H) 7.57 (d, 1H) 5.23 (t, 2H) 3.66 (t, 2H) (two NH protons missing) |
| A159 | 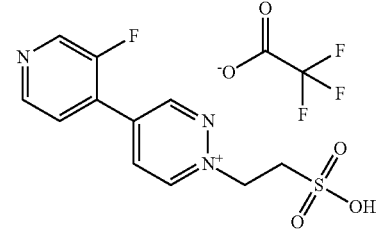 | (400 MHz, D₂O) 9.90 (d, 1H) 9.85 (d, 1H) 8.93 (dd, 1H) 8.79 (d, 1H) 8.67 (d, 1H) 8.01 (t, 1H) 5.12-5.35 (m, 2H) 3.63-3.81 (m, 2H) (one SO₃H proton missing) |
| A160 | 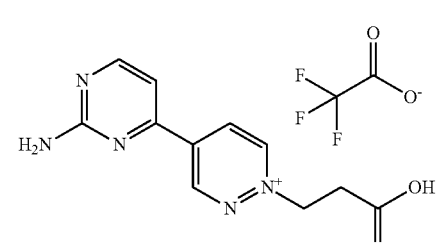 | (400 MHz, CD₃OD) 10.16 (d, 1H) 10.00 (d, 1H) 9.18 (dd, 1H) 8.57 (d, 1H) 7.53 (d, 1H) 5.12 (t, 2H) 3.25 (t, 2H) (two NH₂ protons and one CO₂H proton missing) |
| A161 | 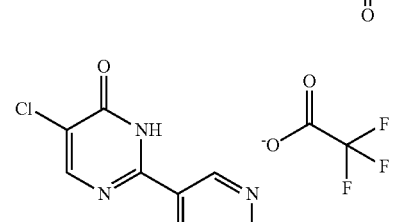 | (400 MHz, D₂O) 9.95 (s, 1H) 9.87 (d, 1H) 9.00 (dd, 1H) 8.44 (s, 1H) 5.09 (t, 2H) 3.22 (t, 2H) (one CO₂H proton missing) |
| A162 | 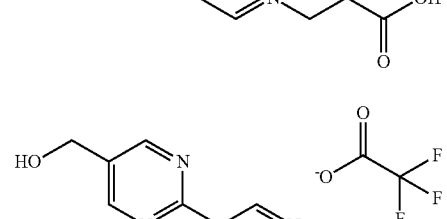 | (400 MHz, D₂O) 10.21 (s, 1H) 9.87 (d, 1H) 9.23 (dd, 1H) 9.02 (s, 2H) 5.16 (t, 2H) 4.81 (s, 2H) 3.26 (t, 2H) (one OH proton and one CO₂H proton missing) |

TABLE A-continued

Physical Data for Compounds of the Invention

| Compound Number | Structure | $^1$H NMR |
|---|---|---|
| A163 | 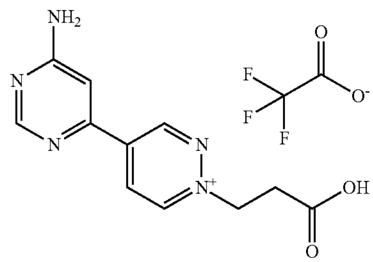 [SMILES: Nc1cc(-c2cc[n+](CCC(=O)O)nc2)ncn1 ; O=C([O-])C(F)(F)F] | (400 MHz, CD$_3$OD) 10.12-10.06 (m, 1H) 10.01-9.93 (m, 1H) 9.10 (dd, 1H) 8.63 (d, 1H) 7.43 (d, 1H) 5.14 (t, 2H) 3.26 (t, 2H) (two NH$_2$ protons and one CO$_2$H proton missing) |
| A164 | 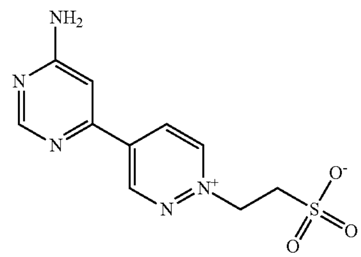 [SMILES: Nc1cc(-c2cc[n+](CCS(=O)(=O)[O-])nc2)ncn1] | (400 MHz, D$_2$O) 9.92-9.86 (m, 1H) 9.82-9.76 (m, 1H) 8.90 (dd, 1H) 8.58-8.49 (m, 1H) 7.32 (d, 1H) 5.23-5.18 (m, 2H) 3.67-3.63 (m, 2H) (two NH$_2$ protons missing) |
| A165 | 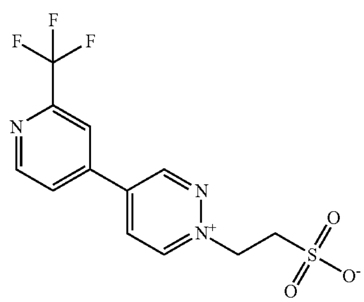 [SMILES: O=S(=O)([O-])CC[n+]1ccc(-c2ccnc(C(F)(F)F)c2)cn1] | (400 MHz, D$_2$O) 9.82-10.02 (m, 2H) 8.86-9.05 (m, 2H) 8.44 (s, 1H) 8.22 (dd, 1H) 5.24-5.34 (m, 2H) 3.66-3.77 ppm (m, 2H) |
| A166 | 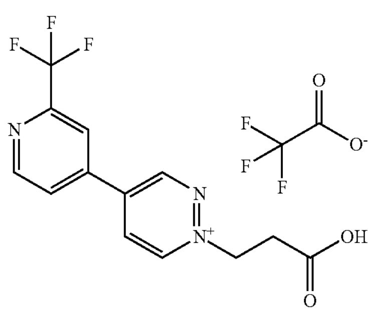 [SMILES: O=C(O)CC[n+]1ccc(-c2ccnc(C(F)(F)F)c2)cn1 ; O=C([O-])C(F)(F)F] | (400 MHz, D$_2$O) 9.78-9.94 (m, 2H) 8.84-9.04 (m, 2H) 8.43 (s, 1H) 8.21 (dd, 1H) 5.15 (t, 2H) 3.28 (t, 2H) (one CO$_2$H proton missing) |
| A167 | 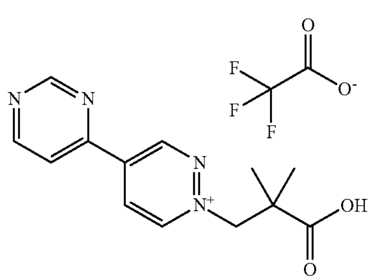 [SMILES: CC(C)(C[n+]1ccc(-c2ccncn2)cn1)C(=O)O ; O=C([O-])C(F)(F)F] | (400 MHz, D$_2$O) 10.03-10.10 (m, 1H) 9.83-9.89 (m, 1H) 9.38 (s, 1H) 9.15 (dd, 1H) 9.07 (d, 1H) 8.31 (dd, 1H) 5.08 (s, 2H) 1.28 (s, 6H) (one CO$_2$H proton missing) |

TABLE A-continued

Physical Data for Compounds of the Invention

| Compound Number | Structure | ¹H NMR |
|---|---|---|
| A168 | 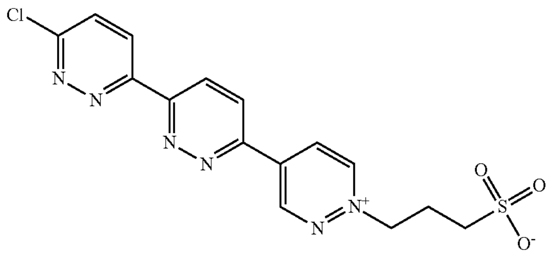 [SMILES: O=S(=O)([O-])CCC[n+]1ccc(-c2ccc(-c3ccc(Cl)nn3)nn2)cn1] | (400 MHz, D$_2$O) 10.23 (d, 1H) 9.86 (d, 1H) 9.20 (dd, 1H) 8.82 (d, 1H) 8.70 (d, 2H) 8.03 (d, 1H) 5.04 (t, 2H) 3.00 (t, 2H) 2.56 (quin, 2H) |
| A169 | 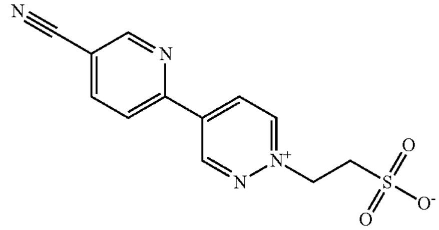 [SMILES: N#Cc1ccc(-c2cc[n+](CCS(=O)(=O)[O-])nc2)nc1] | (400 MHz, D$_2$O) 10.1 (d, 1H) 9.85 (d, 1H) 9.14-9.13 (m, 1H) 9.09 (dd, 1H) 8.47-8.41 (m, 2H) 5.25 (t, 2H) 3.70 (t, 2H) |
| A170 | 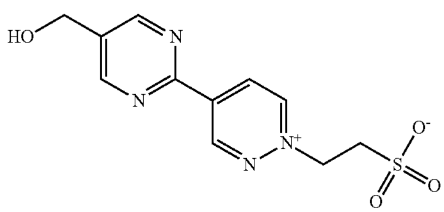 [SMILES: O=S(=O)([O-])CC[n+]1ccc(-c2ncc(CO)cn2)cn1] | (400 MHz, D$_2$O) 10.24 (d, 1H) 9.87 (d, 1H) 9.24 (m, 1H) 9.02 (s, 2H) 5.26 (m, 2H) 4.80 (s, 2H) 3.70 (m, 2H) (one OH proton missing) |
| A171 | 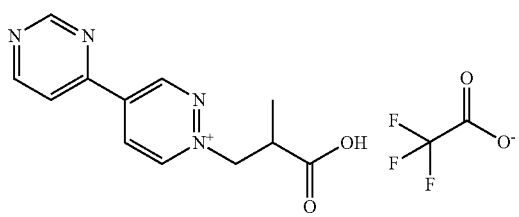 [SMILES: CC(C[n+]1ccc(-c2ccncn2)cn1)C(=O)O ; O=C([O-])C(F)(F)F] | (400 MHz, D$_2$O) 10.07 (d, 1H) 9.88 (d, 1H) 9.37 (s, 1H) 9.13 (dd, 1H) 9.03-9.08 (m, 1H) 8.26-8.33 (m, 1H) 5.14 (dd, 1H) 4.98 (dd, 1H) 3.41-3.45 (m, 1H) 1.30 (d, 3H) (one CO$_2$H proton missing) |
| A172 | 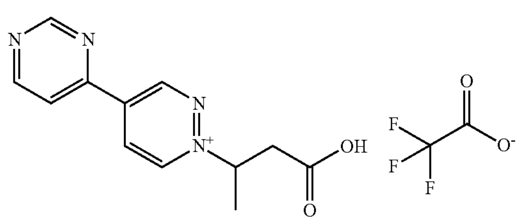 [SMILES: CC(CC(=O)O)[n+]1ccc(-c2ccncn2)cn1 ; O=C([O-])C(F)(F)F] | (400 MHz, D$_2$O) 10.12 (d, 1H) 9.95 (d, 1H) 9.39 (d, 1H) 9.06-9.16 (m, 2H) 8.31 (dd, 1H) 5.50-5.60 (m, 1H) 3.37 (dd, 1H) 3.14 (dd, 1H) 1.72 (d, 3H) (one CO$_2$H proton missing) |
| A173 | 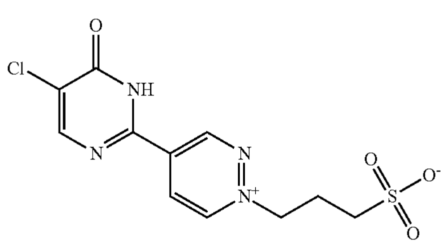 [SMILES: O=c1[nH]c(-c2cc[n+](CCCS(=O)(=O)[O-])nc2)ncc1Cl] | (400 MHz, D$_2$O) 10.24 (m, 1H) 9.80 (m, 1H) 9.04 (m, 1H) 8.44 (s, 1H) 5.03 (m, 2H) 3.04 (m, 2H) 2.50 (m, 2H) (one NH proton missing) |

TABLE A-continued

Physical Data for Compounds of the Invention

| Compound Number | Structure | $^1$H NMR |
|---|---|---|
| A174 | 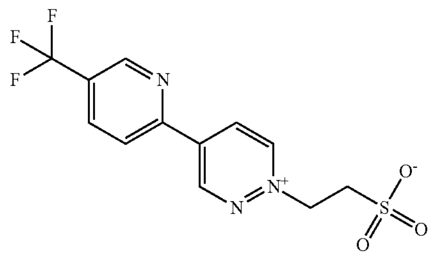 [SMILES: O=S(=O)([O-])CC[n+]1ccc(-c2ccc(C(F)(F)F)cn2)cn1] | (400 MHz, D$_2$O) 10.10 (d, 1H) 9.84 (d, 1H) 9.13 (s, 1H) 9.08 (dd, 1H) 8.45-8.39 (m, 2H) 5.25 (t, 2H) 3.71 (t, 2H) |
| A175 | 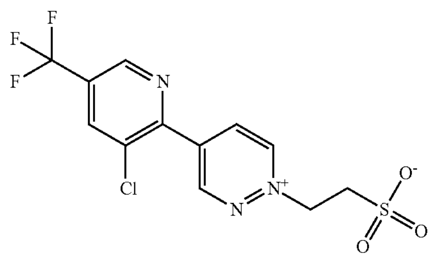 [SMILES: O=S(=O)([O-])CC[n+]1ccc(-c2ncc(C(F)(F)F)cc2Cl)cn1] | (400 MHz, D$_2$O) 9.91-9.89 (m, 2H) 9.04-9.02 (m, 2H) 8.51 (s, 1H) 5.27 (t, 2H) 3.71 (t, 2H) |
| A176 | 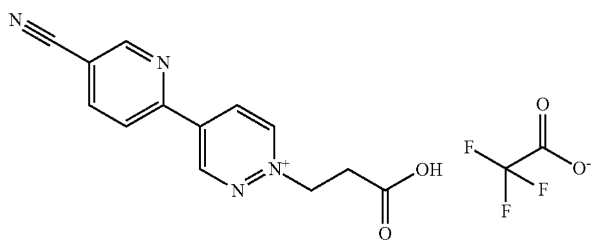 [SMILES: N#Cc1ccc(-c2cc[n+](CCC(=O)O)nc2)nc1 ; O=C([O-])C(F)(F)F] | (400 MHz, D$_2$O) 10.07 (d, 1H) 9.86 (d, 1H) 9.14-9.13 (m, 1H) 9.08 (dd, 1H) 8.47-8.40 (m, 2H) 5.13 (t, 2H) 3.25 (t, 2H) (one CO$_2$H proton missing) |
| A177 | 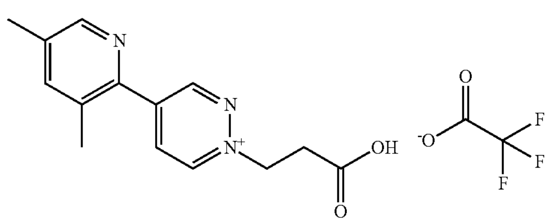 | (400 MHz, D$_2$O) 9.77 (d, 1H) 9.65 (d, 1H) 8.69 (dd, 1H) 8.42 (s, 1H) 7.76 (s, 1H) 5.10 (t, 2H) 3.24 (t, 2H) 2.41 (s, 3H) 2.36 ppm (s, 3H) (one CO$_2$H proton missing) |
| A178 | 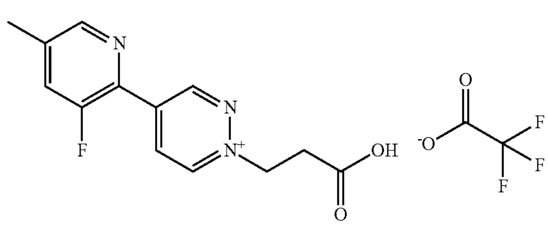 | (400 MHz, D$_2$O) 9.95 (s, 1H) 9.74 (d, 1H) 8.93 (dd, 1H) 8.48 (s, 1H) 7.70 (s, 1H) 5.07 (t, 2H) 3.22 (m, 2H) 2.44 (s, 3H) (one CO$_2$H proton missing) |
| A179 | 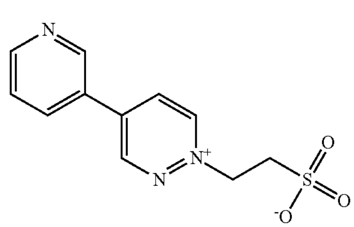 | (400 MHz, D$_2$O) 10.36 (d, 1H) 9.66 (d, 1H) 9.29 (d, 1H) 8.97 (dd, 1H) 8.92 (dd, 1H) 8.85 (m, 1H) 8.12 (m, 1H) 5.36 (t, 2H) 3.76 (t, 2H) |

TABLE A-continued

Physical Data for Compounds of the Invention

| Compound Number | Structure | $^1$H NMR |
|---|---|---|
| A180 | 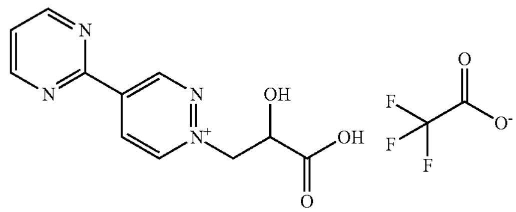 [SMILES: O=C(O)C(O)C[n+]1ccc(-c2ncccn2)cn1 ; O=C([O-])C(F)(F)F] | (400 MHz, D$_2$O) 10.25 (d, 1H) 9.83 (dd, 1H) 9.28 (dd, 1H) 9.06 (m, 2H) 7.73 (dd, 1H) 5.33 (dd, 1H) 5.23 (dd, 1H) 4.98 (m, 1H) (one OH proton and one CO$_2$H proton missing) |
| A181 | 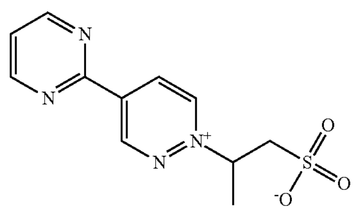 | (400 MHz, CD$_3$OD) 10.43-10.37 (m, 1H) 9.93 (dd, 1H) 9.34 (dd, 1H) 9.11 (d, 2H) 7.68 (t, 1H) 5.66-5.53 (m, 1H) 3.66 (dd, 1H) 3.43 (dd, 1H) 1.83 (d, 3H) |
| A182 | 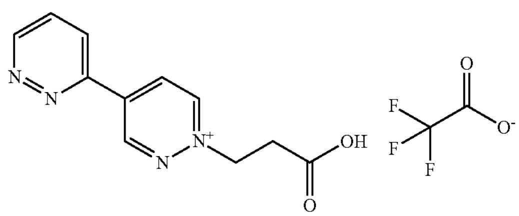 [SMILES: O=C(O)CC[n+]1ccc(-c2cccnn2)cn1 ; O=C([O-])C(F)(F)F] | (400 MHz, D$_2$O) 10.11 (d, 1H) 9.88 (d, 1H) 9.32 (dd, 1H) 9.10 (dd, 1H) 8.50 (dd, 1H) 7.99 (dd, 1H) 5.13 (t, 2H) 3.26 (t, 2H) (one CO$_2$H proton missing) |
| A183 | 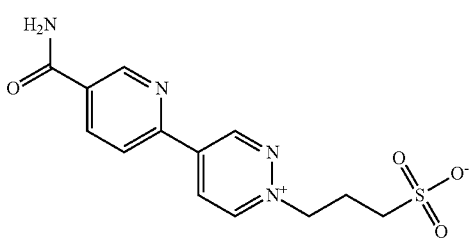 [SMILES: NC(=O)c1ccc(-c2cc[n+](CCCS(=O)(=O)[O-])nc2)nc1] | (400 MHz, D$_2$O) 9.83 (d, 1H) 9.54 (d, 1H) 8.92 (d, 1H) 8.81 (dd, 1H) 8.17-8.23 (m, 1H) 8.10-8.16 (m, 1H) 4.79-4.81 (m, 2H) 2.78 (t, 2H) 2.33 (q, 2H) (two NH protons missing) |
| A184 | 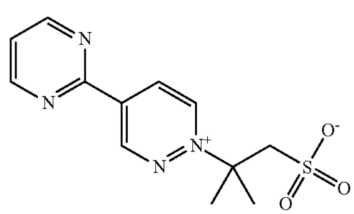 [SMILES: CC(C)(CS(=O)(=O)[O-])[n+]1ccc(-c2ncccn2)cn1] | (400 MHz, CD$_3$OD) 10.41-10.35 (m, 1H) 10.05-9.99 (m, 1H) 9.31 (dd, 1H) 9.12 (d, 2H) 7.67 (t, 1H) 3.67 (s, 2H) 2.10 (s, 6H) |
| A185 | 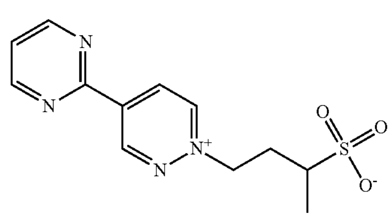 [SMILES: CC(CC[n+]1ccc(-c2ncccn2)cn1)S(=O)(=O)[O-]] | (400 MHz, D$_2$O) 10.22-10.14 (m, 1H) 9.85-9.77 (m, 1H) 9.24-9.16 (m, 1H) 9.04-8.95 (m, 2H) 7.70-7.60 (m, 1H) 5.13-4.96 (m, 2H) 3.05-2.91 (m, 1H) 2.66-2.51 (m, 1H) 2.42-2.25 (m, 1H) 1.36-1.26 (m, 3H) |

TABLE A-continued

Physical Data for Compounds of the Invention

| Compound Number | Structure | $^1$H NMR |
|---|---|---|
| A186 | 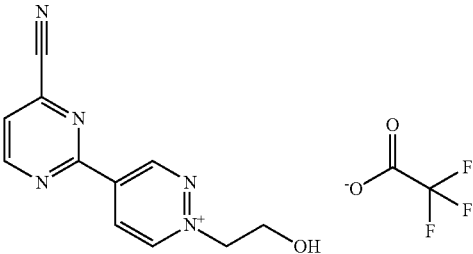 | (400 MHz, D$_2$O) 10.25 (s, 1H) 9.82 (d, 1H) 9.30 (dd, 1H) 9.27 (d, 1H) 8.08 (d, 1H) 4.98 (t, 2H) 4.15 (t, 2H) (one OH proton missing) |
| A187 | 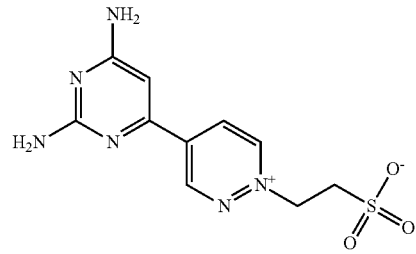 [SMILES: Nc1cc(-c2cc[n+](CCS(=O)(=O)[O-])nc2)nc(N)n1] | (400 MHz, CD$_3$OD) 10.01 (d, 1H) 9.94 (d, 1H) 9.00-8.95 (m, 1H) 6.87 (s, 1H) 5.39-5.25 (m, 2H) 3.30-3.22 (m, 2H) (Four NH protons missing) [isolated as a 1:1 mixture of isomers with 10.36 (s, 1H) 9.71 (d, 1H) 8.95-8.90 (m, 1H) 6.82 (s, 1H), 5.39-5.25 (m, 2H) 3.30-3.22 (m, 2H) (Four NH protons missing)] |
| A188 | 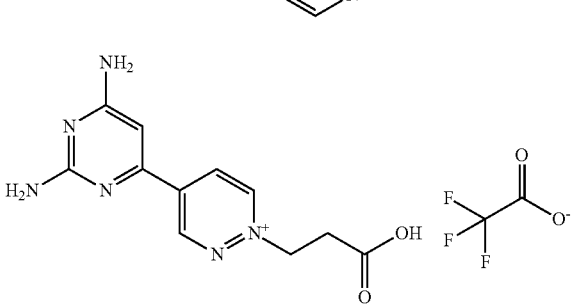 | (400 MHz, CD$_3$OD) 10.00-9.98 (m, 1H) 9.96 (d, 1H) 9.01 (dd, 1H) 6.78 (s, 1H) 5.13 (t, 2H) 3.29-3.23 (m, 2H) (Four NH protons and one CO$_2$H proton missing) |
| A189 | 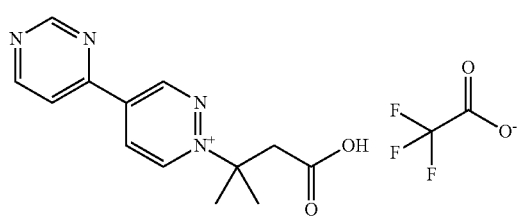 [SMILES: CC(C)(CC(=O)O)[n+]1ccc(-c2ccncn2)cn1 ; O=C([O-])C(F)(F)F] | (400 MHz, D$_2$O) 10.13 (d, 1H) 10.03 (d, 1H) 9.42 (d, 1H) 9.17 (dd, 1H) 9.10 (d, 1H) 8.35 (dd, 1H) 3.39 (s, 2H) 1.96 (s, 6H) (one CO$_2$H proton missing) |
| A190 | 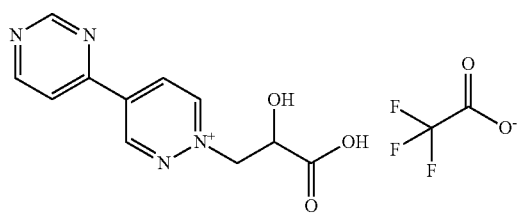 [SMILES: O=C(O)C(O)C[n+]1ccc(-c2ccncn2)cn1 ; O=C([O-])C(F)(F)F] | (400 MHz, D$_2$O) 10.12 (d, 1H) 9.83 (d, 1H) 9.41 (s, 1H) 9.19 (dd, 1H) 9.10 (br s, 1H) 8.34 (dd, 1H) 5.30 (dd, 1H) 5.18 (dd, 1H) 4.86 (dd, 1H) (one OH proton and one CO$_2$H proton missing) |

TABLE A-continued

Physical Data for Compounds of the Invention

| Compound Number | Structure | ¹H NMR |
|---|---|---|
| A191 | 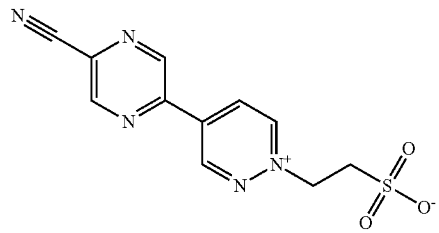 [SMILES: N#Cc1cnc(-c2cc[n+](CCS(=O)(=O)[O-])nc2)cn1] | (400 MHz, D$_2$O) 10.21 (d, 1H) 9.94 (d, 1H) 9.61 (d, 1H) 9.31 (d, 1H) 9.24 (dd, 1H) 5.30 (t, 2H) 3.73 (t, 2H) |
| A192 | 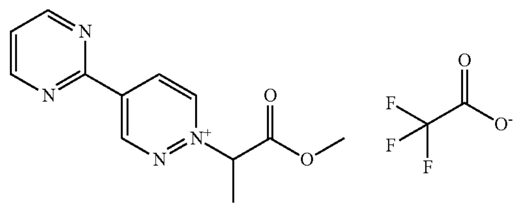 [SMILES: COC(=O)C(C)[n+]1ccc(-c2ncccn2)cn1 ; O=C([O-])C(F)(F)F] | (400 MHz, CD$_3$OD) 10.47-10.41 (m, 1H) 10.07-10.00 (m, 1H) 9.49 (dd, 1H) 9.13 (d, 2H) 7.71 (t, 1H) 6.14 (q, 1H) 3.84 (s, 3H) 2.07 (d, 3H) |
| A193 | 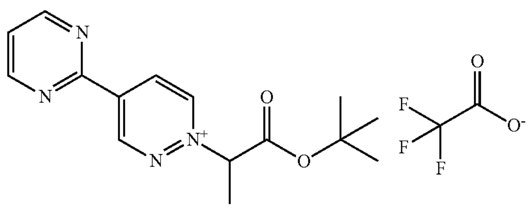 [SMILES: CC(C(=O)OC(C)(C)C)[n+]1ccc(-c2ncccn2)cn1 ; O=C([O-])C(F)(F)F] | (400 MHz, CD$_3$OD) 10.50-10.40 (m, 1H) 10.07-9.98 (m, 1H) 9.51 (dd, 1H) 9.15 (d, 2H) 7.70 (t, 1H) 6.02 (q, 1H) 2.02 (d, 3H) 1.48 (s, 9H) |
| A194 | 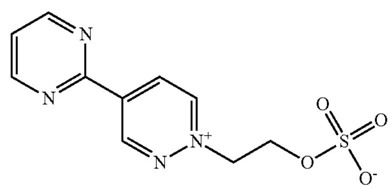 [SMILES: O=S(=O)([O-])OCC[n+]1ccc(-c2ncccn2)cn1] | (400 MHz, D$_2$O) 10.28 (d, 1H) 9.87 (d, 1H) 9.29 (dd, 1H) 9.07 (d, 2H) 7.72 (t, 1H) 5.18-5.28 (m, 2H) 4.62-4.72 (m, 2H) |
| A195 | 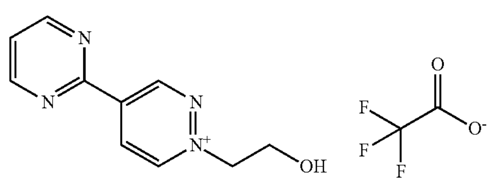 [SMILES: OCC[n+]1ccc(-c2ncccn2)cn1 ; O=C([O-])C(F)(F)F] | (400 MHz, D$_2$O) 10.25 (d, 1H) 9.81 (d, 1H) 9.26 (dd, 1H) 9.05 (d, 2H) 7.70 (t, 1H) 4.94-5.08 (m, 2H) 4.17-4.22 (m, 2H) (one OH proton missing) |
| A196 | 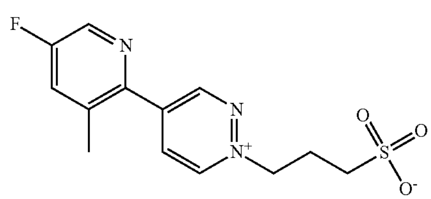 [SMILES: Cc1cc(F)cnc1-c1cc[n+](CCCS(=O)(=O)[O-])nc1] | (400 MHz, D$_2$O) 9.75 (m, 1H) 9.70 (m, 1H) 8.75 (m, 1H) 8.49 (m, 1H) 7.72 (m, 1H) 5.04 (m, 2H) 3.03 (m, 2H) 2.57 (m, 2H) 2.48 (m, 3H) |
| A197 | 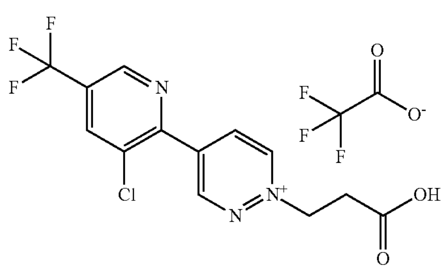 [SMILES: O=C(O)CC[n+]1ccc(-c2ncc(C(F)(F)F)cc2Cl)cn1 ; O=C([O-])C(F)(F)F] | (400 MHz, D$_2$O) 9.92 (d, 1H) 9.89 (d, 1H) 9.04 (td, 2H) 8.54 (d, 1H) 5.16 (t, 2H) 3.24 (t, 2H) (one CO$_2$H proton missing) |

TABLE A-continued

Physical Data for Compounds of the Invention

| Compound Number | Structure | $^1$H NMR |
|---|---|---|
| A198 | 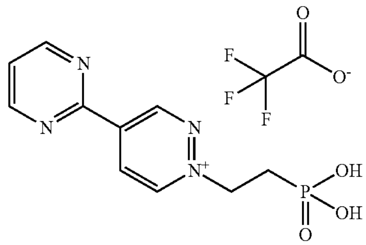 [SMILES: O=P(O)(O)CC[n+]1ccc(-c2ncccn2)cn1 ; O=C([O-])C(F)(F)F] | (400 MHz, D$_2$O) 10.21 (d, 1H) 9.81-9.89 (m, 1H) 9.18-9.26 (m, 1H) 9.02 (d, 2H) 7.67 (t, 1H) 5.09 (dt, 2H) 2.46-2.60 (m, 2H) (two POH protons missing) |
| A199 | 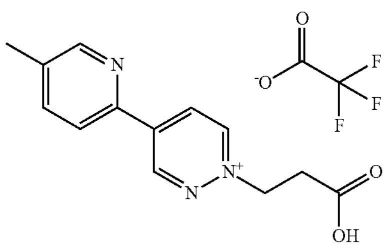 | (400 MHz, D$_2$O) 9.95 (d, 1H) 9.72 (d, 1H) 8.91 (dd, 1H) 8.65 (d, 1H) 8.16 (d, 1H) 7.98-7.87 (m, 1H) 5.08 (t, 2H) 3.26 (t, 2H) 2.42 (s, 3H) (one CO$_2$H proton missing) |
| A200 | 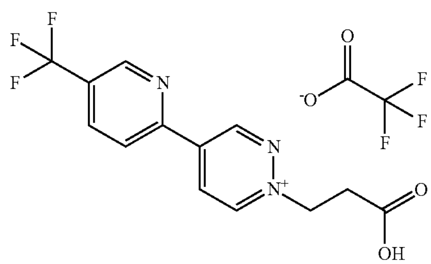 | (400 MHz, D$_2$O) 10.07 (d, 1H) 9.86 (d, 1H) 9.13 (s, 1H) 9.07 (dd, 1H) 8.44-8.38 (m, 2H) 5.14 (t, 2H) 3.28 (t, 2H) (one CO$_2$H proton missing) |
| A201 | 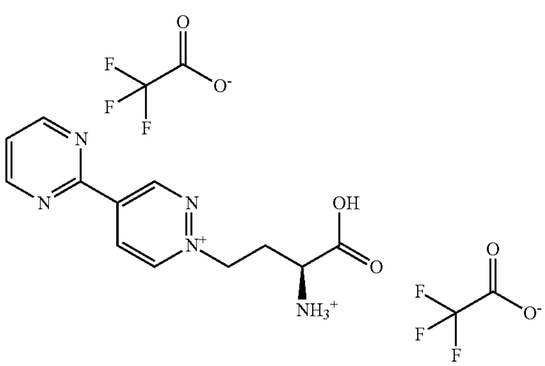 [SMILES: [NH3+][C@@H](CC[n+]1ccc(-c2ncccn2)cn1)C(=O)O ; O=C([O-])C(F)(F)F ; O=C([O-])C(F)(F)F] | (400 MHz, D$_2$O) 10.26 (d, 1H) 9.90 (d, 1H) 9.27 (dd, 1H) 9.06 (d, 2H) 7.72 (t, 1H) 5.17 (t, 2H) 4.09 (dd, 1H) 2.76-2.79 (m, 2H) (Three NH protons and one CO$_2$H proton missing) |
| A202 | 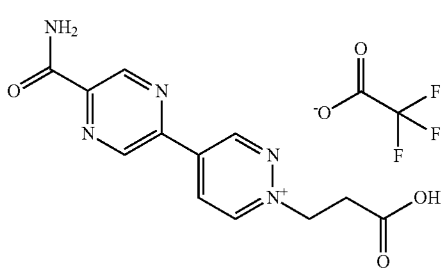 | (400 MHz, D$_2$O) 10.18 (d, 1H) 9.92 (d, 1H) 9.51 (d, 1H) 9.43 (d, 1H) 9.20 (dd, 1H) 5.18 (t, 2H) 3.31 (t, 2H) (two NH protons and one CO$_2$H proton missing) |

TABLE A-continued

Physical Data for Compounds of the Invention

| Compound Number | Structure | $^1$H NMR |
|---|---|---|
| A203 | 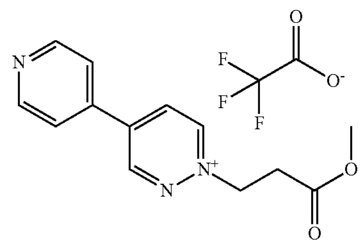 [SMILES: COC(=O)CC[n+]1ccc(-c2ccncc2)cn1 ; O=C([O-])C(F)(F)F] | (400 MHz, D$_2$O) 9.84-9.78 (m, 2H) 8.87 (dd, 1H) 8.80-8.75 (m, 2H) 8.02-7.96 (m, 2H) 5.10 (t, 2H) 3.61 (s, 3H) 3.26 (t, 2H) |
| A204 | 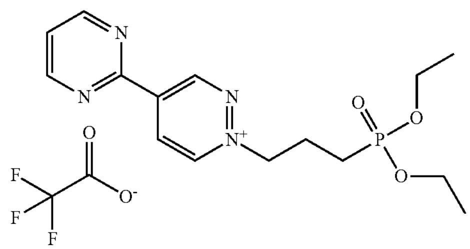 [SMILES: O=C([O-])C(F)(F)F ; CCOP(=O)(CCC[n+]1ccc(-c2ncccn2)cn1)OCC] | (400 MHz, D$_2$O) 10.23 (d, 1H) 9.83 (d, 1H) 9.24 (dd, 1H) 9.04 (d, 2H) 7.69 (t, 1H) 4.97 (t, 2H) 4.05-4.15 (m, 4H) 2.35-2.48 (m, 2H) 1.93-2.09 (m, 2H) 1.27 (t, 6H) |
| A205 | 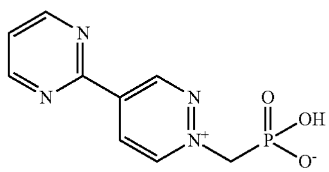 [SMILES: O=P([O-])(O)C[n+]1ccc(-c2ncccn2)cn1] | (400 MHz, D$_2$O) 10.16-10.13 (m, 1H) 9.72-9.68 (m, 1H) 9.20 (dd, 1H) 8.99 (d, 2H) 7.64 (t, 1H) 5.11 (d, 2H) (one OH proton missing) |
| A206 | 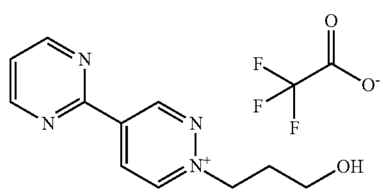 [SMILES: OCCC[n+]1ccc(-c2ncccn2)cn1 ; O=C([O-])C(F)(F)F] | (400 MHz, D$_2$O) 10.21 (d, 1H) 9.85 (d, 1H) 9.22 (dd, 1H) 9.04 (d, 2H) 7.69 (t, 1H) 5.00 (t, 2H) 3.70 (t, 2H) 2.31-2.39 (m, 2H) (one OH proton missing) |
| A207 | 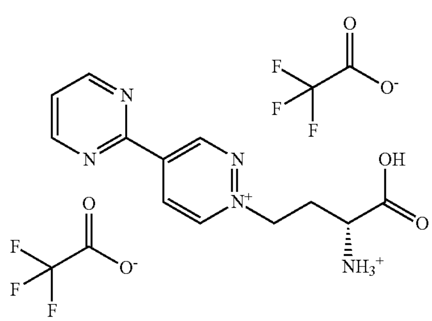 [SMILES: O=C([O-])C(F)(F)F ; [NH3+][C@H](CC[n+]1ccc(-c2ncccn2)cn1)C(=O)O ; O=C([O-])C(F)(F)F] | (400 MHz, D$_2$O) 10.22 (s, 1H) 9.87 (d, 1H) 9.24 (d, 1H) 8.99-9.04 (m, 2H) 7.66 (t, 1H) 5.16 (t, 2H) 4.17 (dd, 1H) 2.69-2.85 (m, 2H) (Three NH protons and one CO$_2$H proton missing) |
| A208 | 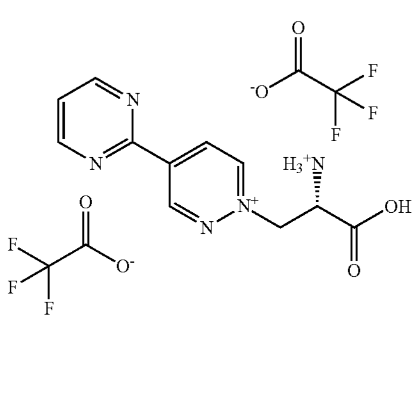 | (400 MHz, D$_2$O) 10.26 (s, 1H) 9.94 (d, 1H) 9.31-9.34 (m, 1H) 9.04 (dd, 2H) 7.69 (t, 1H) 5.48 (d, 2H) 4.75 (t, 1H) (Three NH protons and one CO$_2$H proton missing) |

TABLE A-continued

Physical Data for Compounds of the Invention

| Compound Number | Structure | $^1$H NMR |
|---|---|---|
| A209 | 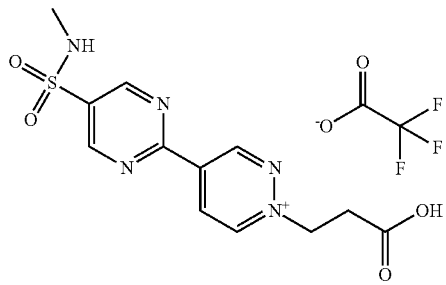 | (400 MHz, D$_2$O) 10.34 (s, 1H) 9.99 (d, 1H) 9.46 (s, 2H) 9.39 (m, 1H) 5.21 (t, 2H) 3.28 (t, 2H) 2.72 (s, 3H) (one NH proton and one CO$_2$H proton missing) |
| A210 | 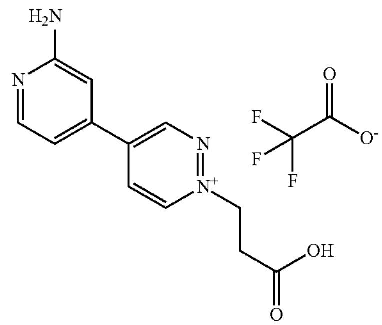 [SMILES: Nc1cc(-c2cc[n+](CCC(=O)O)nc2)ccn1 ; O=C([O-])C(F)(F)F] | (400 MHz, D$_2$O) 9.93 (d, 1H) 9.83 (d, 1H) 8.90 (dd, 1H) 8.03 (d, 1H) 7.53 (d, 1H) 7.30 (d, 1H) 5.23-5.15 (m, 2H) 3.29 (t, 2H) (two NH protons and one CO$_2$H proton missing) |
| A211 | 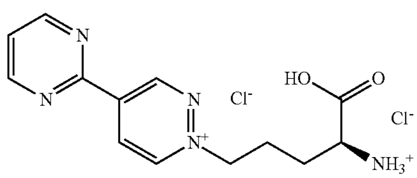 [SMILES: [NH3+][C@@H](CCC[n+]1ccc(-c2ncccn2)cn1)C(=O)O ; [Cl-] ; [Cl-]] | (400 MHz, D$_2$O) 10.24 (dd, 1H) 9.87 (dd, 1H) 9.27 (dd, 1H) 9.06 (d, 2H) 7.72 (t, 1H) 4.99 (t, 2H) 4.08 (t, 1H) 2.23-2.44 (m, 2H) 2.00-2.16 (m, 2H) (three NH protons and one CO$_2$H proton missing) |
| A212 | 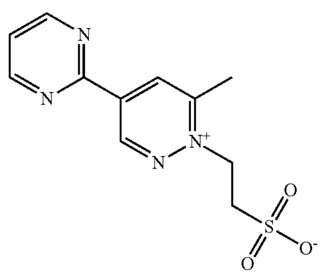 [SMILES: Cc1cc(-c2ncccn2)cn[n+]1CCS(=O)(=O)[O-]] | $^1$H NMR (400 MHz, D$_2$O) 10.00 (d, 1H) 9.08 (d, 1H) 9.00 (d, 2H) 7.65 (t, 1H) 5.16 (t, 2H) 3.68 (t, 2H) 3.12 (s, 3H) |
| A213 | 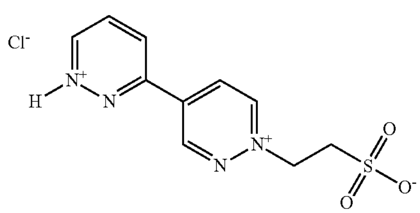 [SMILES: [Cl-] ; O=S(=O)([O-])CC[n+]1ccc(-c2ccc[nH+]n2)cn1] | (400 MHz, D$_2$O) 10.13 (d, 1H) 9.86 (d, 1H) 9.35 (dd, 1H) 9.11 (dd, 1H) 8.57 (dd, 1H) 8.05 (dd, 1H) 5.27-5.21 (m, 2H) 3.71-3.64 (m, 2H) (one NH proton missing) |
| A214 | 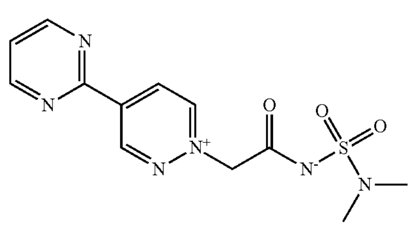 [SMILES: CN(C)S(=O)(=O)[N-]C(=O)C[n+]1ccc(-c2ncccn2)cn1] | (400 MHz, d$_6$-DMSO) 10.36 (s, 1H) 10.06-10.10 (m, 1H) 9.56-9.62 (m, 1H) 9.18-9.22 (m, 2H) 7.82-7.86 (m, 1H) 5.88-5.94 (m, 2H) 2.80-2.86 (m, 6H) |

TABLE A-continued

Physical Data for Compounds of the Invention

| Compound Number | Structure | $^1$H NMR |
|---|---|---|
| A215 | 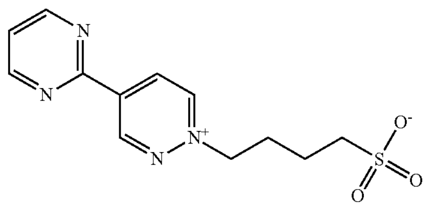 [SMILES: O=S(=O)([O-])CCCC[n+]1ccc(-c2ncccn2)cn1] | (400 MHz, D$_2$O) 10.18 (s, 1H) 9.78-9.82 (m, 1H) 9.16-9.20 (m, 1H) 8.96-9.02 (m, 2H) 7.62-7.66 (m, 1H) 4.86-4.94 (m, 2H) 2.88-2.94 (m, 2H) 2.18-2.28 (m, 2H) 1.72-1.82 (m, 2H) |
| A216 | 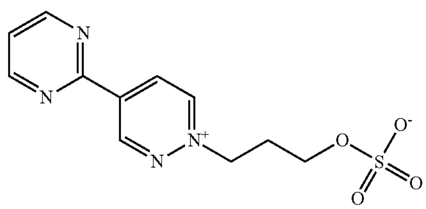 [SMILES: O=S(=O)([O-])OCCC[n+]1ccc(-c2ncccn2)cn1] | (400 MHz, D$_2$O) 10.16 (s, 1H) 9.80 (d, 1H) 9.14-9.20 (m, 1H) 8.96-9.00 (m, 2H) 7.60-7.66 (m, 1H) 4.96-5.04 (m, 2H) 4.06-4.12 (m, 2H) 2.44-2.52 (m, 2H) |
| A217 | 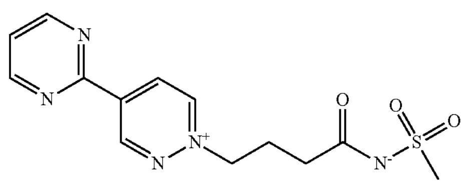 [SMILES: CS(=O)(=O)[N-]C(=O)CCC[n+]1ccc(-c2ncccn2)cn1] | (400 MHz, D$_2$O) 10.16 (s, 1H) 9.78-9.82 (m, 1H) 9.16-9.20 (m, 1H) 8.96-9.00 (m, 2H) 7.62-7.66 (m, 1H) 4.88-4.94 (m, 2H) 3.16 (s, 3H) 2.52-2.58 (m, 2H) 2.36-2.42 (m, 2H) |
| A218 | 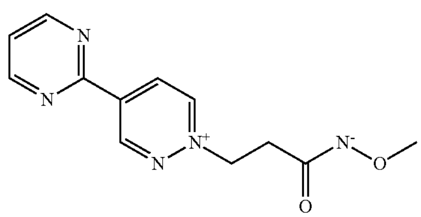 [SMILES: CO[N-]C(=O)CC[n+]1ccc(-c2ncccn2)cn1] | (400 MHz, D$_2$O) 10.18 (s, 1H) 9.82-9.86 (m, 1H) 9.18-9.24 (m, 1H) 8.98-9.02 (m, 2H) 7.64-7.68 (m, 1H) 5.12-5.18 (m, 2H) 3.60 (s, 3H) 3.00-3.04 (m, 2H) |
| A219 | 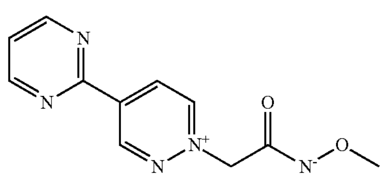 [SMILES: CO[N-]C(=O)C[n+]1ccc(-c2ncccn2)cn1] | (400 MHz, D$_2$O) 10.22 (s, 1H) 9.84-9.88 (m, 1H) 9.28-9.32 (m, 1H) 8.99-9.04 (m, 2H) 7.64-7.68 (m, 1H) 5.64-5.68 (m, 2H) 3.72 (s, 3H) |
| A220 | 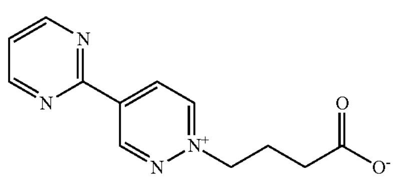 [SMILES: O=C([O-])CCC[n+]1ccc(-c2ncccn2)cn1] | (400 MHz, D$_2$O) 10.18 (s, 1H) 9.81 (d, 1H) 9.18-9.22 (m, 1H) 8.98-9.02 (m, 2H) 7.64-7.68 (m, 1H) 4.90-4.96 (m, 2H) 2.50-2.56 (m, 2H) 2.34-2.42 (m, 2H) |
| A221 | 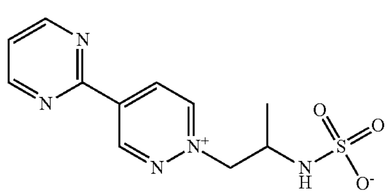 [SMILES: CC(C[n+]1ccc(-c2ncccn2)cn1)NS(=O)(=O)[O-]] | (400 MHz, D$_2$O) 10.18 (s, 1H) 9.68-9.76 (m, 1H) 9.18-9.22 (m, 1H) 9.00-9.06 (m, 2H) 7.64-7.70 (m, 1H) 4.96-5.04 (d, 1H) 4.60-4.68 (m, 1H) 3.82-3.92 (m, 1H) 1.36 (d, 3H) (one NH proton missing) |

TABLE A-continued

Physical Data for Compounds of the Invention

| Compound Number | Structure | ¹H NMR |
|---|---|---|
| A222 | 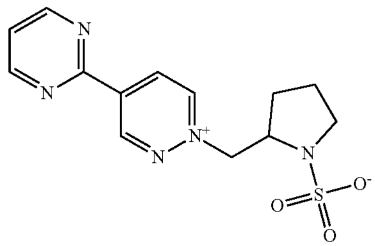 [SMILES: O=S(=O)([O-])N1CCCC1C[n+]1ccc(-c2ncccn2)cn1] | (400 MHz, D$_2$O) 10.12 (s, 1H) 9.62-9.68 (m, 1H) 9.12-9.18 (m, 1H) 8.94-9.02 (m, 2H) 7.60-7.66 (m, 1H) 4.94 (d, 1H) 4.58-4.66 (m, 1H) 4.04-4.14 (m, 1H) 3.16-3.28 (m, 2H) 2.04-2.18 (m, 1H) 1.72-1.98 (m, 3H) |
| A223 | 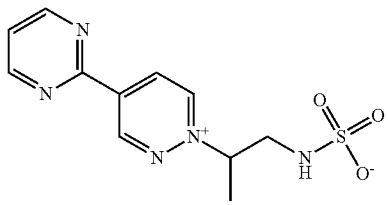 [SMILES: CC(CNS(=O)(=O)[O-])[n+]1ccc(-c2ncccn2)cn1] | (400 MHz, D$_2$O) 10.18 (s, 1H) 9.68-9.74 (m, 1H) 9.14-9.18 (m, 1H) 8.96-9.02 (m, 2H) 7.62-7.66 (m, 1H) 5.14-5.24 (m, 1H) 3.38-3.54 (m, 2H) 1.68 (d, 3H) (one NH proton missing) |
| A224 | 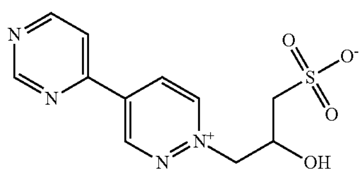 [SMILES: O=S(=O)([O-])CC(O)C[n+]1ccc(-c2ccncn2)cn1] | (400 MHz, D$_2$O) 10.16 (d, 1H) 9.85 (dd, 1H) 9.41-9.44 (m, 1H) 9.21 (dd, 1H) 9.11 (d, 1H) 8.36 (dd, 1H) 5.26 (dd, 1H) 4.97 (dd, 1H) 4.71-4.78 (m, 1H) 3.21-3.37 (m, 2H) (one OH proton missing) |
| A225 | 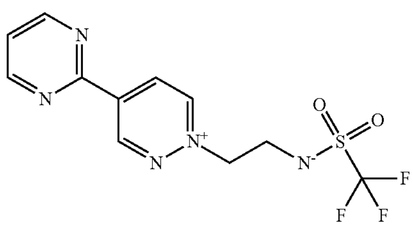 [SMILES: O=S(=O)([N-]CC[n+]1ccc(-c2ncccn2)cn1)C(F)(F)F] | (400 MHz, D$_2$O) 10.14-10.18 (m, 1H) 9.64-9.68 (m, 1H) 9.16-9.22 (m, 1H) 8.96-9.00 (m, 2H) 7.60-7.64 (m, 1H) 4.82-4.88 (m, 2H) 3.58-3.64 (m, 2H) |
| A226 | 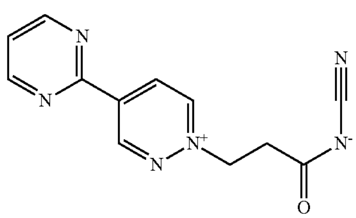 [SMILES: N#C[N-]C(=O)CC[n+]1ccc(-c2ncccn2)cn1] | (400 MHz, D$_2$O) 10.16 (s, 1H) 9.86 (d, 1H) 9.16-9.20 (m, 1H) 8.96-9.02 (m, 2H) 7.60-7.66 (m, 1H) 5.08-5.14 (m, 2H) 3.20-3.28 (m, 2H) |
| A227 | 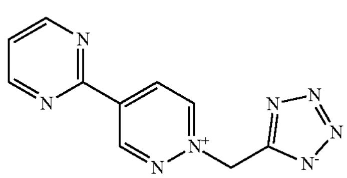 [SMILES: c1cnc(-c2cc[n+](Cc3nnn[n-]3)nc2)nc1] | (400 MHz, D$_2$O) 10.18 (s, 1H) 10.00-10.04 (m, 1H) 9.26-9.30 (m, 1H) 8.96-9.02 (m, 2H) 7.62-7.66 (m, 1H) 6.42-6.48 (m, 2H) |
| A228 | 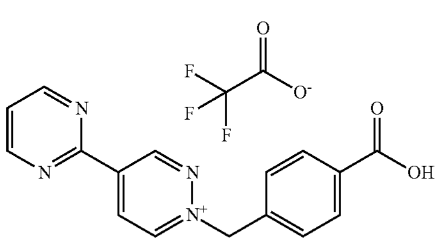 [SMILES: O=C(O)c1ccc(C[n+]2ccc(-c3ncccn3)cn2)cc1 ; O=C([O-])C(F)(F)F] | (400 MHz, CD$_3$OD) 10.44-10.30 (m, 1H) 10.12-10.05 (m, 1H) 9.42 (dd, 1H) 9.10 (d, 2H) 8.10 (d, 2H) 7.74-7.67 (m, 3H) 6.19 (s, 2H) |

TABLE A-continued

Physical Data for Compounds of the Invention

| Compound Number | Structure | ¹H NMR |
|---|---|---|
| A229 | 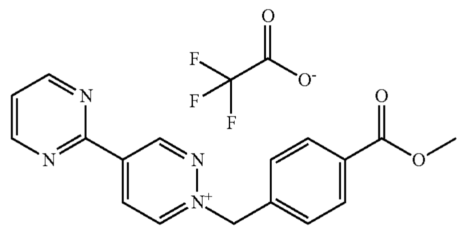 [SMILES: COC(=O)c1ccc(C[n+]2ccc(-c3ncccn3)cn2)cc1 ; O=C([O-])C(F)(F)F] | (400 MHz, CD₃OD) 10.40-10.35 (m, 1H) 10.10-10.05 (m, 1H) 9.43 (dd, 1H) 9.11 (d, 2H) 8.14-8.08 (m, 2H) 7.75-7.68 (m, 3H) 6.18 (s, 2H) 3.91 (s, 3H) |
| A230 | 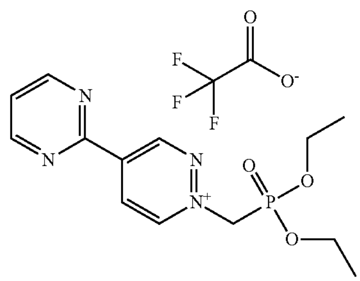 [SMILES: CCOP(=O)(C[n+]1ccc(-c2ncccn2)cn1)OCC ; O=C([O-])C(F)(F)F] | (400 MHz, d₆-DMSO) 10.39-10.35 (m, 1H) 10.01 (d, 1H) 9.47 (dd, 1H) 9.22 (d, 2H) 7.84 (t, 1H) 5.78 (d, 2H) 4.24-4.13 (m, 4H) 1.27 (t, 6H) |
| A231 | 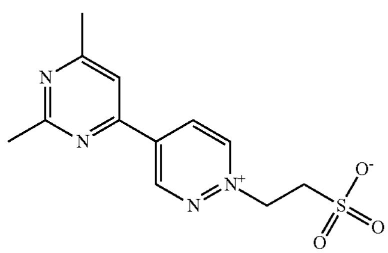 [SMILES: Cc1cc(-c2cc[n+](CCS(=O)(=O)[O-])nc2)nc(C)n1] | (400 MHz, D₂O) 10.04-9.99 (m, 1H) 9.85 (d, 1H) 9.05 (dd, 1H) 8.03 (s, 1H) 5.23 (t, 2H) 3.66 (t, 2H) 2.71 (s, 3H) 2.59 (s, 3H) |
| A232 | 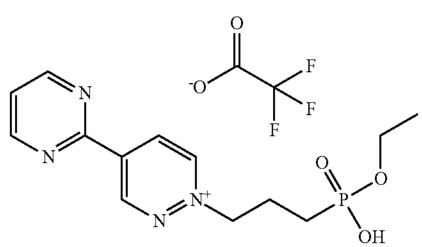 | (400 MHz, D₂O) 10.24 (dd, 1H) 9.86 (dd, 1H) 9.26 (dd, 1H) 9.06 (d, 2H) 7.71 (t, 1H) 4.98 (t, 2H) 3.92 (quin, 2H) 2.37 (ddd, 2H) 1.69-1.80 (m, 2H) 1.23 (t, 3H) (one POH proton missing) |
| A233 | 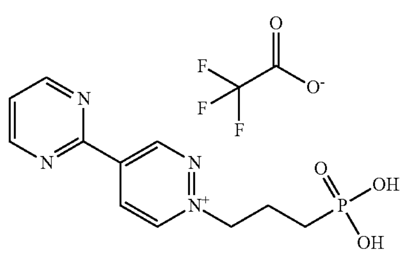 [SMILES: O=P(O)(O)CCC[n+]1ccc(-c2ncccn2)cn1 ; O=C([O-])C(F)(F)F] | (400 MHz, D₂O) 10.22 (d, 1H) 9.84 (d, 1H) 9.23 (dd, 1H) 9.03 (d, 2H) 7.68 (t, 1H) 4.97 (t, 2H) 2.33-2.46 (m, 2H) 1.77-1.89 (m, 2H) (two OH protons missing) |
| A234 | 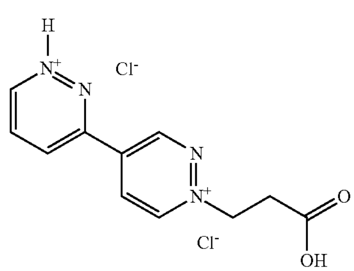 [SMILES: O=C(O)CC[n+]1ccc(-c2ccc[nH+]n2)cn1 ; [Cl-] ; [Cl-]] | (400 MHz, D₂O) 10.11 (d, 1H) 9.88 (d, 1H) 9.36 (br d, 1H) 9.10 (dd, 1H) 8.48-8.56 (m, 1H) 7.92-8.07 (m, 1H) 4.98-5.20 (m, 2H) 3.18-3.32 (m, 2H) (one CO₂H proton missing) |

TABLE A-continued

Physical Data for Compounds of the Invention

| Compound Number | Structure | ¹H NMR |
|---|---|---|
| A235 | 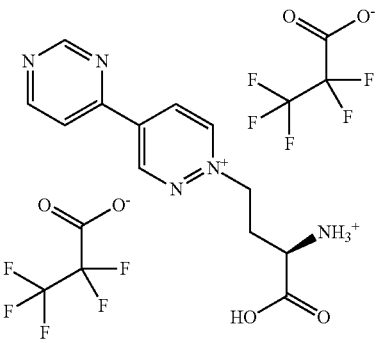 [SMILES: O=C([O-])C(F)(F)C(F)(F)F ; [NH3+][C@H](CC[n+]1ccc(-c2ccncn2)cn1)C(=O)O ; O=C([O-])C(F)(F)C(F)(F)F] | (400 MHz, D₂O) 10.14 (d, 1H) 9.92 (d, 1H) 9.42 (d, 1H) 9.18 (dd, 1H) 9.10 (d, 1H) 8.35 (dd, 1H) 5.09-5.21 (m, 2H) 3.87 (dd, 1H) 2.72 (dd, 2H) (three NH protons and one CO2H proton missing) [Note: pentafluoropropionic acid was used in the HPLC eluent instead of trifluoroacetic acid] |
| A236 | 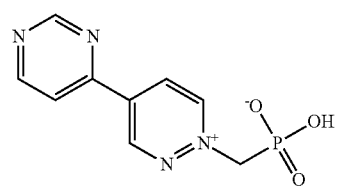 | (400 MHz, D₂O) 10.03 (d, 1H) 9.74-9.69 (m, 1H) 9.34 (s, 1H) 9.14-9.09 (m, 1H) 9.04-9.00 (m, 1H) 8.30-8.26 (m, 1H) 5.11 (d, 2H) (one POH proton missing) |
| A237 | 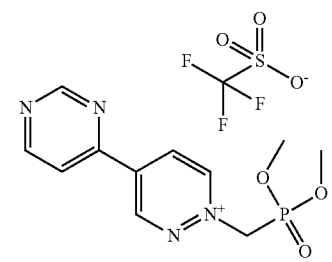 [SMILES: COP(=O)(C[n+]1ccc(-c2ccncn2)cn1)OC ; O=S(=O)([O-])C(F)(F)F] | (400 MHz, D₂O) 10.19-10.13 (m, 1H) 9.93-9.87 (m, 1H) 9.43-9.38 (m, 1H) 9.27-9.22 (m, 1H) 9.11-9.05 (m, 1H) 8.34 (dd, 1H) 5.72-5.65 (m, 2H) 3.90-3.84 (m, 6H) |
| A238 | 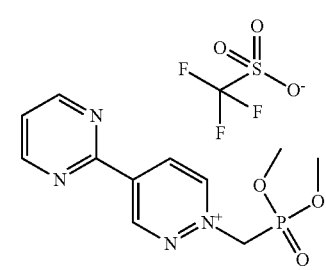 [SMILES: COP(=O)(C[n+]1ccc(-c2ncccn2)cn1)OC ; O=S(=O)([O-])C(F)(F)F] | (400 MHz, D₂O) 10.37 (d, 1H) 10.00 (d, 1H) 9.48-9.42 (m, 1H) 9.23-9.20 (m, 2H) 7.83 (t, 1H) 5.82 (d, 2H) 3.83 (s, 3H) 3.82-3.78 (m, 3H) |
| A239 | 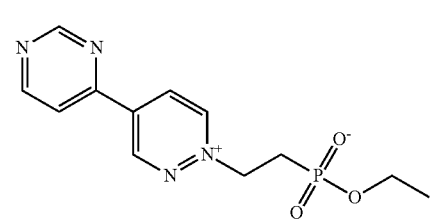 | (400 MHz, D₂O) 10.09 (d, 1H) 9.86 (d, 1H) 9.40-9.35 (m, 1H) 9.13 (dd, 1H) 9.06 (d, 1H) 8.31 (dd, 1H) 5.11-4.98 (m, 2H) 3.88-3.76 (m, 2H) 2.44 (td, 2H) 1.11 (t, 3H) |
| A240 | 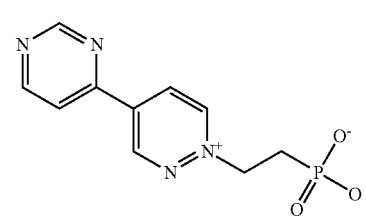 [SMILES: O=P([O-])(O)CC[n+]1ccc(-c2ccncn2)cn1] | (400 MHz, D₂O) 10.10-10.06 (m, 1H) 9.89-9.85 (m, 1H) 9.39-9.36 (m, 1H) 9.15-9.10 (m, 1H) 9.07-9.04 (m, 1H) 8.33-8.28 (m, 1H) 5.11-5.02 (m, 2H) 2.51-2.40 (m, 2H) (one OH proton missing) |

TABLE A-continued

Physical Data for Compounds of the Invention

| Compound Number | Structure | ¹H NMR |
|---|---|---|
| A241 | 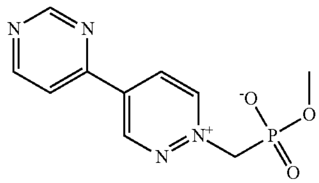 | (400 MHz, D$_2$O) 10.11-10.08 (m, 1H) 9.80-9.75 (m, 1H) 9.41-9.38 (m, 1H) 9.20-9.15 (m, 1H) 9.10-9.06 (m, 1H) 8.36-8.31 (m, 1H) 5.26-5.20 (m, 2H) 3.67-3.61 (m, 3H) |
| A242 | 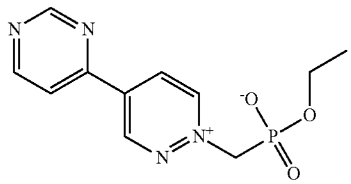 | (400 MHz, D$_2$O) 10.02-9.98 (m, 1H) 9.71-9.64 (m, 1H) 9.33-9.28 (m, 1H) 9.11-9.06 (m, 1H) 9.01-8.96 (m, 1H) 8.26-8.21 (m, 1H) 5.15-5.08 (m, 2H) 3.94-3.84 (m, 2H) 1.12 (t, 3H) |
| A243 | 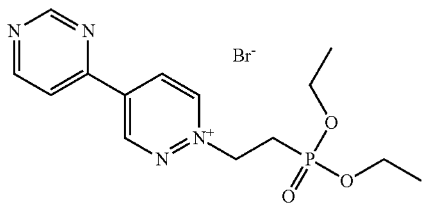 [SMILES: CCOP(=O)(CC[n+]1ccc(-c2ccncn2)cn1)OCC ; [Br-]] | (400 MHz, D$_2$O) 10.14-10.11 (m, 1H) 9.92-9.88 (m, 1H) 9.37 (d, 1H) 9.19-9.14 (m, 1H) 9.05 (d, 1H) 8.32-8.28 (m, 1H) 5.20-5.10 (m, 2H) 4.12-4.02 (m, 4H) 2.88-2.76 (m, 2H) 1.18 (t, 6H) |
| A244 | 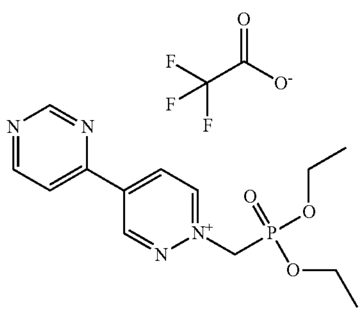 [SMILES: CCOP(=O)(C[n+]1ccc(-c2ccncn2)cn1)OCC ; O=C([O-])C(F)(F)F] | (400 MHz, D$_2$O) 10.17-10.13 (m, 1H) 9.91-9.85 (m, 1H) 9.40-9.36 (m, 1H) 9.25-9.19 (m, 1H) 9.08-9.04 (m, 1H) 8.34-8.29 (m, 1H) 5.66-5.58 (m, 2H) 4.32-4.14 (m, 4H) 1.25 (br t, 6H) |
| A245 | 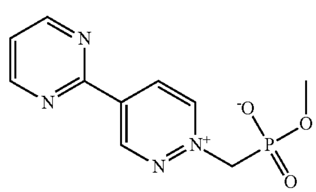 | (400 MHz, D$_2$O) 10.19-10.15 (m, 1H) 9.73-9.69 (m, 1H) 9.25-9.20 (m, 1H) 9.01 (d, 2H) 7.68-7.62 (m, 1H) 5.19 (d, 2H) 3.61 (d, 3H) |
| A246 | 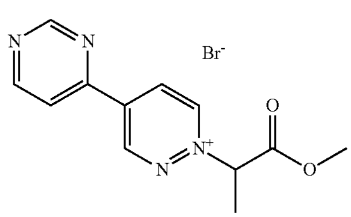 [SMILES: COC(=O)C(C)[n+]1ccc(-c2ccncn2)cn1 ; [Br-]] | (400 MHz, D$_2$O) 10.20 (d, 1H) 10.00 (dd, 1H) 9.45 (d, 1H) 9.28 (dd, 1H) 9.13 (d, 1H) 8.39 (dd, 1H) 6.15 (d, 1H) 3.82 (s, 3H) 2.05 (d, 3H) |

TABLE A-continued

Physical Data for Compounds of the Invention

| Compound Number | Structure | ¹H NMR |
|---|---|---|
| A247 | 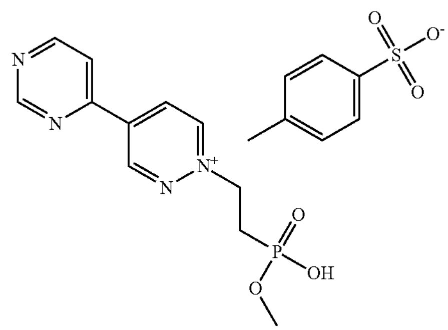 [SMILES: COP(=O)(O)CC[n+]1ccc(-c2ccncn2)cn1 ; Cc1ccc(S(=O)(=O)[O-])cc1] | (400 MHz, D$_2$O) 10.11-10.05 (m, 1H) 9.88-9.83 (m, 1H) 9.39-9.35 (m, 1H) 9.15-9.09 (m, 1H) 9.07-9.03 (m, 1H) 8.32-8.27 (m, 1H) 7.61-7.56 (m, 2H) 7.30-7.25 (m, 2H) 5.09-4.97 (m, 2H) 3.45 (d, 3H) 2.52-2.39 (m, 2H) 2.30 (s, (one POH proton missing) |
| A248 | 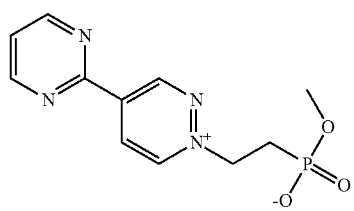 | (400 MHz, D$_2$O) 10.18 (d, 1H) 9.81 (d, 1H) 9.19 (dd, 1H) 8.99 (d, 2H) 7.64 (t, 1H) 5.07-4.97 (m, 2H) 3.46 (d, 3H) 2.53-2.42 (m, 2H) |
| A249 | 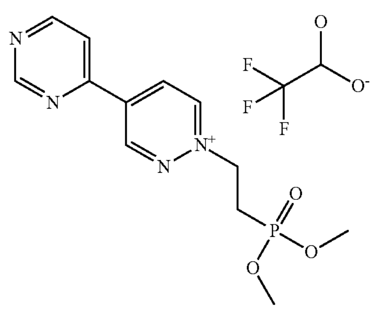 [SMILES: COP(=O)(CC[n+]1ccc(-c2ccncn2)cn1)OC ; [O-]C(O)C(F)(F)F] | (400 MHz, D$_2$O) 10.16-10.13 (m, 1H) 9.94-9.90 (m, 1H) 9.42-9.39 (m, 1H) 9.21-9.16 (m, 1H) 9.11-9.07 (m, 1H) 8.36-8.31 (m, 1H) 5.23-5.13 (m, 2H) 3.76-3.70 (m, 6H) 2.93-2.81 (m, 2H) |
| A250 | 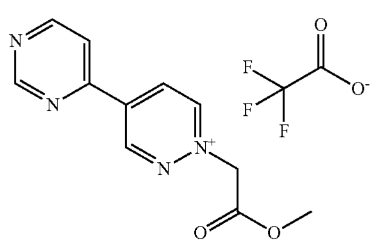 [SMILES: COC(=O)C[n+]1ccc(-c2ccncn2)cn1 ; O=C([O-])C(F)(F)F] | (400 MHz, D$_2$O) 10.16-10.11 (m, 1H) 9.91-9.86 (m, 1H) 9.41-9.37 (m, 1H) 9.26-9.21 (m, 1H) 9.10-9.05 (m, 1H) 8.37-8.30 (m, 1H) 5.87 (s, 2H) 3.80 (s, 3H) |
| A251 | 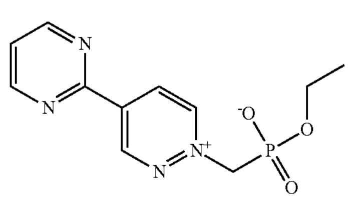 | (400 MHz, D$_2$O) 10.16 (s, 1H) 9.70 (br d, 1H) 9.24-9.18 (m, 1H) 8.99 (d, 2H) 7.64 (t, 1H) 5.15 (br d, 2H) 3.99-3.89 (m, 2H) 1.17 (t, 3H) |

BIOLOGICAL EXAMPLES

Post-Emergence Efficacy
Method A

Seeds of a variety of test species were sown in standard soil in pots. After cultivation for 14 days (post-emergence) under controlled conditions in a glasshouse (at 24/16° C., day/night; 14 hours light; 65% humidity), the plants were sprayed with an aqueous spray solution derived from the dissolution of the technical active ingredient formula (I) in a small amount of acetone and a special solvent and emulsifier mixture referred to as IF50 (11.12% Emulsogen EL360 TM+44.44% N-methylpyrrolidone+44.44% Dowanol DPM glycol ether), to create a 50 g/l solution which was then diluted to required concentration using 0.25% or 1% Empicol ESC70 (Sodium lauryl ether sulphate)+1% ammonium sulphate as diluent.

The test plants were then grown in a glasshouse under controlled conditions (at 24/16° C., day/night; 14 hours light; 65% humidity) and watered twice daily. After 13 days the test was evaluated (100=total damage to plant; 0=no damage to plant).

The results are shown in Table B (below). A value of n/a indicates that this combination of weed and test compound was not tested/assessed.

Test Plants:

*Ipomoea hederacea* (IPOHE), *Euphorbia heterophylla* (EPHHL), *Chenopodium album* (CHEAL), *Amaranthus palmeri* (AMAPA), *Lolium perenne* (LOLPE), *Digitaria sanguinalis* (DIGSA), *Eleusine indica* (ELEIN), *Echinochloa crus-galli* (ECHCG), *Setaria faberi* (SETFA)

TABLE B

Control of weed species by compounds of Formula (I) after post-emergence application

| Compound Number | Application Rate g/Ha | AMAPA | CHEAL | EPHHL | IPOHE | SETFA | ECHCG | ELEIN | DIGSA | LOLPE |
|---|---|---|---|---|---|---|---|---|---|---|
| A1 | 500 | 100 | 100 | 100 | 100 | 100 | 70 | 100 | 100 | 70 |
| A2 | 500 | 60 | 20 | 90 | 10 | 80 | 50 | 30 | 40 | 0 |
| A4 | 500 | 100 | 80 | 100 | 90 | 60 | 60 | 100 | 80 | 100 |
| A5 | 500 | 100 | 100 | 100 | 40 | 90 | 100 | 100 | 100 | 100 |
| A6 | 500 | 100 | 100 | 100 | 60 | 100 | 80 | 100 | 100 | 60 |
| A7 | 500 | 100 | 100 | 100 | 60 | 90 | 80 | 100 | 100 | 60 |
| A8 | 500 | 10 | 10 | 10 | 10 | 20 | 10 | 20 | 20 | 0 |
| A9 | 500 | 100 | 100 | 70 | 30 | 60 | 100 | 100 | 100 | 80 |
| A10 | 500 | 100 | 100 | 100 | 40 | 60 | 30 | 50 | 60 | 90 |
| A11 | 500 | 100 | 100 | 100 | 100 | 30 | 60 | 100 | 80 | 80 |
| A12 | 500 | 100 | 100 | 40 | 30 | 70 | 80 | 100 | 100 | 90 |
| A13 | 500 | 100 | 50 | 70 | 50 | 60 | 50 | 100 | 70 | 50 |
| A14 | 500 | 80 | 60 | 20 | 40 | 60 | 60 | 90 | 90 | 40 |
| A15 | 500 | n/a | 90 | 20 | 10 | 50 | 40 | 80 | 60 | 10 |
| A16 | 500 | 60 | 30 | 50 | 40 | 50 | 60 | 70 | 50 | 10 |
| A17 | 500 | 100 | 30 | 30 | 30 | 40 | 40 | 60 | 60 | 10 |
| A18 | 500 | n/a | 0 | 10 | 10 | 40 | 30 | 60 | 50 | 10 |
| A19 | 500 | 100 | 60 | 60 | 40 | 60 | 40 | 60 | 50 | 20 |
| A20 | 500 | n/a | 100 | 80 | 40 | 100 | 100 | 100 | 100 | 60 |
| A21 | 500 | 100 | 80 | 80 | 40 | 90 | 60 | 100 | 90 | 80 |
| A22 | 500 | n/a | 100 | 70 | 30 | 100 | 100 | 100 | 100 | 80 |
| A23 | 500 | n/a | 80 | 90 | 60 | 100 | 70 | 100 | 80 | 70 |
| A24 | 500 | 90 | 70 | 80 | 70 | 70 | 60 | 40 | 40 | 60 |
| A25 | 500 | 100 | 60 | 40 | 50 | 60 | 70 | 50 | 50 | 40 |
| A26 | 500 | n/a | 100 | 100 | 40 | 100 | 100 | 100 | 100 | 90 |
| A28 | 500 | 100 | 100 | 100 | 100 | 100 | 90 | 100 | 90 | 70 |
| A29 | 500 | 100 | 100 | 100 | 20 | 90 | 90 | 90 | 100 | 50 |
| A30 | 500 | 100 | 90 | 100 | 80 | 100 | 80 | 100 | 100 | 70 |
| A31 | 500 | 100 | 100 | 50 | 100 | 50 | 60 | 80 | 90 | 60 |
| A32 | 500 | n/a | 70 | 70 | 40 | 80 | 70 | 100 | 90 | 30 |
| A33 | 500 | 100 | 80 | 60 | 40 | 60 | 40 | 80 | 60 | 50 |
| A34 | 500 | 100 | 70 | 70 | 70 | 70 | 30 | 90 | 60 | 60 |
| A35 | 500 | 100 | 100 | 100 | n/a | 100 | 80 | 90 | 100 | 90 |
| A36 | 500 | 100 | 90 | 90 | 30 | 100 | 90 | 100 | 90 | 80 |
| A37 | 500 | n/a | 100 | 80 | 30 | 100 | 100 | 100 | 100 | 80 |
| A38 | 500 | 100 | 50 | 30 | 20 | 70 | 30 | 70 | 100 | 40 |
| A39 | 500 | 100 | 90 | 90 | 0 | 40 | 30 | 80 | 70 | 60 |
| A40 | 500 | 90 | 70 | 90 | 100 | 100 | 90 | 90 | 90 | 90 |
| A41 | 500 | n/a | 90 | 90 | 30 | 100 | 100 | 100 | 100 | 70 |
| A42 | 500 | 50 | 0 | 30 | 20 | 50 | 30 | 20 | 50 | 0 |
| A43 | 500 | n/a | 90 | 80 | 30 | 100 | 70 | 100 | 90 | 20 |
| A44 | 500 | 40 | 10 | 20 | 20 | 60 | 30 | 20 | 40 | 20 |
| A45 | 500 | n/a | 60 | 50 | 20 | 100 | 90 | 80 | 80 | 30 |
| A46 | 500 | 70 | 10 | 60 | 10 | 50 | 30 | 50 | 50 | 20 |
| A47 | 500 | n/a | 100 | 80 | 50 | 100 | 70 | 100 | 100 | 60 |
| A48 | 500 | n/a | 100 | 90 | 20 | 100 | 70 | 100 | 90 | 70 |
| A49 | 500 | 100 | 80 | 70 | 60 | 100 | 60 | 100 | 90 | 50 |
| A50 | 500 | 100 | 20 | 90 | 50 | 60 | 40 | 90 | 50 | 60 |
| A51 | 500 | n/a | 70 | 30 | 20 | 70 | 60 | 90 | 90 | 60 |
| A52 | 500 | n/a | 60 | 60 | 20 | 70 | 60 | 70 | 70 | 10 |
| A53 | 500 | n/a | 100 | 80 | 70 | 80 | 70 | 70 | 80 | 40 |
| A54 | 500 | 90 | 90 | 70 | 10 | 100 | 90 | 100 | 100 | 70 |
| A55 | 500 | n/a | 80 | 70 | 70 | 100 | 90 | 100 | 100 | 60 |

TABLE B-continued

Control of weed species by compounds of Formula (I) after post-emergence application

| Compound Number | Application Rate g/Ha | AMAPA | CHEAL | EPHHL | IPOHE | SETFA | ECHCG | ELEIN | DIGSA | LOLPE |
|---|---|---|---|---|---|---|---|---|---|---|
| A56 | 500 | 90 | 90 | 100 | 30 | 100 | 80 | 100 | 100 | 40 |
| A57 | 500 | n/a | 60 | 60 | 10 | 60 | 40 | 40 | 80 | 10 |
| A58 | 500 | 100 | 80 | 60 | 10 | 90 | 60 | 80 | 90 | 50 |
| A59 | 500 | 90 | 90 | 100 | 80 | 100 | 80 | 90 | 100 | 70 |
| A60 | 500 | n/a | 100 | 70 | 60 | 90 | 90 | 100 | 100 | 70 |
| A61 | 500 | n/a | 80 | 90 | 50 | 100 | 90 | 100 | 100 | 70 |
| A62 | 500 | n/a | 100 | 100 | 60 | 100 | 70 | 90 | 100 | 30 |
| A63 | 500 | 40 | 30 | 30 | 20 | 40 | 40 | 50 | 30 | 20 |
| A64 | 500 | 90 | 90 | 100 | 20 | 90 | 60 | 100 | 80 | 80 |
| A65 | 500 | 40 | 10 | 20 | 10 | 40 | 30 | 40 | 30 | 10 |
| A66 | 500 | 40 | 20 | 50 | 40 | 60 | 50 | 40 | 30 | 50 |
| A67 | 500 | 60 | 50 | 80 | 20 | 70 | 80 | 70 | 60 | 40 |
| A68 | 500 | 60 | 70 | 100 | 50 | 60 | 70 | 70 | 40 | 60 |
| A69 | 500 | 100 | 60 | 50 | 40 | 40 | 40 | 60 | 50 | 50 |
| A70 | 500 | 90 | 70 | 50 | 20 | 30 | 30 | 20 | 30 | 20 |
| A71 | 500 | 100 | 60 | 40 | 40 | 30 | 30 | 30 | 30 | 10 |
| A72 | 500 | 60 | 40 | 70 | 40 | 40 | 40 | 30 | 30 | 20 |
| A73 | 500 | 40 | 30 | 60 | 30 | 60 | 60 | 60 | 30 | 40 |
| A74 | 500 | 60 | 30 | 60 | 50 | 80 | 60 | 80 | 50 | 60 |
| A75 | 500 | 60 | 30 | 60 | 20 | 70 | 50 | 60 | 50 | 50 |
| A76 | 500 | 30 | 20 | 30 | 20 | 40 | 30 | 30 | 20 | 30 |
| A77 | 500 | 100 | 80 | 80 | 30 | 100 | 90 | 100 | 100 | 80 |
| A78 | 500 | 0 | 10 | 20 | 20 | 40 | 30 | 30 | 40 | 20 |
| A79 | 500 | 10 | 30 | 10 | 0 | 10 | 10 | 20 | 20 | 0 |
| A81 | 500 | 100 | 90 | 100 | 40 | 90 | 90 | 80 | 100 | 40 |
| A82 | 500 | 70 | 80 | 40 | 20 | 60 | 30 | 60 | 30 | 0 |
| A83 | 500 | 90 | 80 | 90 | 40 | 90 | 50 | 100 | 100 | 70 |
| A84 | 500 | 100 | 80 | 90 | 30 | 50 | 20 | 20 | 50 | 30 |
| A85 | 500 | 90 | 90 | 100 | 30 | 90 | 70 | 90 | 90 | 70 |
| A86 | 500 | 30 | 40 | 50 | 40 | 40 | 20 | 10 | 30 | 10 |
| A87 | 500 | 50 | 30 | 50 | 40 | 70 | 70 | 60 | 70 | 70 |
| A88 | 500 | 100 | 70 | 60 | 30 | 70 | 60 | 90 | 90 | 60 |
| A89 | 500 | 100 | 40 | 100 | 70 | 70 | 60 | 40 | 50 | 40 |
| A90 | 500 | 40 | 20 | 60 | 30 | 30 | 20 | 20 | 30 | 20 |
| A91 | 500 | 40 | 20 | 40 | 20 | 60 | 60 | 60 | 50 | 20 |
| A92 | 500 | 90 | 90 | 70 | 100 | 90 | 80 | 90 | 60 | 50 |
| A93 | 500 | 90 | 80 | 40 | 20 | 100 | 80 | 100 | 100 | 80 |
| A94 | 500 | 70 | 90 | 40 | 30 | 40 | 30 | 20 | 30 | 20 |
| A95 | 500 | 30 | 40 | 40 | 30 | 50 | 50 | 30 | 40 | 20 |
| A96 | 500 | 70 | 20 | 90 | 40 | 70 | 70 | 40 | 40 | 60 |
| A97 | 500 | 90 | 20 | 70 | 30 | 90 | 90 | 90 | 90 | 70 |
| A98 | 500 | 40 | 20 | 40 | 30 | 20 | 20 | 20 | 10 | 0 |
| A99 | 500 | 80 | 30 | 90 | 30 | 50 | 50 | 80 | 40 | 20 |
| A100 | 500 | 60 | 60 | 90 | 20 | 20 | 70 | 60 | 40 | 10 |
| A101 | 500 | 80 | 70 | 80 | 10 | 80 | 60 | 40 | 60 | 70 |
| A102 | 500 | 20 | 50 | 20 | 0 | 10 | 10 | 10 | 10 | 10 |
| A103 | 500 | 0 | 50 | 50 | 30 | 10 | 30 | 30 | 20 | 10 |
| A104 | 500 | 10 | 0 | 20 | 30 | 30 | 30 | 50 | 30 | 10 |
| A105 | 500 | 90 | 20 | 50 | 0 | 90 | 40 | 20 | 60 | 50 |
| A106 | 500 | 80 | 20 | 20 | 10 | 60 | 50 | 80 | 60 | 60 |
| A107 | 500 | 100 | 100 | 100 | 100 | 100 | 100 | 100 | 100 | 70 |
| A108 | 500 | 40 | 80 | 80 | 70 | 60 | 40 | 60 | 50 | 40 |
| A109 | 500 | 60 | 60 | 60 | 50 | 30 | 40 | 50 | 50 | 30 |
| A110 | 500 | 100 | 100 | 80 | 80 | 50 | 50 | 90 | 40 | 50 |
| A112 | 500 | 100 | 100 | 80 | 40 | 70 | 40 | 50 | 40 | 40 |
| A113 | 500 | 40 | 90 | 100 | 60 | 50 | 60 | 40 | 60 | 10 |
| A114 | 500 | 100 | 60 | 80 | 60 | 40 | 60 | 90 | 80 | 70 |
| A115 | 500 | 100 | 100 | 30 | 40 | 60 | 50 | 30 | 30 | 30 |
| A116 | 500 | 100 | 80 | 50 | 10 | 30 | 20 | 20 | 30 | 10 |
| A117 | 500 | 90 | 90 | 100 | 80 | 100 | 90 | 90 | 70 | 50 |
| A118 | 500 | 80 | 80 | 90 | 60 | 70 | 40 | 70 | 90 | 90 |
| A119 | 500 | 100 | 100 | 70 | 50 | 40 | 30 | 30 | 40 | 30 |
| A120 | 500 | 90 | 70 | 50 | 10 | 40 | 40 | 30 | 40 | 20 |
| A121 | 500 | 100 | 80 | 80 | 20 | 30 | 40 | 20 | 40 | 30 |
| A122 | 500 | 100 | 100 | 100 | 70 | 60 | 40 | 90 | 40 | 70 |
| A123 | 500 | 100 | 80 | 100 | 100 | 100 | 90 | 100 | 100 | 60 |
| A124 | 500 | 0 | 0 | 0 | 0 | 20 | 0 | 0 | 10 | 0 |
| A125 | 500 | 100 | 80 | 100 | 30 | 100 | 100 | 100 | 100 | 90 |
| A126 | 500 | 100 | 80 | 100 | 30 | 100 | 80 | 90 | 80 | 70 |
| A127 | 500 | 10 | 20 | 20 | 10 | 30 | 40 | 20 | 80 | 10 |
| A128 | 500 | 30 | 10 | 0 | 0 | 30 | 30 | 50 | 30 | 40 |
| A129 | 500 | 70 | 50 | 70 | 10 | 60 | 90 | 40 | 60 | 80 |
| A130 | 500 | 100 | 90 | 100 | 40 | 100 | 100 | 100 | 90 | 80 |
| A131 | 500 | 100 | 70 | 40 | 50 | 100 | 100 | 100 | 90 | 30 |
| A132 | 500 | 90 | 30 | 30 | 10 | 100 | 70 | 90 | 90 | 50 |

TABLE B-continued

Control of weed species by compounds of Formula (I) after post-emergence application

| Compound Number | Application Rate g/Ha | AMAPA | CHEAL | EPHHL | IPOHE | SETFA | ECHCG | ELEIN | DIGSA | LOLPE |
|---|---|---|---|---|---|---|---|---|---|---|
| A133 | 500 | 60 | 40 | 20 | 20 | 90 | 70 | 90 | 70 | 40 |
| A134 | 500 | 100 | 80 | 90 | 70 | 100 | 80 | 100 | 100 | 80 |
| A135 | 500 | 60 | 20 | 50 | 30 | 50 | 50 | 70 | 30 | 60 |
| A136 | 500 | 60 | 30 | 30 | 30 | 70 | 40 | 50 | 60 | 20 |
| A137 | 500 | 60 | 20 | 20 | 10 | 40 | 30 | 40 | 40 | 20 |
| A138 | 500 | 100 | 100 | 100 | 30 | 100 | 100 | 80 | 100 | 100 |
| A139 | 500 | 80 | 100 | 90 | 10 | 100 | 100 | 100 | 100 | 90 |
| A140 | 500 | 60 | 50 | 50 | 20 | 30 | 20 | 10 | 10 | 0 |
| A141 | 500 | 100 | 60 | 20 | 30 | 50 | 50 | 60 | 40 | 30 |
| A142 | 500 | 10 | 20 | 60 | 20 | 30 | 40 | 60 | 40 | 10 |
| A143 | 500 | 100 | 90 | 80 | 30 | 100 | 100 | 100 | 90 | 70 |
| A144 | 500 | 20 | 10 | 20 | 10 | 20 | 20 | 20 | 30 | 10 |
| A145 | 500 | 10 | 10 | 10 | 10 | 0 | 0 | 0 | 10 | 0 |
| A146 | 500 | 90 | 40 | 50 | 30 | 100 | 90 | 80 | 80 | 50 |
| A147 | 500 | 40 | 50 | 70 | 60 | 40 | 30 | 20 | 20 | 40 |
| A148 | 500 | 100 | 40 | 60 | 20 | 50 | 50 | 40 | 50 | 20 |
| A149 | 500 | 30 | 40 | 30 | 10 | 40 | 50 | 60 | 50 | 40 |
| A151 | 500 | 20 | 20 | 40 | 10 | 20 | 20 | 20 | 20 | 10 |
| A152 | 500 | 20 | 10 | 20 | 0 | 20 | 20 | 20 | 30 | 10 |
| A153 | 500 | 90 | 60 | 40 | 20 | 20 | 40 | 20 | 20 | 0 |
| A154 | 125 | 40 | 50 | 70 | 20 | 30 | 20 | 10 | 20 | 10 |
| A155 | 500 | 20 | 10 | 30 | 20 | 40 | 40 | 30 | 50 | 50 |
| A156 | 500 | 30 | 50 | 50 | 10 | 20 | 10 | 20 | 20 | 0 |
| A157 | 500 | 100 | 100 | 80 | 60 | 80 | 80 | 90 | 70 | 30 |
| A158 | 500 | 100 | 80 | 80 | 30 | 40 | 20 | 50 | 30 | 30 |
| A159 | 500 | 100 | 100 | 80 | 50 | 60 | 70 | 50 | 30 | 40 |
| A160 | 500 | 100 | 100 | 90 | 70 | 90 | 70 | 80 | 70 | 70 |
| A161 | 500 | 30 | 70 | 50 | 20 | 10 | 20 | 20 | 20 | 10 |
| A162 | 500 | 100 | 70 | 80 | 10 | 70 | 90 | 80 | 70 | 90 |
| A163 | 500 | 100 | 60 | 50 | 30 | n/a | 40 | 90 | 50 | 70 |
| A164 | 500 | 100 | 80 | 90 | 40 | 50 | 30 | 80 | 30 | 40 |
| A165 | 500 | 100 | 50 | 50 | 40 | 60 | 70 | 70 | 60 | 60 |
| A166 | 500 | 30 | 50 | 60 | 60 | 40 | 50 | 60 | 70 | 70 |
| A167 | 500 | 20 | 70 | 90 | 100 | 40 | 60 | 80 | 50 | 40 |
| A168 | 500 | 0 | 40 | 30 | 20 | 10 | 20 | 20 | 10 | 10 |
| A169 | 500 | 100 | 70 | n/a | 40 | 50 | 40 | 90 | 50 | 50 |
| A170 | 500 | 100 | 100 | 70 | 40 | 80 | 80 | 40 | 40 | 50 |
| A171 | 500 | 100 | 80 | n/a | 80 | 60 | 60 | 80 | 60 | 70 |
| A172 | 500 | 30 | 60 | 50 | 40 | 50 | 50 | 70 | 80 | 20 |
| A173 | 500 | 30 | 50 | 40 | 20 | 30 | 30 | 10 | 20 | 10 |
| A174 | 500 | 100 | 40 | 60 | 50 | 60 | 50 | 60 | 50 | 60 |
| A175 | 500 | 30 | 60 | 30 | 20 | 30 | 30 | 40 | 40 | 10 |
| A176 | 500 | 40 | 30 | n/a | 40 | 40 | 30 | 70 | 30 | 40 |
| A177 | 500 | 60 | 50 | 30 | 20 | 0 | 0 | 10 | 10 | 0 |
| A178 | 500 | 90 | 70 | 40 | 20 | 10 | 10 | 0 | 10 | 0 |
| A179 | 500 | 30 | 30 | 60 | 20 | 60 | 40 | 50 | 50 | 10 |
| A180 | 500 | 100 | 90 | 80 | 20 | 70 | 70 | 90 | 60 | 30 |
| A181 | 500 | 90 | 90 | n/a | 80 | 60 | 100 | 100 | 80 | 90 |
| A183 | 500 | 10 | 0 | n/a | 20 | 10 | 20 | 10 | 30 | 10 |
| A185 | 500 | 100 | 80 | n/a | 30 | 50 | 40 | 30 | 30 | 30 |
| A186 | 500 | 70 | 70 | 30 | 30 | 60 | 30 | 50 | 60 | 10 |
| A187 | 500 | 50 | 40 | 50 | 20 | 10 | 20 | 10 | 20 | 10 |
| A188 | 500 | 90 | 50 | 30 | 20 | 30 | 50 | 20 | 40 | 20 |
| A189 | 500 | 100 | 100 | 90 | 70 | 70 | 80 | 90 | 50 | 30 |
| A190 | 500 | 100 | 80 | 80 | 70 | 40 | 60 | 70 | 60 | 40 |
| A191 | 500 | 100 | 30 | 30 | 30 | 20 | 10 | 30 | 20 | 30 |
| A192 | 500 | 90 | 60 | 40 | 30 | 20 | 30 | 30 | 30 | 10 |
| A193 | 500 | 70 | 60 | 60 | 60 | 10 | 10 | 30 | 30 | 10 |
| A194 | 500 | 100 | 70 | 70 | 60 | 50 | 70 | 90 | 50 | 50 |
| A195 | 500 | n/a | 60 | n/a | 20 | n/a | 10 | 10 | 20 | 0 |
| A196 | 500 | 30 | 40 | 30 | 20 | 0 | 0 | 10 | 0 | 0 |
| A197 | 500 | 100 | 10 | 10 | 10 | 0 | 0 | 10 | 20 | 0 |
| A198 | 500 | 100 | 100 | 100 | 50 | 90 | 80 | 80 | 80 | 50 |
| A199 | 500 | n/a | 40 | n/a | 10 | 30 | 20 | 10 | 50 | 0 |
| A200 | 500 | 100 | 70 | 70 | 10 | 50 | 40 | 30 | 40 | 40 |
| A201 | 500 | 100 | 100 | 90 | 40 | 80 | 70 | 100 | 80 | 30 |
| A202 | 500 | 100 | 90 | 100 | 60 | 70 | 80 | 20 | 60 | 70 |
| A203 | 500 | 100 | 90 | 50 | 20 | 60 | 50 | 60 | 70 | 0 |
| A204 | 500 | 10 | 20 | 0 | 0 | 0 | 0 | 0 | 0 | 0 |
| A205 | 500 | 80 | 60 | n/a | 80 | 80 | 60 | 60 | 80 | 40 |
| A206 | 500 | 60 | 90 | 60 | 20 | 10 | 20 | 10 | 20 | 0 |
| A207 | 500 | 100 | 100 | 90 | 90 | 100 | 60 | 100 | 90 | 20 |
| A208 | 500 | 100 | 80 | 50 | 20 | 60 | 30 | 60 | 40 | 10 |
| A209 | 125 | 30 | 10 | 0 | 0 | 20 | 10 | 0 | 30 | 10 |
| A210 | 500 | 70 | 10 | 10 | 10 | 30 | 10 | 20 | 60 | 20 |

TABLE B-continued

Control of weed species by compounds of Formula (I) after post-emergence application

| Compound Number | Application Rate g/Ha | AMAPA | CHEAL | EPHHL | IPOHE | SETFA | ECHCG | ELEIN | DIGSA | LOLPE |
|---|---|---|---|---|---|---|---|---|---|---|
| A211 | 500 | 100 | 100 | 100 | 60 | 100 | 100 | 90 | 100 | 60 |
| A212 | 500 | 100 | 100 | 100 | 30 | 80 | 70 | 90 | 90 | 70 |
| A213 | 500 | 100 | 90 | 100 | 70 | 100 | 100 | 100 | 100 | 90 |
| A214 | 500 | 100 | 100 | 100 | 40 | 90 | 100 | 100 | 100 | 80 |
| A215 | 500 | 100 | 60 | 90 | 60 | 20 | 30 | 30 | 60 | 20 |
| A216 | 500 | 100 | 90 | 100 | 60 | 90 | 70 | 100 | 100 | 70 |
| A218 | 500 | 100 | 80 | 80 | 70 | 60 | 60 | 60 | 70 | 70 |
| A219 | 500 | 100 | 80 | 90 | 60 | 90 | 40 | 100 | 70 | 70 |
| A220 | 500 | 100 | 100 | 90 | 80 | 60 | 40 | 20 | 90 | 60 |
| A221 | 500 | 100 | 90 | 90 | 60 | 80 | 60 | 100 | 100 | 60 |
| A222 | 500 | 80 | 60 | n/a | 70 | 80 | 70 | 60 | 90 | 20 |
| A223 | 500 | 100 | 90 | 80 | 60 | 80 | 70 | 90 | 90 | 80 |
| A224 | 500 | 100 | 90 | n/a | 80 | 40 | 40 | 80 | 80 | 40 |
| A225 | 500 | 100 | 90 | 100 | 70 | 30 | 30 | 90 | 60 | 30 |
| A226 | 500 | 100 | 100 | 100 | 50 | 90 | 90 | 100 | 100 | 90 |
| A228 | 500 | 80 | 60 | n/a | 60 | 10 | 10 | 10 | 20 | 0 |
| A229 | 500 | 10 | 0 | n/a | 10 | 10 | 0 | 0 | 20 | 0 |
| A230 | 500 | 50 | 60 | n/a | 20 | 50 | 60 | 10 | 70 | 0 |
| A231 | 500 | 100 | 90 | n/a | 60 | 60 | 50 | 60 | 80 | 60 |
| A232 | 500 | 100 | 90 | n/a | 0 | 80 | 100 | 50 | 90 | 20 |
| A233 | 500 | 100 | 100 | n/a | 70 | 70 | 60 | 50 | 60 | 20 |
| A234 | 500 | 100 | 100 | 100 | 60 | 100 | 100 | 100 | 100 | 90 |
| A235 | 500 | 10 | 40 | 20 | 20 | 30 | 30 | 10 | 40 | 0 |
| A236 | 500 | 90 | 20 | 30 | 40 | 30 | 50 | 10 | 80 | 0 |
| A237 | 500 | 60 | 10 | 0 | 50 | 20 | 10 | 70 | 50 | 10 |
| A238 | 500 | 50 | 20 | 50 | 40 | 50 | 40 | 30 | 50 | 10 |

Method B

An "instant formulation", known as the IF50, containing 50 g/L of the "technical" (i.e. unformulated) active ingredient was prepared by dissolving the active ingredient in a mixture of organic solvents and emulsifier, details of which are provided in the table. This IF50 was then mixed with a small, variable amount of acetone to aid dissolution, before addition of an aqueous solution of 1% v/v ammonium sulphate+1% v/v Empicol ESC70 (Sodium lauryl ether sulphate) adjuvant, as the aqueous diluent, to form an aqueous spray solution which contains a predetermined concentration of the active ingredient (which varies depending on the application rate of the active ingredient to the plants).

Composition of the mixture of organic solvents and emulsifier used as a base for the instant formulation.

| Component | Supplier | Chemical description | CAS Registry number | Amount/ % w/w |
|---|---|---|---|---|
| Emulsogen EL360 ™ | Clariant | Castor oil ethoxylate | 61791-12-6 | 10.6 |
| N-methylpyrrolidone | Widely available | 1-Methyl-2-pyrrolidone | 872-50-4 | 42.2 |
| Dowanol DPM glycol ether | Dow | Dipropylene glycol monomethyl ether | 34590-94-8 | 42.2 |

This aqueous spray solution was then sprayed onto the plants, after about 12 days' cultivation. The plants were grown from seeds sown in standard soil, placed in a glasshouse under controlled conditions (at 24/18° C. or 20/16° C., day/night; 16 hours light; 65% humidity). After spray application the plants were then grown on in a glasshouse under the same conditions and watered twice daily. After 15 days the test was evaluated (100=total damage to plant; 0=no damage to plant).

The results are shown in Table C (below). A value of n/a indicates that this combination of weed and test compound was not tested/assessed.

Test Plants:

*Ipomoea hederacea* (IPOHE), *Euphorbia heterophylla* (EPHHL), *Chenopodium album* (CHEAL), 20 *Amaranthus retroflexus* (AMARE), *Lolium perenne* (LOLPE), *Digitaria sanguinalis* (DIGSA), *Eleusine indica* (ELEIN), *Echinochloa crus-galli* (ECHCG), *Setaria faberi* (SETFA)

TABLE C

Control of weed species by compounds of Formula (I) after post-emergence application

| Compound Number | Application Rate g/Ha | AMARE | CHEAL | EPHHL | IPOHE | SETFA | ECHCG | ELEIN | DIGSA | LOLPE |
|---|---|---|---|---|---|---|---|---|---|---|
| A4 | 500 | 100 | 80 | 100 | 100 | 40 | 70 | 80 | 100 | 90 |
| A28 | 1000 | 100 | 90 | 100 | 100 | 40 | 100 | 100 | 100 | 70 |
| A41 | 1000 | 100 | 90 | 100 | 20 | 100 | 100 | 50 | 100 | 60 |
| A138 | 1000 | 100 | 100 | 100 | 40 | 100 | 100 | 100 | 100 | 100 |
| A207 | 1000 | 100 | 90 | 70 | 100 | 100 | 100 | 100 | 90 | 20 |
| A211 | 500 | 100 | 90 | 80 | 100 | 100 | 100 | 100 | 100 | 10 |
| A213 | 1000 | 100 | 80 | 100 | 80 | 100 | 100 | 100 | 100 | 90 |
| A220 | 1000 | 100 | 90 | 100 | 30 | 30 | 90 | 100 | 100 | 90 |
| A226 | 1000 | 100 | 100 | n/a | 100 | 70 | 100 | n/a | 100 | 70 |

Method C

An "instant formulation", known as the IF50, containing 50 g/L of the "technical" (i.e. unformulated) active ingredient was prepared by dissolving the active ingredient in a mixture of organic solvents and emulsifier, details of which are provided in the table. This IF50 was then mixed with a small, variable amount of acetone to aid dissolution, before addition of a 1% v/v aqueous solution of the adjuvant Empicol ESC70 3EO (Sodium lauryl ether sulphate) and 1% v/v Ammonium sulphate, as the aqueous diluent, to form an aqueous spray solution which contains a predetermined concentration of the active ingredient (which varies depending on the application rate of the active ingredient to the plants).

Composition of the mixture of organic solvents and emulsifier used as a base for the instant formulation.

| Component | Supplier | Chemical description | CAS Registry number | Amount/ % w/w |
|---|---|---|---|---|
| Emulsogen EL360 ™ | Clariant | Castor oil ethoxylate | 61791-12-6 | 10.6 |
| N-methylpyrrolidone | Widely available | 1-Methyl-2-pyrrolidone | 872-50-4 | 42.2 |
| Dowanol DPM glycol ether | Dow | Dipropylene glycol monomethyl ether | 34590-94-8 | 42.2 |

This aqueous spray solution was then sprayed onto the plants after about 21 days' cultivation. The plants were grown from seeds sown in standard soil, placed in a glasshouse under controlled conditions (at 24/18° C., day/night; 14 hours light; 65% humidity). After spray application the plants were then grown on in a glasshouse under the same conditions and watered twice daily. The test was evaluated at 21 days (100=total damage to plant; 0=no damage to plant).

The results are shown in Table D (below). A value of n/a indicates that this combination of weed and test compound was not tested/assessed.

Test Plants:
*Ipomoea hederacea* (IPOHE), *Amaranthus palmeri* (AMAPA), *Lolium perenne* (LOLPE), *Eleusine indica* (ELEIN), *Echinochloa crus-galli* (ECHCG), *Conyza canadensis* (ERICA)

TABLE D

Control of weed species by compounds of Formula (I) after post-emergence application

| Compound Number | Application Rate g/Ha | AMAPA | IPOHE | ECHCG | ELEIN | LOLPE | ERICA |
|---|---|---|---|---|---|---|---|
| A3 | 400 | 65 | 83 | 13 | 15 | 25 | 100 |
| A27 | 400 | 77 | 90 | 43 | 80 | 68 | 65 |

What is claimed is:

1. A compound of Formula (I) or an agronomically acceptable salt or zwitterionic species thereof:

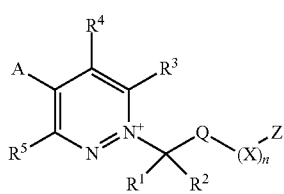

(I)

wherein
R$^1$ is selected from the group consisting of hydrogen, halogen, C$_1$-C$_6$alkyl, C$_2$-C$_6$alkenyl, C$_2$-C$_6$alkynyl, C$_3$-C$_6$cycloalkyl, C$_1$-C$_6$haloalkyl, —OR$^7$, —OR$^{15a}$, —N(R$^6$)S(O)$_2$R$^{15}$, —N(R$^6$)C(O)R$^{15}$, —N(R$^6$)C(O)OR$^{15}$, —N(R$^6$)C(O)NR$^{16}$R$^{17}$, —N(R$^6$)CHO, —N(R$^{7a}$)$_2$ and —S(O)$_r$R$^{15}$;

R$^2$ is selected from the group consisting of hydrogen, halogen, C$_1$-C$_6$alkyl and C$_1$-C$_6$haloalkyl;

and wherein when R$^1$ is selected from the group consisting of —OR$^7$, —OR$^{15a}$, —N(R$^6$)S(O)$_2$R$^{15}$, —N(R$^6$)C(O)R$^{15}$, —N(R$^6$)C(O)OR$^{15}$, —N(R$^6$)C(O)NR$^{16}$R$^{17}$, —N(R$^6$)CHO, —N(R$^{7a}$)$_2$ and —S(O)$_r$R$^{15}$, R$^2$ is selected from the group consisting of hydrogen and C$_1$-C$_6$alkyl; or R$^1$ and R$^2$ together with the carbon atom to which they are attached form a C$_3$-C$_6$cycloalkyl ring or a 3- to 6-membered heterocyclyl, which comprises 1 or 2 heteroatoms individually selected from N and O;

Q is (CR$^{1a}$R$^{2b}$)$_m$,
m is 0, 1, 2 or 3;

each R$^{1a}$ and R$^{2b}$ are independently selected from the group consisting of hydrogen, halogen, C$_1$-C$_6$alkyl, C$_1$-C$_6$haloalkyl, —OH, —OR$^7$, —OR$^{15a}$, —NH$_2$, —NHR$^7$, —NHR$^{15a}$, —N(R$^6$)CHO, —NR$^{7b}$R$^{7c}$ and —S(O)$_r$R$^{15}$; or each R$^{1a}$ and R$^{2b}$ together with the carbon atom to which they are attached form a C$_3$-C$_6$cycloalkyl ring or a 3- to 6-membered heterocyclyl, which comprises 1 or 2 heteroatoms individually selected from N and O; and R$^3$, R$^4$ and R$^5$ are independently selected from the group consisting of hydrogen, halogen, cyano, nitro, —S(O)$_r$ R$^{15}$, C$_1$-C$_6$alkyl, C$_1$-C$_6$fluoroalkyl, C$_1$-C$_6$fluoroalkoxy, C$_1$-C$_6$alkoxy, C$_3$-C$_6$cycloalkyl and —N(R$^6$)$_2$;

each R$^6$ is independently selected from hydrogen and C$_1$-C$_6$alkyl;

each R$^7$ is independently selected from the group consisting of C$_1$-C$_6$alkyl, —S(O)$_2$R$^{15}$, —C(O)R$^{15}$, —C(O)OR$^{15}$ and —C(O)NR$^{16}$R$^{17}$;

each R$^{7a}$ is independently selected from the group consisting of —S(O)$_2$R$^{15}$, —C(O)R$^{15}$, —C(O)OR$^{15}$—C(O)NR$^{16}$R$^{17}$ and —C(O)NR$^6$R$^{15a}$;

R$^{7b}$ and R$^{7c}$ are independently selected from the group consisting of C$_1$-C$_6$alkyl, —S(O)$_2$R$^{15}$, —C(O)R$^{15}$, —C(O)OR$^{15}$, —C(O)NR$^{16}$R$^{17}$ and phenyl, and wherein said phenyl is optionally substituted by 1, 2 or 3 R$^9$ substituents, which may be the same or different; or R$^{7b}$ and R$^{7c}$ together with the nitrogen atom to which they are attached form a 4- to 6-membered heterocyclyl ring which optionally comprises one additional heteroatom individually selected from N, O and S; and A is a 6-membered heteroaryl, which comprises 1, 2, 3 or 4 nitrogen atoms and wherein the heteroaryl may be optionally substituted by 1, 2, 3 or 4 R$^8$ substituents, which may be the same or different, and wherein when A is substituted by 1 or 2 substituents, each R$^8$ is independently selected from the group consisting of halogen, nitro, cyano, —NH$_2$, —NHR$^7$, —N(R$^7$)$_2$, —OH, —OR$^7$, —S(O)$_r$R$^{15}$, —NR$^6$S(O)$_2$R$^{15}$, —C(O)OR$^{10}$, —C(O)R$^{15}$, —C(O)NR$^{16}$R$^{17}$, —S(O)$_2$NR$^{16}$R$^{17}$, C$_1$-C$_6$alkyl, C$_1$-C$_6$haloalkyl, C$_3$-C$_6$cycloalkyl, C$_3$-C$_6$halocycloalkyl, C$_3$-C$_6$cycloalkoxy, C$_2$-C$_6$alkenyl, C$_2$-C$_6$haloalkenyl, $C_2$-$C_6$alkynyl, $C_1$-$C_3$alkoxy$C_1$-$C_3$alkyl-, hydroxy$C_1$-$C_6$alkyl-, $C_1$-$C_3$alkoxy$C_1$-$C_3$alkoxy-, $C_1$-$C_6$haloalkoxy, $C_1$-$C_3$haloalkoxy$C_1$-$C_3$alkyl-, $C_3$-$C_6$alkenyloxy, $C_3$-$C_6$alkynyloxy, N—$C_3$-$C_6$cycloalkylamino, —C($R^6$)=NO$R^6$, phenyl, a 3- to 6-membered heterocyclyl, which comprises 1 or 2 heteroatoms individually selected from N and O, and a 5- or 6-membered heteroaryl, which comprises 1, 2, 3 or 4 heteroatoms individually selected from N, O and S, and wherein said phenyl, heterocyclyl or heteroaryl are optionally substituted by 1, 2 or 3 $R^9$ substituents, which may be the same or different;

and wherein when A is substituted by 3 or 4 substituents, each $R^8$ is independently selected from the group consisting of halogen, —$NH_2$, —NH$R^7$, —N($R^7$)$_2$, —OH, —O$R^7$, —C(O)N$R^{16}R^{17}$, —S(O)$_2$N$R^{16}R^{17}$, $C_1$-$C_6$alkyl and $C_1$-$C_6$haloalkyl; and each $R^9$ is independently selected from the group consisting of halogen, cyano, —OH, —N($R^6$)$_2$, $C_1$-$C_4$alkyl, $C_1$-$C_4$alkoxy, $C_1$-$C_4$haloalkyl and $C_1$-$C_4$haloalkoxy;

X is selected from the group consisting of $C_3$-$C_6$cycloalkyl, phenyl, a 5- or 6-membered heteroaryl, which comprises 1, 2, 3 or 4 heteroatoms individually selected from N, O and S, and a 4- to 6-membered heterocyclyl, which comprises 1, 2 or 3 heteroatoms individually selected from N, O and S, and wherein said cycloalkyl, phenyl, heteroaryl or heterocyclyl moieties are optionally substituted by 1 or 2 $R^9$ substituents, and wherein the aforementioned C$R^1R^2$, Q and Z moieties may be attached at any position of said cycloalkyl, phenyl, heteroaryl or heterocyclyl moieties;

n is 0 or 1;

Z is selected from the group consisting of —C(O)O$R^{10}$, —$CH_2$OH, —CHO, —C(O)NHO$R^{11}$, —C(O)NHCN, —OC(O)NHO$R^{11}$, —OC(O)NHCN, —N$R^6$C(O)NHO$R^{11}$, —N$R^6$C(O)NHCN, —C(O)NHS(O)$_2R^{12}$, —OC(O)NHS(O)$_2R^{12}$, —N$R^6$C(O)NHS(O)$_2R^{12}$, —S(O)$_2$O$R^{10}$, —OS(O)$_2$O$R^{10}$, —N$R^6$S(O)$_2$O$R^{10}$, —N$R^6$S(O)O$R^{10}$, —NHS(O)$_2R^{14}$, —S(O)O$R^{10}$, —OS(O)O$R^{10}$, —S(O)$_2$NHCN, —S(O)$_2$NHC(O)$R^{18}$, —S(O)$_2$NHS(O)$_2R^{12}$, —OS(O)$_2$NHCN, —OS(O)$_2$NHS(O)$_2R^{12}$, —OS(O)$_2$NHC(O)$R^{18}$, —N$R^6$S(O)$_2$NHCN, —N$R^6$S(O)$_2$NHC(O)$R^{18}$, —N(OH)C(O)$R^{15}$, —ONHC(O)$R^{15}$, —N$R^6$S(O)$_2$NHS(O)$_2R^{12}$, —P(O)($R^{13}$)(O$R^{10}$), —P(O)H(O$R^{10}$), —OP(O)($R^{13}$)(O$R^{10}$), —N$R^6$P(O)($R^{13}$)(O$R^{10}$) and tetrazole;

$R^{10}$ is selected from the group consisting of hydrogen, $C_1$-$C_6$alkyl, phenyl and benzyl, and wherein said phenyl or benzyl are optionally substituted by 1, 2 or 3 $R^9$ substituents, which may be the same or different;

$R^{11}$ is selected from the group consisting of hydrogen, $C_1$-$C_6$alkyl and phenyl, and wherein said phenyl is optionally substituted by 1, 2 or 3 $R^9$ substituents, which may be the same or different;

$R^{12}$ is selected from the group consisting of $C_1$-$C_6$alkyl, $C_1$-$C_6$haloalkyl, $C_1$-$C_6$alkoxy, —OH, —N($R^6$)$_2$ and phenyl, and wherein said phenyl is optionally substituted by 1, 2 or 3 $R^9$ substituents, which may be the same or different;

$R^{13}$ is selected from the group consisting of —OH, $C_1$-$C_6$alkyl, $C_1$-$C_6$alkoxy and phenyl;

$R^{14}$ is $C_1$-$C_6$haloalkyl;

$R^{15}$ is selected from the group consisting of $C_1$-$C_6$alkyl and phenyl, and wherein said phenyl is optionally substituted by 1, 2 or 3 $R^9$ substituents, which may be the same or different;

$R^{15a}$ is phenyl, wherein said phenyl is optionally substituted by 1, 2 or 3 $R^9$ substituents, which may be the same or different;

$R^{16}$ and $R^{17}$ are independently selected from the group consisting of hydrogen and $C_1$-$C_6$alkyl; or $R^{16}$ and $R^{17}$ together with the nitrogen atom to which they are attached form a 4- to 6-membered heterocyclyl ring which optionally comprises one additional heteroatom individually selected from N, O and S; and $R^{18}$ is selected from the group consisting of hydrogen, $C_1$-$C_6$alkyl, $C_1$-$C_6$haloalkyl, $C_1$-$C_6$alkoxy, —N($R^6$)$_2$ and phenyl, and wherein said phenyl is optionally substituted by 1, 2 or 3 $R^9$ substituents, which may be the same or different;

and r is 0, 1 or 2.

2. The compound according to claim 1, wherein $R^1$ and $R^2$ are independently selected from the group consisting of hydrogen and $C_1$-$C_6$alkyl.

3. The compound according to claim 1, wherein each $R^{1a}$ and $R^{2b}$ are independently selected from the group consisting of hydrogen, $C_1$-$C_6$alkyl, —OH and —$NH_2$.

4. The compound according to claim 1, wherein m is 1 or 2.

5. The compound according to claim 1, wherein $R^3$, $R^4$ and $R^5$ are independently selected from the group consisting of hydrogen, $C_1$-$C_6$alkyl and $C_1$-$C_6$alkoxy.

6. The compound according to claim 1, wherein $R^3$, $R^4$ and $R^5$ are hydrogen.

7. The compound according to claim 1, wherein A is selected from the group consisting of formula A-I to A-VII below

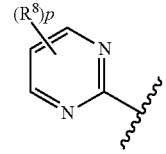

A-I

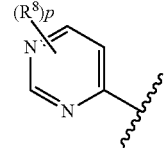

A-II

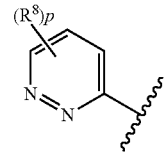

A-III

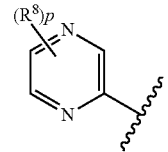

A-IV

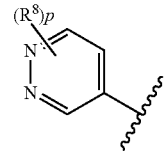

A-V

-continued

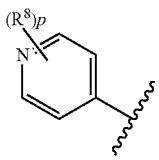

A-VI

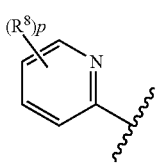

A-VII wherein the jagged line defines the point of attachment to the remaining part of a compound of Formula (I), p is 0, 1 or 2 and $R^8$ is as defined in claim 1.

8. The compound according to claim 1, wherein A is selected from the group consisting of formula A-I to A-V below

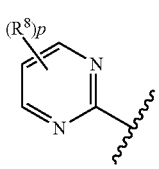

A-I

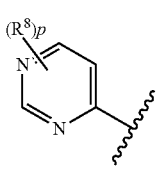

A-II

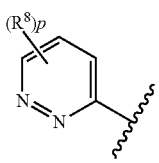

A-III

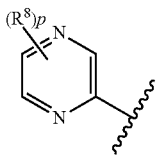

A-IV

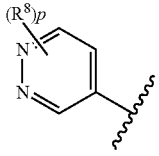

A-V wherein the jagged line defines the point of attachment to the remaining part of a compound of Formula (I), p is 0, 1, or 2 and $R^8$ is as defined in claim 1.

9. The compound according to claim 1, wherein when A is substituted by 1 or 2 substituents, each $R^8$ is independently selected from the group consisting of halogen, nitro, cyano, $-NH_2$, $-NHR^7$, $-N(R^7)_2$, $-OH$, $-OR^7$, $-S(O)_rR^{15}$, $-NR^6S(O)_2R^{15}$, $-C(O)OR^{10}$, $-C(O)R^{15}$, $-C(O)NR^{16}R^{17}$, $-S(O)_2NR^{16}R^{17}$, $C_1$-$C_6$alkyl and $C_1$-$C_6$haloalkyl.

10. The compound according to claim 1, wherein when A is substituted by 1 or 2 substituents, each $R^8$ is independently selected from the group consisting of chloro, fluoro, cyano, $-NH_2$, $-N(Me)_2$, $-OMe$, $-S(O)_2Me$, $-C(O)NHMe$, $-C(O)N(Me)_2$, methyl and trifluoromethyl.

11. The compound according to claim 7, wherein A is selected from the group consisting of formula A-I to A-V and p is 0.

12. The compound according to claim 1, wherein Z is selected from the group consisting of $-C(O)OR^{10}$, $-C(O)NHS(O)_2R^{12}$, $-S(O)_2OR^{10}$, and $-P(O)(R^{13})(OR^{10})$.

13. The compound according to claim 1, wherein Z is $-C(O)OH$ or $-S(O)_2OH$.

14. The compound according to claim 1, wherein n is 0.

15. An agrochemical composition comprising a herbicidally effective amount of a compound of Formula (I) as defined in claim 1 and an agrochemically-acceptable diluent or carrier.

16. A method of controlling plant growth, comprising applying a compound of Formula (T) as defined in claim 1, to the plants or to a locus thereof.

17. A process for preparing a compound of formula (I) as defined in claim 1, comprising:
(i) either
(a) reacting a compound of formula (H)

A-Hal          formula (H)

wherein
A is as defined in claim 1 and Hal is a halogen, triflate, mesylate, or tosylate, with a compound of formula (J)

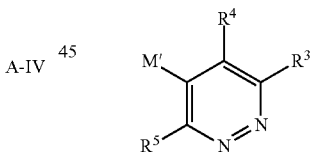

formula (J)

wherein
$R^3$, $R^4$ and $R^5$ are as defined in claim 1 and M' is an organostannane or an organoborane, in the presence of a palladium catalyst, to give a compound of formula (X)

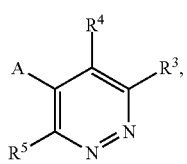

formula (X)

or (b) reacting a compound of formula (K)

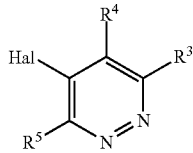
formula (K)

wherein $R^3$, $R^4$ and $R^5$ are as defined in claim 1 and Hal is a halogen triflate, mesylate, or tosylate, with a compound of formula (L)

A-M'  formula (L)

wherein

A is as defined in-claim 1 and M' is an organostannane or an organoborane, in the presence of a palladium catalyst, to give a compound of formula (X);

(ii) reacting a compound of formula (X) with an alkylating agent of formula (W)

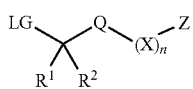
formula (W)

wherein $R^1$, $R^2$, Q, X, Z and n are as defined in claim 1 and LG is a leaving group, in an inert solvent or mixture of inert solvents, at a temperature of from −78° C. to 150° C., to give a compound of formula (I);

(iii) optionally, partially or fully hydrolysing a compound of formula (I) in the presence of a acid.

18. The process of claim 17, wherein for a compound of formula (J), M' is tributylstannane.

19. The process of claim 17, wherein the compound of formula (X) is selected from the group consisting of 2-pyridazin-4-ylpyrimidine, 4-pyridazin-4-ylpyrimidine, 3-pyridazin-4-ylpyridazine, 2-pyridazin-4-ylpyrazine and 4-pyridazin-4-ylpyridazine.

20. A compound selected from the group consisting of 2-pyridazin-4-ylpyrimidine, 3-pyridazin-4-ylpyridazine and 2-pyridazin-4-ylpyrazine.

21. A process, comprising:

(a) reacting a compound of formula (H)

A-Hal  formula (H)

wherein

A is as defined in claim 1 and Hal is a halogen, triflate, mesylate, or tosylate, with a compound of formula (J)

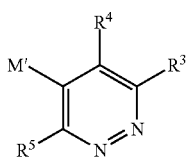
formula (J)

wherein $R^3$, $R^4$ and $R^5$ are as defined in claim 1 and M' is an organostannane or an organoborane, in the presence of a palladium catalyst, to give a compound of formula (X)

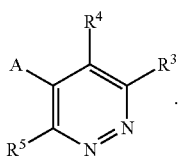
formula (X)

22. A process for preparing a compound of formula (I) as defined in claim 1, comprising:

reacting a compound of formula (X)

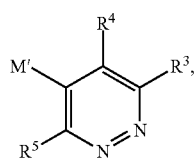
formula (J)

where A, $R^3$, $R^4$ and $R^5$ are as defined in claim 1 with an alkylating agent of formula (W)

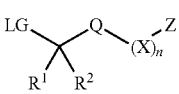
formula (W)

wherein $R^1$, $R^2$, Q, X, Z and n are as defined in claim 1 and LG is a leaving group, in an inert solvent or mixture of inert solvents, at a temperature of from −78° C. to 150° C., to give a compound of formula (I) as defined in claim 1.

23. A compound selected from the group consisting of:

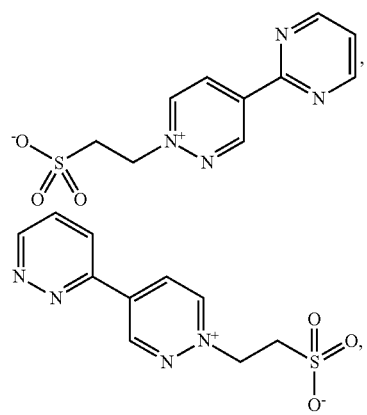

-continued
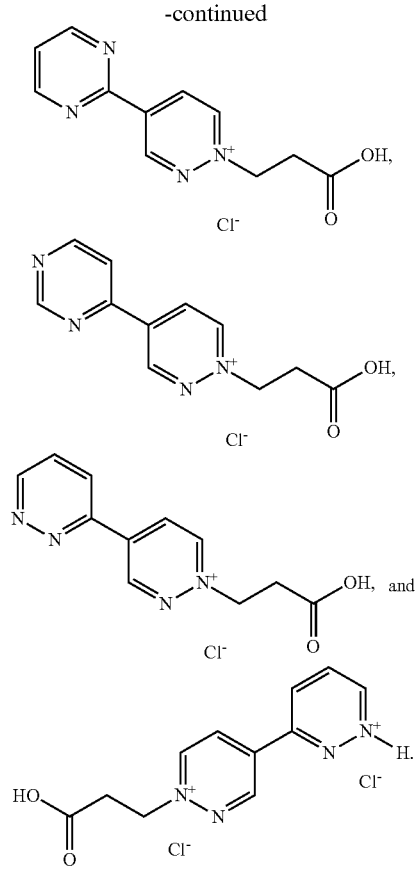
24. The compound of claim 23, wherein the compound is
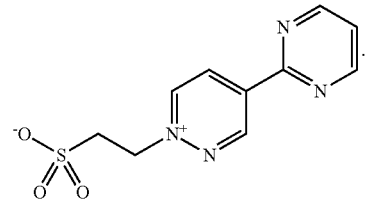
25. The compound of claim 23, wherein the compound is
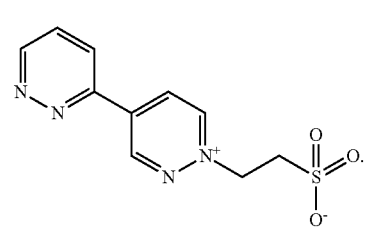 [SMILES: O=S(=O)([O-])CC[n+]1ccc(-c2cccnn2)cn1]
26. The compound of claim 23, wherein the compound is
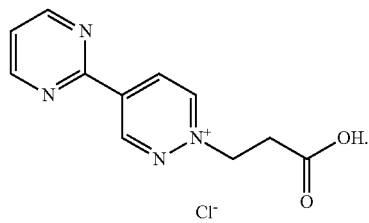 [SMILES: O=C(O)CC[n+]1ccc(-c2ncccn2)cn1 ; [Cl-]]
27. The compound of claim 23, wherein the compound is
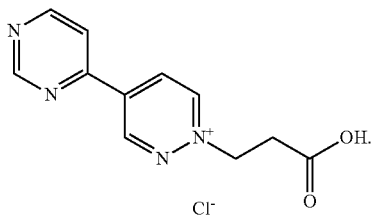 [SMILES: O=C(O)CC[n+]1ccc(-c2ccncn2)cn1 ; [Cl-]]
28. The compound of claim 23, wherein the compound is
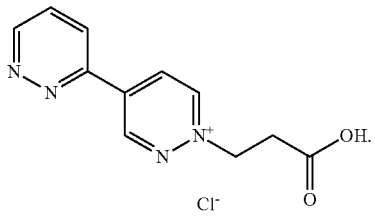 [SMILES: O=C(O)CC[n+]1ccc(-c2cccnn2)cn1 ; [Cl-]]
29. The compound of claim 23, wherein the compound is
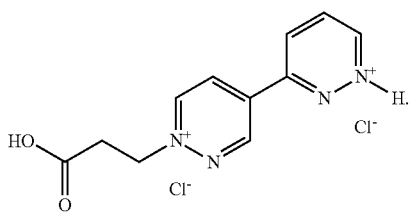
* * * * *